(12) United States Patent
Watanabe et al.

(10) Patent No.: US 9,287,507 B2
(45) Date of Patent: Mar. 15, 2016

(54) ORGANIC ELECTROLUMINESCENT ELEMENT, COMPOUNDS AND MATERIALS USED FOR THE ORGANIC ELECTROLUMINESCENT ELEMENT, AND LIGHT-EMITTING, DISPLAY AND ILLUMINATING DEVICES USING THE ELEMENTS

(71) Applicant: UDC Ireland Limited, Dublin (IE)

(72) Inventors: Kousuke Watanabe, Kanagawa (JP); Koji Takaku, Kanagawa (JP); Wataru Toyama, Kanagawa (JP); Toshihiro Ise, Kanagawa (JP); Masaru Kinoshita, Kanagawa (JP); Saki Takada, Kanagawa (JP)

(73) Assignee: UDC Ireland, Dublin (IE)

( * ) Notice: Subject to any disclaimer, the term of this patent is extended or adjusted under 35 U.S.C. 154(b) by 498 days.

(21) Appl. No.: 13/762,314

(22) Filed: Feb. 7, 2013

(65) Prior Publication Data

US 2013/0214259 A1  Aug. 22, 2013

(30) Foreign Application Priority Data

Feb. 14, 2012 (JP) ................ 2012-029312

(51) Int. Cl.
| | |
|---|---|
| *H01L 51/00* | (2006.01) |
| *C07C 15/28* | (2006.01) |
| *C09K 11/06* | (2006.01) |
| *C07F 7/08* | (2006.01) |
| *C09B 57/00* | (2006.01) |
| *C09B 1/00* | (2006.01) |
| *C09B 3/78* | (2006.01) |
| *H01L 51/50* | (2006.01) |

(52) U.S. Cl.
CPC ............ *H01L 51/0058* (2013.01); *C07C 15/28* (2013.01); *C07F 7/0809* (2013.01); *C07F 7/0818* (2013.01); *C09B 1/00* (2013.01); *C09B 3/78* (2013.01); *C09B 57/00* (2013.01); *C09B 57/001* (2013.01); *C09B 57/008* (2013.01); *C09K 11/06* (2013.01); *H01L 51/0052* (2013.01); *C07B 2200/05* (2013.01); *C07C 2103/24* (2013.01); *C09K 2211/1011* (2013.01); *C09K 2211/1014* (2013.01); *C09K 2211/1044* (2013.01); *C09K 2211/1059* (2013.01); *C09K 2211/1088* (2013.01); *C09K 2211/1092* (2013.01); *H01L 51/006* (2013.01); *H01L 51/5012* (2013.01)

(58) Field of Classification Search
None
See application file for complete search history.

(56) References Cited

U.S. PATENT DOCUMENTS

2006/0216633 A1 * 9/2006 Kubota et al. ............... 430/139

FOREIGN PATENT DOCUMENTS

| | | |
|---|---|---|
| JP | 2002063988 | 2/2002 |
| JP | 200722717 | 9/2007 |
| JP | 20106818 | 1/2010 |
| JP | 2012001449 | 1/2012 |
| KR | 10-2011012370 | 11/2011 |
| WO | 2006104044 | 5/2006 |
| WO | 2006085434 | 8/2006 |

OTHER PUBLICATIONS

STN Structure Search (Jul. 23, 2015).*
STN Structure Search (Jul. 22, 2015).*

* cited by examiner

Primary Examiner — Vu A Nguyen
(74) Attorney, Agent, or Firm — Riverside Law LLP

(57) ABSTRACT

An organic electroluminescent element is provided that has high luminous efficiency, and a slow luminance deterioration rate in the initial stage of lighting. The organic electroluminescent element includes a substrate; a pair of electrodes including an anode and a cathode, disposed on the substrate; and at least one organic layer including a light emitting layer, disposed between the electrodes, wherein at least one organic layer includes a compound represented by the general formula (1). ($R^{11}$ to $R^{15}$ represent hydrogen atoms, alkyl groups, or silyl groups, and any one of $R^{21}$ to $R^{24}$ represents a group represented by general formula (1A) or (1B). $Ph^4$ represents a p-phenylene group, and at least one of $Ph^{4a}$ and $Ph^{4b}$ represents a p-phenylene group.)

General Formula (1)

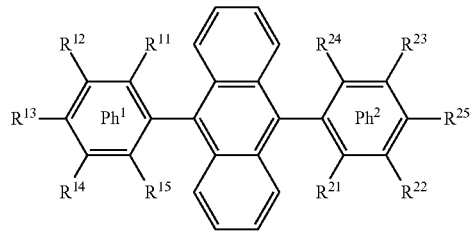

General Formula (1A)

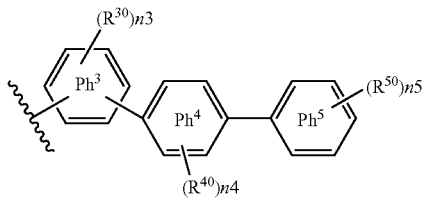

General Formula (1B)

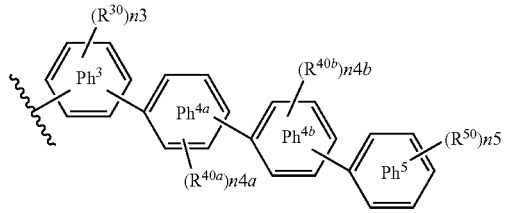

19 Claims, 2 Drawing Sheets

ORGANIC ELECTROLUMINESCENT ELEMENT, COMPOUNDS AND MATERIALS USED FOR THE ORGANIC ELECTROLUMINESCENT ELEMENT, AND LIGHT-EMITTING, DISPLAY AND ILLUMINATING DEVICES USING THE ELEMENTS

CROSS-REFERENCE TO RELATED APPLICATIONS

The present application claims priority benefit from Japanese Patent Application No. 2012-029312, filed 14 Feb. 2012, which is hereby incorporated by reference herein in its entirety.

FIELD OF THE INVENTION

The present invention relates to organic electroluminescent elements, compounds usable therefor, and materials for organic electroluminescent element. The present invention also relates to light emitting devices, display devices, or illumination devices using the organic electroluminescent element.

BACKGROUND OF INVENTION

Since organic electroluminescent elements (which may hereinafter also be referred to as "elements" or "organic EL elements") are capable of high-luminance light emitting using low voltage driving, they have been actively researched and developed. The organic electroluminescent elements have a pair of electrodes and an organic layer between the pair of electrodes, and utilize, for light emitting, energy of the exciton generated as a result of recombination of the electron injected from the cathode and the hole injected from the anode in the organic layer. The organic electroluminescent elements have potential application in a wide range of fields, because they can be provided as elements that have various light emitting wavelengths, and have fast response speed and are relatively thin and light. Particularly important for application to full-color displays or the like is the development of an organic electroluminescent element having high blue color purity and high luminous efficiency, and many research and development results have been reported.

For example, Patent Document 1 describes using arylanthracene derivatives as host material in the light emitting layer of an organic electroluminescent element, and using styrylamine compounds as light emitting material to provide an organic electroluminescent element having high luminous efficiency and a long luminance half life. In Patent Document 1, the arylanthracene derivatives are described as having sufficient glass transition temperatures.

Patent Document 2 describes arylene derivatives having a trivalent aromatic group, and using the arylene derivatives as host material in the light emitting layer of an organic electroluminescent element to provide an organic electroluminescent element having high luminous efficiency, a low luminance drop rate after a 80° C., 500-hour storage period, and heat resistance and a long luminance half life.

Patent Document 3 describes an organic electroluminescent element that uses anthracene derivatives.

Patent Document 4 describes an organic electroluminescent element that uses bisanthracene derivatives, and providing an organic electroluminescent element that has high luminous efficiency and long life also in high luminance regions.

CITATION LIST

Patent Documents

[Patent Document 1] WO2006/104044
[Patent Document 2] JP-A-2010-6818
[Patent Document 3] KR10-2011-0123701
[Patent Document 4] WO2006/85434

SUMMARY OF INVENTION

However, studies conducted by the present inventors found that the organic electroluminescent elements described in Patent Documents 1 to 3 are unsatisfactory from the viewpoint of luminous efficiency.

Patent Documents 1, 2, and 4 describe increasing the luminance half life. However, Patent Documents 1 to 4, including Patent Document 3, neither disclose nor suggest how the luminance is deteriorated particularly at the initial light time. In this respect, the present inventors investigated characteristics of the organic electroluminescent elements described in Patent Documents 1 to 4. As a result, it was noted that dissatisfaction remains from the viewpoint of a luminance deterioration rate at the initial stage of lighting. The matter that the luminance deterioration of an organic electroluminescent element at the initial stage of lighting is fast is not so problematic in the case of use for simple illumination, the use of which is in general not advanced due to issues of cost. However, it was noted that, for example, when such an element in which the luminance deterioration at the initial stage of lighting is fast is used as a light source of blue of a display, a difference in the luminance deterioration rate at the initial stage of lighting from a red or green light source is generated, resulting in a problem of color shift exceeding a range of assumption at the time of manufacture of a usual display. That is, when abrupt luminance deterioration at the initial stage of lighting occurs, although such abrupt luminance deterioration is hardly perceived in the case of a single color, when the color is mixed with other colors as in a display application or the like, it is perceived as a color shift, resulting in a problem.

The present inventors conducted further studies to provide an organic electroluminescent element that has high luminous efficiency, and a slow luminance deterioration rate in the initial stage of lighting. It was found as a result that the foregoing problems can be solved by using anthracene derivatives of specific structures. The present invention was completed on the basis of this finding, as follows.

[1] An organic electroluminescent element comprising a substrate; a pair of electrodes including an anode and a cathode, disposed on the substrate; and at least one organic layer including a light emitting layer, disposed between the electrodes, wherein at least one organic layer includes a compound represented by the following general formula (1):

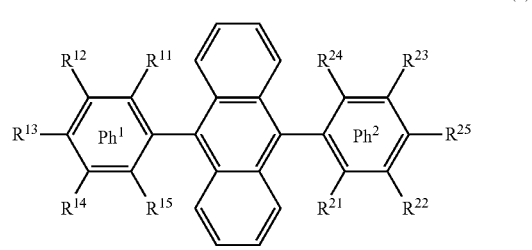

General Formula (1)

(In the general formula (1), $Ph^1$ represents a phenyl group, and $Ph^e$ represents a phenylene group. $R^{11}$ to $R^{15}$ each independently represent a hydrogen atom, an alkyl group, or a silyl group, and $R^{11}$ to $R^{15}$ are not bound to each other to form a ring. Any one of $R^{21}$ to $R^{24}$ represents a group represented by the general formula (1A) or (1B) below, and the other $R^{21}$ to $R^{24}$ each independently represent a hydrogen atom or an alkyl group, and $R^{21}$ to $R^{24}$ are not bound to each other to form a ring. $R^{25}$ represents a hydrogen atom, an alkyl group, or a silyl group.)

General Formula (1A)

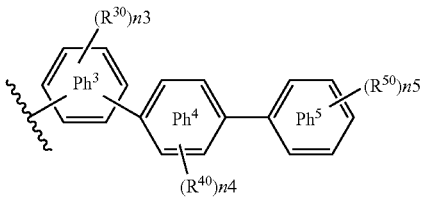

(In the general formula (1A), $Ph^3$ represents a phenylene group, $Ph^4$ represents p-phenylene group, and $Ph^5$ represents a phenyl group. $R^{30}$ and $R^{40}$ each independently represent an alkyl group, n3 and n4 each independently represent an integer of 0 to 4, and, when n3 and n4 are 2 or more, a plurality of $R^{30}$, a plurality of $R^{40}$, and $R^{30}$ and $R^{40}$ are not connected to each other to form a ring. $R^{50}$ represents a substituent, n5 represents an integer of 0 to 5, and when n5 is 2 or more, a plurality of $R^{50}$ may be connected to each other to form an aromatic hydrocarbon ring, but the aromatic hydrocarbon ring is not further substituted with an aromatic hydrocarbon ring. $R^{40}$ and $R^{50}$ are not connected to each other to form a ring.)

General Formula (1B)

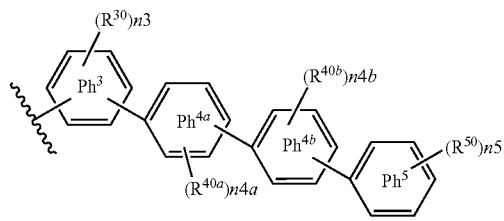

(In the general formula (1B), $Ph^3$, $Ph^{4a}$, and $Ph^{4b}$ each independently represent a phenylene group (at least one of $Ph^{4a}$ and $Ph^{4b}$ representing a p-phenylene group), and $Ph^5$ represents a phenyl group. $R^{30}$, $R^{40a}$, and $R^{40b}$ each independently represent an alkyl group, n3, n4a, and n4b each independently represent an integer of 0 to 4, and, when n3, n4a, and n4b are 2 or more, a plurality of $R^{30}$, a plurality of $R^{40a}$, a plurality $R^{40b}$, $R^{30}$ and $R^{40a}$, and $R^{40a}$ and $R^{40b}$ are not connected to each other to form a ring. $R^{50}$ represents a substituent, $Ph^5$ represents a phenyl group, n5 represents an integer of 0 to 5, and, when n5 is 2 or more, a plurality of $R^{50}$ may be connected to each other to form an aromatic hydrocarbon ring, but the aromatic hydrocarbon ring is not further substituted with an aromatic hydrocarbon ring. $R^{40b}$ and $R^{50}$ are not connected to each other to form a ring.)

[2] It is preferable in the organic electroluminescent element of [1] that the $R^{22}$ or $R^{23}$ in the compound represented by the general formula (1) be a group represented by the general formula (1A) or (1B).

[3] It is preferable in the organic electroluminescent element of [1] or [2] that the $Ph^3$ in the compound represented by the general formula (1) be a m-phenylene group.

[4] It is preferable in the organic electroluminescent element of any one of [1] to [3] that the $Ph^{4a}$, $Ph^{4b}$, and $Ph^5$ in the group represented by the general formula (1A) in the compound represented by the general formula (1) are substituted or unsubstituted p-terphenylene structures, or that the $Ph^{4a}$, $Ph^{4b}$, and $Ph^5$ in the group represented by the general formula (1B) be substituted or unsubstituted p-terphenylene structures.

[5] It is preferable in the organic electroluminescent element of any one of [1] to [4] that one of the $R^{21}$ to $R^{24}$ in the compound represented by the general formula (1) be a group represented by the general formula (1A).

[6] It is preferable in the organic electroluminescent element of any one of [1] to [5] that the compound represented by the general formula (1) be contained in the light emitting layer.

[7] It is preferable in the organic electroluminescent element of any one of [1] to [6] that the same organic layer as the organic layer containing the compound represented by the general formula (1) contain a compound represented by the following general formula (p-1).

General Formula (p-1)

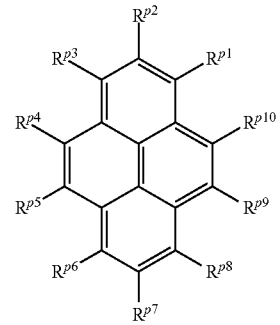

(In the general formula (p-1), $R^{p1}$ to $R^{p10}$ represent hydrogen atoms or substituents.)

[8] It is preferable in the organic electroluminescent element of any one of [1] to [6] that the same organic layer as the organic layer containing the compound represented by the general formula (1) contain a compound represented by the following general formula (PT-1).

General Formula (PT-1)

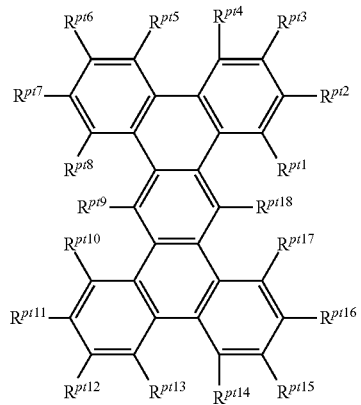

(In the general formula (PT-1), $R^{pt1}$ to $R^{pt18}$ represent hydrogen atoms or substituents.)

[9] It is preferable in the organic electroluminescent element of any one of [1] to [6] that the same organic layer as the organic layer containing the compound represented by the general formula (1) contain a compound represented by the following general formula (ch-1).

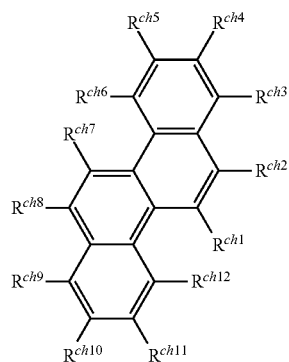

General Formula (ch-1)

(In the general formula (ch-1), $R^{ch1}$ to $R^{ch12}$ represent hydrogen atoms or substituents.)

[10] A light emitting device that uses the organic electroluminescent element of any one of [1] to [9].

[11] A display device that uses the organic electroluminescent element of any one of [1] to [9].

[12] An illumination device that uses the organic electroluminescent element of any one of [1] to [9].

[13] A compound represented by the following general formula (1).

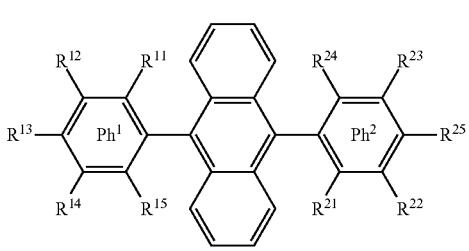

General Formula (1)

(In the general formula (1), $Ph^1$ represents a phenyl group, and $Ph^2$ represents a phenylene group. $R^{11}$ to $R^{15}$ each independently represent a hydrogen atom, an alkyl group, or a silyl group, and $R^{11}$ to $R^{15}$ are not bound to each other to form a ring. Any one of $R^{21}$ to $R^{24}$ represents a group represented by the general formula (1A) or (1B) below, and the other $R^{21}$ to $R^{24}$ each independently represent hydrogen atoms or alkyl groups, and $R^{21}$ to $R^{24}$ are not bound to each other to form a ring. $R^{25}$ represents a hydrogen atom, an alkyl group, or a silyl group.)

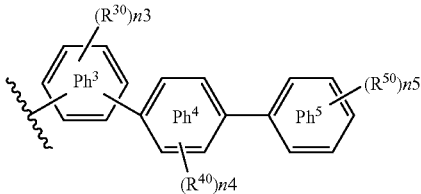

General Formula (1A)

(In the general formula (1A), $Ph^3$ represents a phenylene group, $Ph^4$ represents a p-phenylene group, and $Ph^5$ represents a phenyl group. $R^{30}$ and $R^{40}$ each independently represent an alkyl group, n3 and n4 each independently represent an integer of 0 to 4, and, when n3 and n4 are 2 or more, a plurality of $R^{30}$, a plurality of $R^{40}$, and $R^{20}$ and $R^{40}$ are not connected to each other to form a ring. $R^{50}$ represents a substituent, n5 represents an integer of 0 to 5, and, when n5 is 2 or more, a plurality of $R^{50}$ may be connected to each other to form an aromatic hydrocarbon ring, but the aromatic hydrocarbon ring is not further substituted with an aromatic hydrocarbon ring. $R^{40}$ and $R^{50}$ are not connected to each other to form a ring.)

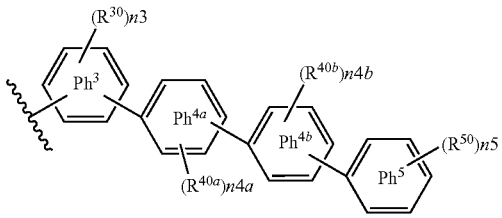

General Formula (1B)

(In the general formula (1B), $Ph^3$, $Ph^{4a}$, and $Ph^{4b}$ each independently represent a phenylene group (at least one of $Ph^{4a}$ and $Ph^{4b}$ representing a p-phenylene group), and $Ph^5$ represents a phenyl group. $R^{30}$, $R^{40a}$, and $R^{40b}$ each independently represent an alkyl group, n3, n4a, and n4b each independently represent an integer of 0 to 4, and, when n3, n4a, and n4b are 2 or more, a plurality of $R^{30}$, a plurality of $R^{40a}$, a plurality of $R^{40b}$, $R^{30}$ and $R^{40a}$, and $R^{40a}$ and $R^{40b}$ are not connected to each other to form a ring. $R^{50}$ represents a substituent, $Ph^5$ represents a phenyl group, n5 represents an integer of 0 to 5, and, when n5 is 2 or more, a plurality of $R^{50}$ may be connected to each other to form an aromatic hydrocarbon ring, but the aromatic hydrocarbon ring is not further substituted with an aromatic hydrocarbon ring. $R^{40b}$ and $R^{50}$ are not connected to each other to form a ring.)

[14] It is preferable in the compound of [13] that the $R^{22}$ or $R^{23}$ in the compound represented by the general formula (1) be a group represented by the general formula (1A) or (1B).

[15] It is preferable in the compound of [13] or [14] that the $Ph^3$ in the compound represented by the general formula (1) be a m-phenylene group.

[16] It is preferable in the compound of any one of [12] to [15] that the $Ph^{4a}$, $Ph^{4b}$, and $Ph^5$ in the group represented by the general formula (1A) in the compound represented by the general formula (1) be substituted or unsubstituted p-terphenylene structures, or that the $Ph^{4a}$, $Ph^{4b}$, and $Ph^5$ in the group represented by the general formula (1B) be substituted or unsubstituted p-terphenylene structures.

[17] It is preferable in the compound of any one of [13] to [16] that one of the $R^{21}$ to $R^{24}$ in the compound represented by the general formula (1) be a group represented by the general formula (1A).

[18] It is preferable that the compound of any one of [13] to [17] be represented by any one of the following (H-1) to (H-14).

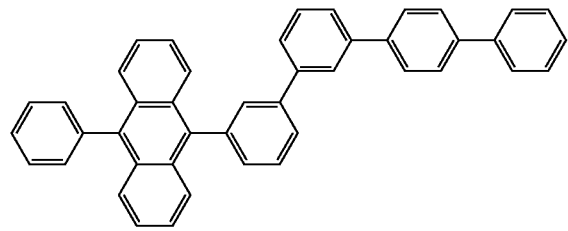
(H-1)

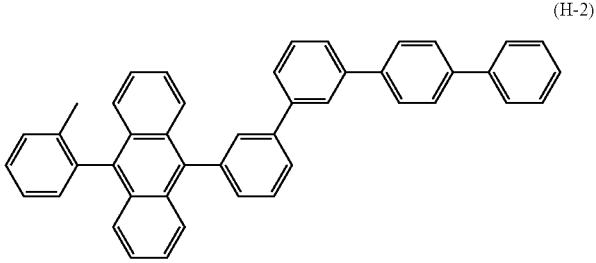
(H-2)

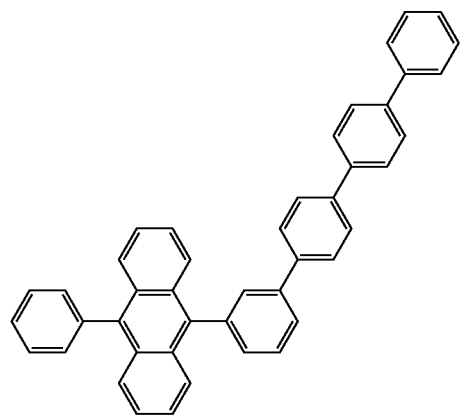
(H-3)

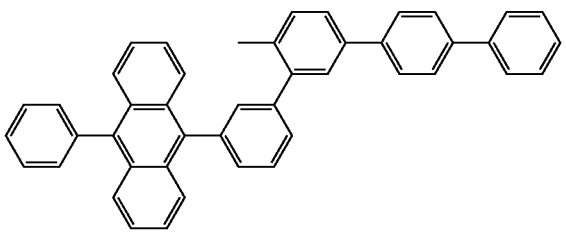
(H-4)

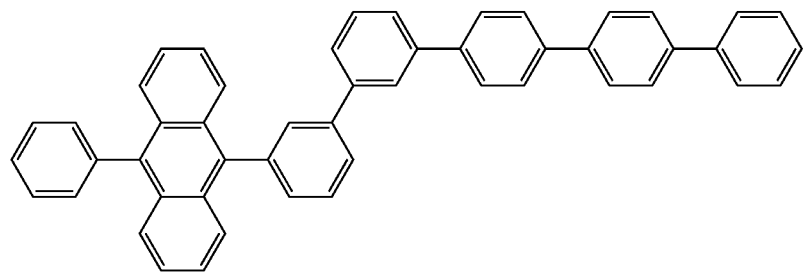
(H-5)

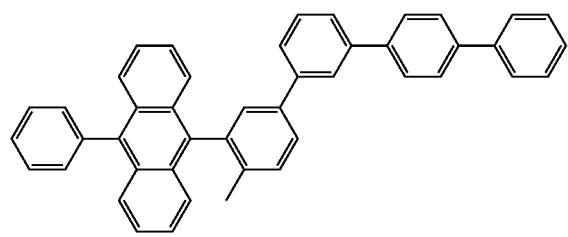
(H-6)

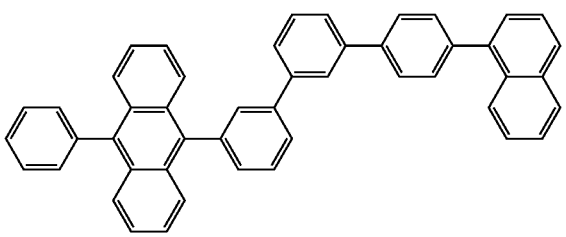
(H-7)

-continued (H-8)
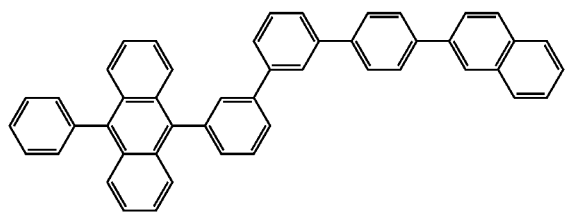

(H-9)

(H-10)
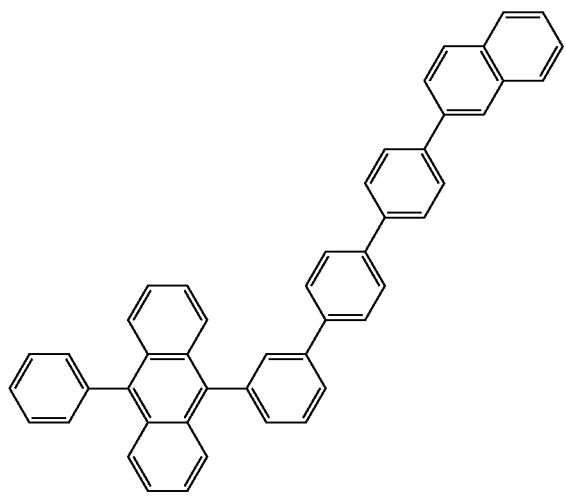

(H-11)
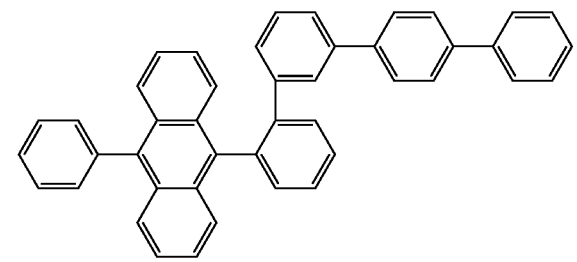

(H-12)
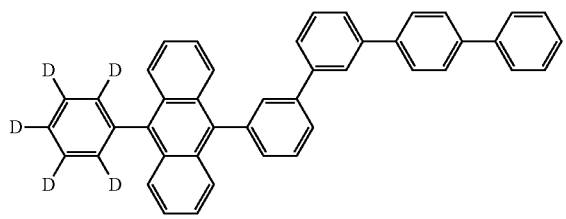

(H-13)
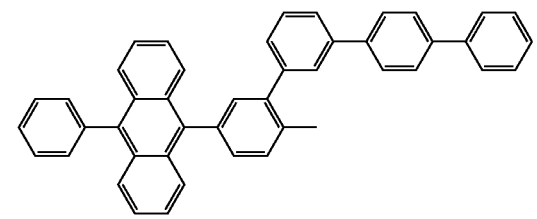

(H-14)
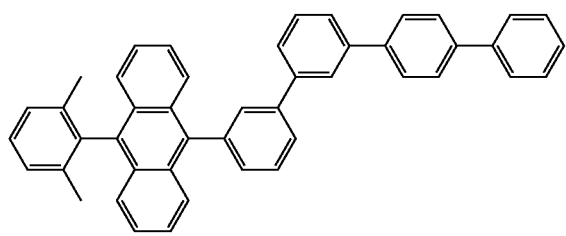

[19] A charge transporting material formed from the compound of any one of [13] to [18].

According to the present invention, it is possible to provide an organic electroluminescent element having high luminous efficiency, and a slow luminance deterioration rate at the initial stage of lighting.

DETAILED DESCRIPTION OF INVENTION

Figure 1:
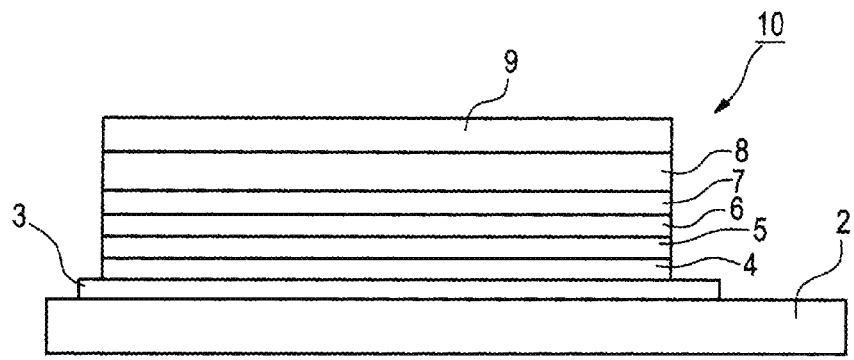
FIG. 1 is a schematic view showing one example of a configuration of the organic electroluminescent element according to the present invention.

Details of the present invention are hereunder described. The description of the configuration requirements below is based on representative embodiments and specific examples of the present invention, but the present invention is not limited to these embodiments and specific examples. Incidentally, in the present specification, the range expressed with "to" means a range including the numerical values before and after "to" as the lower limit and the upper limit, respectively.

[Organic Electroluminescent Element]

The organic electroluminescent element according to the present invention comprises a substrate; a pair of electrodes including an anode and a cathode, disposed on the substrate; and at least one organic layer including a light emitting layer, disposed between the electrodes, wherein at least one organic layer includes a compound represented by the general formula (1).

The organic electroluminescent element of the present invention is desirable, because it contains the compound represented by the general formula (1) in at least one of the organic layers, and has high luminous efficiency, and a slow luminance deterioration rate in the initial stage of lighting.

Without being bound by any theory, it is believed that the improved durability by means of a slow luminance deterioration rate in the initial stage of lighting is attained by (1) improved charge transportability that depends on molecular shape differences (such as whether being chained or branched, or having planarity), and the resulting changes in the carrier balance, (2) the improved reaction deterioration process of compounds as controlled by slight differences in molecular shape (such as whether being chained or branched, or having planarity), and/or (3) the improved compatibility of the host material and the light emitting material. Note that in the second case where the reaction deterioration process of compounds is controlled to improve by differences in molecular shape, it is considered that even a slight difference in molecular shape has a large effect on the luminance deterioration rate in the initial stage of lighting, because the deterioration process differs for different combinations of the host material and the light emitting material, for example, when the compound represented by the general formula (1) is used as host material.

On the other hand, without being bound by any theory, it is believed that the improved luminous efficiency is made possible by the following mechanism, for example, when the compound represented by the general formula (1) is used as host material. The improvement is believed to be due to (1) the increased $S_1$ level of the host material, and/or (2) the improved compatibility of the host material and the light emitting material. In the second case pointing to the improved compatibility of the host material and the light emitting material, the improved efficiency is believed to be due to the suppression of the slight association of the light emitting material, suppressing the inefficient process of association emission.

Particularly, because the compound represented by the general formula (1) includes a group having at least one p-phenylene group therein (i.e., a group including a p-terphenylene structure) at any one of the positions $R^{21}$ to $R^{24}$, using the compound as the host material improves the compatibility with the light emitting material. It is therefore possible to improve the luminous efficiency, and slow the luminance deterioration rate in the initial stage of lighting.

<<Compound Represented by General Formula (1)>>

The compound represented by the general formula (1) is described below in detail.

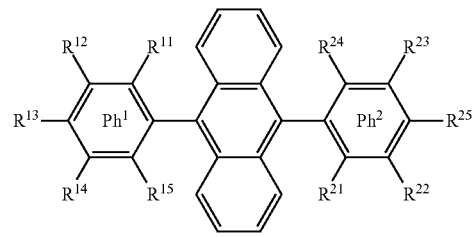

General Formula (1)

(In the general formula (1), $Ph^1$ represents a phenyl group, and $Ph^2$ represents a phenylene group. $R^{11}$ to $R^{15}$ each independently represent a hydrogen atom, an alkyl group, or a silyl group, and $R^{11}$ to $R^{15}$ are not bound to each other to form a ring. Any one of $R^{21}$ to $R^{24}$ represents a group represented by the following general formula (1A) or (1B), and the other $R^{21}$ to $R^{24}$ each independently represent a hydrogen atom or an alkyl group, and $R^{21}$ to $R^{24}$ are not bound to each other to form a ring. $R^{25}$ represents a hydrogen atom, an alkyl group, or a silyl group.)

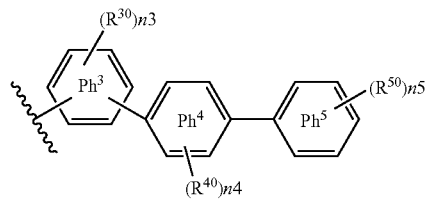

General Formula (1A)

(In the general formula (1A), $Ph^3$ represents a phenylene group, $Ph^4$ represents a p-phenylene group, and $Ph^5$ represents a phenyl group. $R^{30}$ and $R^{40}$ each independently represent an alkyl group, n3 and n4 each independently represent an integer of 0 to 4, and, when n3 and n4 are 2 or more, a plurality of $R^{30}$, a plurality of $R^{40}$, and $R^{30}$ and $R^{40}$ are not connected to each other to form a ring. $R^{50}$ represents a substituent, n5 represents an integer of 0 to 5, and, when n5 is 2 or more, a plurality of $R^{50}$ may be connected to each other to form an aromatic hydrocarbon ring, but the aromatic hydrocarbon ring is not further substituted with an aromatic hydrocarbon ring. $R^{40}$ and $R^{50}$ are not connected to each other to form a ring.)

General Formula (1B)

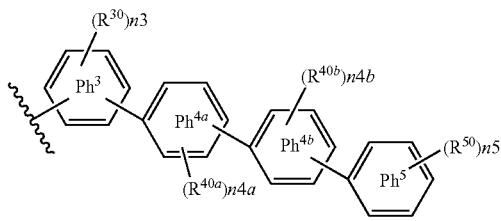

(In the general formula (1B), $Ph^3$, $Ph^{4a}$, and $Ph^{4b}$ each independently represent a phenylene group (at least one of $Ph^{4a}$ and $Ph^{4b}$ representing a p-phenylene group), and $Ph^5$ represents a phenyl group. $R^{30}$, $R^{40a}$, and $R^{40b}$ each independently represent an alkyl group, n3, n4a, and n4b each independently represent an integer of 0 to 4, and, when n3, n4a, and n4b are 2 or more, a plurality of $R^{30}$, a plurality of $R^{40a}$, a plurality of $R^{40b}$, $R^{30}$ and $R^{40a}$, and $R^{40a}$ and $R^{40b}$ are not connected to each other to form a ring. $R^{50}$ represents a substituent, $Ph^5$ represents a phenyl group, n5 represents an integer of 0 to 5, and, when n5 is 2 or more, a plurality of $R^{50}$ may be connected to each other to form an aromatic hydrocarbon ring, but the aromatic hydrocarbon ring is not further substituted with an aromatic hydrocarbon ring. $R^{40b}$ and $R^{50}$ are not connected to each other to form a ring.)

In the present invention, the hydrogen atom in the description of the general formula (1) also includes isotopes (a deuterium atom and the like), and the atoms constituting the substituent are also intended to include isotopes of the atoms.

In the present invention, the "substituent" at each occurrence may be further substituted. For example, in the present invention, the "alkyl group" at each occurrence includes an alkyl group substituted with a fluorine atom (for example, a trifluoromethyl group), an alkyl group substituted with an aryl group (for example, a triphenylmethyl group), and the like, but "an alkyl group of 1 to 6 carbon atoms" represents one having from 1 to 6 carbon atoms, as a whole group also including substituted groups thereof.

In the general formula (1), $Ph^1$ represents a phenyl group. In the compound represented by the general formula (1), $R^{11}$ to $R^{15}$ are not bound to each other to form a ring (described later), and thus $Ph^1$ does not form a fused ring. From the viewpoint of increasing the $S_1$ level and further improving the efficiency of the organic electroluminescent element, a compound represented by the general formula (1) in which $Ph^1$ is a phenyl group is superior to a compound in which the substituent adjacent to the anthracene skeleton corresponding to $Ph^1$ is a fused ring such as a naphthyl group.

In the general formula (1), $R^{11}$ to $R^{15}$ each independently represent a hydrogen atom, an alkyl group, or a silyl group, and $R^{11}$ to $R^{15}$ are not bound to each other to form a ring.

The alkyl groups represented by the $R^{11}$ to $R^{15}$ are preferably alkyl groups of 1 to 10 carbon atoms, more preferably alkyl groups of 1 to 5 carbon atoms, particularly preferably methyl groups, ethyl groups, n-propyl groups, isopropyl groups, and tert-butyl groups, even more preferably methyl groups. The alkyl groups represented by the $R^{11}$ to $R^{15}$ may be further substituted, but preferably do not have a substituent.

The silyl groups represented by the $R^{11}$ to $R^{15}$ are preferably silyl groups having a substituent, more preferably trisubstituted silyl groups. The substituents of the silyl groups represented by the $R^{11}$ to $R^{15}$ are not particularly limited, and are preferably alkyl groups and aryl groups, more preferably alkyl groups of 1 to 5 carbon atoms, and aryl groups of 6 to 12 carbon atoms, particularly preferably alkyl groups of 1 to 5 carbon atoms. The silyl groups represented by $R^{11}$ to $R^{15}$ are particularly preferably trimethylsilyl groups or triphenylsilyl groups, even more preferably trimethylsilyl groups.

The total number of the alkyl groups or silyl groups in $R^{11}$ to $R^{15}$ is preferably 0 to 3, more preferably 0 to 2, particularly preferably 0 or 1. Preferably, at least one of $R^{11}$ and $R^{15}$ has an alkyl group or a silyl group, and more preferably only one of $R^{11}$ and $R^{15}$ has an alkyl group or a silyl group when the $S_1$ level of the compound represented by the general formula (1) needs to be further increased to further improve the efficiency of the organic electroluminescent element, and when $R^{21}$ and $R^{24}$ are hydrogen atoms.

In the general formula (1), the anthracene skeleton including $Ph^1$ and $Ph^2$ may have other substituents. It is, however, preferable that the anthracene skeleton do not have a substituent from the viewpoint of providing short light emitting wavelengths for the organic electroluminescent element, and increasing the $S_1$ level of the compound represented by the general formula (1) to improve the efficiency of the organic electroluminescent element.

In the general formula (1), $Ph^2$ represents a phenylene group. In the compound represented by the general formula (1), $R^{21}$ to $R^{24}$ are not bound to each other to form a ring (described later), and thus $Ph^2$ does not form a fused ring. From the viewpoint of further increasing the $S_1$ level to further improve the efficiency of the organic electroluminescent element, a compound represented by the general formula (1) in which $Ph^2$ is a phenyl group is superior to a compound in which the substituent adjacent to the anthracene skeleton corresponding to $Ph^2$ is a fused ring such as a naphthyl group.

In the compound represented by the general formula (1), any one of $R^{21}$ to $R^{24}$ (described later) has a group represented by the general formula (1A) or (1B). Thus, from the relationship between the anthracene skeleton and the group represented by the general formula (1A) or (1B), $Ph^2$ represents an o-phenylene group or a m-phenylene group, and is preferably an o-phenylene group or a m-phenylene group, rather than a p-phenylene group, from the viewpoint of improving the luminous efficiency. From the viewpoint of durability, $Ph^2$ is more preferably a m-phenylene group from the relationship between the anthracene skeleton and the group represented by the general formula (1A) or (1B). $Ph^2$ is also preferably an o-phenylene group from the viewpoint of improving efficiency.

In the general formula (1), any one of $R^{21}$ to $R^{24}$ has a group represented by the general formula (1A) or (1B), and the other $R^{21}$ to $R^{24}$ each independently represent a hydrogen atom or an alkyl group.

$R^{25}$ represents a hydrogen atom, an alkyl group, or a silyl group, preferably a hydrogen atom, or an alkyl group, more preferably a hydrogen atom. The preferred range of the alkyl group represented by $R^{25}$ is the same as the preferred range of the alkyl groups represented by $R^{11}$ to $R^{15}$. The preferred range of the silyl group represented by $R^{25}$ is the same as the preferred range of the silyl groups represented by $R^{11}$ to $R^{15}$.

When any one of $R^{11}$ to $R^{15}$ and $R^{21}$ to $R^{25}$ represents an alkyl group, the alkyl group may be further substituted and form a polymer. Preferably, the alkyl group does not form a polymer from the viewpoints of efficiency and durability.

In the following, the groups represented by $R^{21}$ to $R^{24}$ other than the groups represented by the general formula (1A) or (1B) are described first, followed by the groups represented by the general formula (1A) or (1B).

The alkyl groups represented by the other $R^{21}$ to $R^{24}$ are preferably alkyl groups of 1 to 10 carbon atoms, more preferably alkyl groups of 1 to 5 carbon atoms, particularly preferably methyl groups, ethyl groups, n-propyl groups, isopropyl groups, and tert-butyl groups, even more preferably methyl groups. The alkyl groups represented by the other $R^{21}$ to $R^{24}$ may be further substituted, but preferably do not have a substituent.

The total number of the alkyl groups in the other $R^{21}$ to $R^{24}$ is preferably 0 to 2, more preferably 0 or 1, particularly preferably 0. Preferably, at least one of $R^{21}$ and $R^{24}$ has an alkyl group or the general formula (1A) or (1B), and more preferably, $R^{11}$ and $R^{15}$ are hydrogen atoms, and only one of $R^{21}$ and $R^{24}$ has the general formula (1A) or (1B) when the $S_1$ level of the compound represented by the general formula (1) needs to be further increased to further improve the efficiency of the organic electroluminescent element, and when $R^{11}$ and $R^{15}$ are hydrogen atoms.

In the general formula (1), any one of $R^{21}$ to $R^{24}$ represents a group represented by the general formula (1A) or (1B). In the compound represented by the general formula (1), $R^{22}$ or $R^{23}$ is preferably a group represented by the general formula (1A) or (1B).

Preferred embodiments of the groups represented by the general formula (1A), and the groups represented by the general formula (1B) are described below, in order.

General Formula (1A)

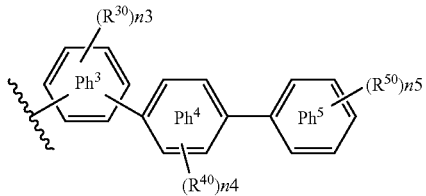

In the general formula (1A), $Ph^3$ represents a phenylene group, $Ph^4$ represents a p-phenylene group, and $Ph^5$ represents a phenyl group. $R^{30}$ and $R^{40}$ each independently represent an alkyl group, n3 and n4 each independently represent an integer of 0 to 4, and, when n3 and n4 are 2 or more, a plurality of $R^{30}$, a plurality of $R^{40}$, and $R^{30}$ and $R^{40}$ are not connected to each other to form a ring. $R^{50}$ represents a substituent, n5 represents an integer of 0 to 5, and, when n5 is 2 or more, a plurality of $R^{50}$ may be connected to each other to form an aromatic hydrocarbon ring, but the aromatic hydrocarbon ring is not further substituted with an aromatic hydrocarbon ring. $R^{40}$ and $R^{50}$ are not connected to each other to form a ring.

In the general formula (1A), $Ph^3$ represents a phenylene group, and is preferably a p-phenylene group or a m-phenylene group, more preferably a m-phenylene group from the viewpoint of durability.

In the general formula (1A), $R^{30}$ each independently represent an alkyl group, n3 represents an integer of 0 to 4, and, when n3 is 2 or more, a plurality of $R^{30}$ may be the same or different.

The preferred range of the alkyl group represented by $R^{30}$ is the same as the preferred range of the alkyl groups represented by $R^{11}$ to $R^{15}$.

n3 represents an integer of 0 to 4, preferably 0 to 2, more preferably 0 or 1, particularly preferably 0.

In the general formula (1A), $Ph^4$ represents a p-phenylene group.

In the general formula (1A), $R^{40}$ each independently represent an alkyl group, n4 represents an integer of 0 to 4, and, when n4 is 2 or more, a plurality of $R^{40}$ may be the same or different.

The preferred range of the alkyl group represented by $R^{40}$ is the same as the preferred range of the alkyl groups represented by $R^{11}$ to $R^{15}$.

n4 represents an integer of 0 to 4, preferably 0 to 2, more preferably 0 or 1, particularly preferably 0.

In the general formula (1A), $Ph^5$ represents a phenyl group.

However, when $R^{50}$ are connected to each other to form an aromatic hydrocarbon ring, $Ph^5$ as a whole may represent an aryl group of 10 or less carbon atoms. The ring formed when $R^{50}$ are connected to each other is an aromatic hydrocarbon ring, and the aromatic hydrocarbon ring is less likely to have adverse effects on the luminance deterioration rate in the initial stage of lighting, compared to other fused rings such as carbazole.

The aromatic hydrocarbon ring formed when $R^{50}$ are connected to each other is preferably an aromatic hydrocarbon ring of 10 or less carbon atoms, rather than rings of 14 or more carbon atoms such as an anthracene ring and a triphenylene ring, from the viewpoint of luminous efficiency. More preferably, the aromatic hydrocarbon ring is a naphthalene ring.

In the general formula (1A), $R^{50}$ represents a substituent, n5 represents an integer of 0 to 5, and, when n5 is 2 or more, a plurality of $R^{50}$ may be connected to each other to form an aromatic hydrocarbon ring, but the aromatic hydrocarbon ring is not further substituted with an aromatic hydrocarbon ring.

The substituent represented by $R^{50}$ is not particularly limited, and is preferably an alkyl group.

The preferred range of the alkyl group represented by $R^{50}$ is the same as the preferred range of the alkyl groups represented by $R^{11}$ to $R^{15}$.

n5 represents an integer of 0 to 4, and is preferably 0 to 2, more preferably 0 or 1, particularly preferably 0.

In the group represented by the general formula (1A), it is preferable that $R^{50}$ are not connected to each other to form an aromatic hydrocarbon ring, and that $Ph^3$, $Ph^4$, and $Ph^5$ represent substituted or unsubstituted p-terphenylene structures. More preferably, $Ph^3$, $Ph^4$, and $Ph^5$ represent unsubstituted p-terphenylene structures.

General Formula (1B)

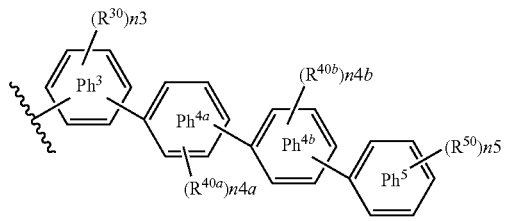

In the general formula (1B), $Ph^3$, $Ph^{4a}$, and $Ph^{4b}$ each independently represent a phenylene group (at least one of $Ph^{4a}$ and $Ph^{4b}$ representing a p-phenylene group), and $Ph^5$ represents a phenyl group. $R^{30}$, $R^{40a}$, and $R^{40b}$ each independently represent an alkyl group, n3, n4a, and n4b each independently represent an integer of 0 to 4, and, when n3, n4a, and n4b are 2 or more, a plurality of $R^{30}$, a plurality of $R^{40a}$, a plurality of $R^{40b}$, $R^{30}$ and $R^{40a}$, and $R^{40a}$ and $R^{40b}$ are not connected to each other to form a ring. $R^{50}$ represents a substituent, $Ph^5$ represents a phenyl group, n5 represents an integer of 0 to 5, and, when n5 is 2 or more, a plurality of $R^{50}$ may be connected to each other to form an aromatic hydrocarbon ring, but the aromatic hydrocarbon ring is not further substituted with an aromatic hydrocarbon ring. $R^{40b}$ and $R^{50}$ are not connected to each other to form a ring.

The definition and the preferred range of $R^{30}$ in the general formula (1B) are the same as the definition and the preferred range of $R^{30}$ in the general formula (1A).

The definition and the preferred range of n3 in the general formula (1B) are the same as the definition and the preferred range of n3 in the general formula (1A).

In the general formula (1A), $Ph^{4a}$ and $Ph^{4b}$ each independently represent a phenylene group. Note, however, that at least one of $Ph^{4a}$ and $Ph^{4b}$ represents a p-phenylene group.

Preferably, at least $Ph^{4a}$ in $Ph^{4a}$ and $Ph^{4b}$ is a p-phenylene group. When $Ph^{4a}$ is a p-phenylene group, $Ph^{4b}$ is preferably a p-phenylene group or a m-phenylene group, preferably a p-phenylene group from the viewpoint of improving the luminance deterioration rate in the initial stage of lighting.

In the general formula (1A), $R^{40a}$ and $R^{40b}$ each independently represent an alkyl group, n4a and n4b each independently represent an integer of 0 to 4, and, when n4a and n4b are 2 or more, a plurality of $R^{40a}$ and $R^{40b}$ may be the same or different.

The preferred range of the alkyl group represented by $R^{40a}$ and $R^{40b}$ are the same as the preferred range of the alkyl groups represented by $R^{11}$ to $R^{15}$.

n4a and n4b each independently represent an integer of 0 to 4, and is preferably 0 to 2, more preferably 0 or 1, particularly preferably 0.

In the general formula (1A), $Ph^5$ represents a phenyl group.

Note, however, that, when $R^{50}$ are connected to each other to form an aromatic hydrocarbon ring (described later), $Ph^5$ as a whole may represent an aryl group of 10 or less carbon atoms. The aromatic hydrocarbon ring formed when $R^{50}$ are connected to each other is preferably an aromatic hydrocarbon ring of 10 carbon atoms, preferably a naphthalene ring.

$R^{50}$ in the general formula (1B) is preferably an alkyl group or an aryl group, preferably an aryl group. The preferred range of the alkyl group represented by $R^{50}$ is the same as the preferred range of the alkyl groups represented by $R^{11}$ to $R^{15}$. The aryl group represented by $R^{50}$ is preferably an aryl group of 6 to 10 carbon atoms, more preferably a phenyl group.

The definition and the preferred range of n5 in the general formula (1B) are the same as the definition and the preferred range of n5 in the general formula (1A).

In the group represented by the general formula (1B), it is preferable that $R^{50}$ are not connected to each other to form an aromatic hydrocarbon ring, and that $Ph^{4a}$, $Ph^{4b}$, and $Ph^5$ represent p-terphenylene structures. More preferably, $Ph^{4a}$, $Ph^{4b}$, and $Ph^5$ represent unsubstituted p-terphenylene structures.

In the compound represented by the general formula (1), it is preferable that one of $R^{21}$ to $R^{24}$ is a group represented by the general formula (1A) from among the groups represented by the general formulae (1A) and (1B).

The compound represented by the general formula (1) preferably has a molecular weight of 1,000 or less, more preferably 900 or less, further preferably 800 or less, particularly preferably 700 or less. Lower molecular weights make it possible to lower sublimation temperature, and can thus prevent the pyrolysis of the compound during the deposition. Further, the deposition time can be reduced to save the required energy for the deposition. Materials with high sublimation temperatures are likely to undergo pyrolysis during the deposition of extended time periods, and excessively high sublimation temperatures are not desirable from the viewpoint of suitability for deposition. The compound represented by the general formula (1) has a sublimation temperature (as used herein, 10% by mass reduction temperature) of preferably 500° C. or less, more preferably 450° C. or less, further preferably 400° C. or less, most preferably 350° C. or less.

Specific examples of the compound represented by the general formula (1) are given below. It should be noted that the compounds of general formula (1) used in the present invention should not be narrowly construed as being limited to these specific examples. Of these specific examples, the compound of the present invention represented by the general formula (1) is preferably represented by any one of the following compounds (H-1) to (H-14).

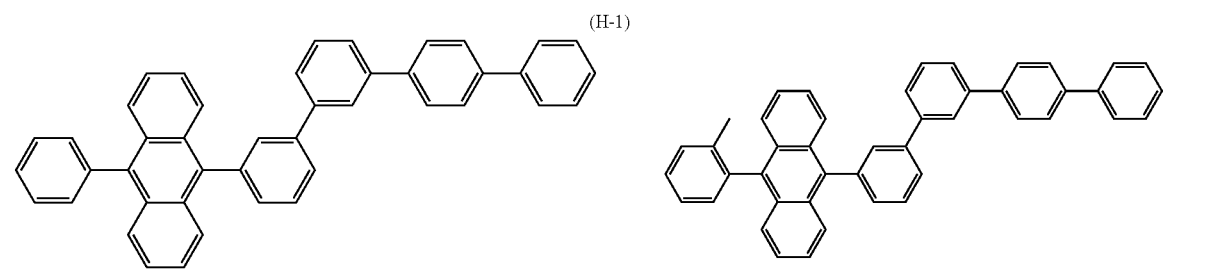

(H-3)
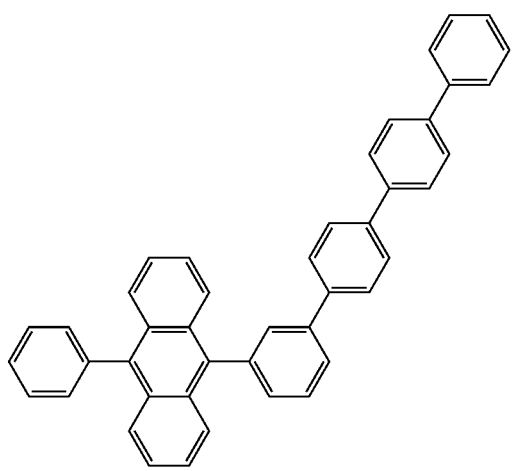
(H-4)
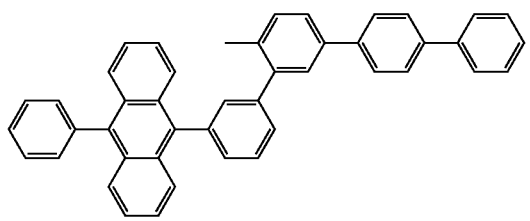
(H-5)
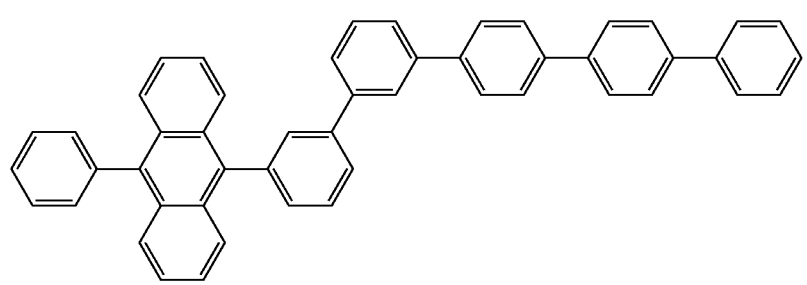
(H-6)
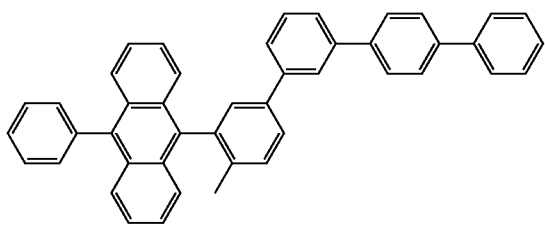
(H-7)
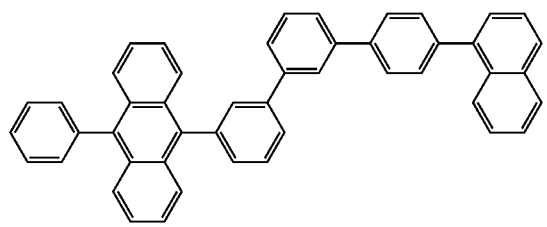
(H-8)
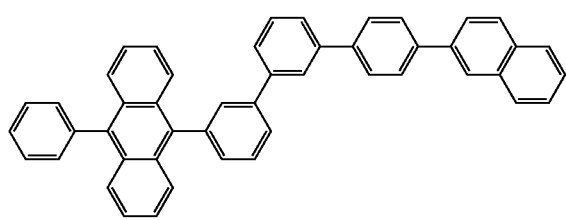
(H-9)
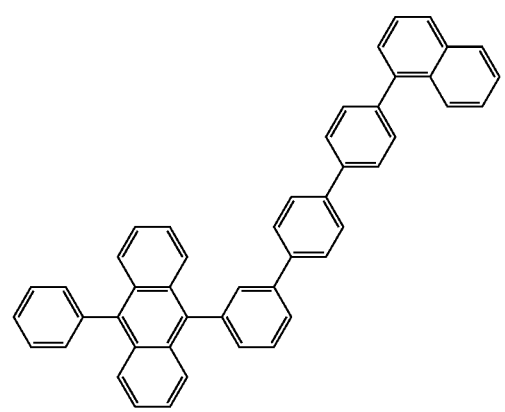

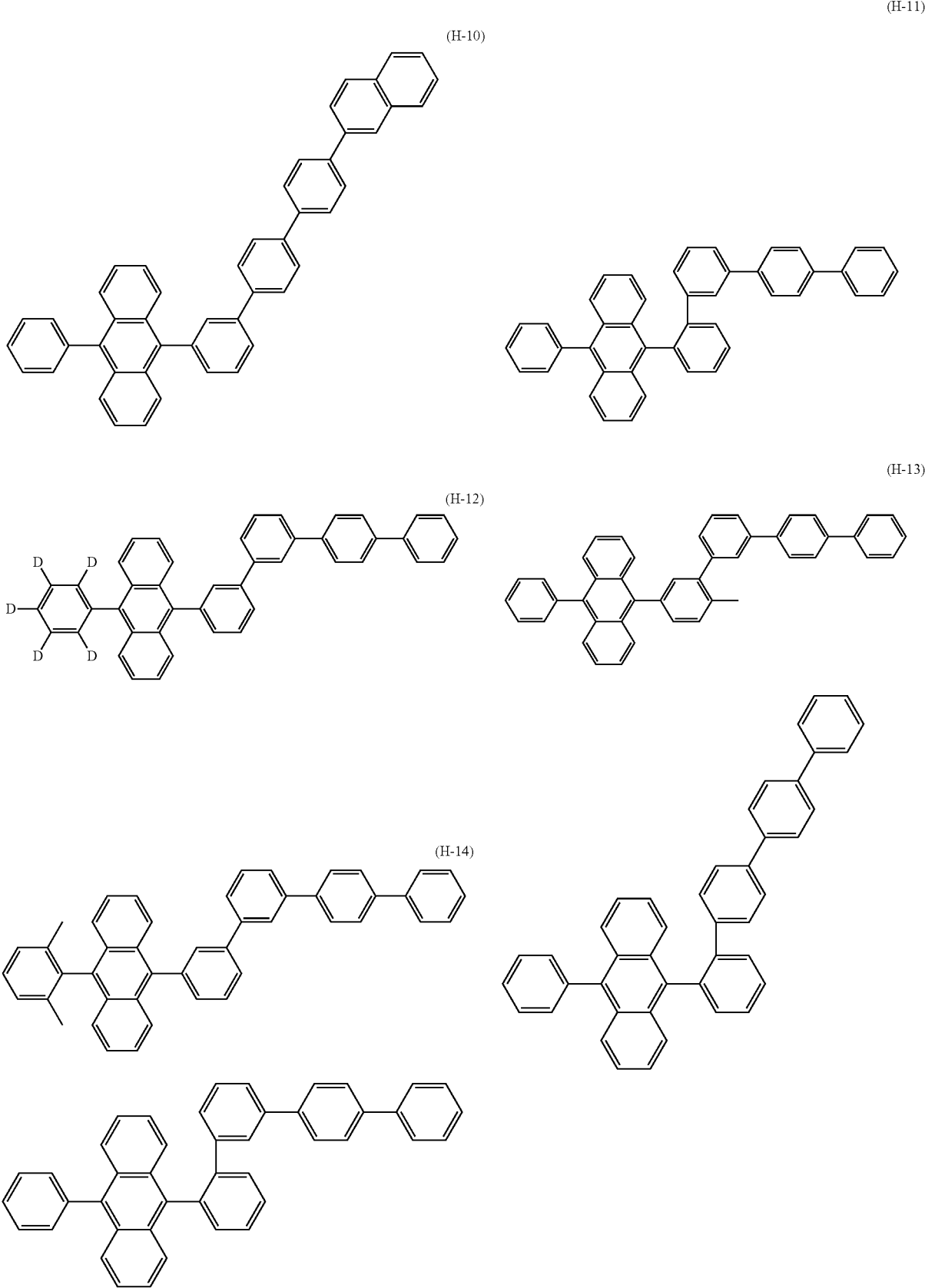

-continued
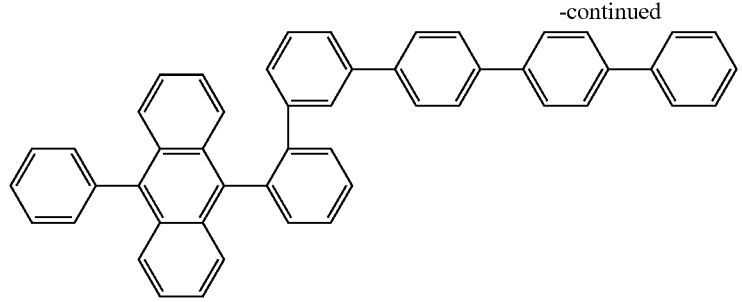
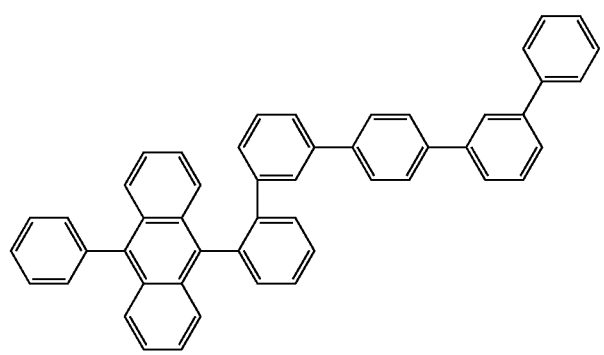
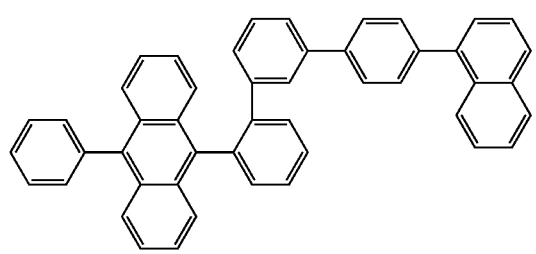
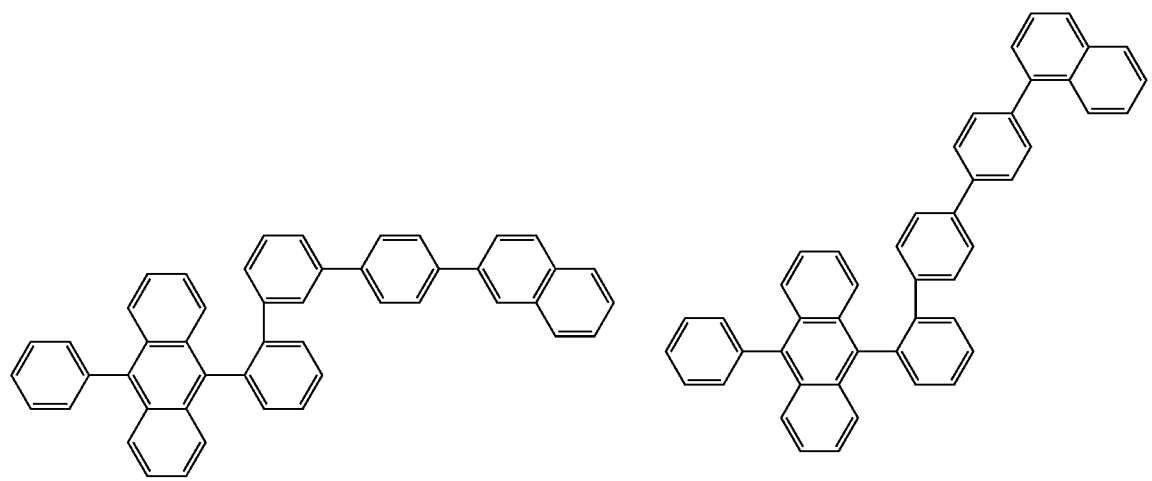
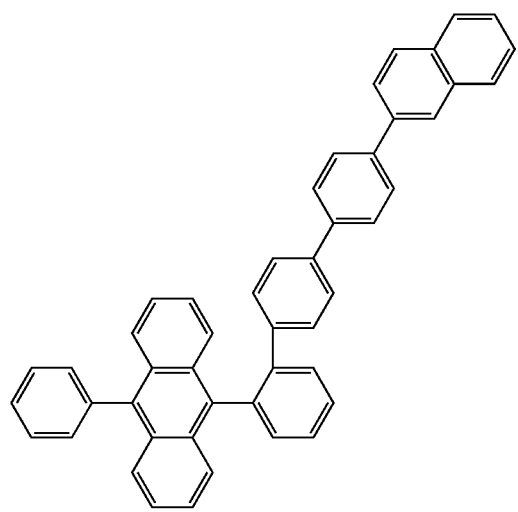
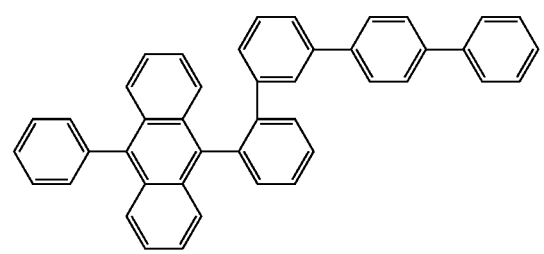

-continued
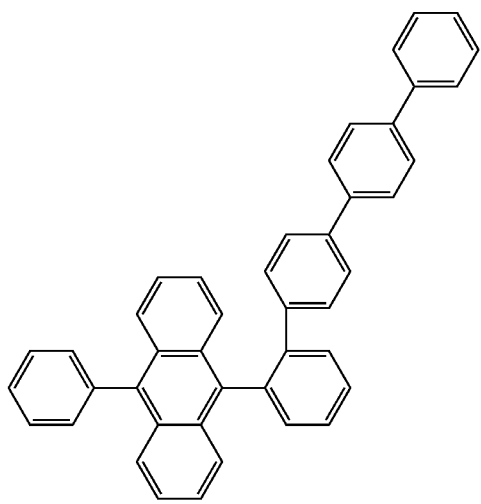
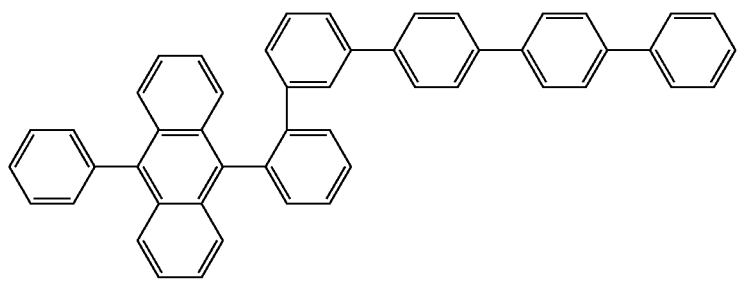
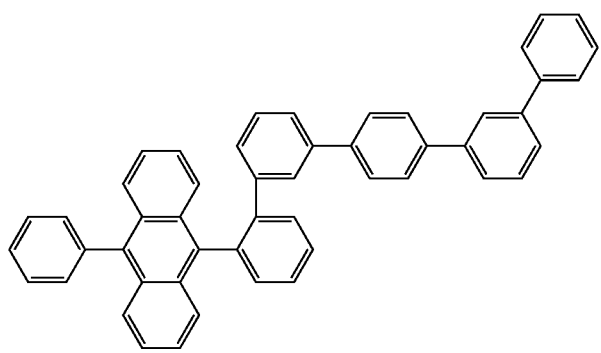
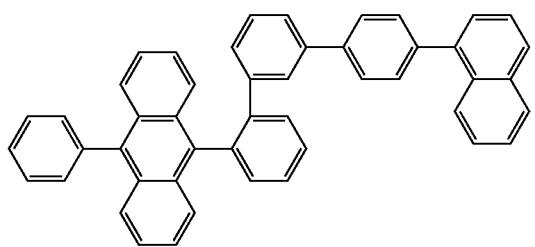
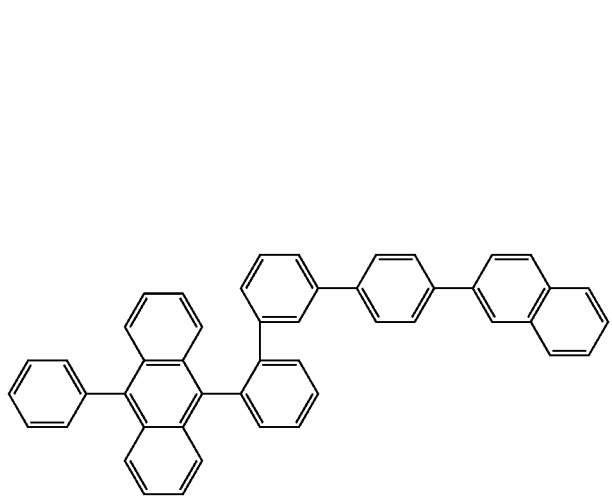
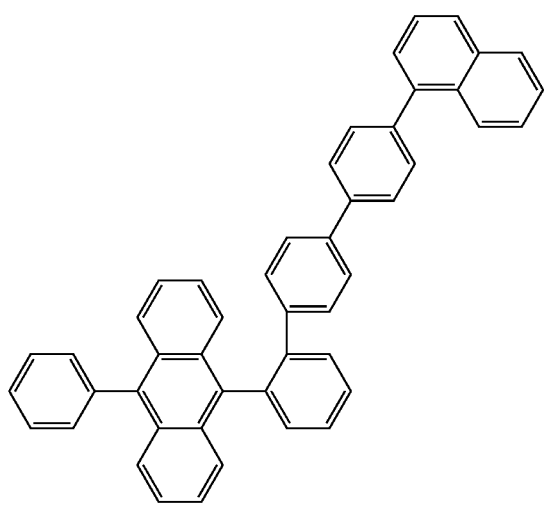

-continued
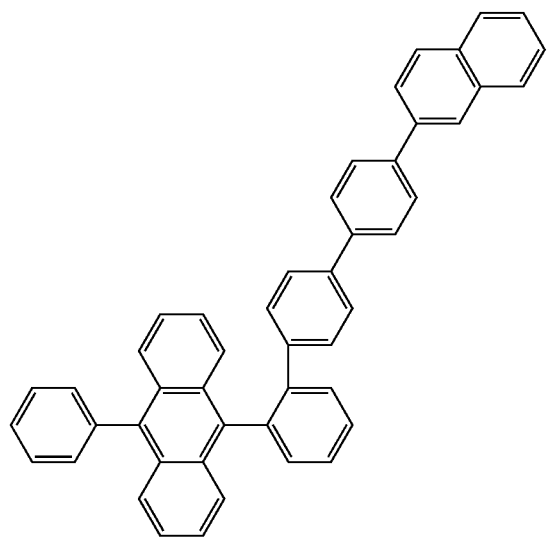
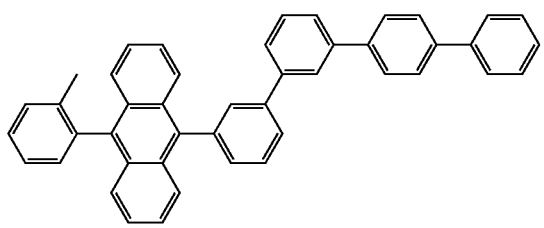
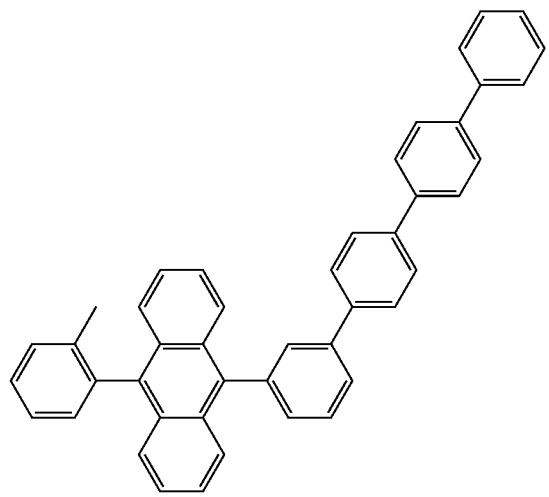
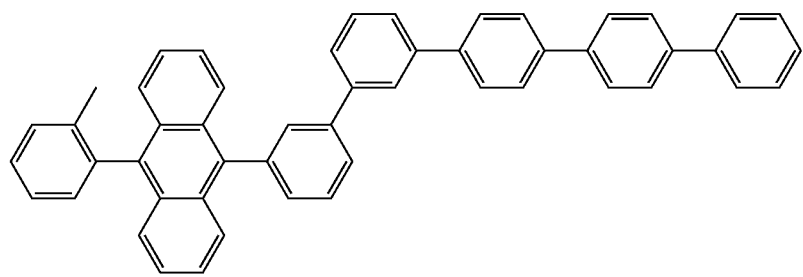
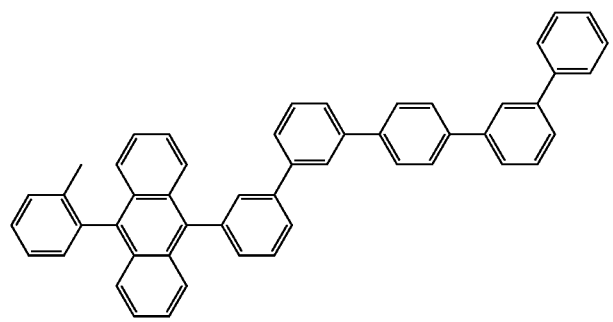
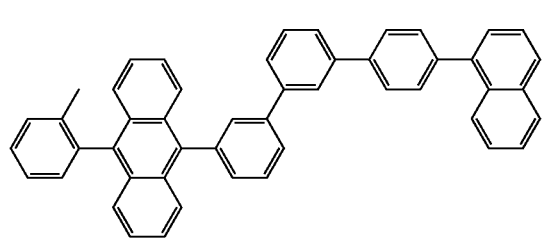

-continued
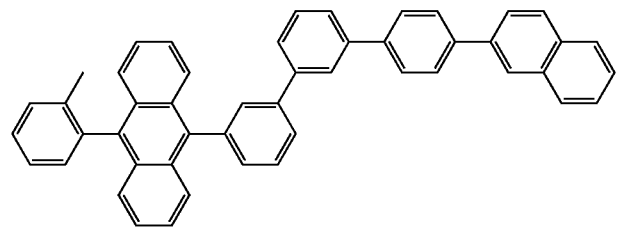
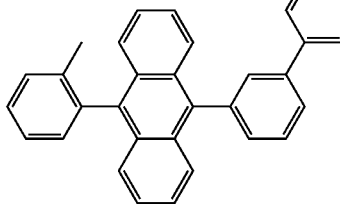
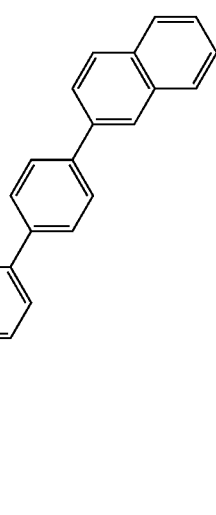
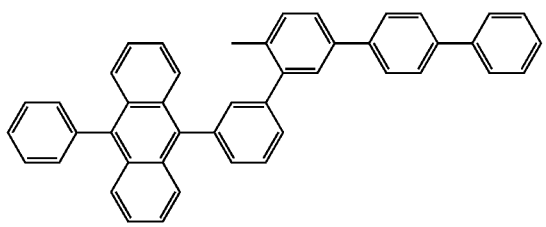
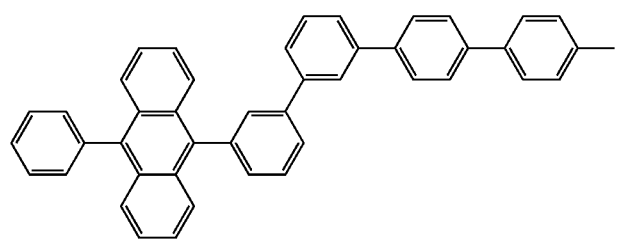
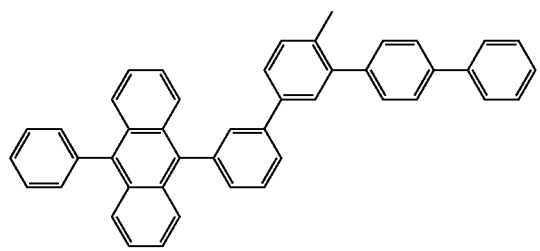
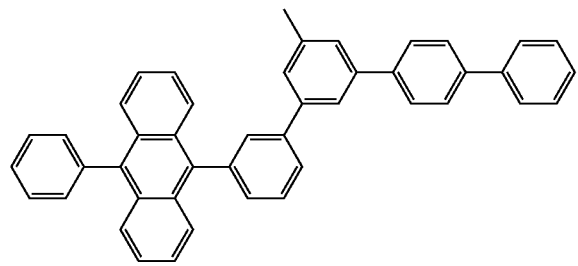
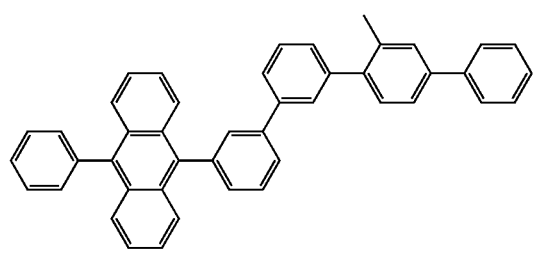
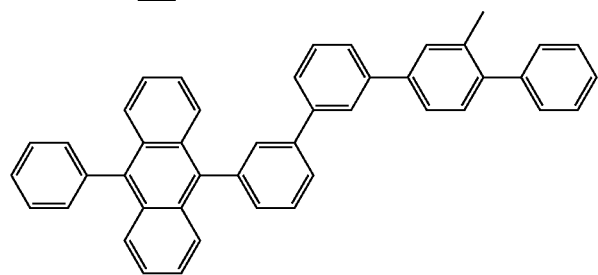
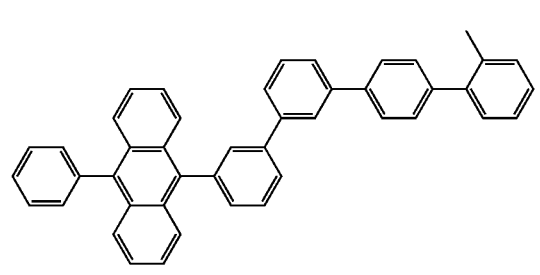

-continued
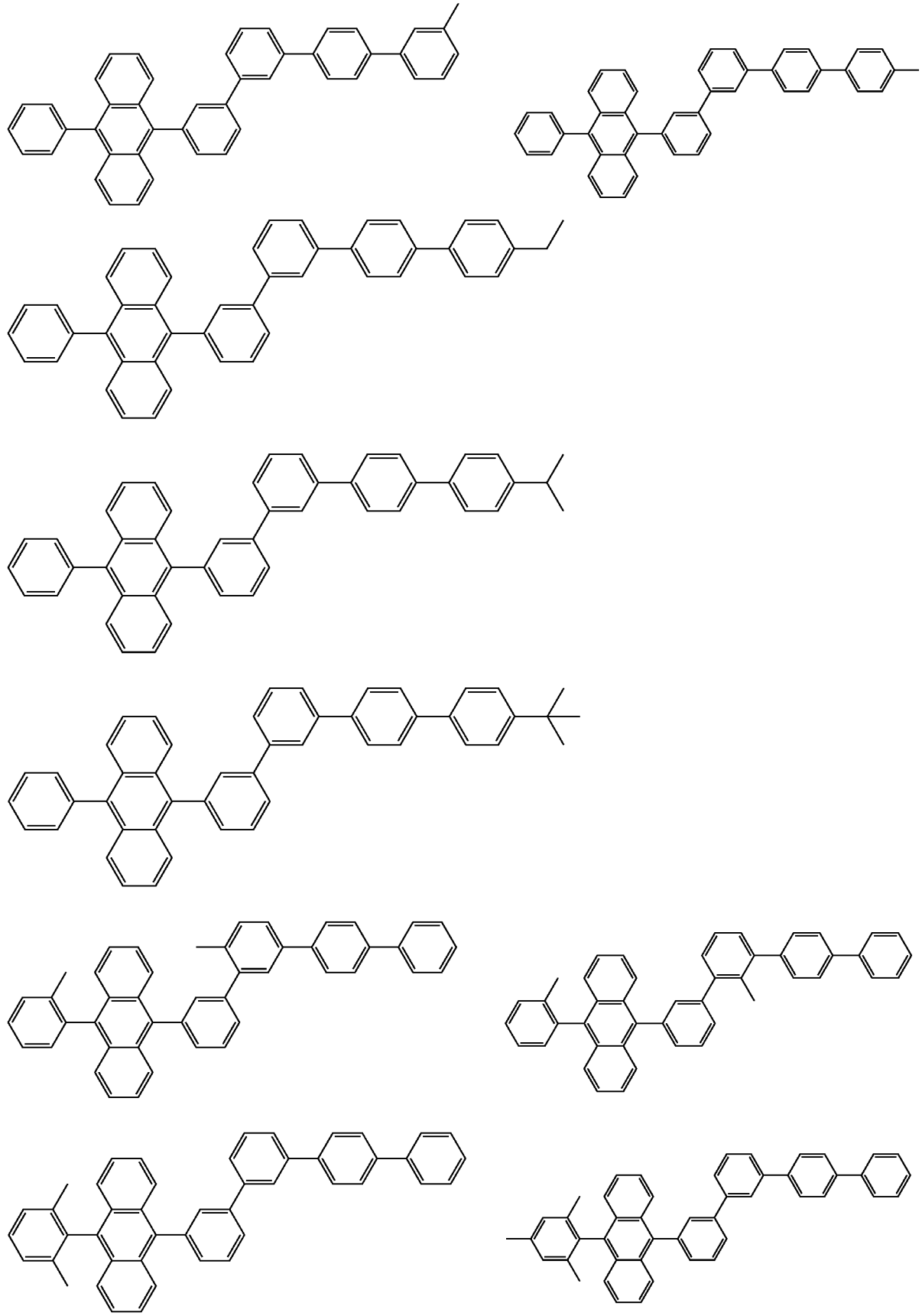

33 34
-continued
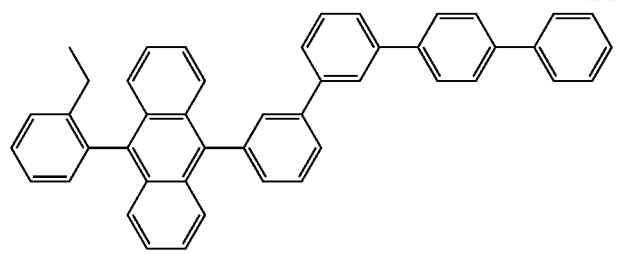
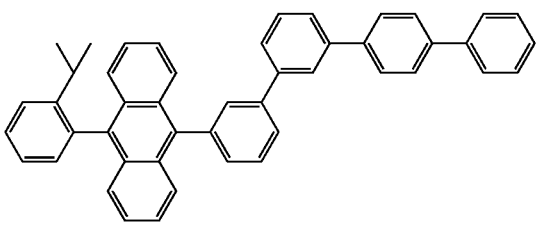
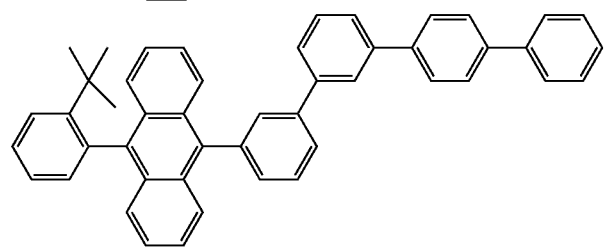
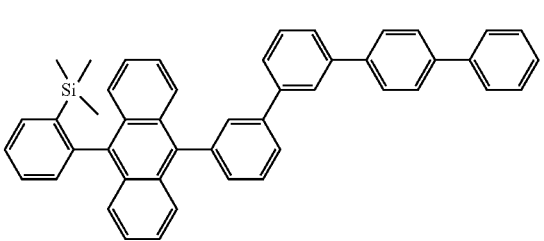
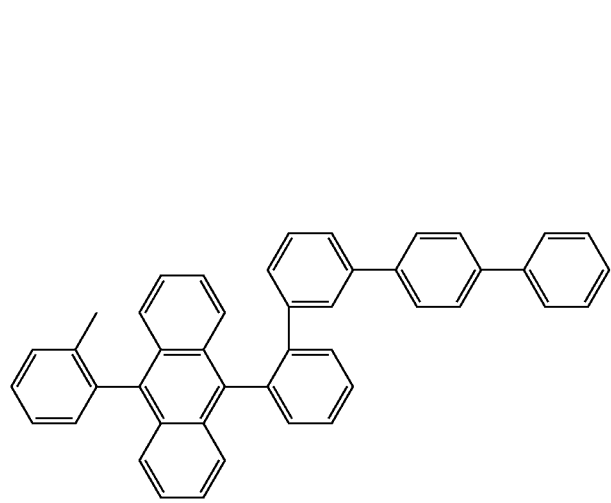
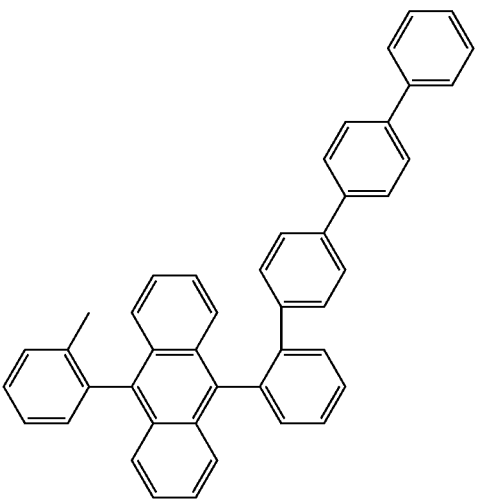
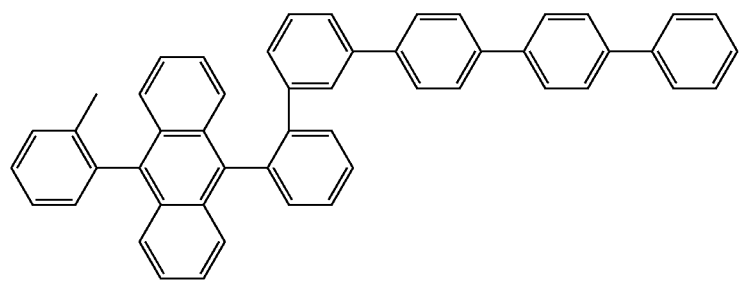
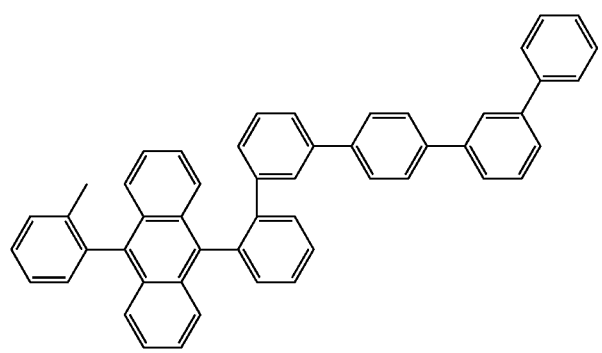
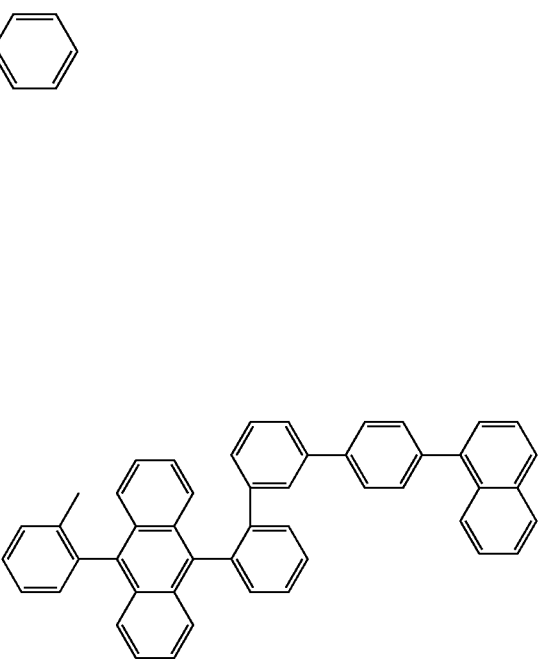

-continued

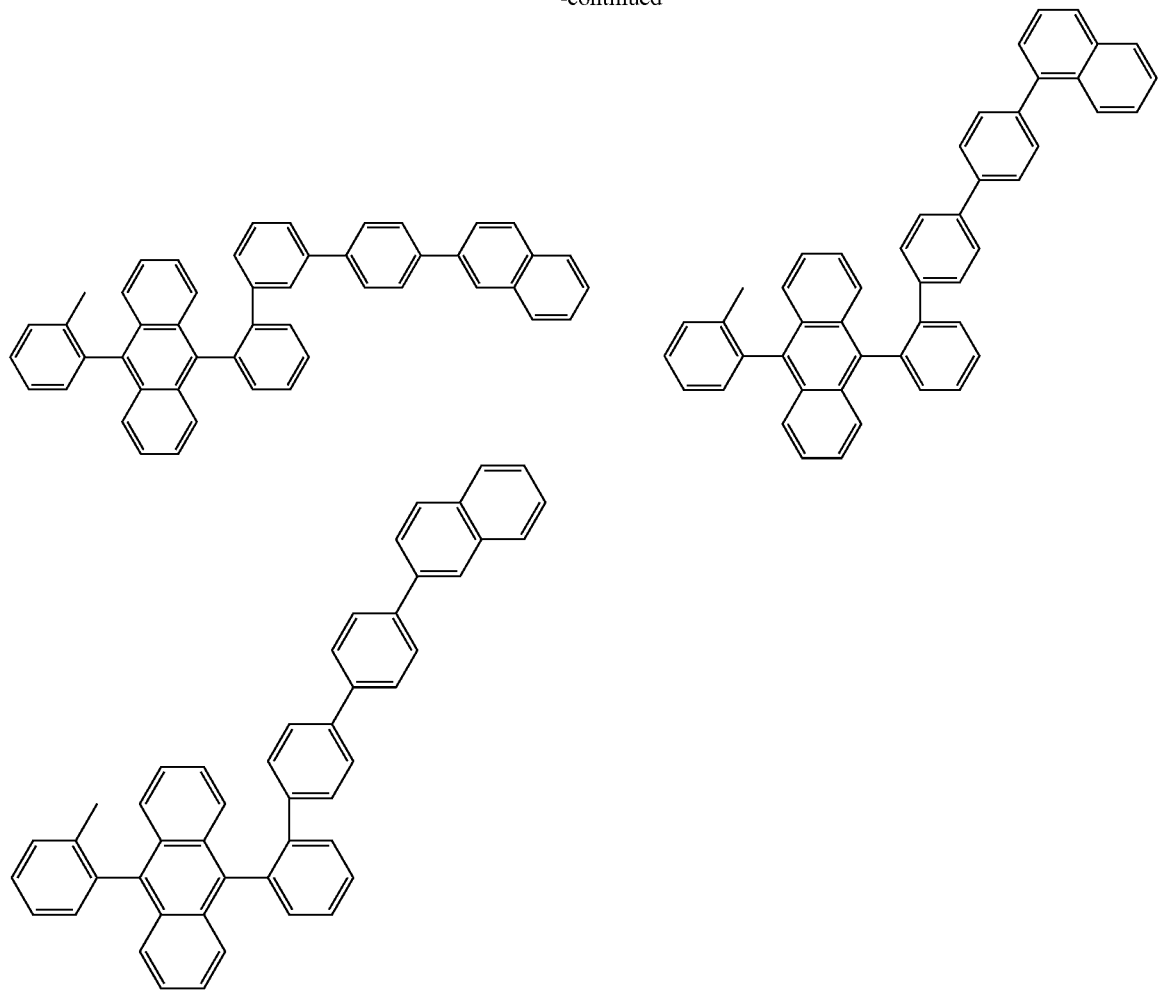

The compounds represented by the general formula (1) can be synthesized by combinations of known reactions, for example, by referring to JP-A-2008-50308.

It is preferable that after the synthesis, the product is purified by means of column chromatography, recrystallization, or the like and then purified by means of sublimation purification. By the sublimation purification, not only organic impurities can be separated, but inorganic salts, a residual solvent, and the like can be effectively removed.

<<Configuration of Organic Electroluminescent Element>>

The organic electroluminescent element of the present invention includes a substrate; a pair of electrodes including an anode and a cathode, disposed on the substrate; and at least one organic layer including a light emitting layer, disposed between the electrodes, wherein at least one light emitting layer includes the compound represented by the general formula (1).

The configuration of the organic electroluminescent element according to the present invention is not particularly limited. FIG. 1 shows one example of the configuration of the organic electroluminescent element according to the present invention. An organic electroluminescent element 10 of FIG. 1 has an organic layer between a pair of electrodes (an anode 3 and a cathode 9) on a substrate 2.

The element configuration of the organic electroluminescent element, the substrate, the cathode, and the anode are described in detail in, for example, JP-A-2008-270736, and the detailed description thereon in this patent document can be applied to the present invention.

Preferred embodiments of the organic electroluminescent element according to the present invention are hereunder described in detail in the order of the substrate, the electrodes, the organic layer, a protective layer, a sealing enclosure, a driving method, a light emitting wavelength, and applications.

<Substrate>

The organic electroluminescent element according to the present invention has a substrate.

The substrate used in the present invention is preferably a substrate that does not scatter or decay light emitted from the organic layer. In the case of an organic material, those having excellent heat resistance, dimensional stability, solvent resistance, electrical insulating properties, and processability are preferable.

<Electrodes>

The organic electroluminescent element according to the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be usually one having a function as an electrode of supplying holes into an organic layer, and is not particularly limited from the viewpoints of its shape, structure, size, or the like. Further, depending on the use and purpose of the light emitting element, the anode can be suitably selected from the known electrode materials. As described above, the anode is usually provided as a transparent anode.

(Cathode)

The cathode may be usually one having a function as an electrode of injecting electrons to an organic layer, and is not particularly limited from the viewpoints of its shape, structure, size, or the like. Further, depending on the use and purpose of the light emitting element, the cathode can be suitably selected from the known electrode materials.

<Organic Layer>

The organic electroluminescent element of the present invention includes at least one organic layer disposed between the electrodes, and that includes a light emitting layer, wherein at least one light emitting layer includes the compound represented by the general formula (1).

The organic layer is not particularly limited and can be suitably selected depending on the use and purpose of the organic electroluminescent element. However, the organic layer is preferably formed on the transparent electrode or the semi-transparent electrode. In that case, the organic layer is formed on the whole surface or one surface of the transparent electrode or the semi-transparent electrode.

The shape, the size, the thickness, and the like of the organic layer are not particularly limited and can be suitably selected depending on the purpose.

The configuration of the organic layer, the method for forming the organic layer, preferred embodiments of the respective layers constituting the organic layer, and the materials used in the respective layers in the organic electroluminescent element according to the present invention are hereunder described in detail in order.

(Configuration of Organic Layer)

In the organic electroluminescent element of the present invention, the organic layer includes the light emitting layer. The organic layer preferably includes a charge transporting layer. The charge transporting layer refers to a layer in which charges move when voltage is applied to the organic electroluminescent element. Specifically, examples thereof include a hole injecting layer, a hole transporting layer, an electron blocking layer, a light emitting layer, a hole blocking layer, an electron transporting layer, and an electron injecting layer. A low-cost and high-efficiency organic electroluminescent element can be produced when the charge transporting layer is the hole injecting layer, the hole transporting layer, the electron blocking layer, or the light emitting layer.

The compound represented by the general formula (1) is contained in at least one light emitting layer in the organic layers disposed between the electrodes of the organic electroluminescent element.

The compound represented by the general formula (1) may be contained in the other organic layers of the organic electroluminescent element of the present invention so far as the gist of the present invention is not deviated. Examples of the organic layer other than the light emitting layer that may contain the compound represented by the general formula (1) include the hole injecting layer, the hole transporting layer, the electron transporting layer, the electron injecting layer, the exciton blocking layer, the charge blocking layer (such as the hole blocking layer, and the electron blocking layer). Preferred is one of the hole injecting layer, the hole transporting layer, the exciton blocking layer, and the charge blocking layer. More preferred is the hole transporting layer, the exciton blocking layer, or the charge blocking layer.

When the compound represented by the general formula (1) is contained in the light emitting layer, the compound represented by the general formula (1) is contained in preferably 0.1 to 100% by mass, more preferably 1 to 50% by mass, further preferably 2 to 20% by mass with respect to the total mass of the light emitting layer.

When the compound represented by the general formula (1) is contained in organic layers other than the light emitting layer, the compound represented by the general formula (1) is contained in preferably 70 to 100% by mass, more preferably 80 to 100% by mass, further preferably 90 to 100% by mass with respect to the total mass of the organic layers.

(Organic Layer Forming Method)

The respective organic layers in the organic electroluminescent element according to the present invention can be suitably formed by any of dry type film forming methods such as a deposition method and a sputtering method, wet type film forming methods (solution coating methods) such as a transfer method, a printing method, a spin coating method, and a bar coating method.

In the organic electroluminescent element of the present invention, it is preferable that the organic layer disposed between the pair of electrodes is formed by the deposition of at least one layer of a composition that includes the compound represented by the general formula (1).

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting. However, the light emitting layer in the present invention is not necessarily limited to the light emitting by such a mechanism.

The light emitting layer in the organic electroluminescent element according to the present invention may be constituted of only the light emitting material, or may be constituted as a mixed layer of the host material and the light emitting material. The light emitting material may be made of a single kind or two or more kinds thereof. The host material is preferably a charge transporting material. The host material may be made of a single kind or two or more kinds thereof. Examples thereof include a configuration in which an electron transporting host material and a hole transporting host material are mixed. Furthermore, the light emitting layer may include a material which does not have charge transporting properties and which does not emit light.

In addition, the light emitting layer may be made of a single layer or multiple layers of two or more layers. The respective layers may include the same light emitting material or host material, or may also include a different material in every layer. In the case where plural light emitting layers are present, the respective light emitting layers may emit light in a different luminous color from each other.

The thickness of the light emitting layer is not particularly limited, but it is usually from 2 nm to 500 nm, and above all, from the viewpoint of external quantum efficiency, it is more preferably from 3 nm to 200 nm, and still more preferably from 5 nm to 100 nm.

Host Material

The organic electroluminescent element of the present invention preferably uses the compound represented by the general formula (1) as the host material. However, even in this case, a host material different from the compound represented by the general formula (1) may be used in combination. Here, the host material as referred to in the present specification is a compound which chiefly plays a role in injecting or transporting charges in the light emitting layer and is also a compound which does not substantially emit light in itself. As used herein, it is meant by the terms "which does not substantially emit light" that the amount of light emission from the compound which does not substantially emit light is preferably not more than 5%, more preferably not more than 3%, and still more preferably not more than 1% relative to the total amount of light emission in the whole of the element.

Examples of the host materials that can be used in the organic electroluminescent element of the present invention include the compounds represented by the general formula (1), and the following compounds.

Pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkanes, pyrazoline, pyrazolone, phenylenediamine, arylamines, amino-substituted chalcone, styrylanthracene, fluorenone, hydrazone, stilbene, silazane, aromatic tertiary amine compounds, styrylamine compounds, porphyrin-based compounds, fused aromatic hydrocarbon compounds (such as fluorene, naphthalene, phenanthrene, and triphenylene) other than the compounds represented by the general formula (1), conductive polymeric oligomers (such as polysilane-based compounds, poly(N-vinylcarbazole), aniline-based copolymers, thiophene oligomers, and polythiophene), organic silanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, phthalocyanine, and a variety of metal complexes typified by metal complexes of 8-quinolinol derivatives and metal complexes having metal phthalocyanine, benzoxazole, or benzothiazole as a ligand thereof, and derivatives thereof (which may have a substituent or a fused ring). Compounds described in paragraphs [0081] and [0083] of JP-A-2010-111620 also may be used.

Of these, carbazole, dibenzothiophene, dibenzofuran, arylamine, fused aromatic hydrocarbon compounds other than the compounds represented by the general formula (1), and metal complexes are preferred, and fused aromatic hydrocarbon compounds are particularly preferred for their stability. Preferred examples of the fused aromatic hydrocarbon compounds other than the compounds represented by the general formula (1) include naphthalene-based compounds, phenanthrene-based compounds, triphenylene-based compounds, and pyrene-based compounds, and pyrene-based compounds are more preferred.

The host material that can be used in the light emitting layer in the organic electroluminescent element of the present invention may be a hole-transporting host material, or an electron-transporting host material.

In the light emitting layer, it is preferable that the singlet lowest excitation energy ($S_1$ energy) of the host material in the film state be higher than the $S_1$ energy of the light emitting material from the viewpoints of color purity, luminous efficiency, and driving durability. The $S_1$ of the host material exceeds the $S_1$ of the light emitting material preferably by 0.1 eV or more, more preferably 0.2 eV or more, further preferably 0.3 eV or more.

The host material requires a larger $S_1$ than the light emitting material, because the emission extinction occurs when the $S_1$ of the host material in the film state is smaller than the $S_1$ of the light emitting material. Further, even when the host material has a larger $S_1$ than the light emitting material, the reverse energy movement occurs from the light emitting material to the host material when the $S_1$ difference is small. This may lead to low efficiency, low color purity, or low durability. The host material is therefore required to have a sufficiently larger $S_1$, and high chemical stability and carrier injecting and transporting properties.

The content of the host compound in the light emitting layer in the organic electroluminescent element of the present invention is not particularly limited. However, from the viewpoints of luminous efficiency and driving voltage, the host compound content is preferably 15 to 99% by mass with respect to the total compound mass forming the light emitting layer. When the light emitting layer contains more than one host compounds containing the compound represented by the general formula (1), the compound represented by the general formula (1) is preferably 50 to 99% by mass or less of the total host compound.

Light Emitting Material

A light emitting material different from the compound represented by the general formula (1) may be used for the light emitting layer in the organic electroluminescent element of the present invention, or in the organic electroluminescent element of the present invention that uses the compound represented by the general formula (1) as the light emitting material of the light emitting layer or in organic layers other than the light emitting layer.

The light emitting material that can be used in the present invention may be a phosphorescent material, a fluorescent material, or the like. Further, the light emitting layer in the present invention may contain two or more light emitting materials to improve color purity or widen the light emitting wavelength region.

The fluorescent materials and phosphorescent materials that can be used in the organic electroluminescent element of the present invention are described, for example, in paragraphs [0100] to [0164] of JP-A-2008-270736, and paragraphs [0088] to [0090] of JP-A-2007-266458, and the detailed descriptions in these publications may be applied to the present invention.

Examples of the phosphorescent materials that can be used in the present invention include those described in, for example, U.S. Pat. No. 6,303,238, U.S. Pat. No. 6,097,147, WO00/57676, WO00/70655, WO01/08230, WO01/39234, WO01/41512, WO02/02714, WO02/15645, WO02/44189, WO05/19373, JP-A-2001-247859, JP-A-2002-302671, JP-A-2002-117978, JP-A-2003-133074, JP-A-2002-235076, JP-A-2003-123982, JP-A-2002-170684, European patent publication 1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259. Examples of more preferred light emitting materials include phosphorescent metal complex compounds such as Ir complexes, Pt complexes, Cu complexes, Re complexes, W complexes, Rh complexes, Ru complexes, Pd complexes, Os complexes, Eu complexes, Tb complexes, Gd complexes, Dy complexes, and Ce complexes. Particularly preferred are Ir complexes, Pt complexes, and Re complexes, of which Ir complexes, Pt complexes, or Re complexes containing at least one coordination mode of a metal-carbon bond, a metal-nitrogen bond, a metal-oxygen bond, and a metal-sulfur bond are preferred. Furthermore, from the viewpoints of luminous efficiency, driving durability, chromaticity, and the like, Ir complexes and Pt complexes are especially preferable, and Ir complexes are most preferable.

The type of the fluorescent material that can be used in the present invention is not particularly limited. Aside from the compounds represented by the general formula (1), the following compounds may be used. Benzooxazole, benzoimidazole, benzothiazole, styrylbenzene, polyphenyl, diphenylbutadiene, tetraphenylbutadiene, naphthalimide, coumalin, pyran, perinone, oxadiazole, aldazine, pyrralidine, cyclopentadiene, bisstyrylanthracene, quinacridone, pyrrolopyridine, thiadiazolopyridine, cyclopentadiene, styrylamine, fused polycyclic aromatic compounds (such as anthracene, phenanthroline, pyrene, perylene, rubrene, and pentacene), various metal complexes as represented by metal complexes of 8-quinolinol, pyrromethene complexes, and rare earth complexes, polymer compounds such as polythiophene, polyphenylene, and polyphenylenevinylene, organic silanes, and derivatives of these.

Compounds described in paragraph [0082] of JP-A-2010-111620 also may be used as the light emitting material.

When the compound represented by the general formula (1) is used as the host material of the light emitting layer, the organic electroluminescent element of the present invention preferably uses a fluorescent material as the light emitting material, more preferably a blue emitting fluorescent material.

The maximum light emitting wavelength of the organic electroluminescent element of the present invention is preferably less than 460 nm, more preferably 400 nm or more and less than 460 nm, particularly preferably 420 nm or more and less than 455 nm, further preferably 430 nm or more and less than 455 nm, and from the viewpoint of obtaining blue emission of high color purity, most preferably 440 nm or more and less than 455 nm.

The organic electroluminescent element of the present invention preferably has a maximum light emitting wavelength of 440 nm or more and less than 455 nm, because it produces blue emission of particularly high color purity. From the viewpoints of obtaining a sharp spectrum and improving the blue color purity while realizing high luminous efficiency and improving the luminance deterioration rate in the initial stage of lighting, it is preferable to use pyrene derivatives, phenanthrotriphenylene derivatives, and chrysene derivatives as light emitting materials for obtaining such organic electroluminescent elements.

Without being bound by any theory, reducing the light emitting wavelength is known to be useful for obtaining desirable blue color purity. However, reducing the light emitting wavelength of the light emitting material increases the $S_1$ (lowest excitation singlet energy level) of the light emitting material, and either decreases the $S_1$ difference between the light emitting material and the host material, or makes the $S_1$ of the host material greater than the $S_1$ of the light emitting material. This is problematic, because it lowers the luminous efficiency, and lowers the blue color purity by inclusion of the side emission of the host material. On the other hand, when pyrene derivatives, phenanthrotriphenylene derivatives, and chrysene derivatives are used as light emitting material with the compound of the present invention represented by the general formula (1) used for the light emitting layer, it is possible to improve blue color purity while maintaining high luminous efficiency.

The pyrene derivatives are not particularly limited, but include the compounds represented by the following general formula (p-1).

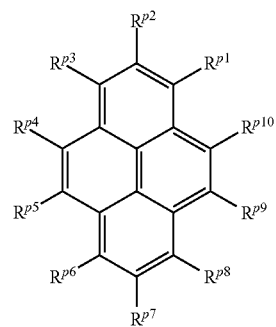

General Formula (p-1)

[In the general formula (p-1), $R^{p1}$ to $R^{p10}$ represent hydrogen atoms or substituents.]

Examples of the substituents represented by $R^{p1}$ to $R^{p10}$ include those given in the substituent group A below, and the adjacent substituents may be bound to each other via a single bond or a linking group to form a ring. Further, the substituents given in the substituent group A may be further substituted, and the adjacent substituents on the substituent group A may be bound to each other via a single bond or a linking group to form a ring.

(Substituent Group A)

An alkyl group (having preferably from 1 to 30 carbon atoms, more preferably from 1 to 20 carbon atoms, and especially preferably from 1 to 10 carbon atoms; for example, methyl, ethyl, isopropyl, tert-butyl, n-octyl, n-decyl, n-hexadecyl, cyclopropyl, cyclopentyl, and cyclohexyl), an alkenyl group (having preferably from 2 to 30 carbon atoms, more preferably from 2 to 20 carbon atoms, and especially preferably from 2 to 10 carbon atoms; for example, vinyl, allyl, 2-butenyl, and 3-pentenyl), an alkynyl group (having preferably from 2 to 30 carbon atoms, more preferably from 2 to 20 carbon atoms, and especially preferably from 2 to 10 carbon atoms; for example, propargyl and 3-pentynyl), an aryl group (having preferably from 6 to 30 carbon atoms; for example, phenyl, p-methylphenyl, naphthyl, and anthranyl), an amino group (having preferably from 0 to 30 carbon atoms; for example, amino, methylamino, dimethylamino, diethylamino, dibenzylamino, diphenylamino, and ditolylamino), an alkoxy group (having preferably from 1 to 30 carbon atoms, more preferably from 1 to 20 carbon atoms, and especially preferably from 1 to 10 carbon atoms; for example, methoxy, ethoxy, butoxy, and 2-ethylhexyloxy), an aryloxy group (having preferably from 6 to 30 carbon atoms, more preferably from 6 to 20 carbon atoms, and especially preferably from 6 to 12 carbon atoms; for example, phenyloxy, 1-naphthyloxy, and 2-naphthyloxy), a heterocyclic oxy group (having preferably from 1 to 30 carbon atoms, more preferably from 1 to 20 carbon atoms, and especially preferably from 1 to 12 carbon atoms; for example, pyridyloxy, pyrazyloxy, pyrimidyloxy, and quinolyloxy), an acyl group (having preferably from 2 to 30 carbon atoms, more preferably from 2 to 20 carbon atoms, and especially preferably from 2 to 12 carbon atoms; for example, acetyl, benzoyl, formyl, and pivaloyl), an alkoxycarbonyl group (having preferably from 2 to 30 carbon atoms, more preferably from 2 to 20 carbon atoms, and especially preferably from 2 to 12 carbon atoms; for example, methoxycarbonyl and ethoxycarbonyl), an aryloxycarbonyl group (having preferably from 7 to 30 carbon atoms, more preferably from 7 to 20 carbon atoms, and especially preferably from 7 to 12 carbon atoms; for example, phenyloxycarbonyl), an acyloxy group (having preferably from 2 to 30 carbon atoms, more preferably from 2 to 20 carbon atoms, and especially preferably from 2 to 10 carbon atoms; for example, acetoxy and benzoyloxy), an acylamino group (having preferably from 2 to 30 carbon atoms, more preferably from 2 to 20 carbon atoms, and especially preferably from 2 to 10 carbon atoms; for example, acetylamino and benzoylamino), an alkoxycarbonylamino group (having preferably from 2 to 30 carbon atoms, more preferably from 2 to 20 carbon atoms, and especially preferably from 2 to 12 carbon atoms; for example, methoxycarbonylamino), an aryloxycarbonylamino group (having preferably from 7 to 30 carbon atoms, more preferably from 7 to 20 carbon atoms, and especially preferably from 7 to 12 carbon atoms; for example, phenyloxycarbonylamino), a sulfonylamino group (having preferably from 1 to 30 carbon atoms, more preferably from 1 to 20 carbon atoms, and especially preferably from 1 to 12 carbon atoms; for example, methanesulfonylamino and benzenesulfonylamino), a sulfamoyl group (having preferably from 0 to 30 carbon atoms, more preferably from 0 to 20 carbon atoms, and especially preferably from 0 to 12 carbon atoms; for example, sulfamoyl, methyl sulfamoyl, dimethyl sulfamoyl, and phenyl sulfamoyl), a carbamoyl group (having preferably from 1 to 30 carbon atoms, more preferably from 1 to 20 carbon atoms, and especially preferably from 1 to 12 carbon atoms; for example, carbamoyl, methyl carbamoyl, diethyl carbamoyl, and phenyl carbamoyl), an alkylthio group (having preferably from 1 to 30 carbon atoms, more preferably from 1 to 20 carbon atoms, and especially preferably from 1 to 12 carbon atoms; for example, methylthio and ethylthio), an arylthio group (having preferably from 6 to 30 carbon atoms, more preferably from 6 to 20 carbon atoms, and especially preferably from 6 to 12 carbon atoms; for example, phenylthio), a heterocyclic thio group (having preferably from 1 to 30 carbon atoms, more preferably from 1 to 20 carbon atoms, and especially preferably from 1 to 12 carbon atoms; for example, pyridylthio, 2-benzimizolylthio, 2-benzoxazolylthio, and 2-benzthiazolylthio), a sulfonyl group (having preferably from 1 to 30 carbon atoms, more preferably from 1 to 20 carbon atoms, and especially preferably from 1 to 12 carbon atoms; for example, mesyl and tosyl), a sulfinyl group (having preferably from 1 to 30 carbon atoms, more preferably from 1 to 20 carbon atoms, and especially preferably from 1 to 12 carbon atoms; for example, methane sulfinyl and benzene sulfinyl), a ureido group (having preferably from 1 to 30 carbon atoms, more preferably from 1 to 20 carbon atoms, and especially preferably from 1 to 12 carbon atoms; for example, ureido, methylureido, and phenylureido), a phosphoramide group (having preferably from 1 to 30 carbon atoms, more preferably from 1 to 20 carbon atoms, and especially preferably from 1 to 12 carbon atoms; for example, diethylphosphoramide and phenylphosphoramide), a hydroxyl group, a mercapto group, a halogen atom (for example, a fluorine atom, a chlorine atom, a bromine atom, and an iodine atom), a cyano group, a sulfo group, a carboxyl group, a nitro group, a hydroxamic group, a sulfino group, a hydrazino group, an imino group, a heterocyclic group (inclusive of an aromatic heterocyclic group, which has preferably from 1 to 30 carbon atoms, and more preferably from 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenienyl, tellelienyl, piperidyl, piperidino, morpholino, pyrrolidyl, pyrrolidino, benzoxazolyl, benzimidazolyl, benzothiazolyl, a carbazolyl group, an azepinyl group, and a silolyl group), a silyl group (having preferably from 3 to 40 carbon atoms, more preferably from 3 to 30 carbon atoms, and especially preferably from 3 to 24 carbon atoms; for example, trimethylsilyl and triphenylsilyl), a silyloxy group (having preferably from 3 to 40 carbon atoms, more preferably from 3 to 30 carbon atoms, and especially preferably from 3 to 24 carbon atoms; for example, trimethylsilyloxy and triphenylsilyloxy), and a phosphoryl group (for example, a diphenylphosphoryl group and a dimethylphosphoryl group).

From the viewpoints of color purity and durability, it is preferable that at least one of $R^{p1}$ to $R^{p10}$ is an aryl group, a heteroaryl group, or an amino group (including an alkylamino group, a dialkylamino group, an arylamino group, and a diarylamino group), more preferably an aryl group, or an amino group.

The compounds represented by the general formula (p-1) are preferably compounds represented by the following general formula (p-2), (p-3), or (p-4).

General Formula (p-2)

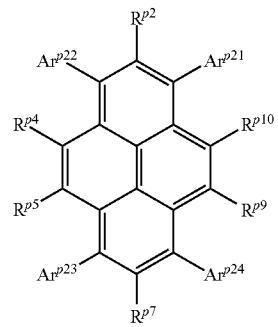

[In the general formula (p-2), $R^{p2}$, $R^{p4}$, $R^{p5}$, $R^{p7}$, $R^{p9}$, and $R^{p10}$ have the same definitions as the $R^{p2}$, $R^{p4}$, $R^{p5}$, $R^{p7}$, $R^{p9}$, $R^{p10}$ in the general formula (p-1). $Ar^{p21}$ to $Ar^{p24}$ represent hydrogen atoms or aryl groups, or heteroaryl groups. At least one of $Ar^{p21}$ to $Ar^{p24}$ represents an aryl group, or a heteroaryl group.]

From the viewpoints of color purity and durability, $R^{p2}$, $R^{p4}$, $R^{p5}$, $R^{p7}$, $R^{p9}$, $R^{p10}$ are preferably hydrogen atoms, alkyl groups, aryl groups, or heteroaryl groups, more preferably hydrogen atoms, alkyl groups, or aryl groups, further preferably hydrogen atoms, or alkyl groups, particularly preferably hydrogen atoms.

From the viewpoint of color purity, $Ar^{p21}$ to $Ar^{p24}$ are preferably hydrogen atoms or aryl groups. More preferably, one or two, or four of $Ar^{p21}$ to $Ar^{p24}$ are aryl groups. Further preferably, two or four of $Ar^{p21}$ to $Ar^{p24}$ are aryl groups. Particularly preferably, four of $Ar^{p21}$ to $Ar^{p24}$ are aryl groups.

Specific examples of the compounds represented by the general formula (p-2) are given below. It should be noted that the present invention is not limited to the following.

(p2-1)
(p2-2)
(p2-3)
(p2-4)
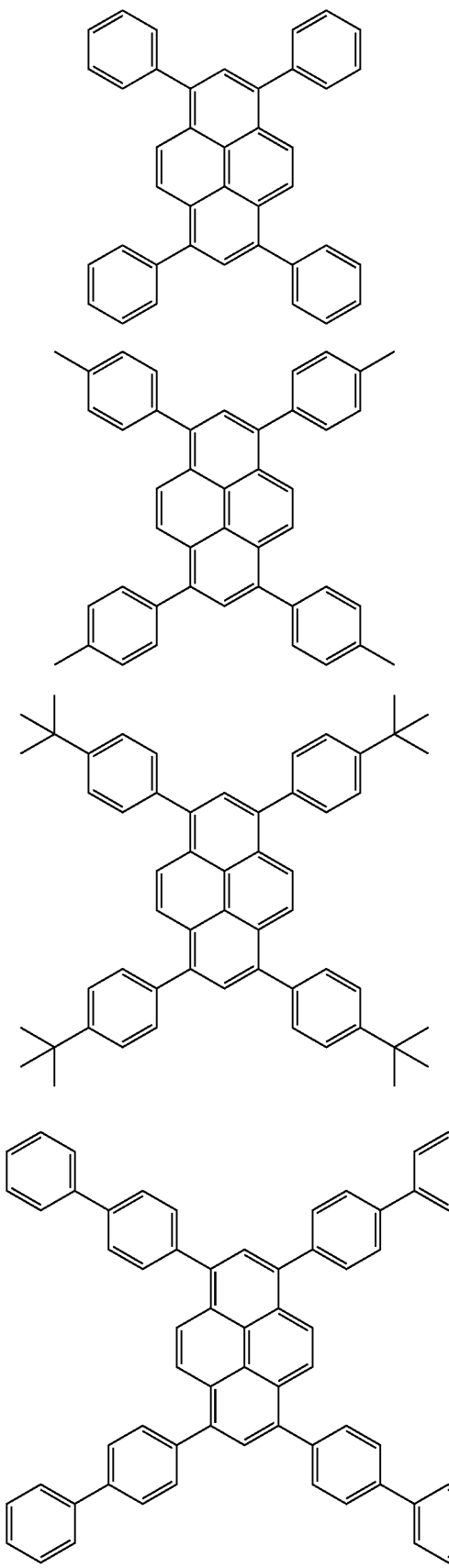
(p2-5)
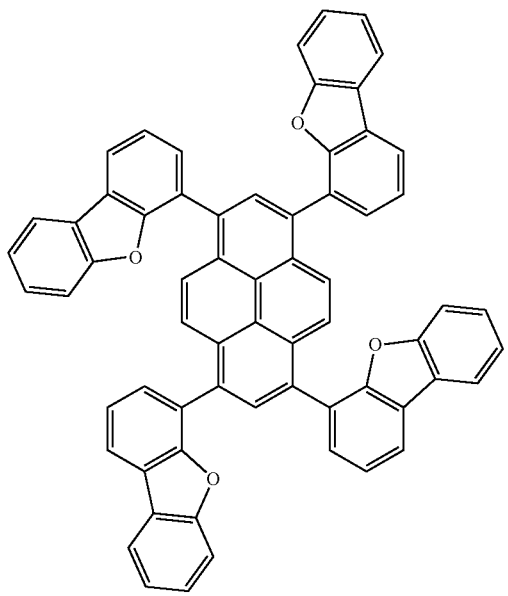
(p2-6)
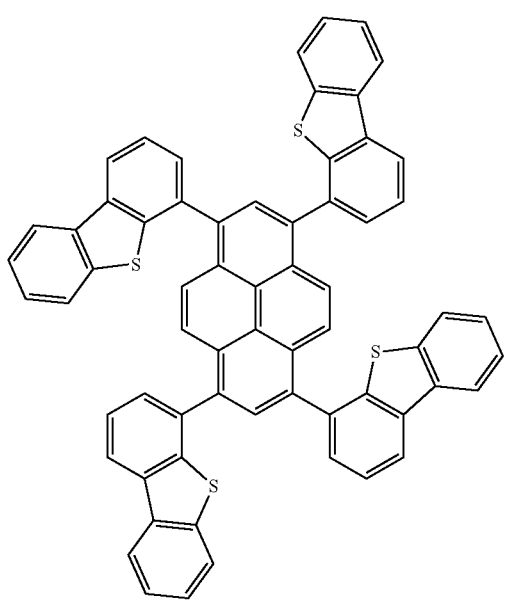
(p2-7)
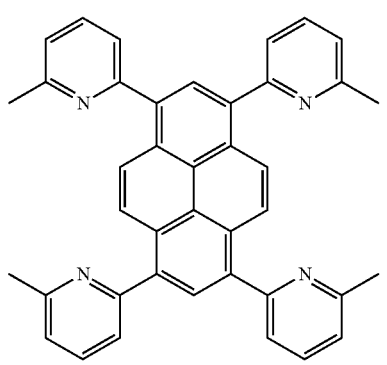

(p2-8) 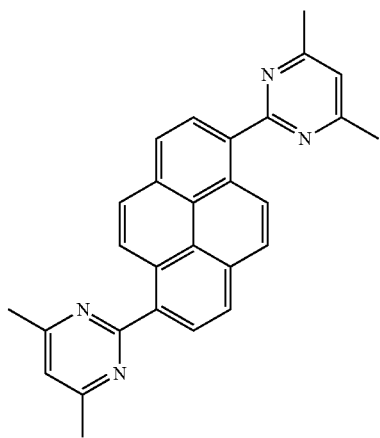
(p2-9) 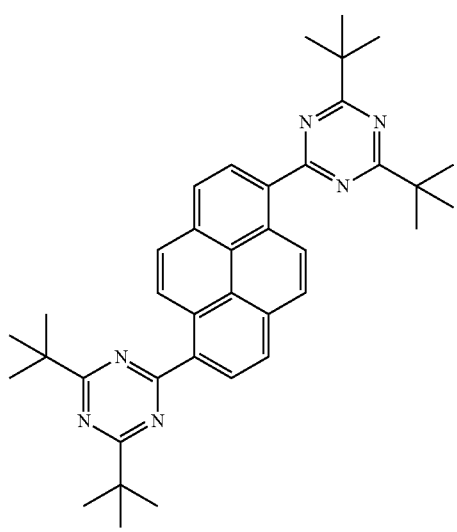
(p2-10) 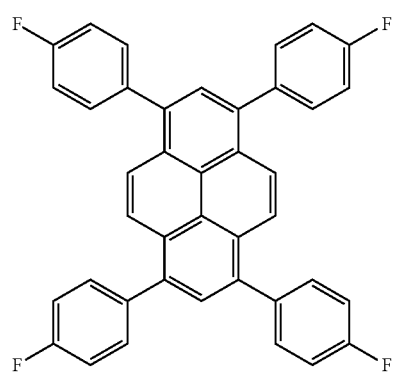
(p2-11) 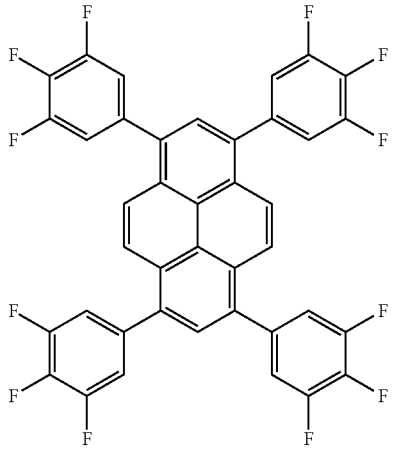
(p2-12) 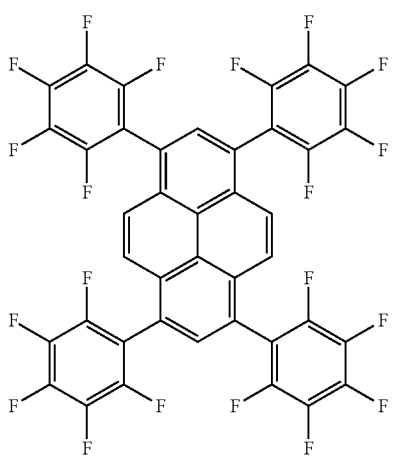
(p2-13) 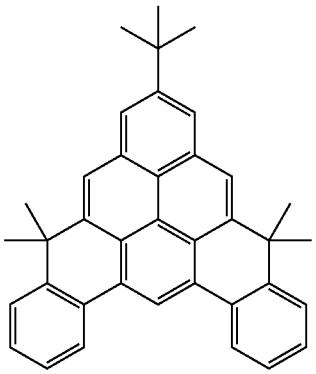

-continued (p2-14)

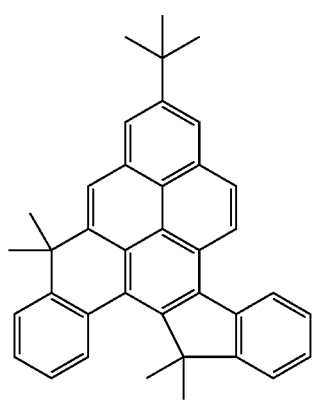

(p2-15)

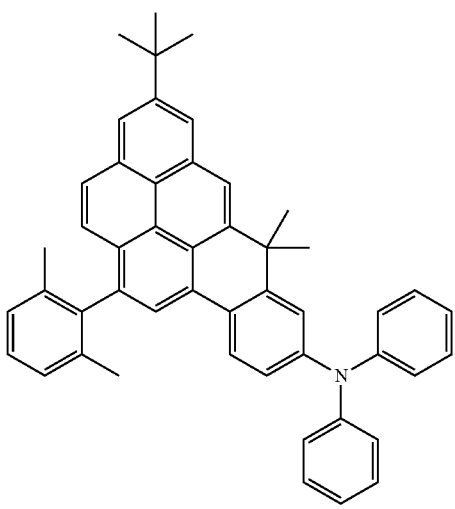

General Formula (p-3)

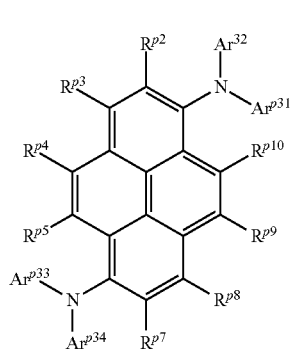

[In the general formula (p-3), $R^{p2}$ to $R^{p5}$, and $R^{p7}$ to $R^{p10}$ have the same definitions as $R^{P2}$ to $R^{P5}$, and $R^{P7}$ to $R^{P10}$ in the general formula (p-1). $Ar^{p31}$ to $Ar^{p34}$ represent substituents.]

From the viewpoints of color purity and durability, $R^{p2}$ to $R^{p5}$, and $R^{p7}$ to $R^{p10}$ are preferably hydrogen atoms, alkyl groups, aryl groups, or heteroaryl groups, more preferably hydrogen atoms, alkyl groups, or aryl groups, further preferably hydrogen atoms, or aryl groups, particularly preferably hydrogen atoms.

$Ar^{p31}$ to $Ar^{p34}$ represent substituents. Examples of the substituents include those given in the substituent group B, and the adjacent substituents may be bound to each other via a single bond or a linking group to form a ring. The substituents given in the substituent group B may be further substituted, and the adjacent substituents on the substituent group B may be bound to each other via a single bond or a linking group to form a ring.

(Substituent Group B)

An alkyl group (having preferably 1 to 30 carbon atoms, more preferably 1 to 20 carbon atoms, particularly preferably 1 to 10 carbon atoms; for example, methyl, ethyl, isopropyl, tert-butyl, n-octyl, n-decyl, n-hexadecyl, cyclopropyl, cyclopentyl, and cyclohexyl), an alkenyl group (having preferably 2 to 30 carbon atoms, more preferably 2 to 20 carbon atoms, particularly preferably 2 to 10 carbon atoms; for example, vinyl, allyl, 2-butenyl, and 3-pentenyl), an alkynyl group (having preferably 2 to 30 carbon atoms, more preferably 2 to 20 carbon atoms, particularly preferably 2 to 10 carbon atoms; for example, propargyl, and 3-pentynyl), an aryl group (having preferably 6 to 30 carbon atoms; for example, phenyl, p-methylphenyl, naphthyl, and anthranyl), a cyano group, and a heterocyclic group (including aromatic heterocyclic groups, and having preferably 1 to 30 carbon atoms, more preferably 1 to 12 carbon atoms; the heteroatom being, for example, a nitrogen atom, an oxygen atom, a sulfur atom, a phosphorus atom, a silicon atom, a selenium atom, or a tellurium atom; specific examples include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenienyl, tellelienyl, piperidyl, piperidino, morpholino, pyrrolidyl, pyrrolidino, benzooxazolyl, benzoimidazolyl, benzothiazolyl, carbazolyl group, azepinyl group, and silolyl group)

As used herein, the "number of carbon atoms" in substituents such as the alkyl groups is inclusive of substitution of substituents such as alkyl groups with other substituents, and is intended to include the number of the carbon atoms in such other substituents.

From the viewpoints of color purity and durability, $Ar^{p31}$ to $Ar^{p34}$ are preferably aryl groups or heteroaryl groups, more preferably aryl groups. Of aryl groups, phenyl groups having substituents are further preferable, and phenyl groups in which one of $Ar^{p31}$ and $Ar^{p32}$, and one of $Ar^{p33}$ and $Ar^{p34}$ are substituted with at least one fluorine atom are particularly preferable.

Specific examples of the compounds represented by the general formula (p-3) are described below. It should be noted that the present invention is not limited to the following.

(p2-1)

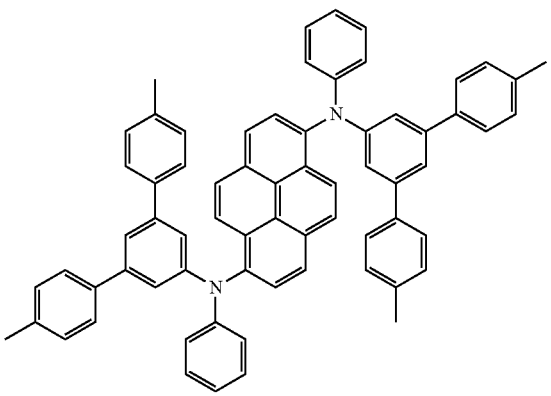

(p2-2)
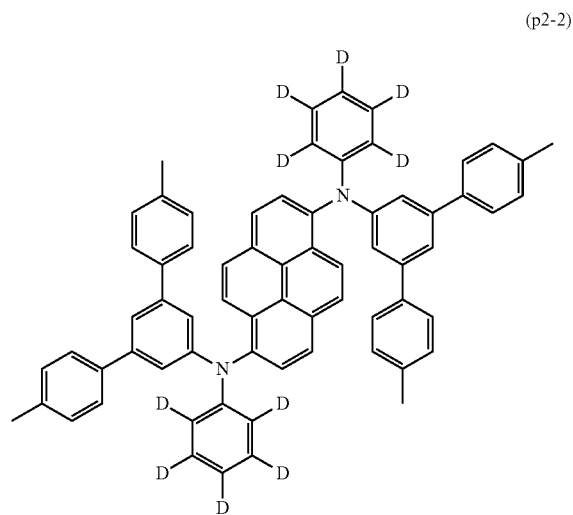
(p2-3)
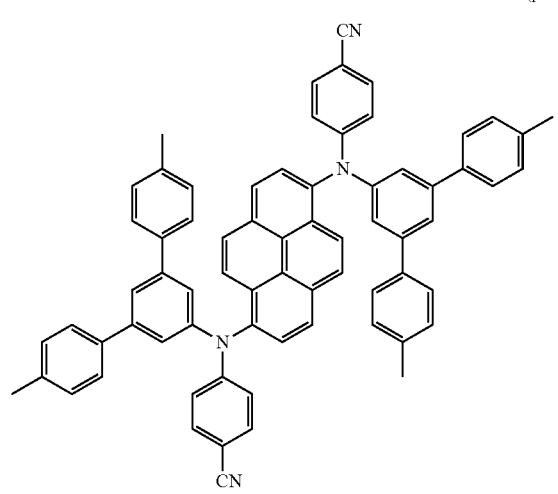
(p3-4)
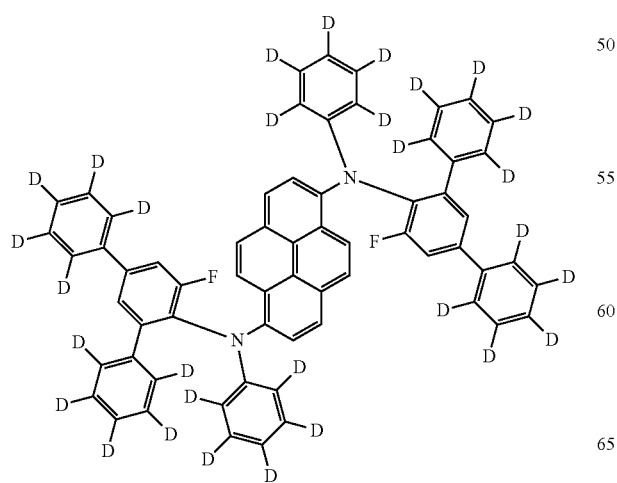
(p3-5)
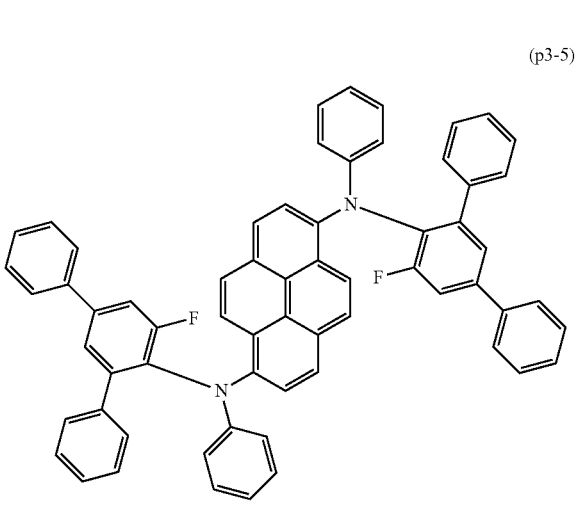
(p3-6)
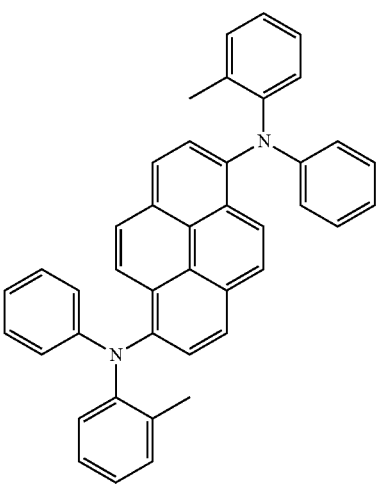
(p3-7)
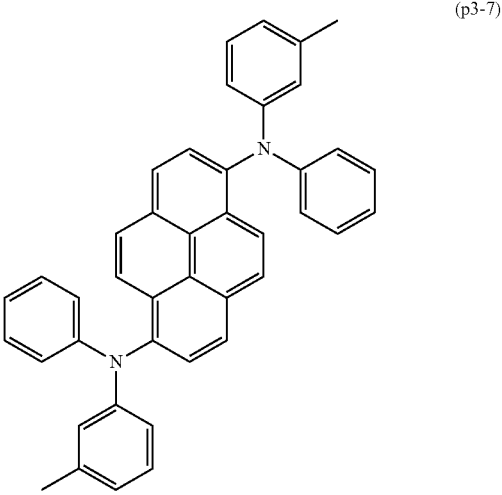

-continued
(p3-8)
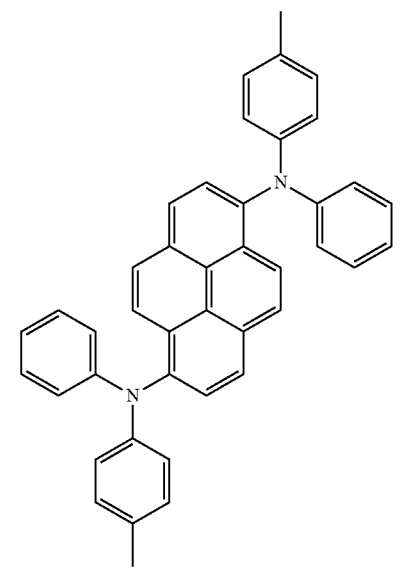
(p3-9)
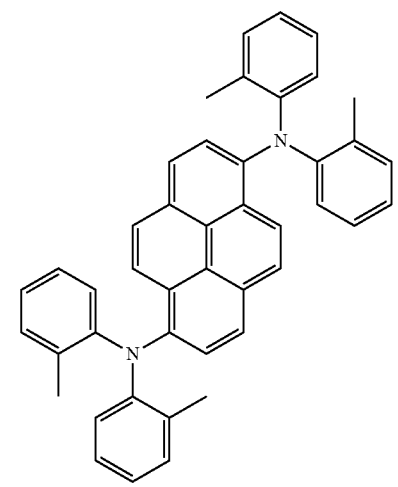
(p3-10)
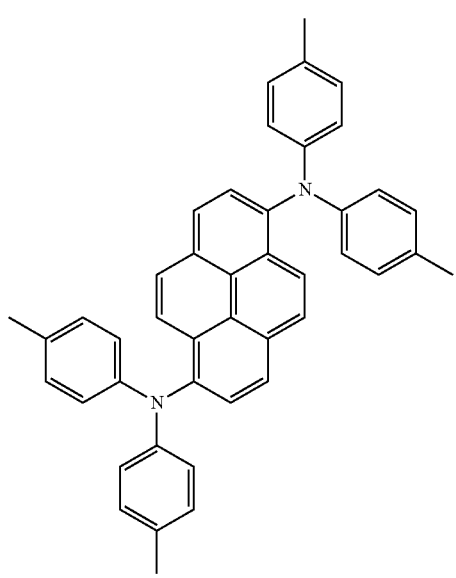
-continued
(p3-11)
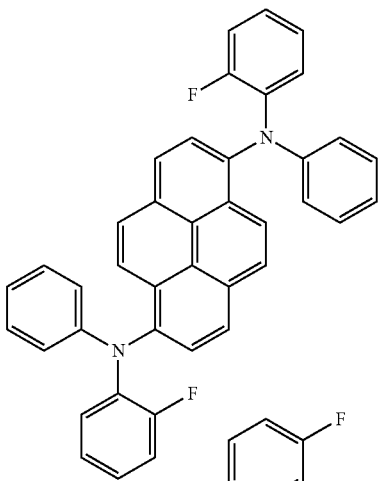
(p3-12)
(p3-13)
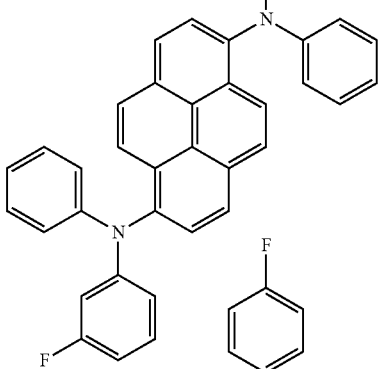
(p3-14)
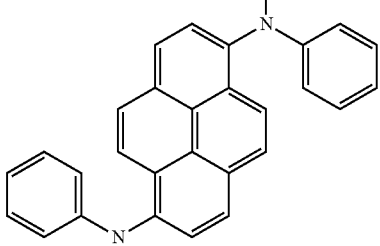

General Formula (p-4)

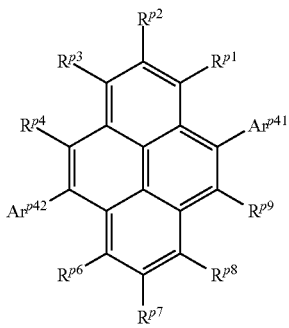

[In the general formula (p-4), $R^{p1}$ to $R^{p4}$, and $R^{p6}$ to $R^{p9}$ have the same definitions as $R^{p1}$ to $R^{p4}$, and $R^{p6}$ to $R^{p9}$ in the general formula (p-1). $Ar^{p41}$ and $Ar^{p42}$ represent hydrogen atoms or aryl groups, or heteroaryl groups. One of $Ar^{p41}$ and $Ar^{p42}$ represents an aryl group, or a heteroaryl group.]

From the viewpoints of color purity and durability, $R^{p1}$ to $R^{p4}$, and $R^{p6}$ to $R^{p9}$ are preferably hydrogen atoms, alkyl groups, aryl groups, or heteroaryl groups, more preferably hydrogen atoms, alkyl groups, or aryl groups, further preferably hydrogen atoms or alkyl groups, particularly preferably hydrogen atoms.

From the viewpoints of color purity and durability, $Ar^{p41}$ and $Ar^{p42}$ are preferably aryl groups. Of aryl groups, phenyl groups having substituents are more preferable, and phenyl groups substituted with amino groups are further preferable.

Specific examples of the compounds represented by the general formula (p-4) are described below. It should be noted that the present invention is not limited to the following.

(p4-1)

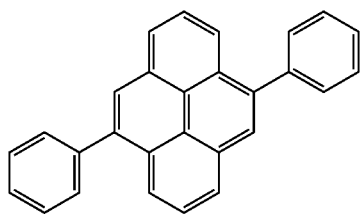

(p4-2)

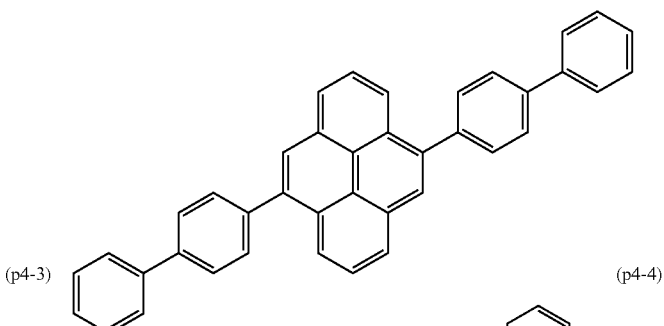

(p4-3)

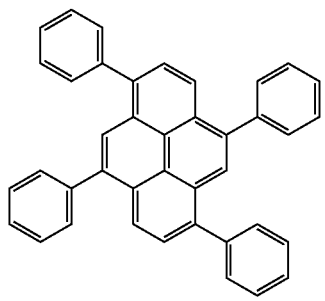

(p4-4)

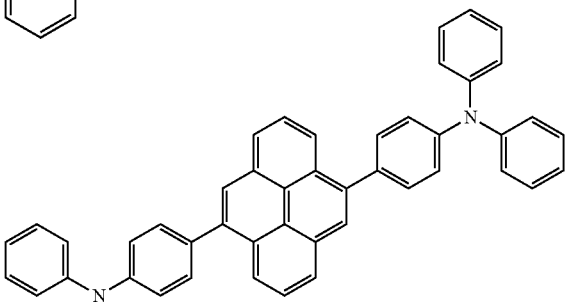

(p4-5)

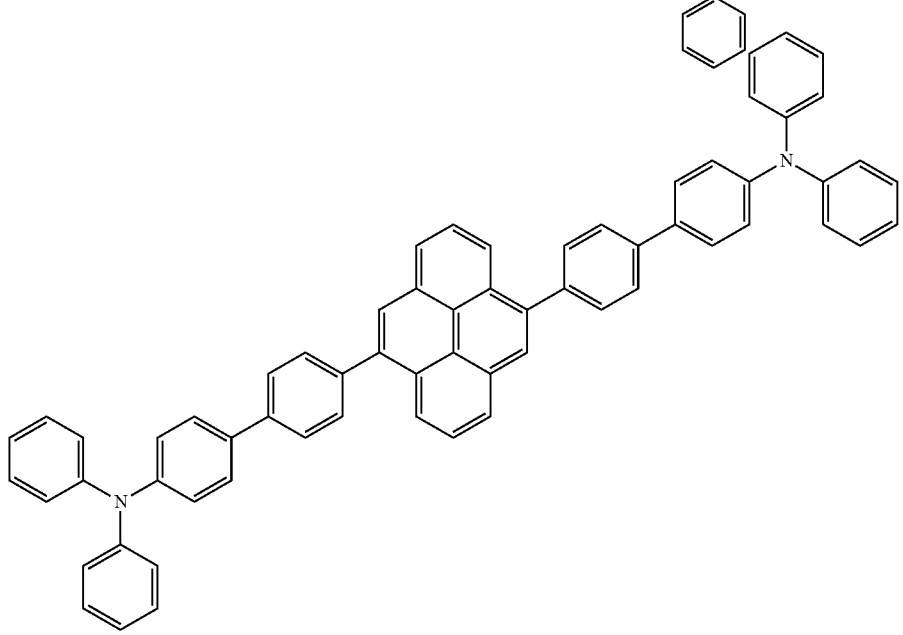

-continued
(p4-6)
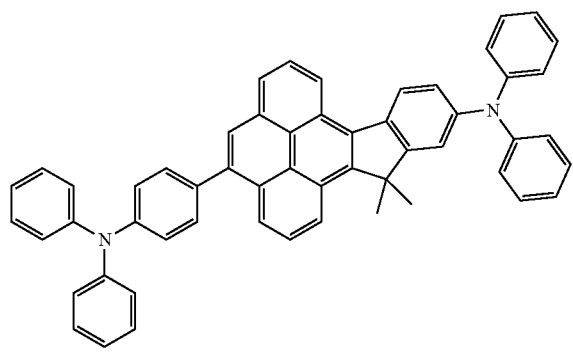
(p4-7)
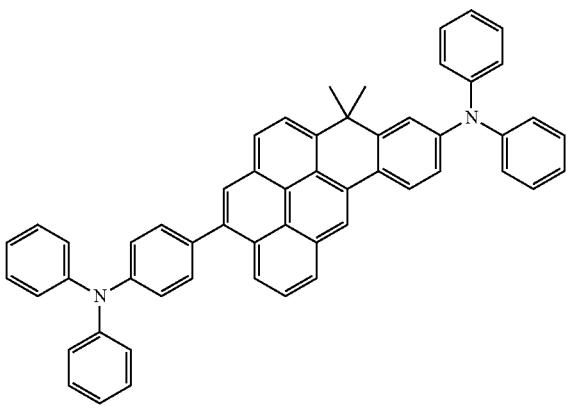
(p4-8)
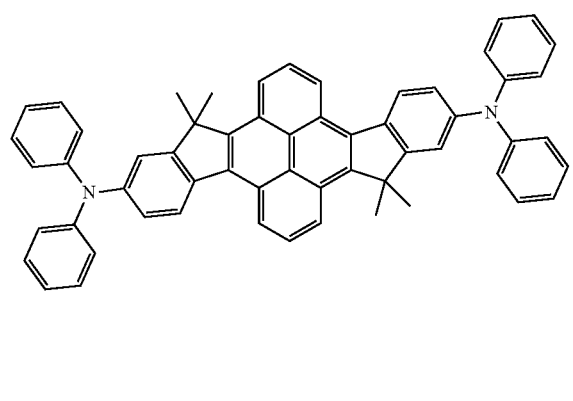
(p4-9)
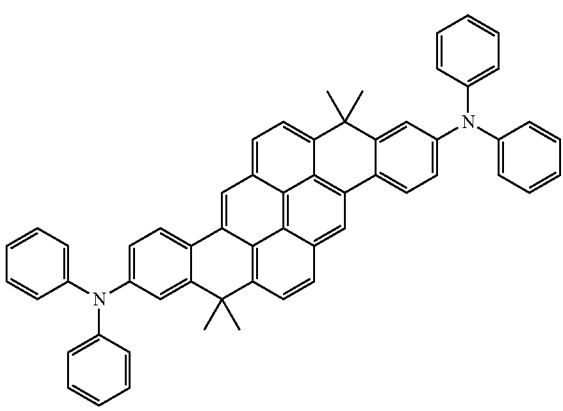
(p4-10)
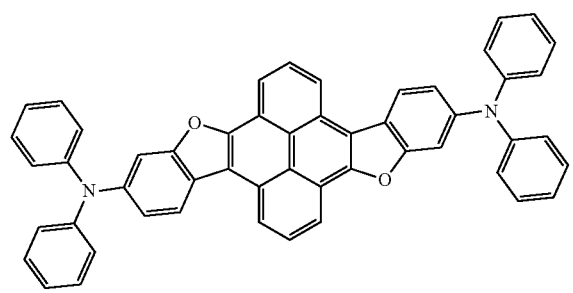
(p4-11)
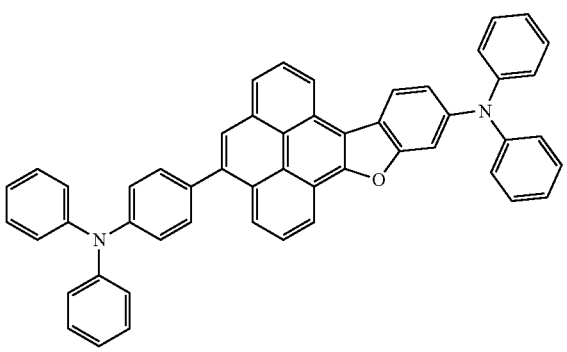
(p4-12)
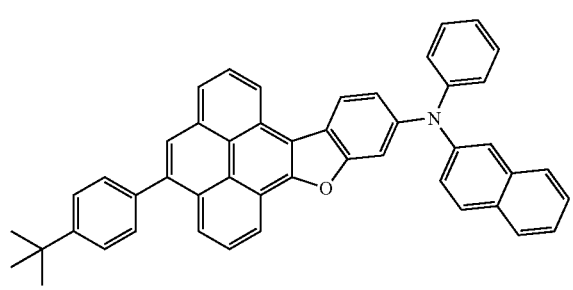

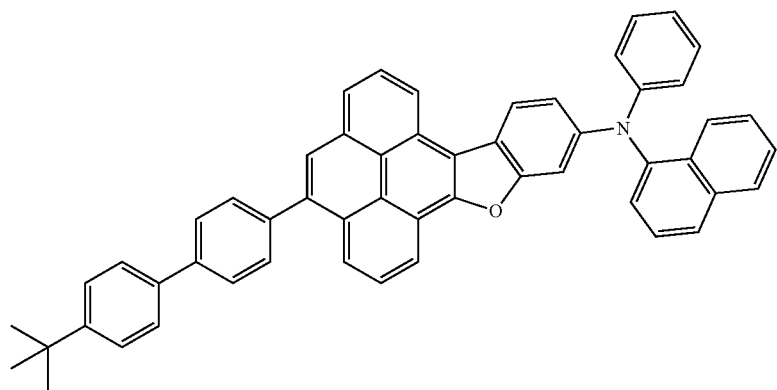
(p4-13)

Preferred examples of the phenanthrotriphenylene derivatives include compounds represented by the following general formula (PT-1).

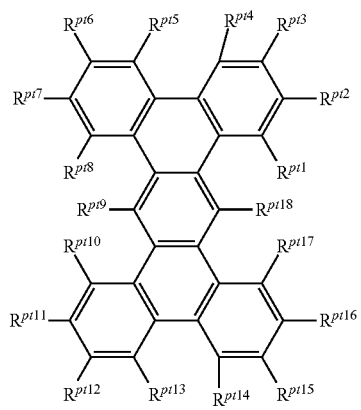

General Formula (PT-1)

[In the general formula (PT-1), $R^{pt1}$ to $R^{pt18}$ represent hydrogen atoms or substituents.]

Examples of the substituents represented by $R^{pt1}$ to $R^{pt18}$ include those given in the substituent group A, and the adjacent substituents may be bound to each other via a single bond or a linking group to form a ring.

From the viewpoints of color purity and durability, it is preferable that at least one of $R^{pt1}$ to $R^{pt18}$ is an aryl group, a heteroaryl group, or an amino group, more preferably an aryl group, or an amino group.

Specific examples of the compounds represented by the general formula (PT-1) are described below. It should be noted that the present invention is not limited to the following.

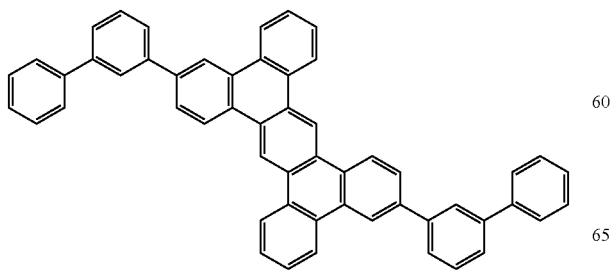
(pt1-1)

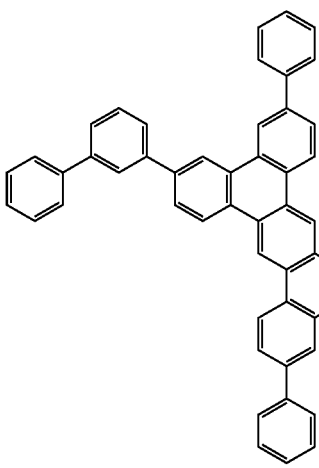
(pt1-2)

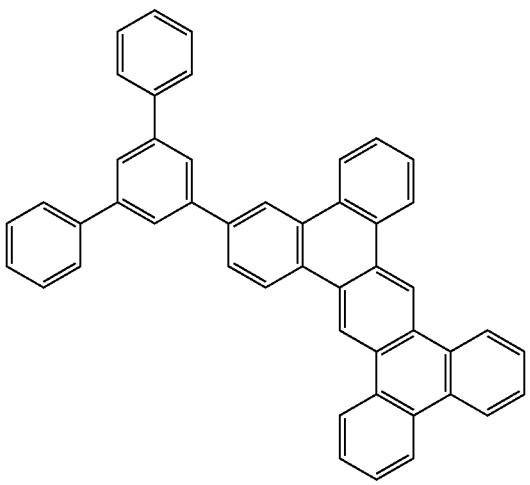
(pt1-3)

(pt1-4)

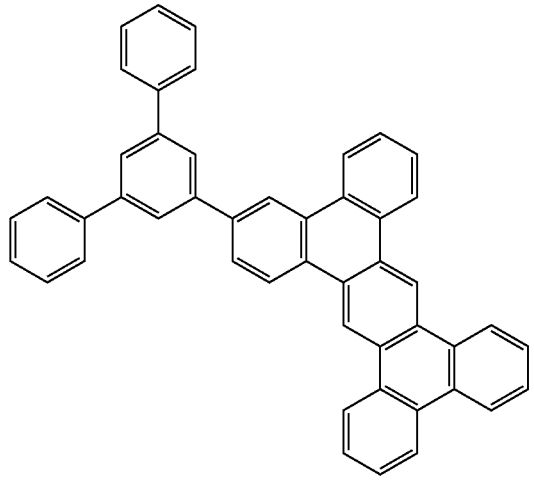

(pt1-5)

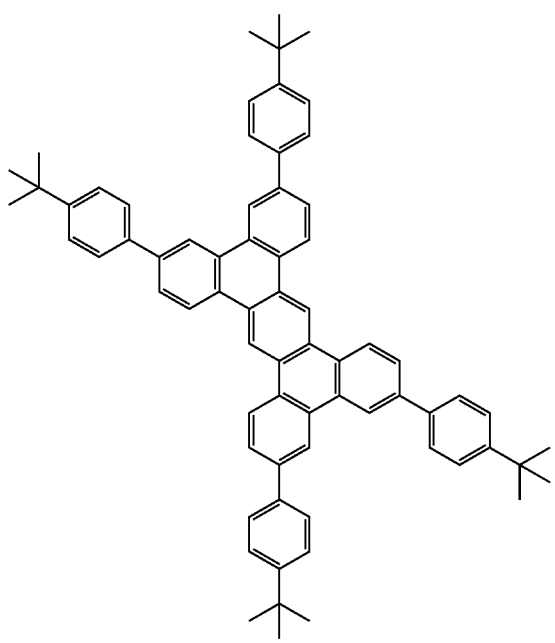

The compounds represented by the general formula (PT-1) are preferably compounds represented by the following general formula (PT-2).

General Formula (PT-2)

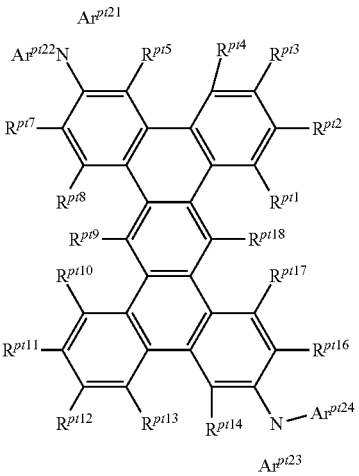

[In the general formula (PT-2), $R^{pt1}$ to $R^{pt5}$, $R^{pt7}$ to $R^{pt14}$, and $R^{pt16}$ to $R^{pt18}$ represent hydrogen atoms or substituents. $Ar^{pt21}$ to $Ar^{pt24}$ represent substituents.]

$R^{pt1}$ to $R^{pt5}$, $R^{pt7}$ to $R^{pt14}$, and $R^{pt16}$ to $R^{pt18}$ represent hydrogen atoms or substituents. Examples of the substituents represented by $R^{pt1}$ to $R^{pt5}$, $R^{pt7}$ to $R^{pt14}$, and $R^{pt16}$ to $R^{pt18}$ include those given in the substituent group A. The substituents given in the substituent group A may be further substituted.

$Ar^{pt21}$ to $Ar^{pt24}$ represent substituents. Examples of the substituents represented by $Ar^{pt21}$ to $Ar^{pt24}$ include those given in the substituent group B, and the substituents given in the substituent group B may be further substituted. $Ar^{pt21}$ to $Ar^{pt24}$ are preferably aryl groups that may be substituted.

Specific examples of the compounds represented by the general formula (PT-2) are described below. It should be noted that the present invention is not limited to the following.

(pt2-1)

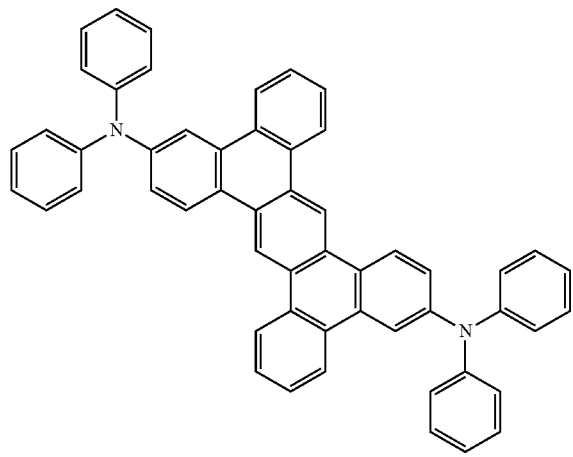

(pt2-2)

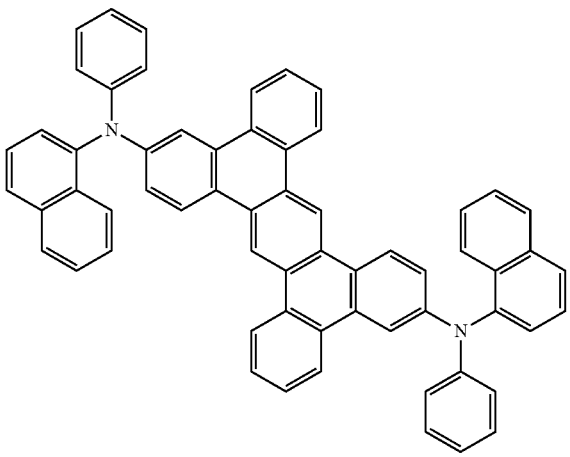

-continued
(pt2-3)
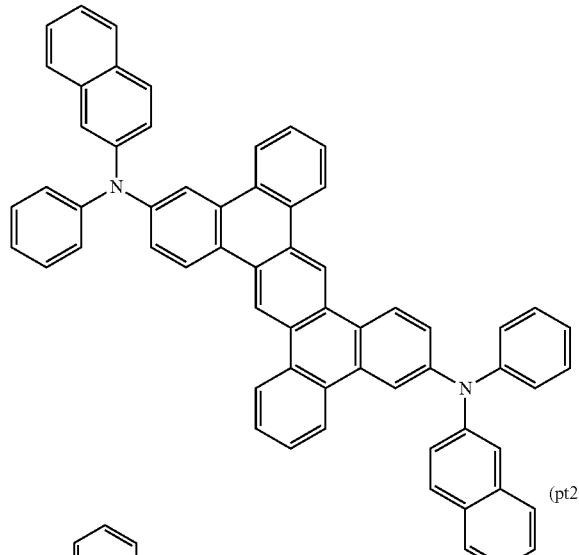
(pt2-4)
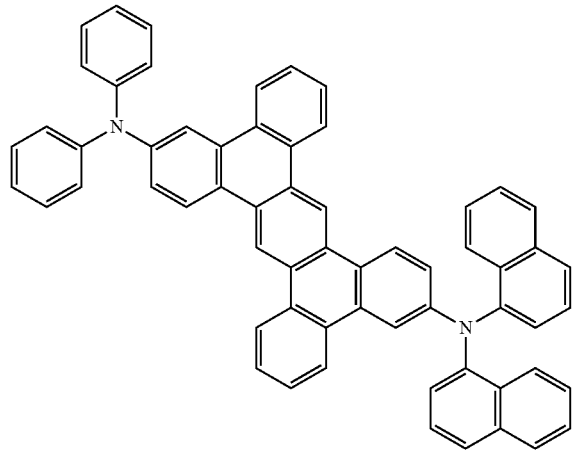
(pt2-5)
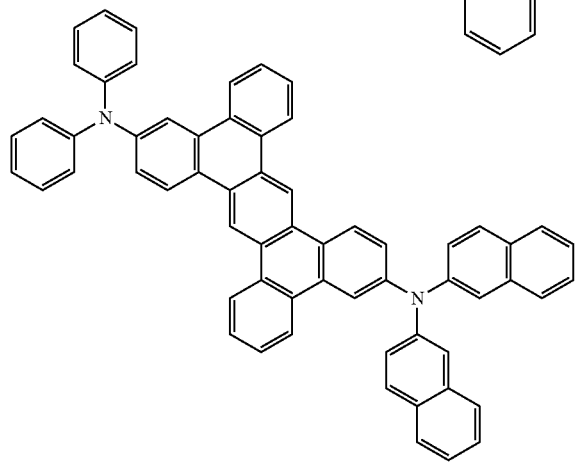
(pt2-6)
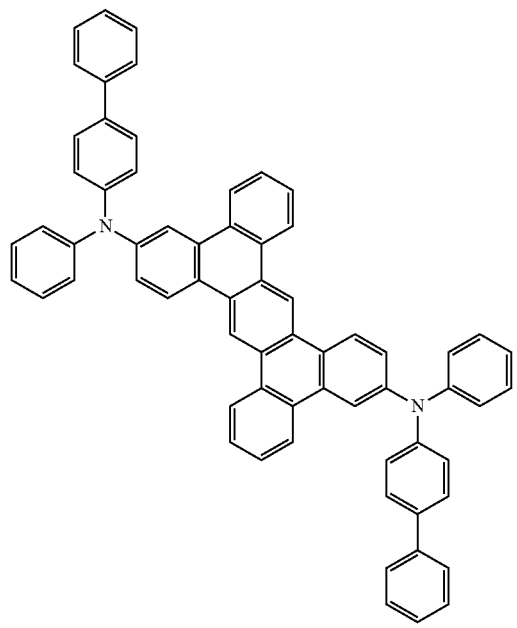
(pt2-7)
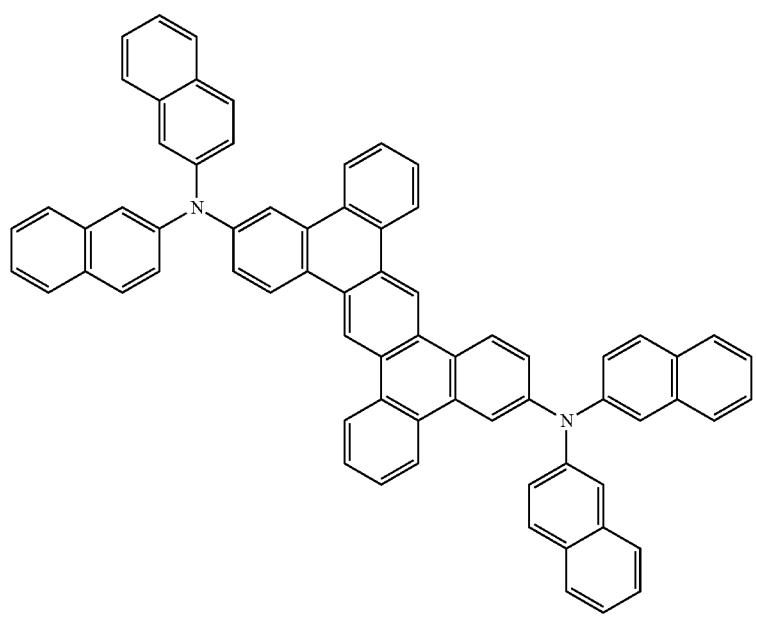

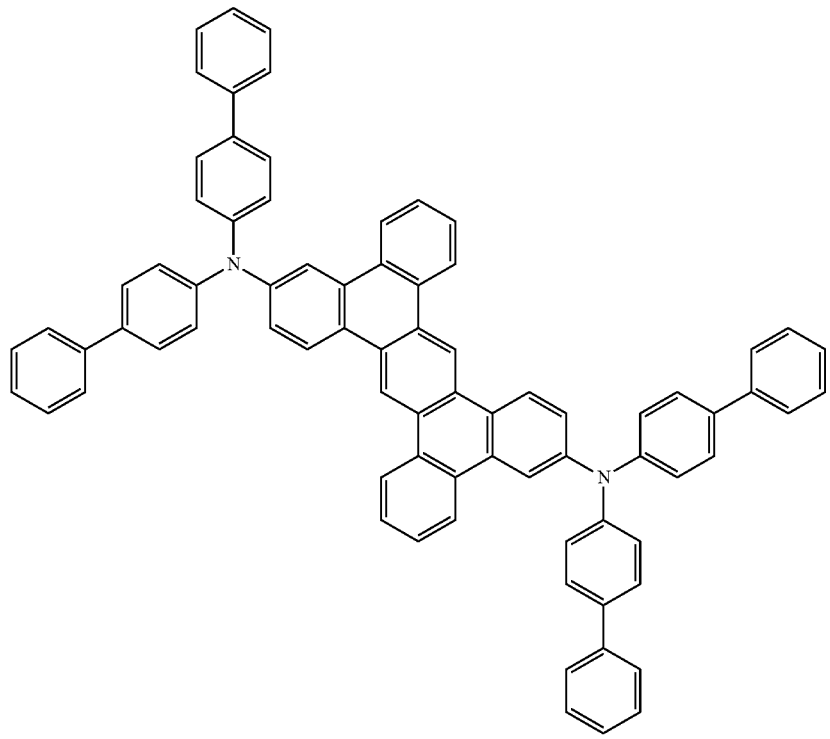

(pt2-8)

Preferred examples of the chrysene derivatives include compounds represented by the following general formula (ch-1).

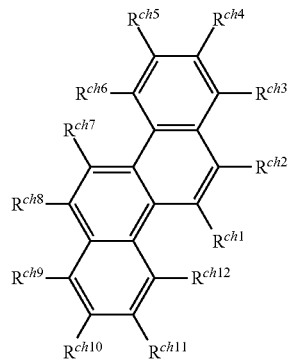

General Formula (ch-1)

[In the general formula (ch-1), $R^{ch1}$ to $R^{ch12}$ represent hydrogen atoms or substituents.]

Examples of the substituents represented by $R^{ch1}$ to $R^{ch12}$ include those given in the substituent group A, and the adjacent substituents may be bound to each other via a single bond or a linking group to form a ring.

From the viewpoints of color purity and durability, it is preferable that at least one of $R^{ch1}$ to $R^{ch12}$ is an aryl group, a heteroaryl group, or an amino group, more preferably an aryl group, or an amino group, further preferably an amino group, particularly preferably a diarylamino group.

Preferably, at least two of $R^{ch1}$ to $R^{ch12}$ are diarylamino groups.

Specific examples of the compounds represented by the general formula (ch-1) are described below. It should be noted that the present invention is not limited to the following.

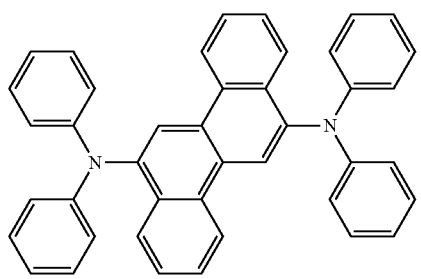
(ch-1)

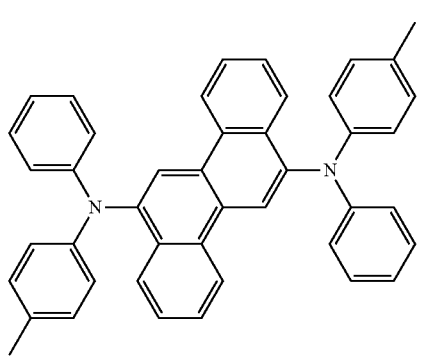
(ch-2)

(ch-3)
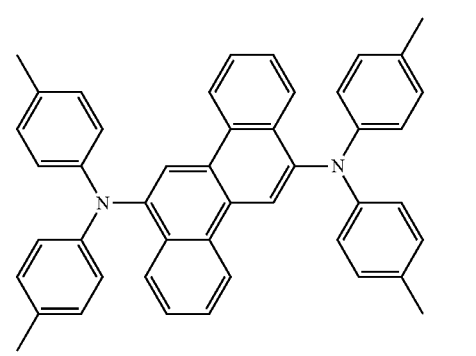
(ch-4)
(ch-5)
(ch-6)
(ch-7)
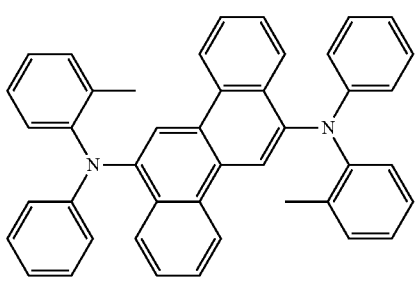
(ch-8)
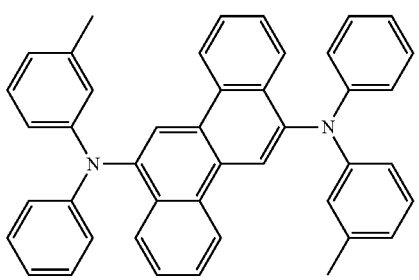
(ch-9)
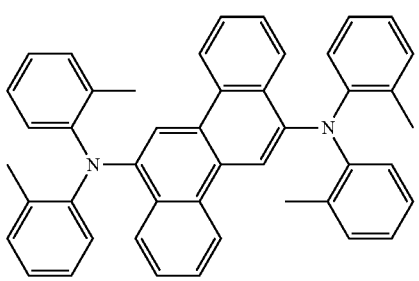
(ch-10)
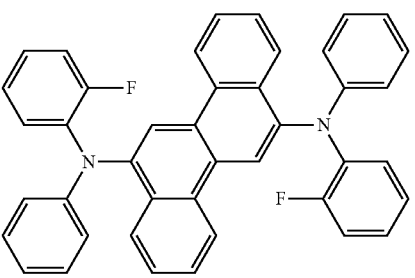
(ch-11)
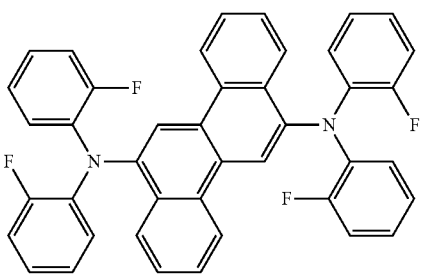

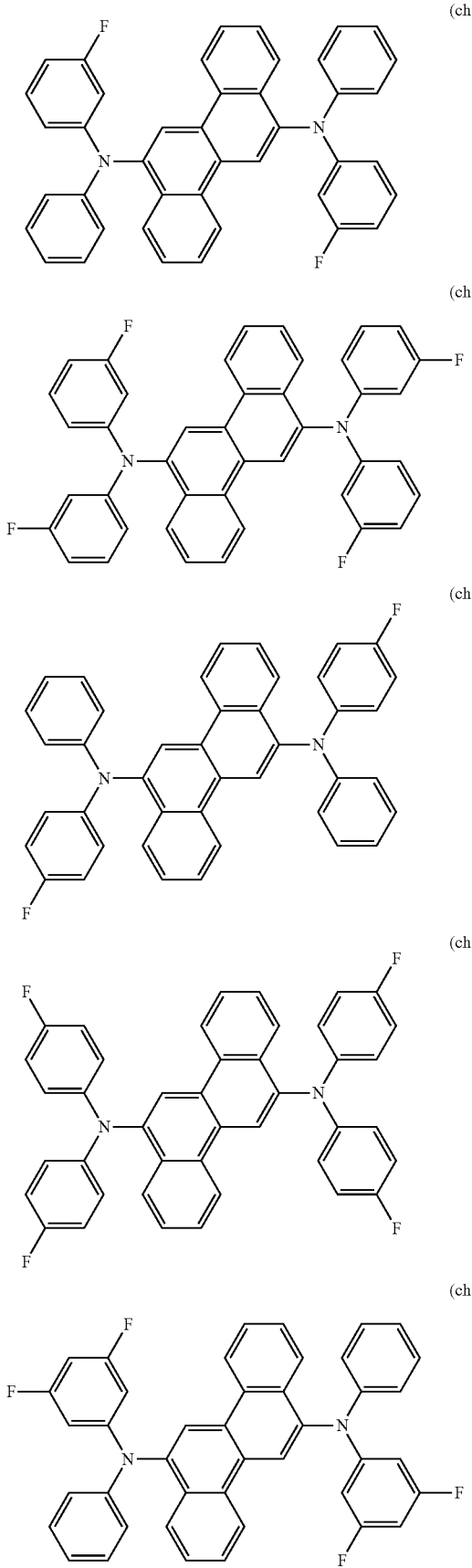
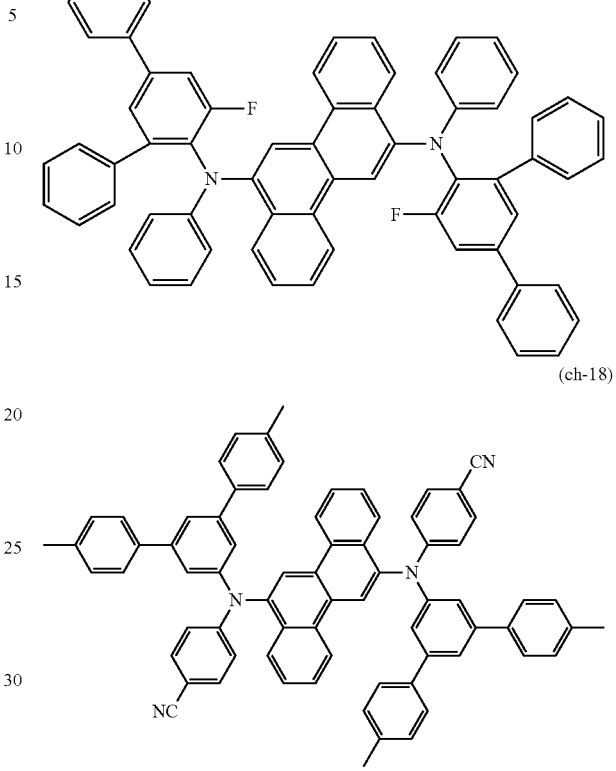

Among the compounds represented by the general formulae (p-1), (PT-1), and (ch-1), as the light emitting material used in the organic electroluminescent element of the present invention, preferably the compounds represented by the general formulae (p-1) and (PT-1), more preferably the compound represented by the general formula (PT-1), are used.

The light emitting layer in the organic electroluminescent element according to the present invention may be constituted of only the light emitting material, or may be constituted as a mixed layer of the host material and the light emitting material. The light emitting material may be made of a single kind or two or more kinds thereof. The host material is preferably a charge transporting material. The host material may be made of a single kind or two or more kinds thereof. Examples thereof include a configuration in which an electron transporting host material and a hole transporting host material are mixed. Furthermore, the light emitting layer may include a material which does not have charge transporting properties and which does not emit light.

In addition, the light emitting layer may be made of a single layer or multiple layers of two or more layers. The respective layers may include the same light emitting material or host material, or may also include a different material in every layer. In the case where plural light emitting layers are present, the respective light emitting layers may emit light in a different luminous color from each other.

(Other Layers)

The organic electroluminescent element according to the present invention may include layers other than the light emitting layer.

Examples of the organic layer other than the light emitting layer which may be included in the organic layer include a hole injecting layer, a hole transporting layer, a blocking layer (e.g., a hole blocking layer, an exciton blocking layer, and the like), and an electron transporting layer. Specifically, examples of the layer configuration include those described below, but it should not be construed that the present invention is limited to these configurations.

Anode/hole transporting layer/light emitting layer/electron transporting layer/cathode Anode/hole transporting layer/light emitting layer/blocking layer/electron transporting layer/cathode Anode/hole transporting layer/light emitting layer/blocking layer/electron transporting layer/electron injecting layer/cathode Anode/hole injecting layer/hole transporting layer/light emitting layer/blocking layer/electron transporting layer/cathode Anode/hole injecting layer/hole transporting layer/light emitting layer/electron transporting layer/electron injecting layer/cathode Anode/hole injecting layer/hole transporting layer/light emitting layer/blocking layer/electron transporting layer/electron injecting layer/cathode Anode/hole injecting layer/hole transporting layer/blocking layer/light emitting layer/blocking layer/electron transporting layer/electron injecting layer/cathode The organic electroluminescent element according to the present invention preferably includes at least one (A) organic layer which is preferably disposed between the anode and the light emitting layer. Examples of (A) the organic layer which is preferably disposed between the anode and the light emitting layer include a hole injecting layer, a hole transporting layer, and an electron blocking layer from the anode side.

The organic electroluminescent element according to the present invention preferably includes at least one (B) organic layer which is preferably disposed between the cathode and the light emitting layer. Examples of (B) the organic layer which is preferably disposed between the cathode and the light emitting layer include an electron injecting layer, an electron transporting layer, and a hole blocking layer from the cathode side.

Specifically, an example of the preferred embodiments of the organic electroluminescent element according to the present invention is the embodiment shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

These layers other than the light emitting layer which the organic electroluminescent element according to the present invention may have are hereunder described.

(A) Organic Layer Preferably Disposed Between Anode and Light Emitting Layer

First, (A) the organic layer preferably disposed between the anode and the light emitting layer is described.

(A-1) Hole Injecting Layer and Hole Transporting Layer

Each of the hole injecting layer and the hole transporting layer is a layer having a function of receiving holes from the anode or the anode side to transport them into the cathode side.

The light-emitting element of the present invention preferably includes at least one organic layer between the light emitting layer and the anode, and the organic layer preferably contains at least one compound selected from the compounds represented by the following general formulae (Sa-1), (Sb-1), and (Sc-1).

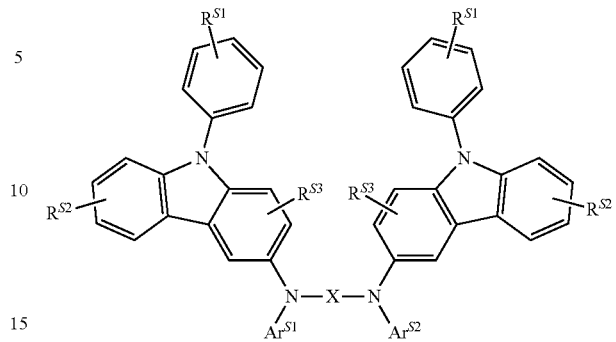

General Formula (Sa-1)

(In the formula, X represents a substituted or unsubstituted alkylene group of 1 to 30 carbon atoms, a substituted or unsubstituted alkenylene group of 2 to 30 carbon atoms, a substituted or unsubstituted arylene group of 6 to 30 carbon atoms, a substituted or unsubstituted heteroarylene group of 2 to 30 carbon atoms, a substituted or unsubstituted heterocyclic group of 2 to 30 carbon atoms, or a group as a combination of these groups. $R^{S1}$, $R^{S2}$ and $R^{S3}$ each independently represent a hydrogen atom, a substituted or unsubstituted alkyl group of 1 to 30 carbon atoms, a substituted or unsubstituted alkoxy group of 1 to 30 carbon atoms, a substituted or unsubstituted aryl group of 6 to 30 carbon atoms, a substituted or unsubstituted aryloxy group of 6 to 30 carbon atoms, a substituted or unsubstituted heterocyclic ring of 2 to 30 carbon atoms, a substituted or unsubstituted fused polycyclic group of 5 to 30 carbon atoms, a hydroxyl group, a cyano group, or a substituted or unsubstituted amino group. The adjacent $R^{S1}$, $R^{S2}$ and $R^{S3}$ may be bound to each other to form a saturated carbon ring or an unsaturated carbon ring. $Ar^{S1}$ and $Ar^{S2}$ each independently represent a substituted or unsubstituted aryl group of 6 to 30 carbon atoms, or a substituted or unsubstituted heteroaryl group of 2 to 30 carbon atoms.)

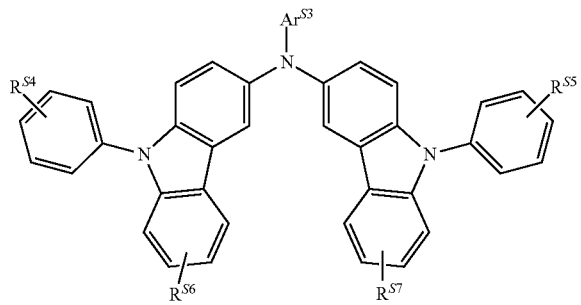

General Formula (Sb-1)

(In the formula, $R^{S4}$, $R^{S5}$, $R^{S6}$, and $R^{S7}$ each independently represent a hydrogen atom, a substituted or unsubstituted alkyl group of 1 to 30 carbon atoms, a substituted or unsubstituted alkoxy group of 1 to 30 carbon atoms, a substituted or unsubstituted aryl group of 6 to 30 carbon atoms, a substituted or unsubstituted aryloxy group of 6 to 30 carbon atoms, a substituted or unsubstituted heterocyclic ring of 2 to 30 carbon atoms, a substituted or unsubstituted fused polycyclic group of 5 to 30 carbon atoms, a hydroxyl group, a cyano group, or a substituted or unsubstituted amino group. The adjacent $R^{S4}$, $R^{S5}$, $R^{S6}$, and $R^{S7}$ may be bound to each other to form a saturated carbon ring or an unsaturated carbon ring.

Ar$^{S3}$ represents a substituted or unsubstituted aryl group of 6 to 30 carbon atoms, or a substituted or unsubstituted heteroaryl group of 2 to 30 carbon atoms.)

General Formula (Sc-1)

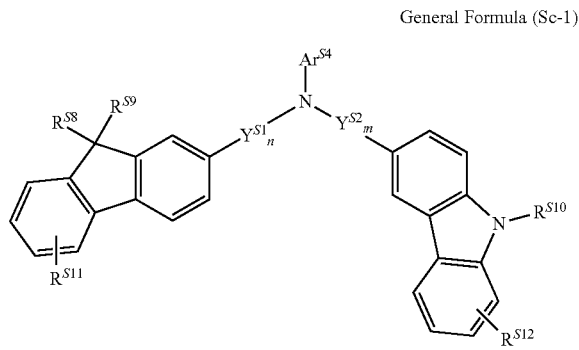

(In the formula, R$^{S8}$ and R$^{S9}$ each independently represent a hydrogen atom, a substituted or unsubstituted alkyl group of 1 to 30 carbon atoms, a substituted or unsubstituted aryl group of 6 to 30 carbon atoms, a substituted or unsubstituted heterocyclic group of 2 to 30 carbon atoms, or a substituted or unsubstituted fused polycyclic group of 5 to 30 carbon atoms. R$^{S10}$ represents a substituted or unsubstituted alkyl group of 1 to 30 carbon atoms, a substituted or unsubstituted aryl group of 6 to 30 carbon atoms, a substituted or unsubstituted heterocyclic group of 2 to 30 carbon atoms, or a substituted or unsubstituted fused polycyclic group of 5 to 30 carbon atoms. R$^{S11}$ and R$^{S12}$ each independently represent a hydrogen atom, a substituted or unsubstituted alkyl group of 1 to 30 carbon atoms, a substituted or unsubstituted alkoxy group of 1 to 30 carbon atoms, a substituted or unsubstituted aryl group of 6 to 30 carbon atoms, a substituted or unsubstituted aryloxy group of 6 to 30 carbon atoms, a substituted or unsubstituted heterocyclic ring of 2 to 30 carbon atoms, a substituted or unsubstituted fused polycyclic group of 5 to 30 carbon atoms, a hydroxyl group, a cyano group, or a substituted or unsubstituted amino group. The adjacent R$^{S11}$ and R$^{S12}$ may be bound to each other to form a saturated carbon ring or an unsaturated carbon ring. Ar$^{S4}$ represents a substituted or unsubstituted aryl group of 6 to 30 carbon atoms, or a substituted or unsubstituted heteroaryl group of 2 to 30 carbon atoms. Y$^{S1}$ and Y$^{S2}$ each independently represent a substituted or unsubstituted alkylene group of 1 to 30 carbon atoms, or a substituted or unsubstituted arylene group of 6 to 30 carbon atoms. n and m each independently represent an integer of 0 to 5.)

The general formula (Sa-1) is described below.

In the general formula (Sa-1), X represents a substituted or unsubstituted alkylene group of 1 to 30 carbon atoms, a substituted or unsubstituted alkenylene group of 2 to 30 carbon atoms, a substituted or unsubstituted arylene group of 6 to 30 carbon atoms, a substituted or unsubstituted heteroarylene group of 2 to 30 carbon atoms, a substituted or unsubstituted heterocyclic group of 2 to 30 carbon atoms, or a group as a combination of these groups. X is preferably a substituted or unsubstituted arylene group of 6 to 30 carbon atoms, more preferably substituted or unsubstituted phenylene, substituted or unsubstituted biphenylene, or substituted or unsubstituted naphthylene, further preferably substituted or unsubstituted biphenylene.

R$^{S1}$, R$^{S2}$, and R$^{S3}$ each independently represent a hydrogen atom, a substituted or unsubstituted alkyl group of 1 to 30 carbon atoms, a substituted or unsubstituted alkoxy group of 1 to 30 carbon atoms, a substituted or unsubstituted aryl group of 6 to 30 carbon atoms, a substituted or unsubstituted aryloxy group of 6 to 30 carbon atoms, a substituted or unsubstituted heterocyclic ring of 2 to 30 carbon atoms, a substituted or unsubstituted fused polycyclic group of 5 to 30 carbon atoms, a hydroxyl group, a cyano group, or a substituted or unsubstituted amino group. The adjacent R$^{S1}$, R$^{S2}$, and R$^{S3}$ may be bound to each other to form a saturated carbon ring or an unsaturated carbon ring. Examples of the saturated carbon ring and the unsaturated carbon ring include naphthalene, azulene, anthracene, fluorene, and phenalene. R$^{S1}$, R$^{S2}$ and R$^{S3}$ are preferably hydrogen atoms, substituted or unsubstituted alkyl groups of 1 to 30 carbon atoms, substituted or unsubstituted aryl groups of 6 to 30 carbon atoms, substituted or unsubstituted fused polycyclic groups of 5 to 30 carbon atoms, or cyano groups, more preferably hydrogen atoms.

Ar$^{S1}$ and Ar$^{S2}$ each independently represent a substituted or unsubstituted aryl group of 6 to 30 carbon atoms, or a substituted or unsubstituted heteroaryl group of 2 to 30 carbon atoms. Ar$^{S1}$ and Ar$^{S2}$ are preferably substituted or unsubstituted phenyl groups.

The general formula (Sb-1) is described below.

In the general formula (Sb-1), R$^{S4}$, R$^{S5}$, R$^{S6}$, and R$^{S7}$ each independently represent a hydrogen atom, a substituted or unsubstituted alkyl group of 1 to 30 carbon atoms, a substituted or unsubstituted alkoxy group of 1 to 30 carbon atoms, a substituted or unsubstituted aryl group of 6 to 30 carbon atoms, a substituted or unsubstituted aryloxy group of 6 to 30 carbon atoms, a substituted or unsubstituted heterocyclic ring of 2 to 30 carbon atoms, a substituted or unsubstituted fused polycyclic group of 5 to 30 carbon atoms, a hydroxyl group, a cyano group, or a substituted or unsubstituted amino group. The adjacent R$^{S4}$, R$^{S5}$, R$^{S6}$, and R$^{S7}$ may be bound to each other to form a saturated carbon ring or an unsaturated carbon ring. Examples of the saturated carbon ring and the unsaturated carbon ring include naphthalene, azulene, anthracene, fluorene, and phenalene. R$^{S4}$, R$^{S5}$, R$^{S6}$, and R$^{S7}$ are preferably hydrogen atoms, substituted or unsubstituted alkyl groups of 1 to 30 carbon atoms, substituted or unsubstituted aryl groups of 6 to 30 carbon atoms, substituted or unsubstituted fused polycyclic groups of 5 to 30 carbon atoms, and cyano groups, more preferably hydrogen atoms.

Ar$^{S3}$ represents a substituted or unsubstituted aryl group of 6 to 30 carbon atoms, or a substituted or unsubstituted heteroaryl group of 2 to 30 carbon atoms. Ar$^{S3}$ is preferably a substituted or unsubstituted phenyl group.

The general formula (Sc-1) is described below.

In the general formula (Sc-1), R$^{S8}$ and R$^{S9}$ each independently represent a hydrogen atom, a substituted or unsubstituted alkyl group of 1 to 30 carbon atoms, a substituted or unsubstituted aryl group of 6 to 30 carbon atoms, a substituted or unsubstituted heterocyclic group of 2 to 30 carbon atoms, or a substituted or unsubstituted fused polycyclic group of 5 to 30 carbon atoms. R$^{S8}$ and R$^{S9}$ are preferably substituted or unsubstituted alkyl groups of 1 to 30 carbon atoms, or substituted or unsubstituted aryl groups of 6 to 30 carbon atoms, more preferably methyl groups or phenyl groups. R$^{S10}$ represents a substituted or unsubstituted alkyl group of 1 to 30 carbon atoms, a substituted or unsubstituted aryl group of 6 to 30 carbon atoms, a substituted or unsubstituted heterocyclic group of 2 to 30 carbon atoms, or a substituted or unsubstituted fused polycyclic group of 5 to 30 carbon atoms. R$^{S10}$ is preferably a substituted or unsubstituted aryl group of 6 to 30 carbon atoms, more preferably a phenyl group. R$^{S11}$ and R$^{S12}$ each independently represent a hydrogen atom, a substituted or unsubstituted alkyl group of 1 to 30 carbon atoms, a substituted or unsubstituted alkoxy group of 1 to 30 carbon atoms, a substituted or unsubstituted aryl group of 6 to 30 carbon atoms, a substituted or unsubstituted aryloxy group of 6 to 30 carbon atoms, a substituted or unsubstituted heterocyclic ring of 2 to 30 carbon atoms, a substituted or unsubstituted fused polycyclic group of 5 to 30 carbon atoms, a hydroxyl group, a cyano group, or a substituted or unsubstituted amino group. The adjacent R$^{S11}$ and R$^{S12}$ may be bound to each other to form a saturated carbon ring or an unsaturated carbon ring. Examples of the saturated carbon ring and the unsaturated carbon ring include naphthalene, azulene, anthracene, fluorene, and phenalene. $R^{S11}$ and $R^{S12}$ are preferably hydrogen atoms, substituted or unsubstituted alkyl groups of 1 to 30 carbon atoms, substituted or unsubstituted aryl groups of 6 to 30 carbon atoms, substituted or unsubstituted fused polycyclic groups of 5 to 30 carbon atoms, or cyano groups, more preferably hydrogen atoms. $Ar^{S4}$ represents a substituted or unsubstituted aryl group of 6 to 30 carbon atoms, or a substituted or unsubstituted heteroaryl group of 2 to 30 carbon atoms. $Y^{S1}$ and $Y^{S2}$ represent substituted or unsubstituted alkylene of 1 to 30 carbon atoms, or substituted or unsubstituted arylene of 6 to 30 carbon atoms. $Y^{S1}$ and $Y^{S2}$ are preferably substituted or unsubstituted arylene of 6 to 30 carbon atoms, more preferably substituted or unsubstituted phenylene. n is an integer of 0 to 5, preferably 0 to 3, more preferably 0 to 2, further preferably 0. m is an integer of 0 to 5, preferably 0 to 3, more preferably 0 to 2, further preferably 1.

Preferably, the general formula (Sa-1) represents the compound represented by the following general formula (Sa-2).

The general formula (Sa-2) is described below. $R^{S1}$, $R^{S2}$, and $R^{S3}$ have the same definitions as their counterparts in the general formula (Sa-1), and the preferred ranges are the same. $Q^{Sa}$ each independently represent a hydrogen atom, a cyano group, a fluorine atom, an alkoxy group of 1 to 30 carbon atoms, a substituted or unsubstituted alkyl group of 1 to 30 carbon atoms, an aryloxy group of 6 to 30 carbon atoms, a substituted or unsubstituted aryl group of 6 to 30 carbon atoms, a substituted or unsubstituted heterocyclic ring of 2 to 30 carbon atoms, or a substituted or unsubstituted amino group. $Q^{Sa}$ is preferably a hydrogen atom, a cyano group, a fluorine atom, a substituted or unsubstituted alkyl group of 1 to 30 carbon atoms, or a substituted or unsubstituted aryl group of 6 to 30 carbon atoms, more preferably a hydrogen atom, or a substituted or unsubstituted alkyl group of 1 to 30 carbon atoms, further preferably a hydrogen atom.

Preferably, the general formula (Sb-1) represents the compound represented by the following general formula (Sb-2).

General Formula (Sa-2)

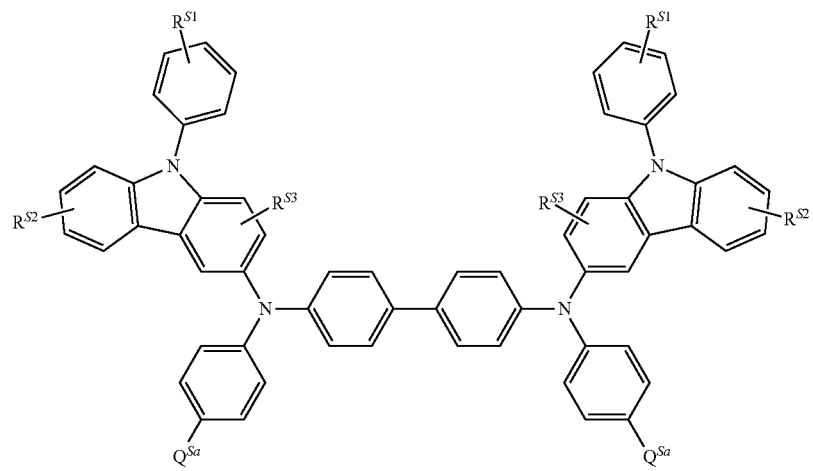

(In the formula, $R^{S1}$, $R^{S2}$, and $R^{S3}$ each independently represent a hydrogen atom, a substituted or unsubstituted alkyl group of 1 to 30 carbon atoms, a substituted or unsubstituted alkoxy group of 1 to 30 carbon atoms, a substituted or unsubstituted aryl group of 6 to 30 carbon atoms, a substituted or unsubstituted aryloxy group of 6 to 30 carbon atoms, a substituted or unsubstituted heterocyclic ring of 2 to 30 carbon atoms, a substituted or unsubstituted fused polycyclic group of 5 to 30 carbon atoms, a hydroxyl group, a cyano group, or a substituted or unsubstituted amino group. The adjacent $R^{S1}$, $R^{S2}$ and $R^{S3}$ may be bound to each other to form a saturated carbon ring or an unsaturated carbon ring. $Q^{Sa}$ each independently represent a hydrogen atom, a cyano group, a fluorine atom, an alkoxy group of 1 to 30 carbon atoms, a substituted or unsubstituted alkyl group of 1 to 30 carbon atoms, an aryloxy group of 6 to 30 carbon atoms, a substituted or unsubstituted aryl group of 6 to 30 carbon atoms, a substituted or unsubstituted heterocyclic ring of 2 to 30 carbon atoms, or a substituted or unsubstituted amino group.)

General Formula (Sb-2)

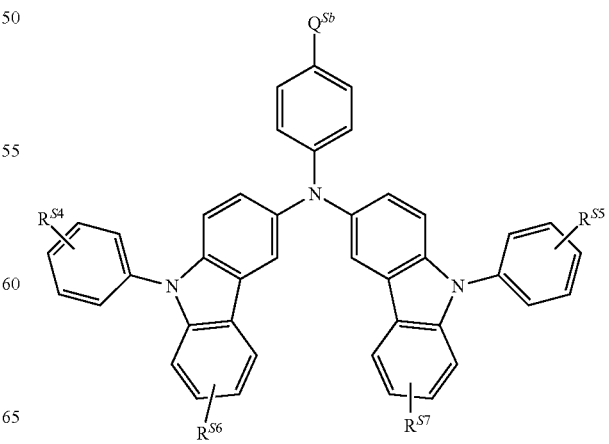

(In the formula, $R^{S4}$, $R^{S5}$, $R^{S6}$, and $R^{S7}$ each independently represent a hydrogen atom, a substituted or unsubstituted alkyl group of 1 to 30 carbon atoms, a substituted or unsubstituted alkoxy group of 1 to 30 carbon atoms, a substituted or unsubstituted aryl group of 6 to 30 carbon atoms, a substituted or unsubstituted aryloxy group of 6 to 30 carbon atoms, a substituted or unsubstituted heterocyclic ring of 2 to 30 carbon atoms, a substituted or unsubstituted fused polycyclic group of 5 to 30 carbon atoms, a hydroxyl group, a cyano group, or a substituted or unsubstituted amino group. The adjacent $R^{S4}$, $R^{S5}$, $R^{S6}$, and $R^{S7}$ may be bound to each other to form a saturated carbon ring or an unsaturated carbon ring. $Q^{Sb}$ represents a hydrogen atom, a cyano group, a fluorine atom, an alkoxy group of 1 to 30 carbon atoms, a substituted or unsubstituted alkyl group of 1 to 30 carbon atoms, an aryloxy group of 6 to 30 carbon atoms, a substituted or unsubstituted aryl group of 6 to 30 carbon atoms, a substituted or unsubstituted heterocyclic ring of 2 to 30 carbon atoms, or a substituted or unsubstituted amino group.)

The general formula (Sb-2) is described below. $R^{S4}$, $R^{S5}$, $R^{S6}$, and $R^{S7}$ have the same definitions as their counterparts in the general formula (Sb-1), and the preferred ranges are the same. $Q^{Sa}$ represents a hydrogen atom, a cyano group, a fluorine atom, an alkoxy group of 1 to 30 carbon atoms, a substituted or unsubstituted alkyl group of 1 to 30 carbon atoms, an aryloxy group of 6 to 30 carbon atoms, a substituted or unsubstituted aryl group of 6 to 30 carbon atoms, a substituted or unsubstituted heterocyclic ring of 2 to 30 carbon atoms, or a substituted or unsubstituted amino group. $Q^{Sa}$ is preferably a hydrogen atom, a cyano group, a fluorine atom, a substituted or unsubstituted alkyl group of 1 to 30 carbon atoms, or a substituted or unsubstituted aryl group of 6 to 30 carbon atoms, more preferably a hydrogen atom, or a substituted or unsubstituted alkyl group of 1 to 30 carbon atoms, further preferably a hydrogen atom.

Preferably, the general formula (Sc-1) represents the compound represented by the following general formula (Sc-2).

General Formula (Sc-2)

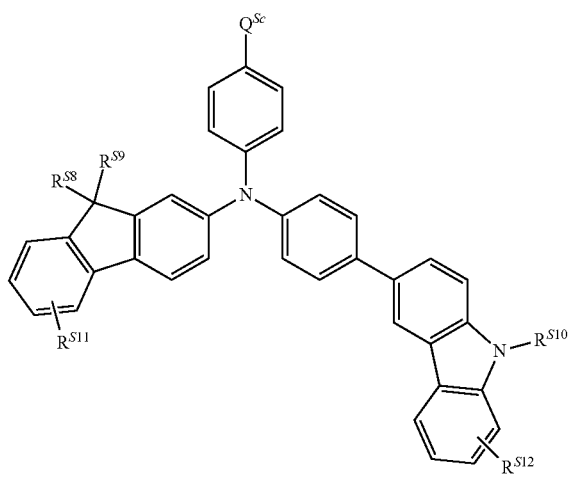

(In the formula, $R^{S8}$ and $R^{S9}$ each independently represent a hydrogen atom, a substituted or unsubstituted alkyl group of 1 to 30 carbon atoms, a substituted or unsubstituted aryl group of 6 to 30 carbon atoms, a substituted or unsubstituted heterocyclic group of 2 to 30 carbon atoms, or a substituted or unsubstituted fused polycyclic group of 5 to 30 carbon atoms. $R^{S10}$ represents a substituted or unsubstituted alkyl group of 1 to 30 carbon atoms, a substituted or unsubstituted aryl group of 6 to 30 carbon atoms, a substituted or unsubstituted heterocyclic group of 2 to 30 carbon atoms, or a substituted or unsubstituted fused polycyclic group of 5 to 30 carbon atoms. $R^{S11}$ and $R^{S12}$ each independently represent a hydrogen atom, a substituted or unsubstituted alkyl group of 1 to 30 carbon atoms, a substituted or unsubstituted alkoxy group of 1 to 30 carbon atoms, a substituted or unsubstituted aryl group of 6 to 30 carbon atoms, a substituted or unsubstituted aryloxy group of 6 to 30 carbon atoms, a substituted or unsubstituted heterocyclic ring of 2 to 30 carbon atoms, a substituted or unsubstituted fused polycyclic group of 5 to 30 carbon atoms, a hydroxyl group, a cyano group, or a substituted or unsubstituted amino group. The adjacent $R^{S11}$ and $R^{S12}$ may be bound to each other to form a saturated carbon ring or an unsaturated carbon ring. $Q^{Sc}$ represents a hydrogen atom, a cyano group, a fluorine atom, an alkoxy group of 1 to 30 carbon atoms, a substituted or unsubstituted alkyl group of 1 to 30 carbon atoms, an aryloxy group of 6 to 30 carbon atoms, a substituted or unsubstituted aryl group of 6 to 30 carbon atoms, a substituted or unsubstituted heterocyclic ring of 2 to 30 carbon atoms, or a substituted or unsubstituted amino group.)

The general formula (Sc-2) is described below. $R^{S8}$, $R^{S9}$, $R^{S10}$, $R^{S11}$, and $R^{S12}$ have the same definitions as their counterparts in the general formula (Sc-1), and the preferred ranges are the same. $Q^{Sc}$ represents a hydrogen atom, a cyano group, a fluorine atom, an alkoxy group of 1 to 30 carbon atoms, a substituted or unsubstituted alkyl group of 1 to 30 carbon atoms, an aryloxy group of 6 to 30 carbon atoms, a substituted or unsubstituted aryl group of 6 to 30 carbon atoms, a substituted or unsubstituted heterocyclic ring of 2 to 30 carbon atoms, or a substituted or unsubstituted amino group. $Q^{Sc}$ is preferably a hydrogen atom, a cyano group, a fluorine atom, a substituted or unsubstituted alkyl group of 1 to 30 carbon atoms, or a substituted or unsubstituted aryl group of 6 to 30 carbon atoms, more preferably a hydrogen atom, a substituted or unsubstituted aryl group of 6 to 30 carbon atoms, further preferably a phenyl group.

Specific examples of the compounds represented by the general formulae (Sa-1), (Sb-1), and (Sc-1) include those given below. It should be noted that the present invention is not limited to the following specific examples.

79 80
1
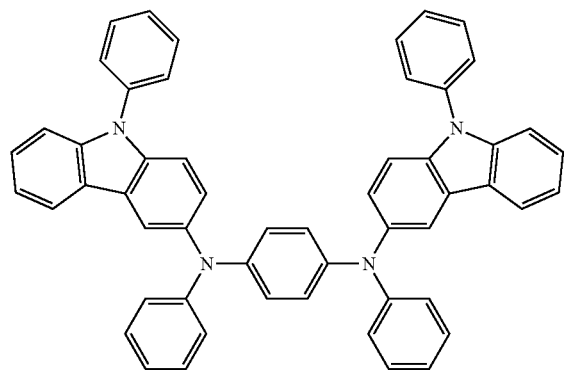
2
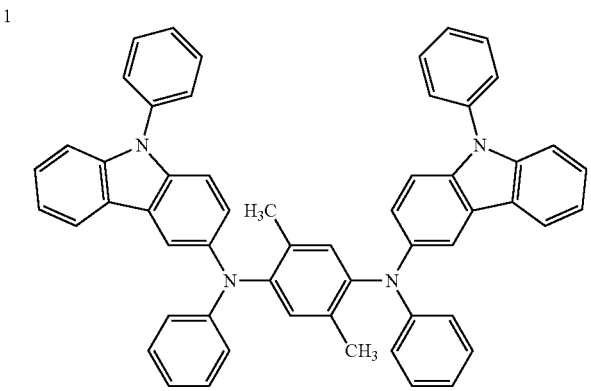
3
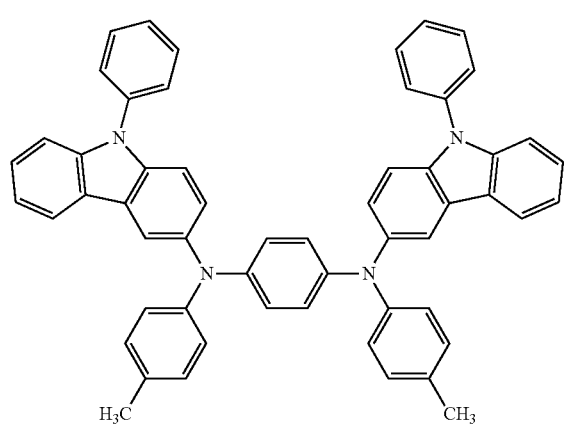
4
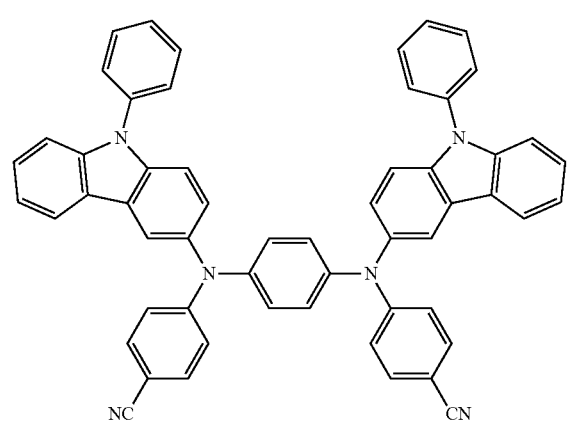
5
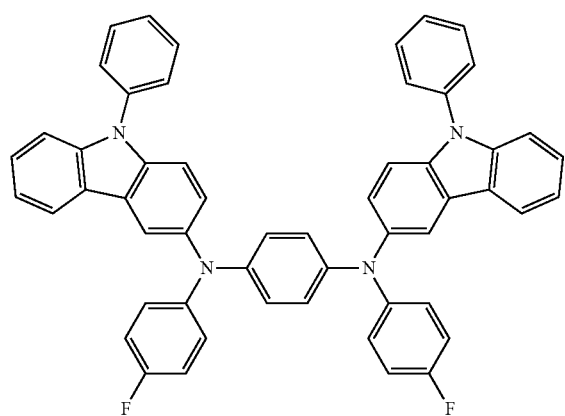
6
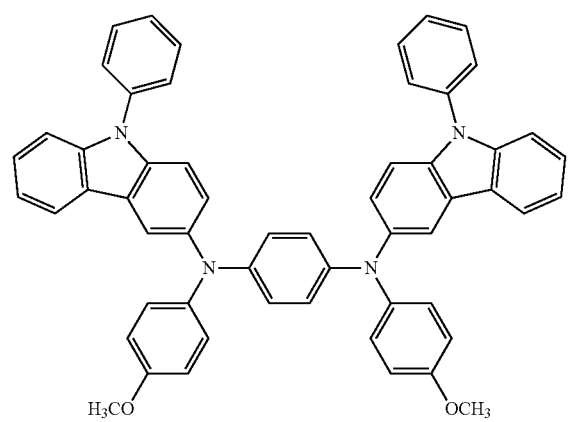
7
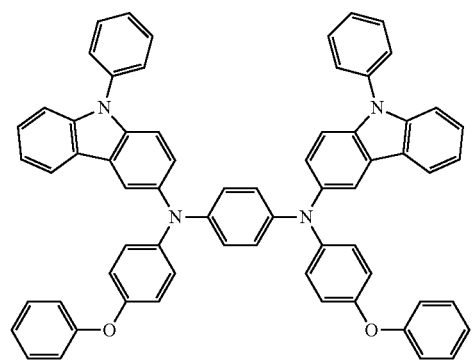
8
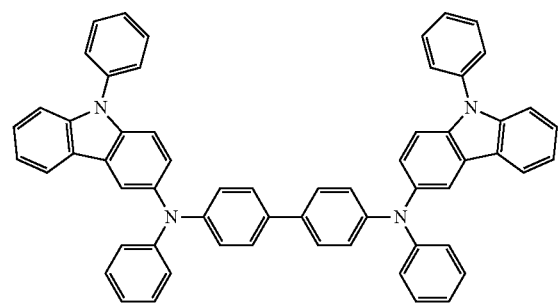

-continued
9
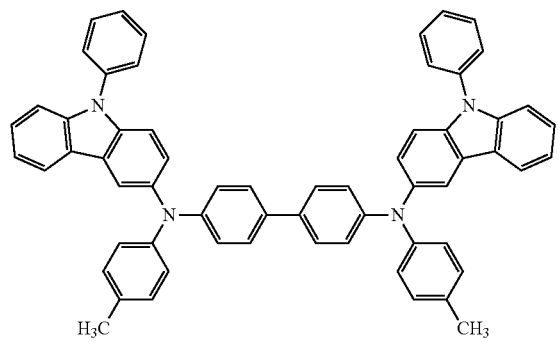
10
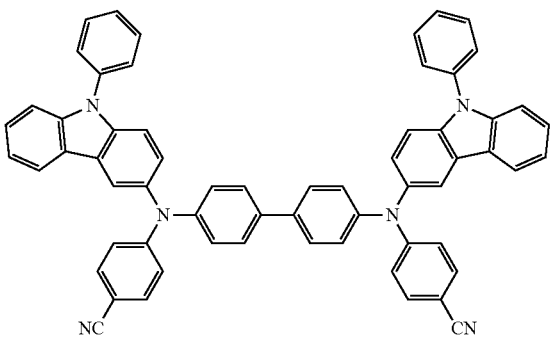
11
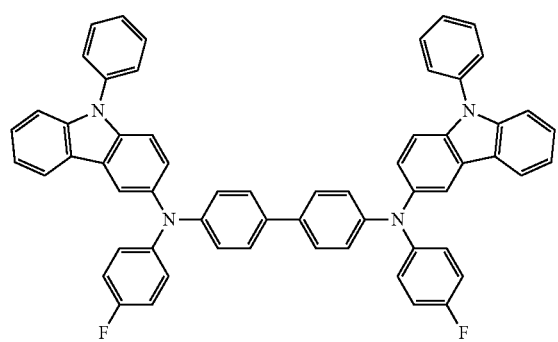
12
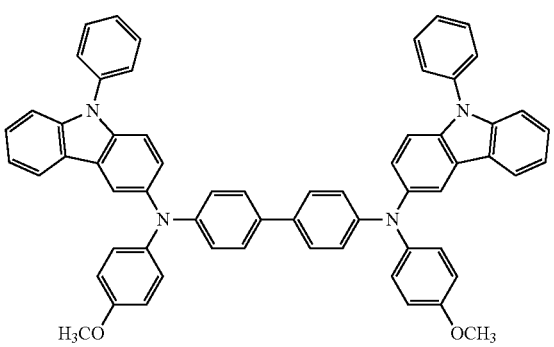
13
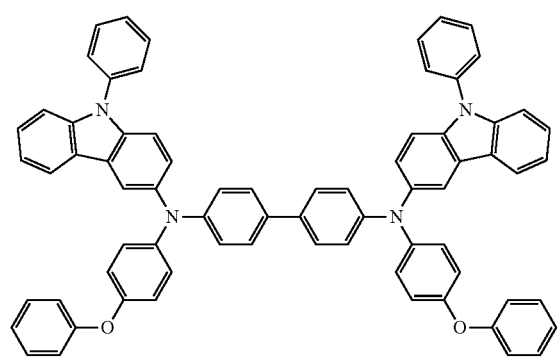
14
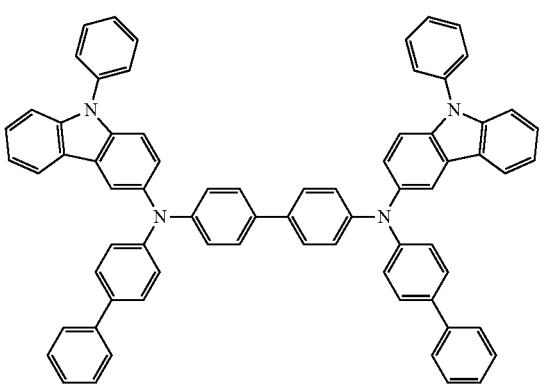
15
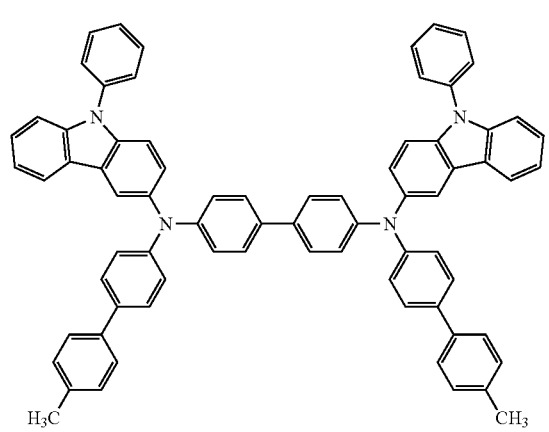
16
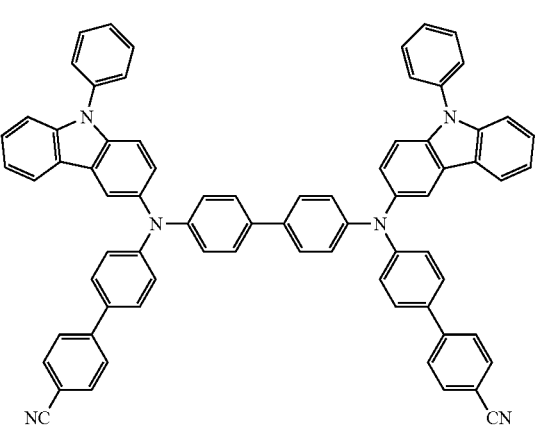

-continued
17
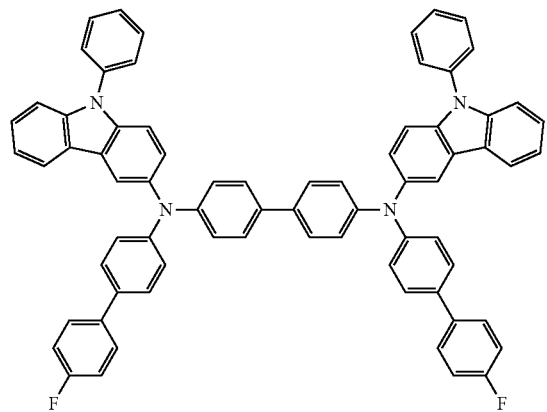
18
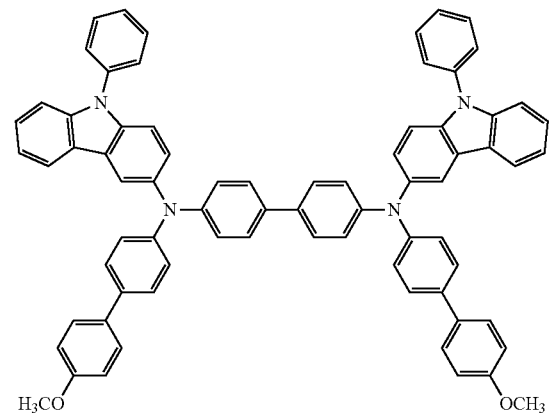
19
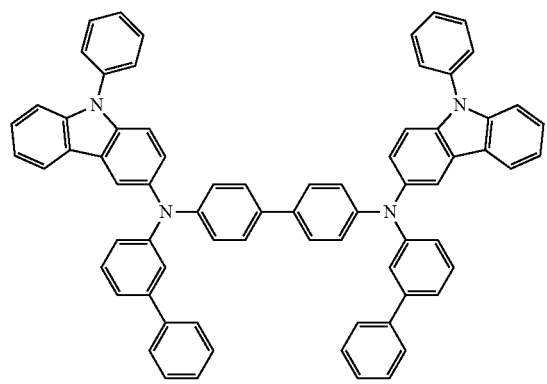
20
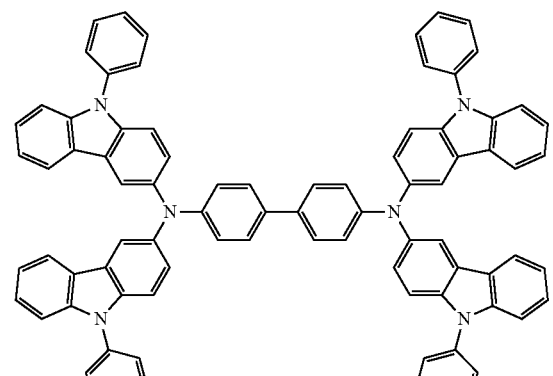
21
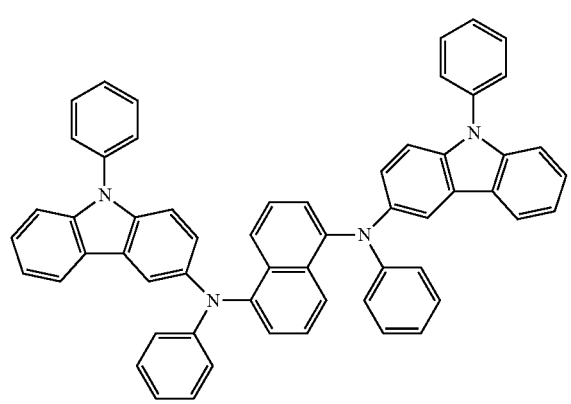
22
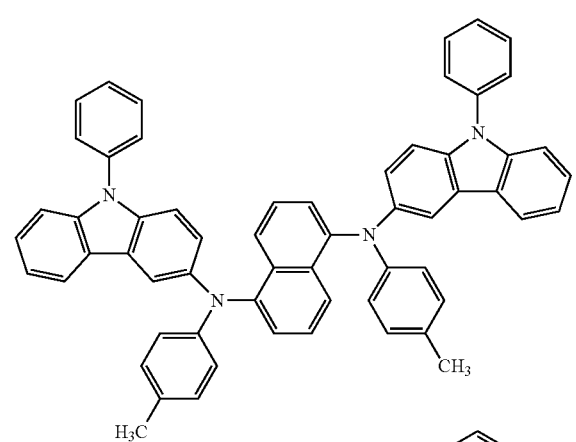
23
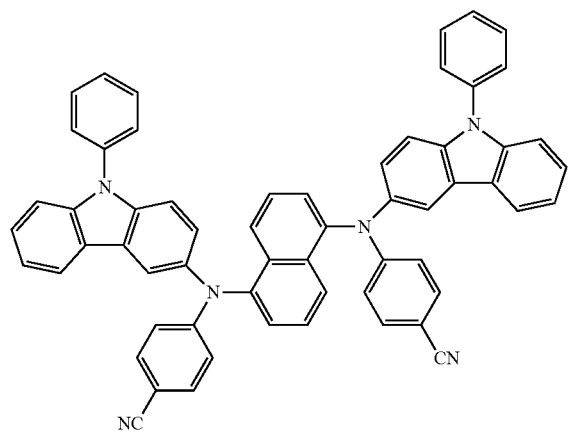
24
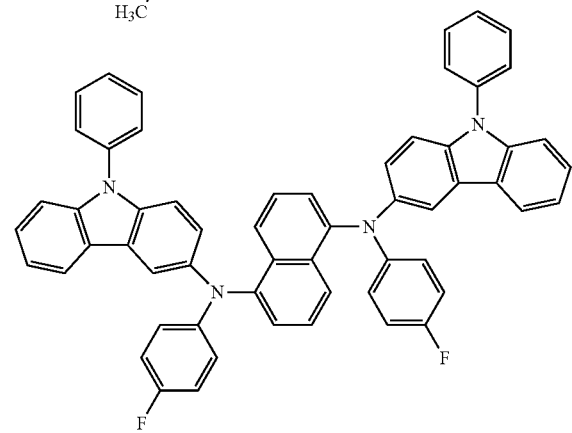

-continued
25
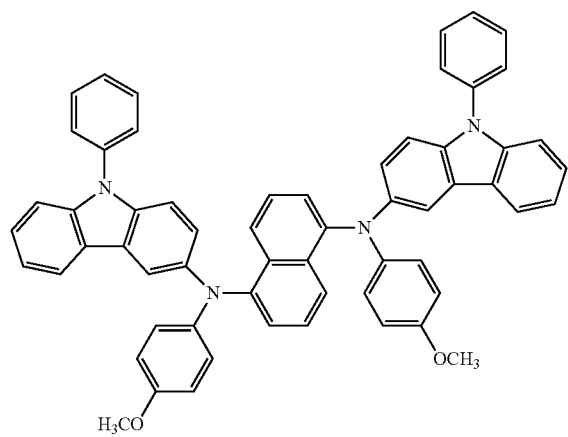
26
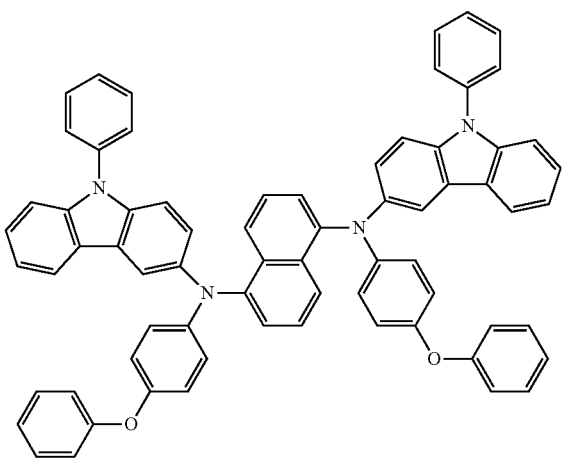
27
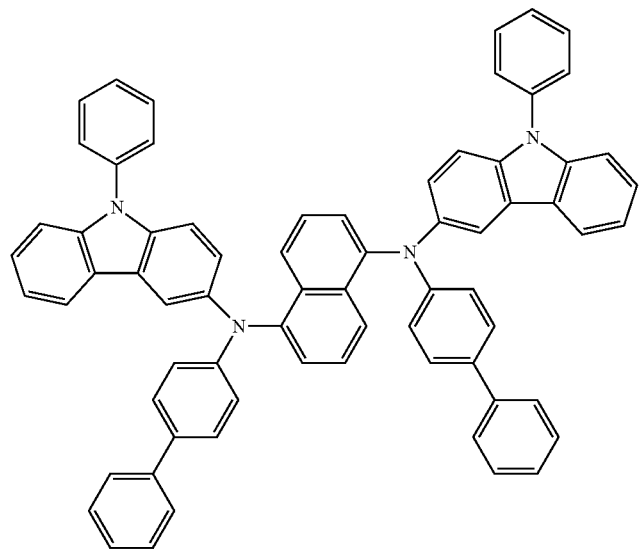
28
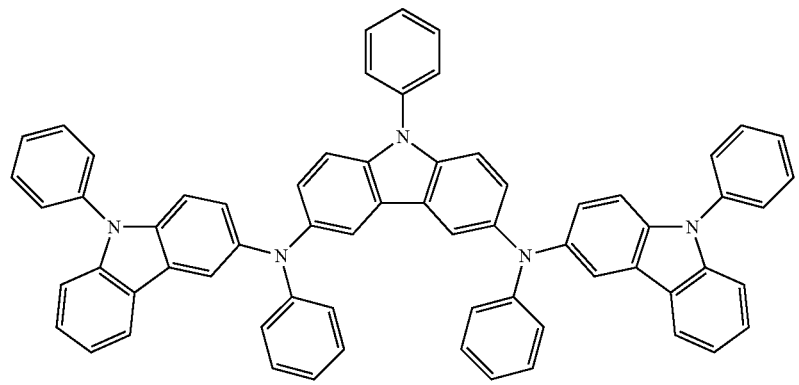

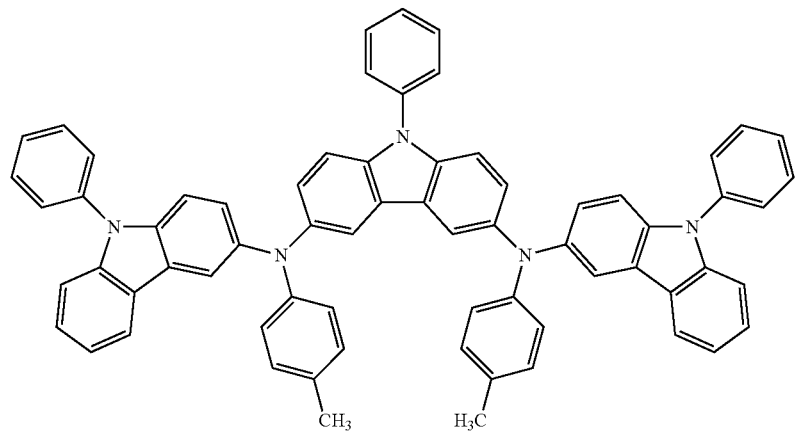
29
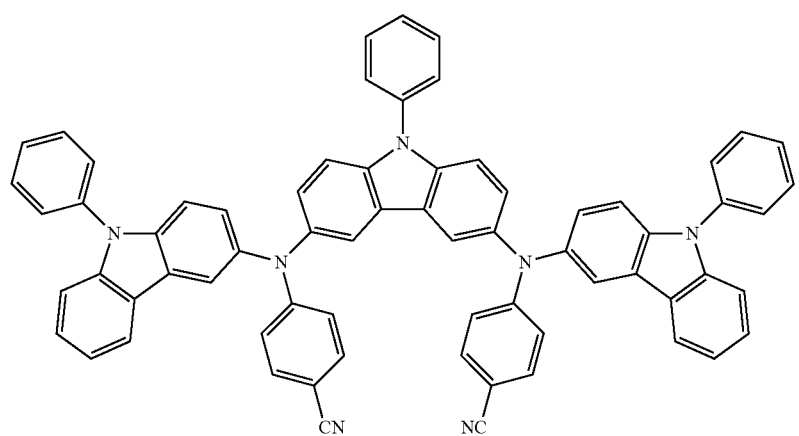
30
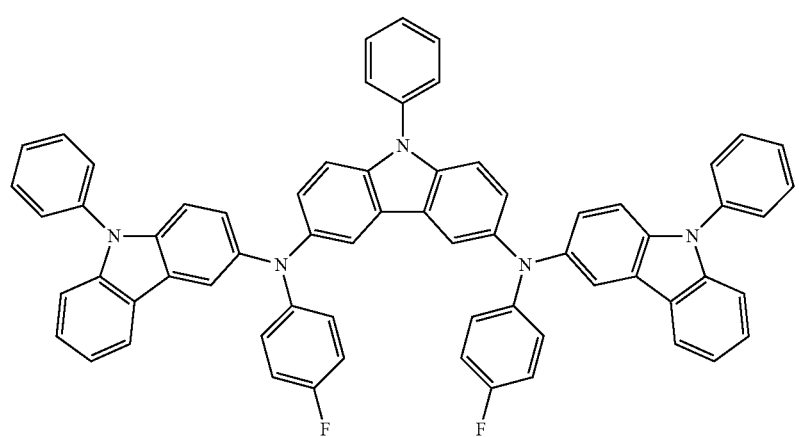
31

32
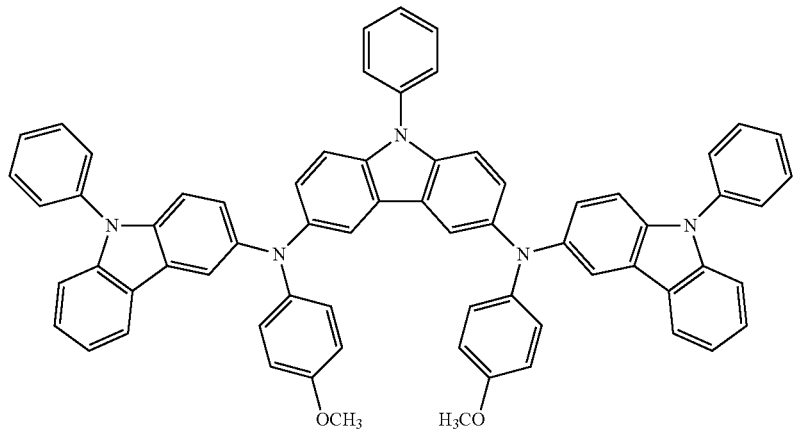
33
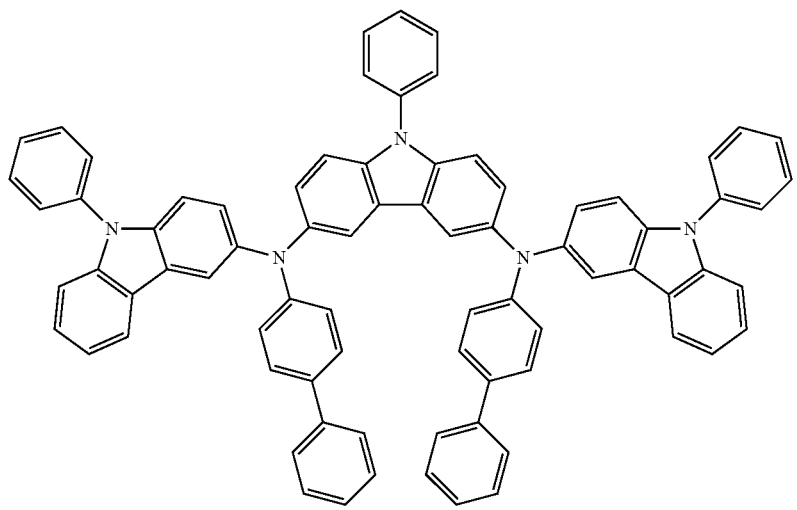
34
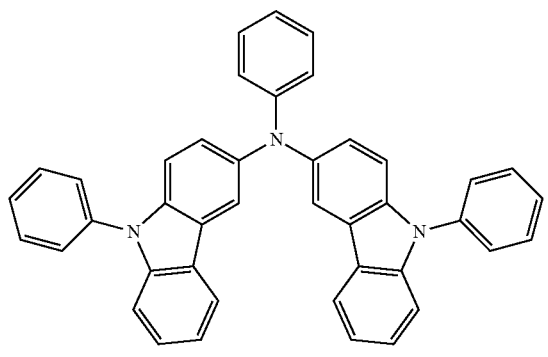
35
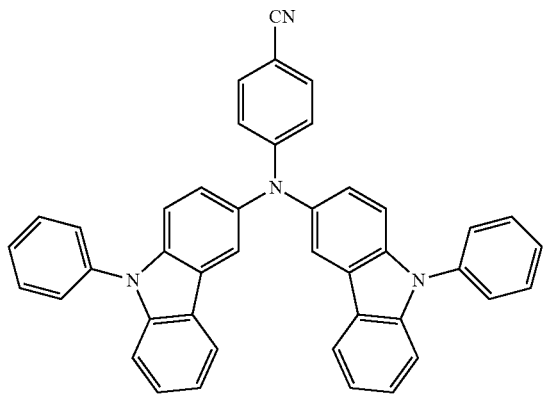

36
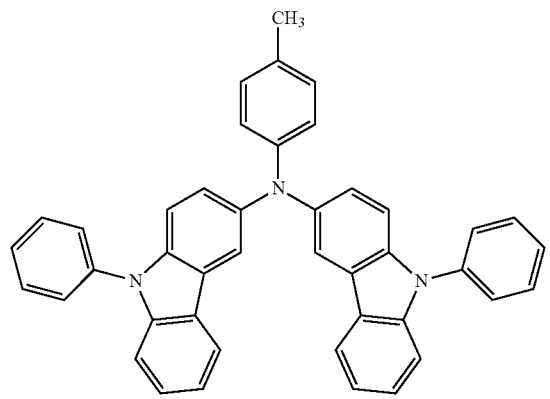
37
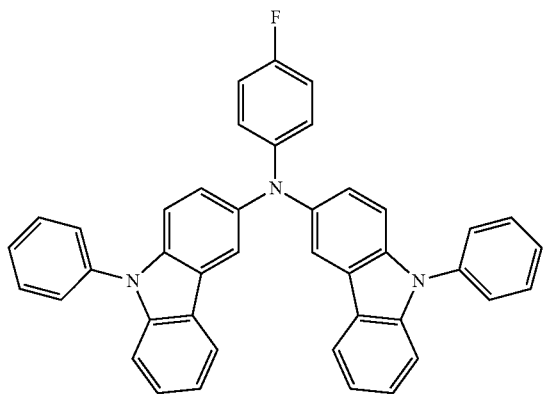
38
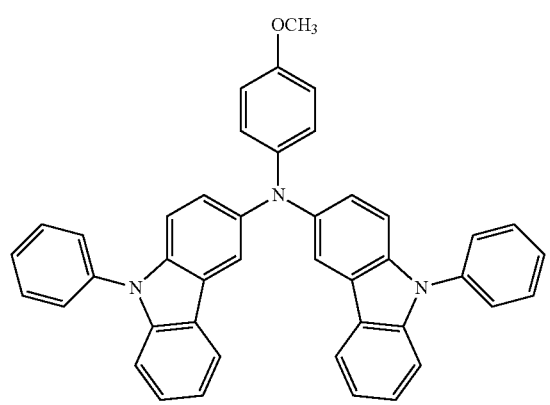
39
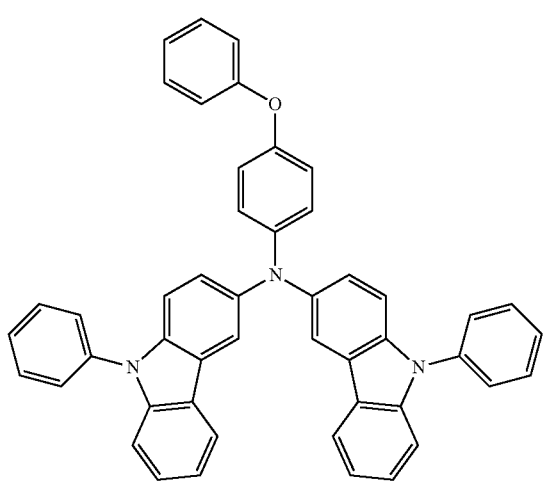
40
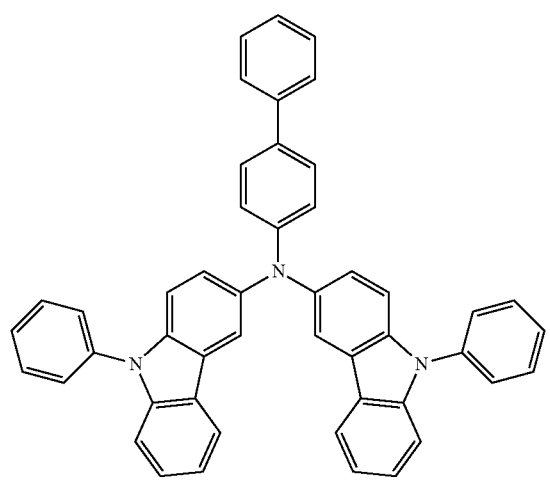
41
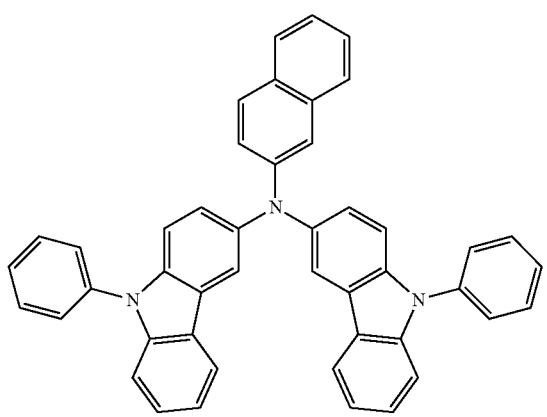

-continued
42
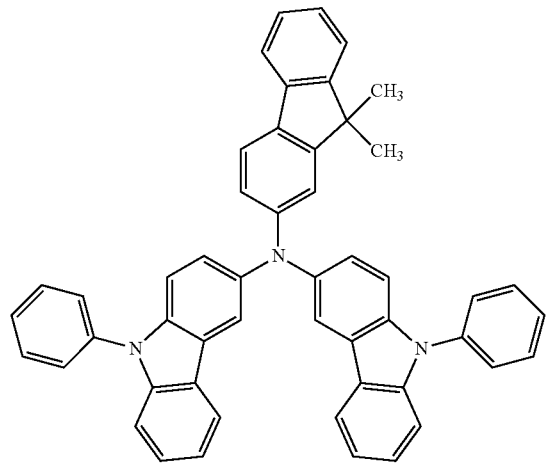
43
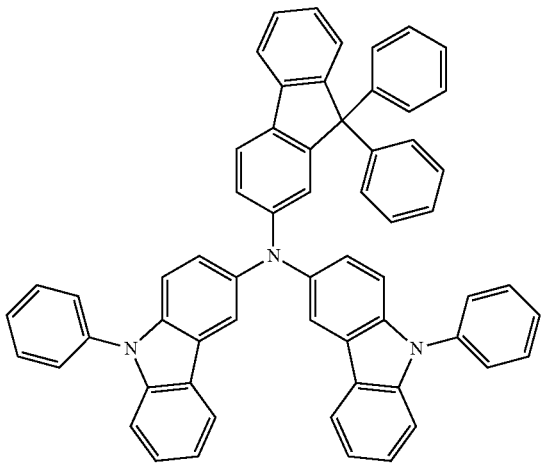
44
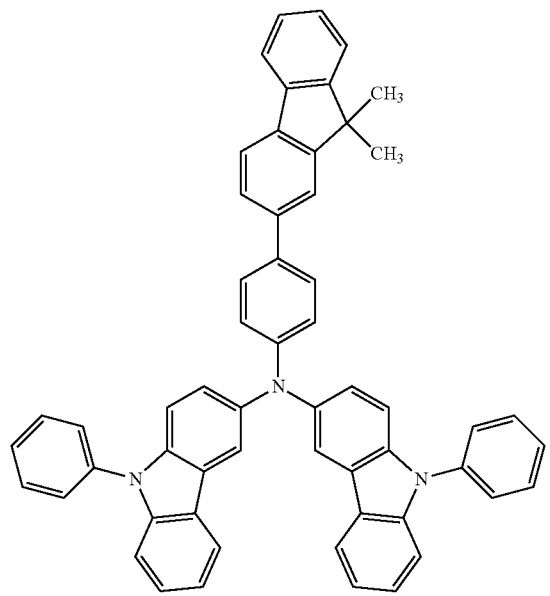
45
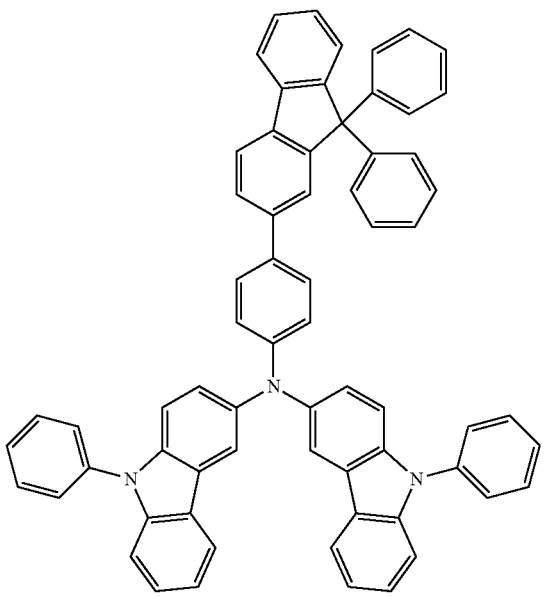
46
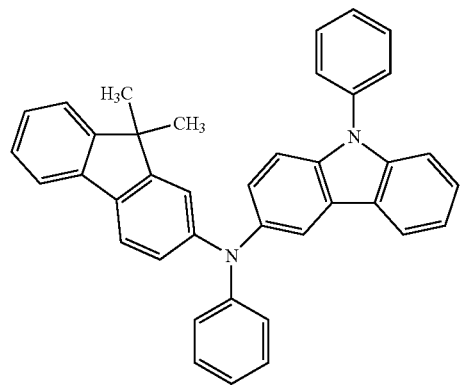
47
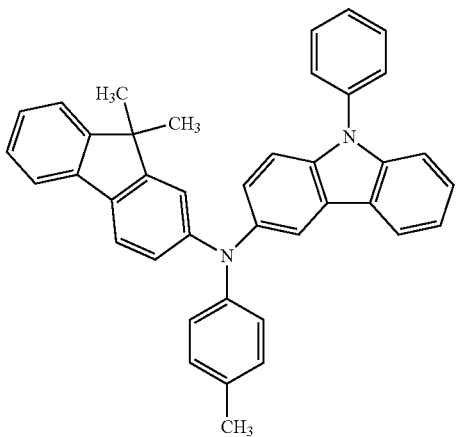

-continued
48
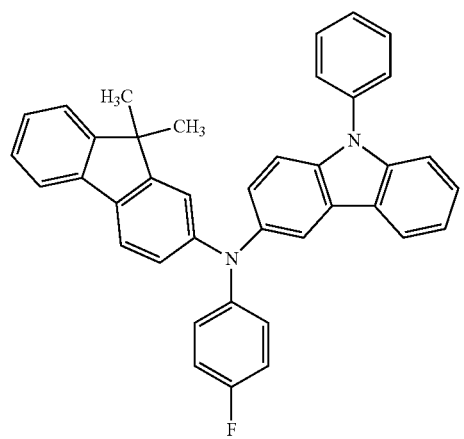
49
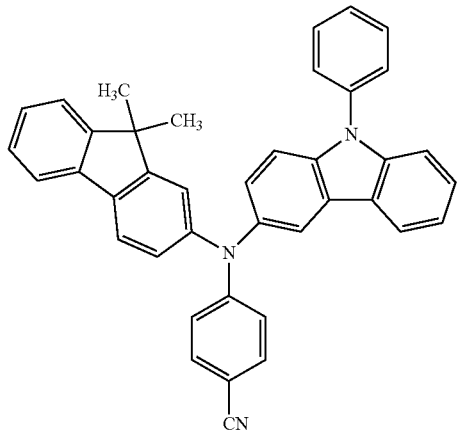
50
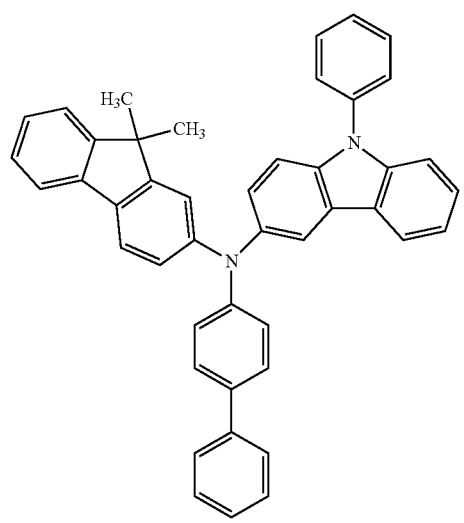
51
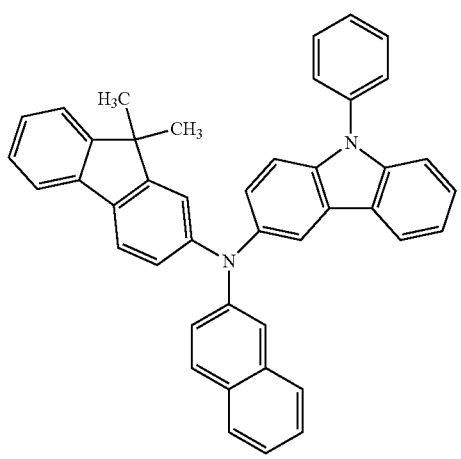
52
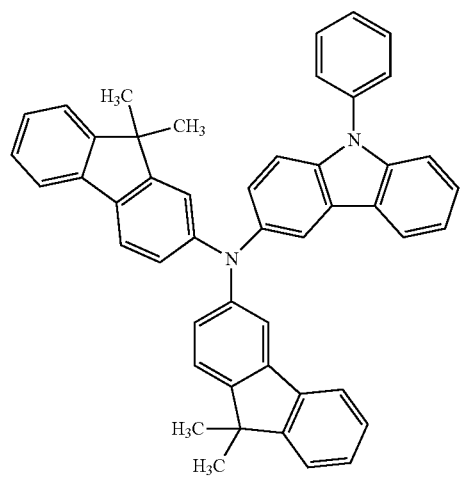
53
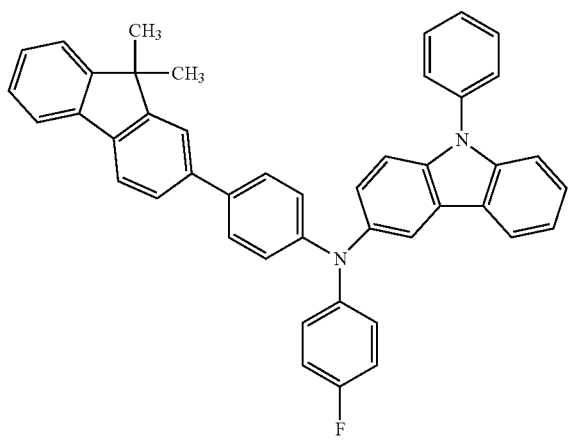

54
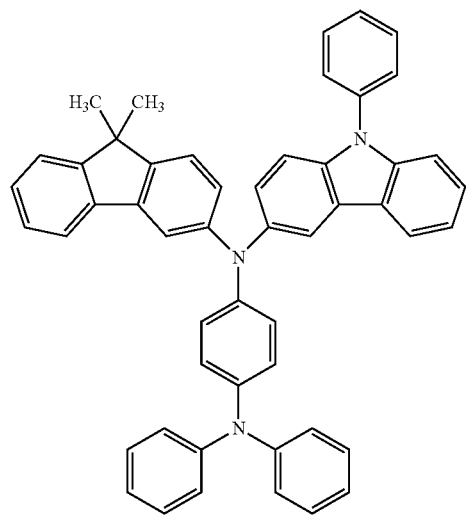
55
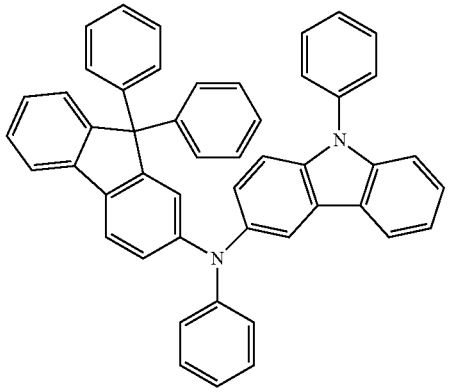
56
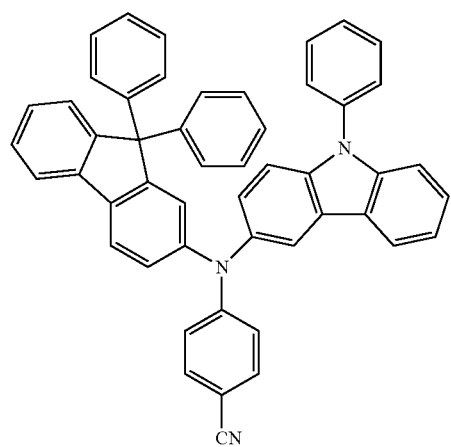
57
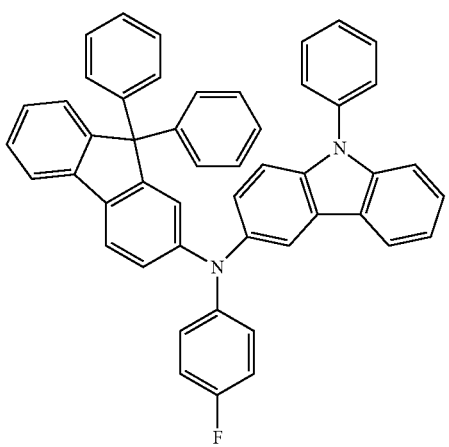
58
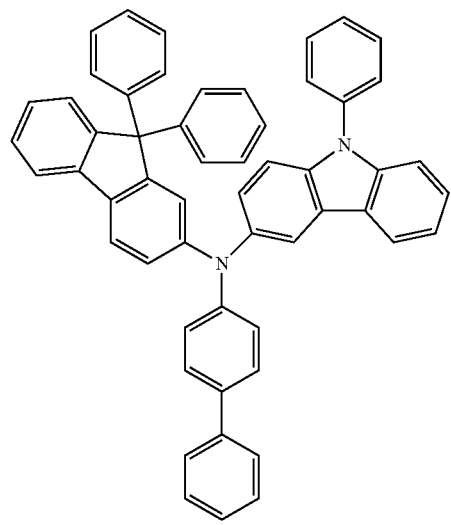
59
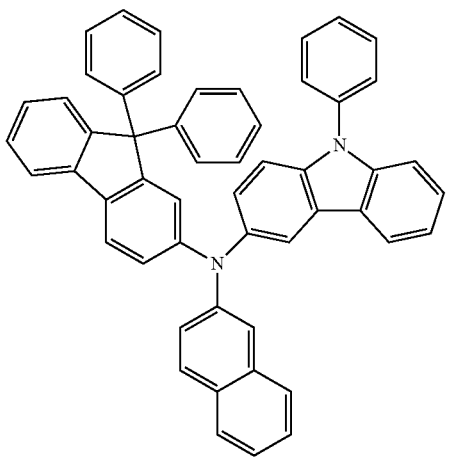

-continued

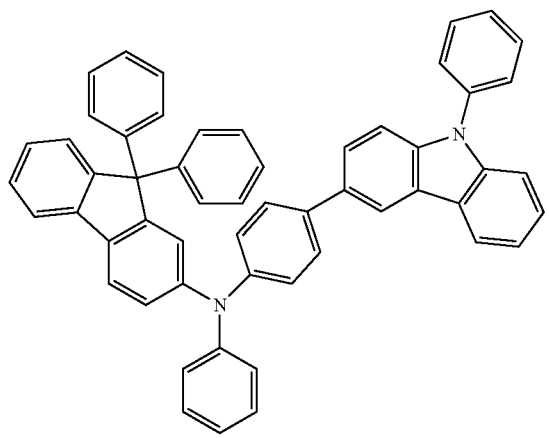
60

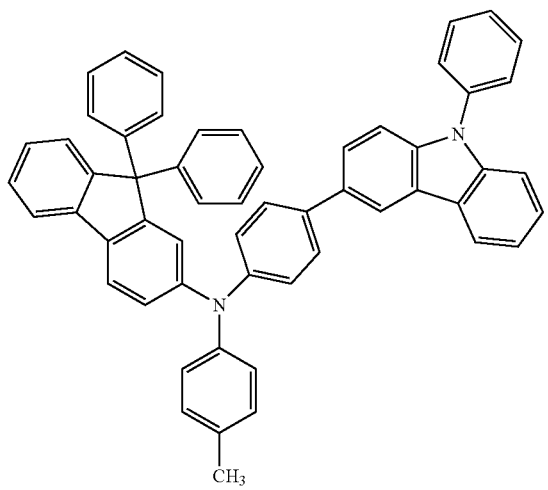
61

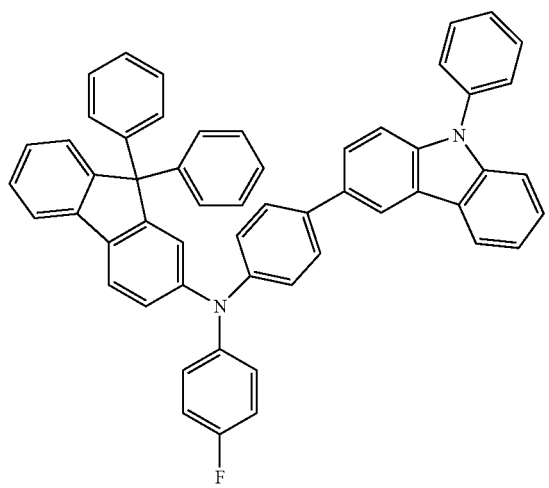
62

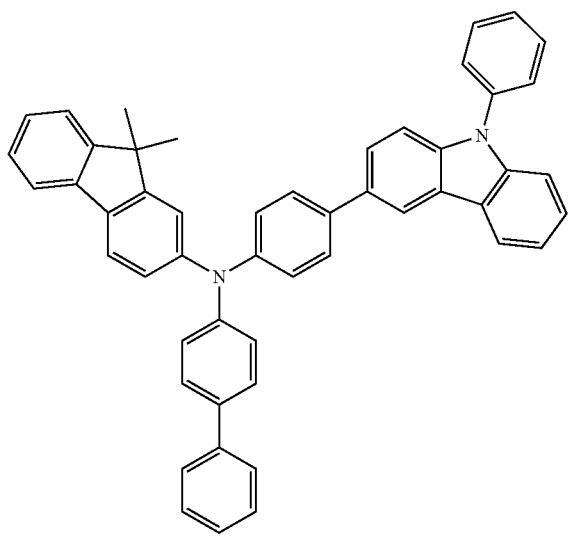
63

The compound represented by the general formula (Sa-1), (Sb-1), or (Sc-1) can be synthesized by the method described in JP-A-2007-318101. It is preferable that after the synthesis, the product is purified by means of column chromatography, recrystallization, reprecipitation, or the like and then purified by means of sublimation purification. By the sublimation purification, not only organic impurities can be separated, but inorganic salts, a residual solvent, a moisture, and the like can be effectively removed.

In the light-emitting element of the present invention, the compound represented by the general formula (Sa-1), (Sb-1), or (Sc-1) is preferably contained in the organic layer between the light emitting layer and the anode, more preferably in the anode-side layer adjacent to the light emitting layer. Particularly preferably, the compound represented by the general formula (Sa-1), (Sb-1), or (Sc-1) is a hole transporting material contained in the hole transporting layer.

The compounds represented by the general formula (Sa-1), (Sb-1), or (Sc-1) are contained in preferably 70 to 100% by mass, more preferably 85 to 100% by mass with respect to the total mass of the organic layer added.

[Compounds Represented by General Formula (M-3)]

In the organic electroluminescent element of the present invention, at least one compound represented by the general formula (M-3) below can be exemplified as the material particularly preferably used for (A) the organic layer preferably disposed between the anode and the light emitting layer.

The compounds represented by the general formula (M-3) are preferably contained in the organic layer between the light emitting layer and the anode, and adjacent to the light emitting layer. However, the compounds are not limited with respect to an application thereof and may be contained in any of the organic layers. As for the layer into which the compounds represented by the general formula (M-3) are introduced, the compounds can be contained in any one or plural layers of the light emitting layer, the hole injecting layer, the hole transporting layer, the electron transporting layer, the electron injecting layer, and the charge blocking layer.

The organic layer in which the compounds represented by the general formula (M-3) are contained, and which is located between the light emitting layer and the anode and adjacent to the light emitting layer, is more preferably the electron blocking layer or the hole transporting layer.

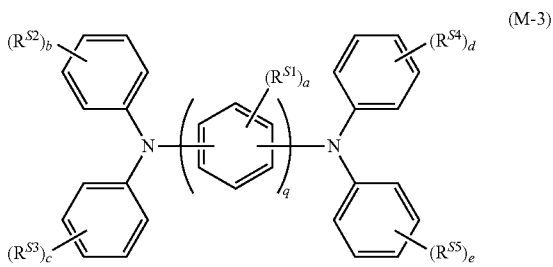

(M-3)

In the general formula (M-3), $R^{S1}$ to $R^{S5}$ each independently represent an alkyl group, a cycloalkyl group, an alkenyl group, an alkynyl group, —CN, a perfluoroalkyl group, a trifluorovinyl group, —$CO_2$R, —C(O)R, —$NR_2$, —$NO_2$, —OR, a halogen atom, an aryl group, or a heteroaryl group, and may further have a substituent Z. R each independently represent a hydrogen atom, an alkyl group, a perhaloalkyl group, an alkenyl group, an alkynyl group, a heteroalkyl group, an aryl group, or a heteroaryl group. When a plurality of $R^{S1}$ to $R^{S5}$ exist, these may be bound to each other to form a ring, and may further have a substituent Z.

a represents an integer of 0 to 4, and when a plurality of $R^{S1}$ exist, these may be the same or different, and may be bound to each other to form a ring. b to e each independently represent an integer of 0 to 5, and when a plurality of $R^{S2}$ to $R^{S5}$ exist, these may be the same or different, and any two may be bound to each other to form a ring.

q is an integer of 1 to 5, and when q is 2 or more, a plurality of $R^{S1}$ may be the same or different, and may be bound to each other to form a ring.

The alkyl group may have a substituent, and may be saturated or unsaturated. Examples of the groups that may be substituted include the substituent Z. Examples of the alkyl groups represented by $R^{S1}$ to $R^{S5}$ include preferably alkyl groups of 1 to 8 carbon atoms in total, more preferably alkyl groups of 1 to 6 carbon atoms in total, for example, such as a methyl group, an ethyl group, an i-propyl group, a cyclohexyl group, and a tert-butyl group.

The cycloalkyl group may have a substituent, and may be saturated or unsaturated. Examples of the groups that may be substituted include the substituent Z. Examples of the cycloalkyl groups represented by $R^{S1}$ to $R^{S5}$ include preferably cycloalkyl groups of 4 to 7 rings, more preferably cycloalkyl groups of 5 to 6 carbon atoms in total, for example, such as a cyclopentyl group, and a cyclohexyl group.

Examples of the alkenyl groups represented by $R^{S1}$ to $R^{S5}$ include preferably alkenyl groups of 2 to 30 carbon atoms, more preferably 2 to 20 carbon atoms, particularly preferably 2 to 10 carbon atoms, for example, such as vinyl, allyl, 1-propenyl, 1-isopropenyl, 1-butenyl, 2-butenyl, and 3-pentenyl.

Examples of the alkynyl groups represented by $R^{S1}$ to $R^{S5}$ include preferably alkynyl groups of 2 to 30 carbon atoms, more preferably 2 to 20 carbon atoms, particularly preferably 2 to 10 carbon atoms, for example, such as ethinyl, propargyl, 1-propynyl, and 3-pentynyl.

Examples of the perfluoroalkyl groups represented by $R^{S1}$ to $R^{S5}$ include those in which all of the hydrogen atoms in the alkyl groups are substituted with fluorine atoms.

Examples of the aryl groups represented by $R^{S1}$ to $R^{S5}$ include preferably substituted or unsubstituted aryl groups of 6 to 30 carbon atoms, for example, such as a phenyl group, a tolyl group, a biphenyl group, and a terphenyl group.

Examples of the heteroaryl groups represented by $R^{S1}$ to $R^{S5}$ include preferably heteroaryl groups of 5 to 8 carbon atoms, more preferably five- or six-membered substituted or unsubstituted heteroaryl groups, for example, such as a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a triazolyl group, a benzothiazolyl group, an isothiazolyl group, a benzisothiazolyl group, a thiadiazolyl group, an isooxazolyl group, a benzisooxazolyl group, a pyrrolidinyl group, a piperidinyl group, a piperazinyl group, an imidazolidinyl group, a thiazolinyl group, a sulfolanyl group, a carbazolyl group, a dibenzofuryl group, a dibenzothienyl group, and a pyridoindolyl group. Preferred examples include a pyridyl group, a pyrimidinyl group, an imidazolyl group, and a thienyl group. More preferred examples include a pyridyl group, and a pyrimidinyl group.

$R^{S1}$ to $R^{S5}$ are preferably hydrogen atoms, alkyl groups, cyano groups, trifluoromethyl groups, perfluoroalkyl groups, dialkylamino groups, fluoro groups, aryl groups, or heteroaryl groups, more preferably hydrogen atoms, alkyl groups, cyano groups, trifluoromethyl groups, fluoro groups, or aryl groups, further preferably hydrogen atoms, alkyl groups, or aryl groups. The substituent Z is preferably an alkyl group, an alkoxy group, a fluoro group, a cyano group, or a dialkylamino group, more preferably a hydrogen atom, or an alkyl group.

Any two of $R^{S1}$ to $R^{S5}$ may be bound to each other to form a fused 4- to 7-membered ring. The fused 4- to 7-membered ring is cycloalkyl, aryl, or heteroaryl, and may further have a substituent Z. The cycloalkyl, aryl, and heteroaryl have the same definitions and preferred ranges as the cycloalkyl group, the aryl group, and the heteroaryl group defined for $R^{S1}$ to $R^{S5}$.

When the compound represented by the general formula (M-3) is used in the hole transporting layer, the compound represented by the general formula (M-3) is contained preferably in 50 to 100% by mass, preferably 80 to 100% by mass, particularly preferably 95 to 100% by mass.

When used in a plurality of organic layers, the compound represented by the general formula (M-3) is preferably contained in each layer in the foregoing range.

The hole transporting layer containing the compound represented by the general formula (M-3) has a thickness of preferably 1 nm to 500 nm, more preferably 3 nm to 200 nm, further preferably 5 nm to 100 nm. Further, the hole transporting layer is preferably provided in contact with the light emitting layer.

Specific examples of the compounds represented by the general formula (M-3) are given below. It should be noted, however, that the present invention is not limited to the following.

103
104
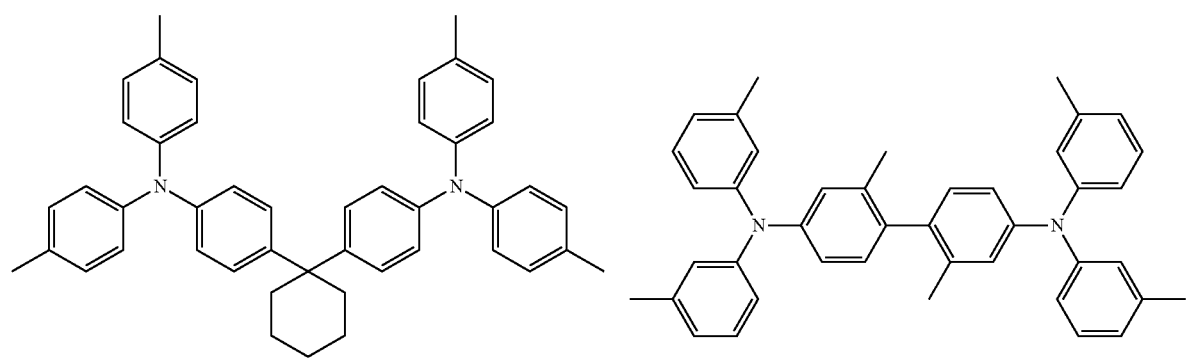
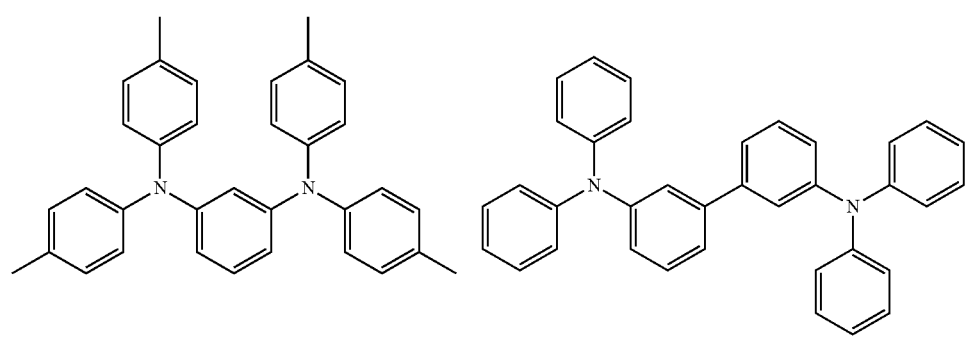
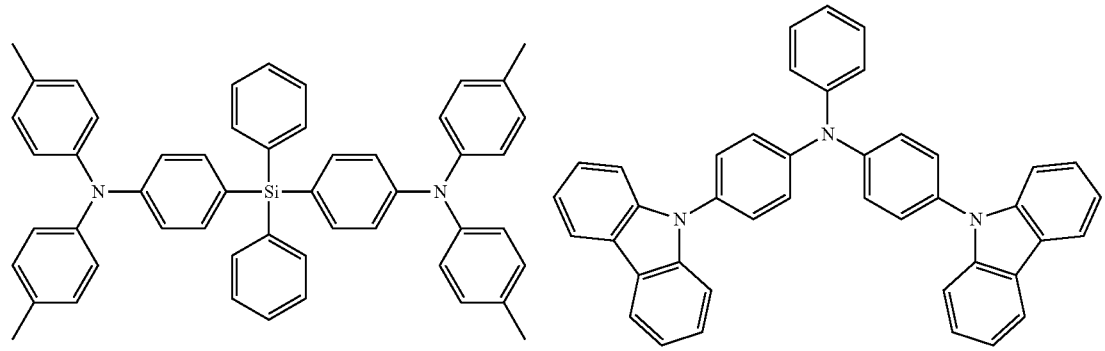
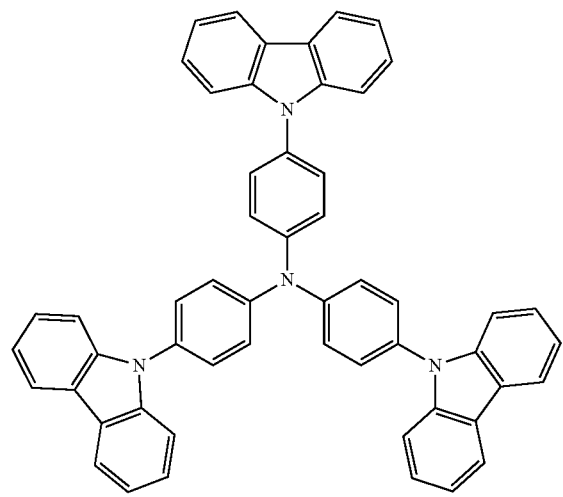

-continued
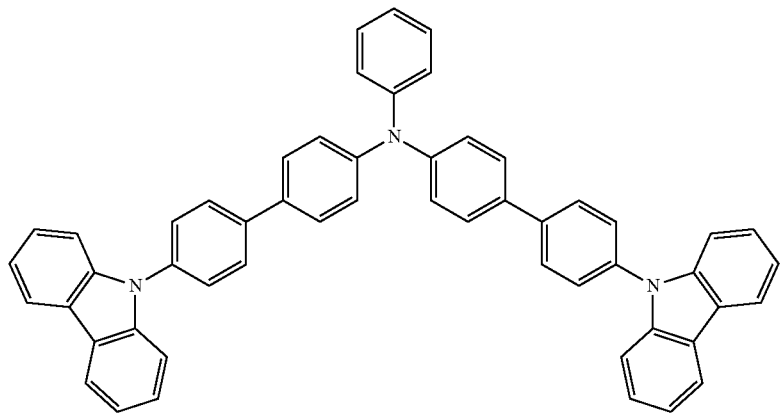
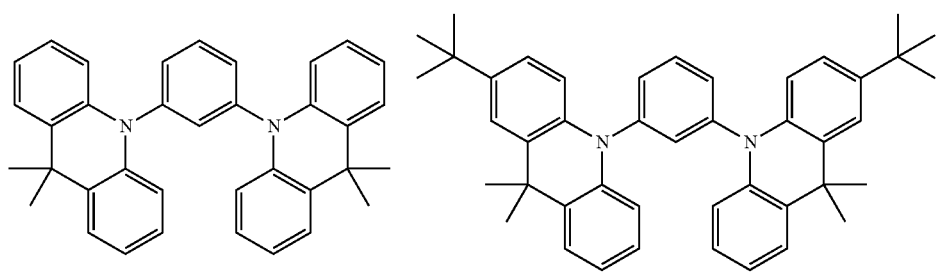
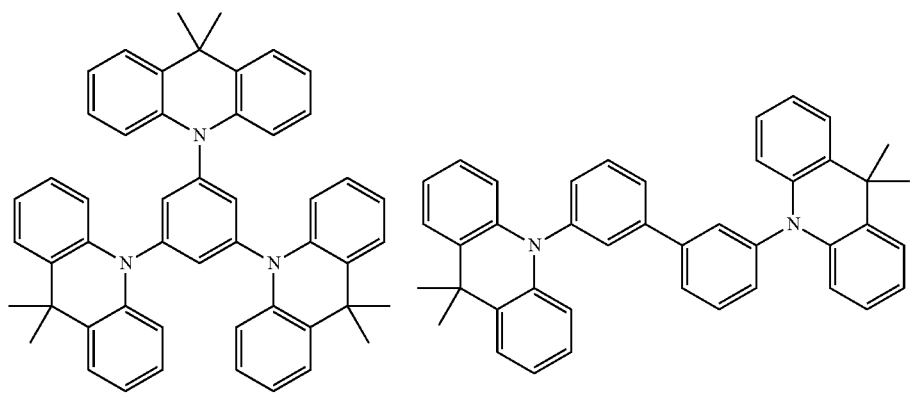
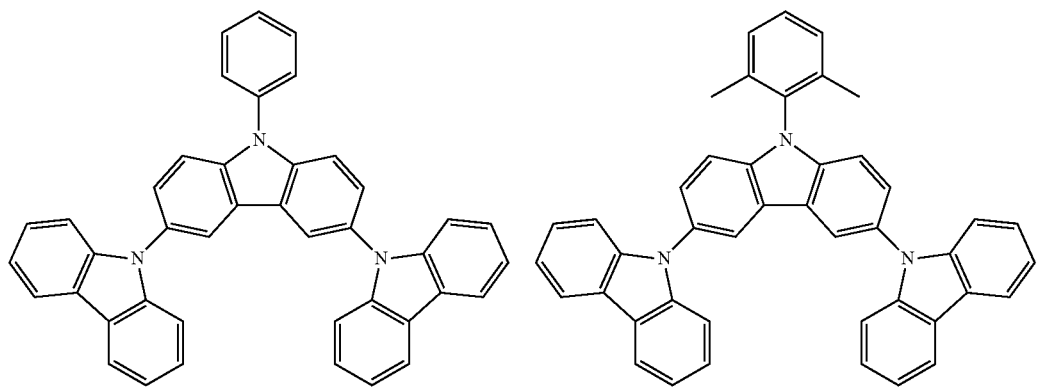

107 108
-continued
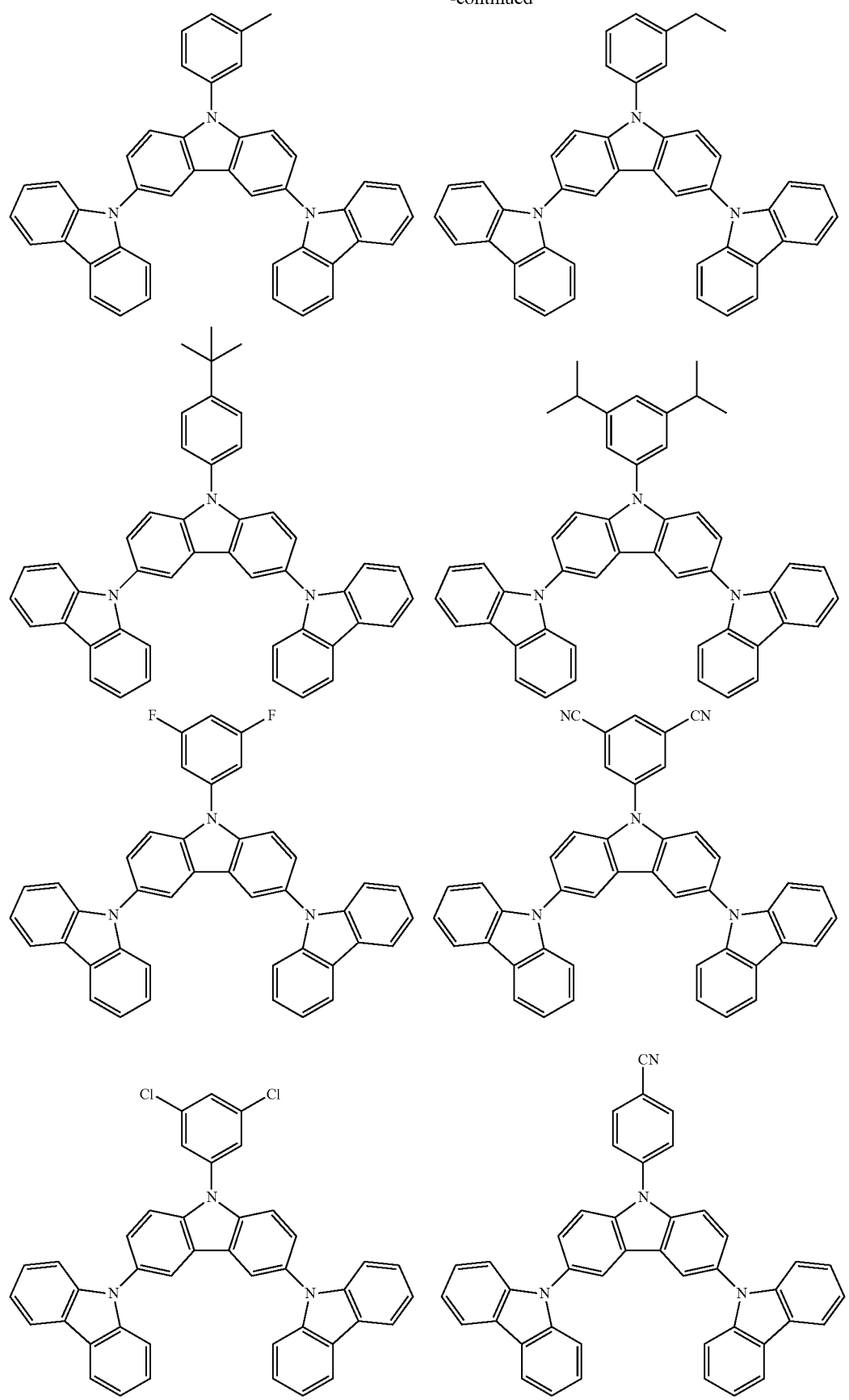

-continued
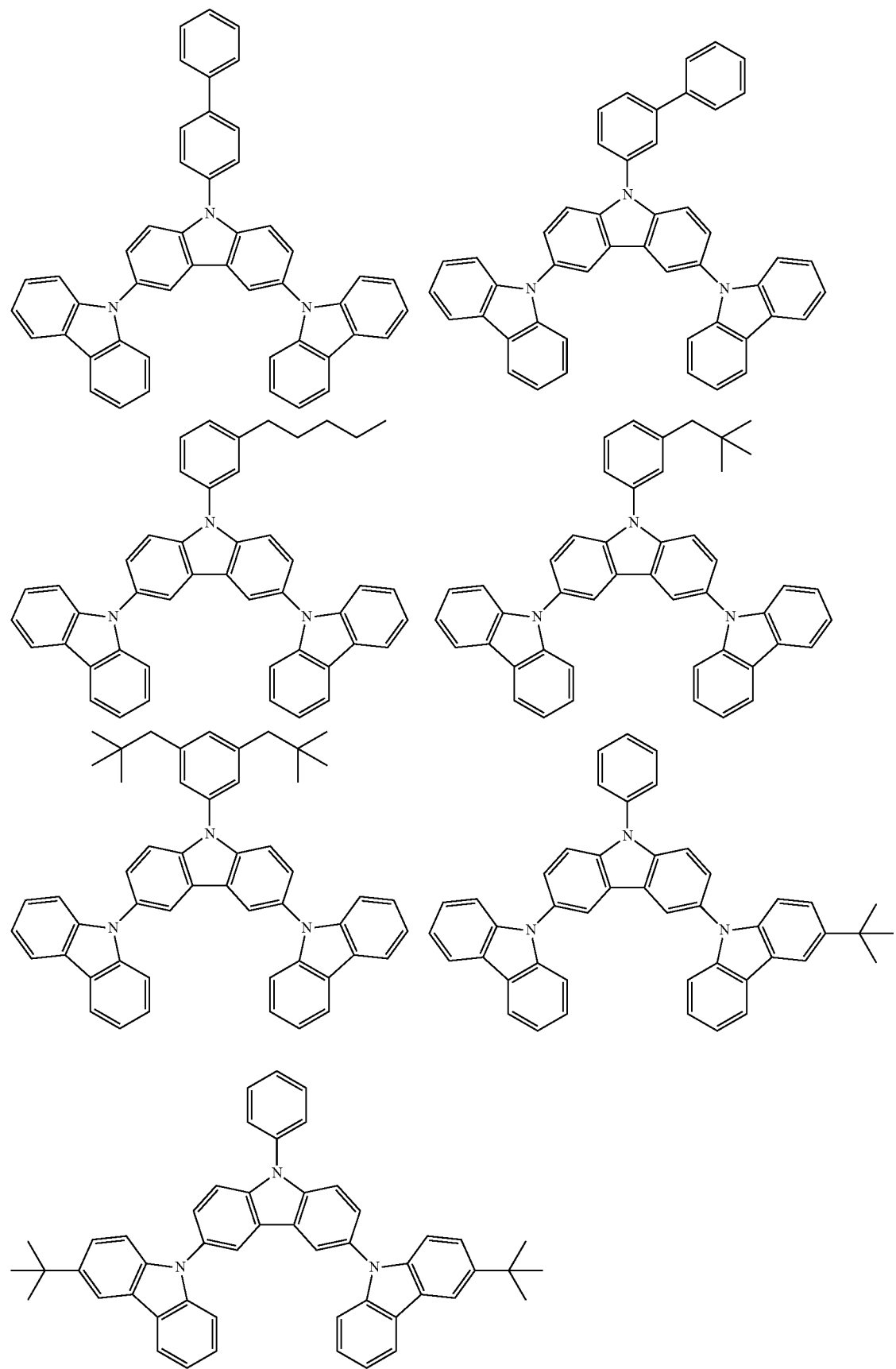

-continued
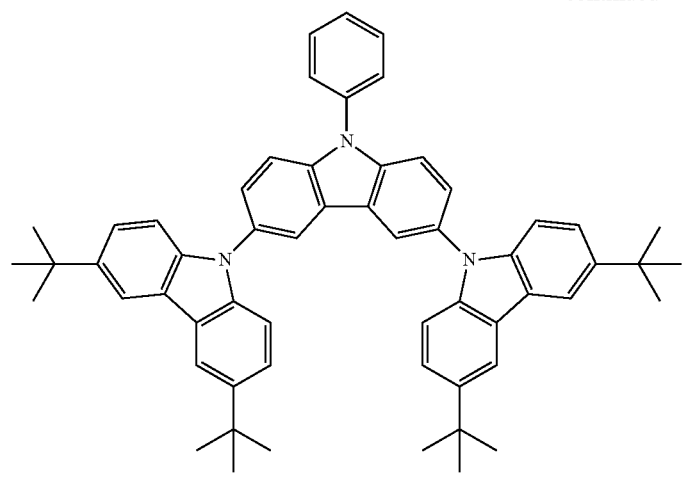
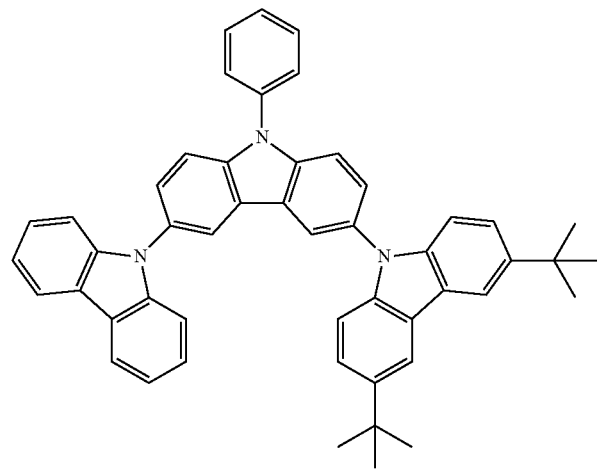
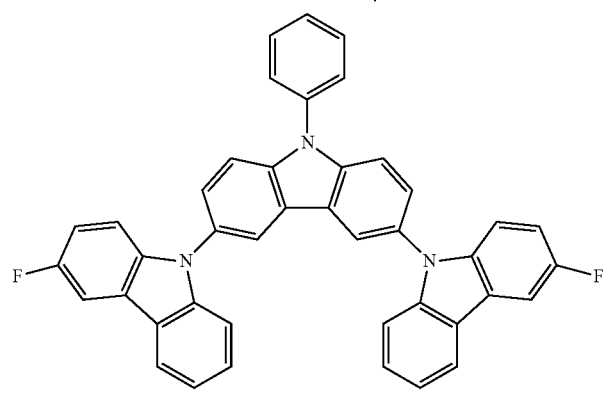
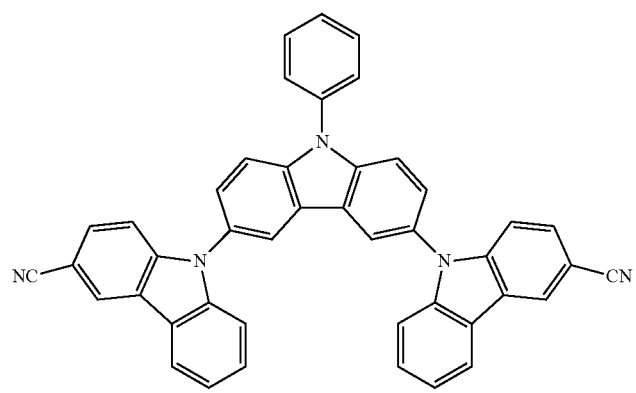

-continued
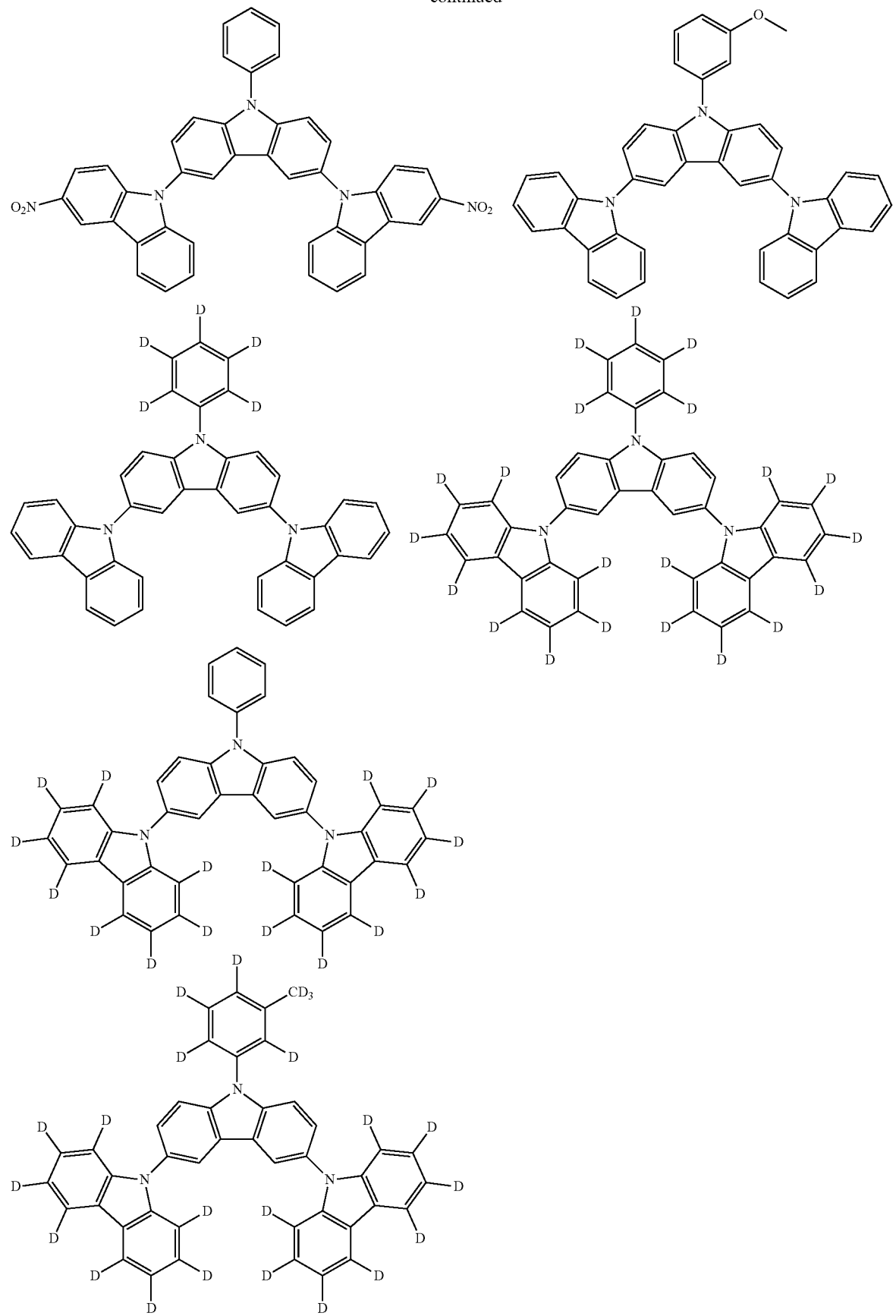

-continued
115
116
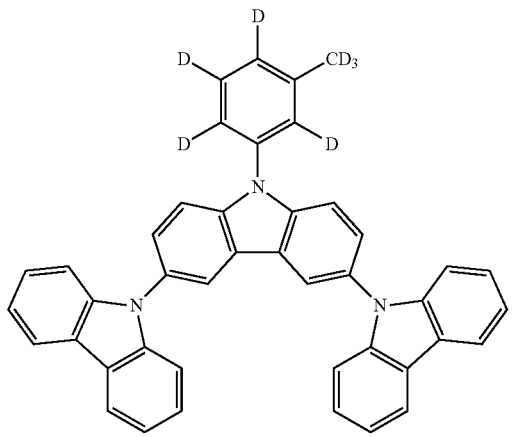
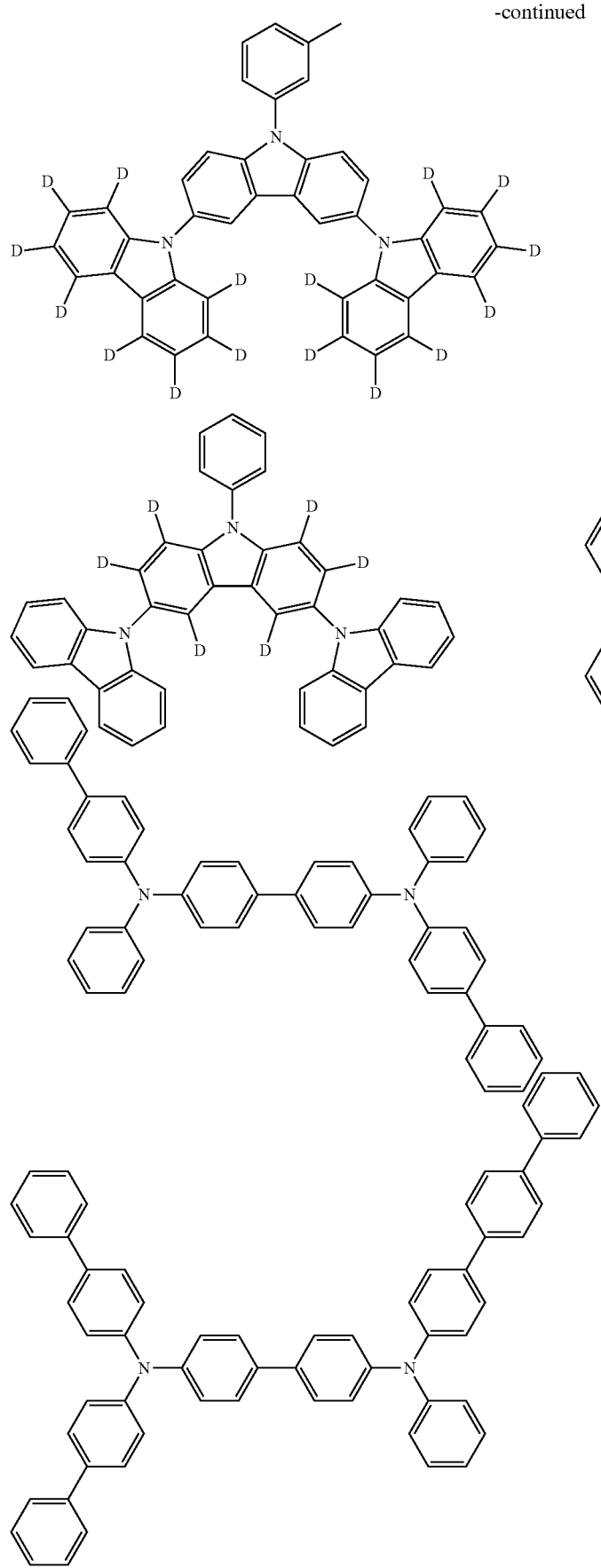
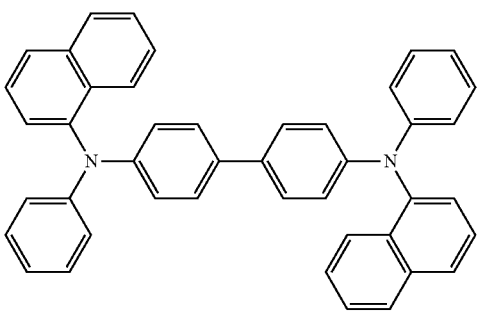

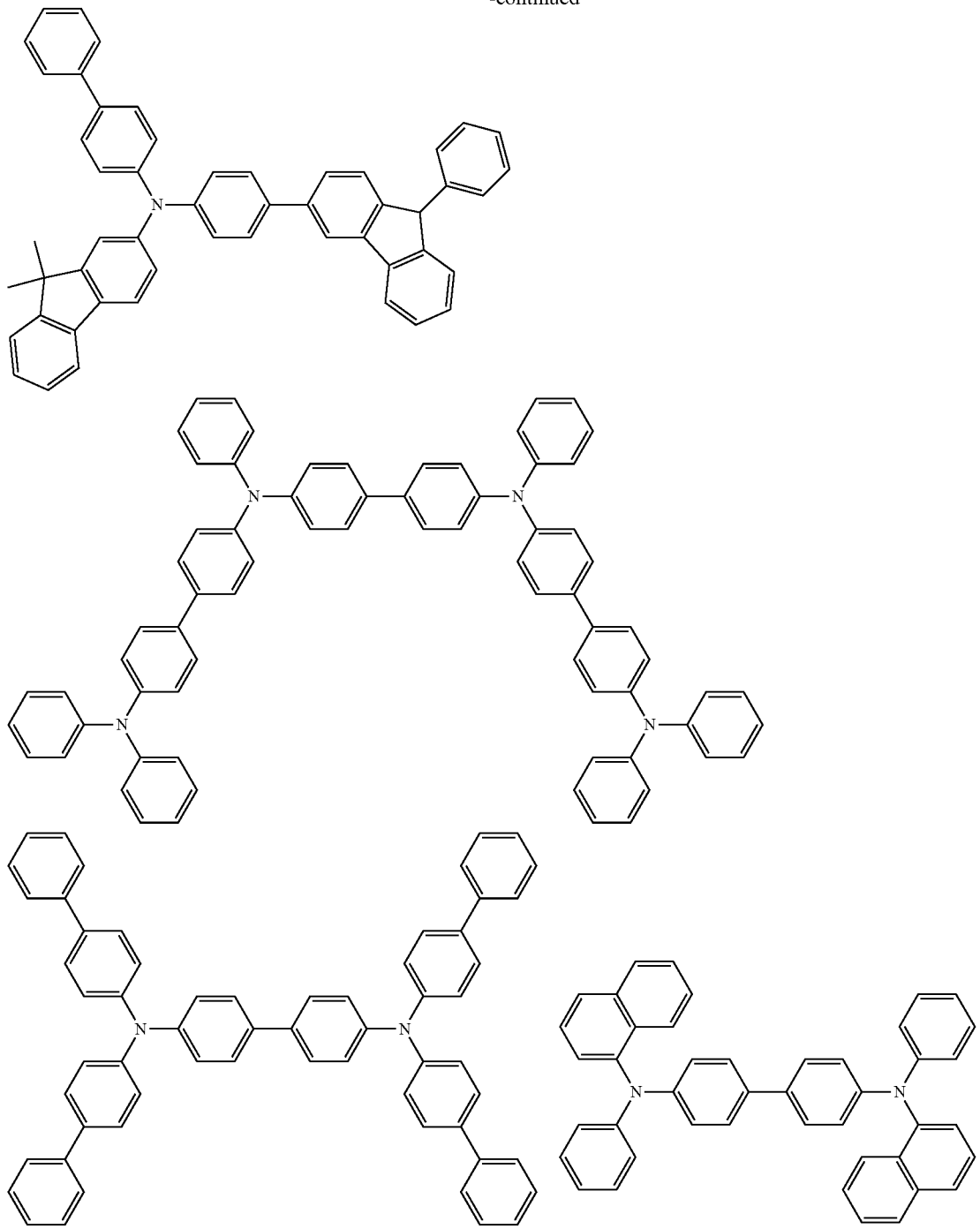

With regard to the hole injecting layer and the hole transporting layer, the detailed descriptions in paragraphs [0165] to [0167] of JP-A-2008-270736 may be applied to the present invention. The detailed descriptions in paragraphs [0250] to [0339] of JP-A-2011-71452 also may be applied with regard to the hole injecting layer and the hole transporting layer of the present invention. Further, the compounds represented by the general formula (1) can preferably be applied to the hole injecting layer and the hole transporting layer.

The hole injecting layer preferably contains an electron-accepting dopant. Containing an electron-accepting dopant in the hole injecting layer is effective, because it improves hole injectability, lowers driving voltage, and improves efficiency. Any organic material or inorganic material may be used as the electron-accepting dopant, provided that electrons can be drawn out of the doped material, and radical cations can be generated. Examples include TCNQ compounds such as tetracyanoquinodimethane (TCNQ), and tetrafluorotetracyanoquinodimethane (F4-TCNQ), and hexaazatriphenylene compounds such as hexacyanohexaazatriphenylene (HAT-CN), and molybdenum oxides.

The electron-accepting dopant is contained in the hole injecting layer in preferably 0.01 to 50% by mass, more preferably 0.1 to 40% by mass, further preferably 0.2 to 30% by mass with respect to the total compound mass forming the hole injecting layer.

(A-2) Electron Blocking Layer

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

As the organic compound constituting the electron blocking layer, for example, those exemplified above as the hole transporting material can be used.

The thickness of the electron blocking layer is preferably from 1 nm to 500 nm, more preferably from 3 nm to 100 nm, and still more preferably from 5 nm to 50 nm.

The electron blocking layer may have either a single layer structure composed of one or two or more kinds of materials selected from the above-exemplified materials or a multilayer structure composed of a plurality of layers having the same composition or different compositions.

The material used for the electron blocking layer preferably has a higher $S_1$ energy than the light emitting material from the viewpoints of color purity, luminous efficiency, and driving durability. The $S_1$ of the material used for the electron blocking layer in the film state is higher than the $S_1$ of the light emitting material by preferably 0.1 eV or more, more preferably 0.2 eV or more, further preferably 0.3 eV or more.

(B) Organic Layer Preferably Disposed Between Cathode and Light Emitting Layer:

Next, the (B) organic layer preferably disposed between the cathode and the light emitting layer is described.

(B-1) Electron Injecting Layer and Electron Transporting Layer

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by the general formula (1) can be used. As other electron transporting materials, any one of compounds selected from aromatic ring tetracarboxylic acid anhydrides such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof, organic silane derivatives typified by silole; hydrocarbon compounds with fused rings, such as naphthalene, anthracene, phenanthrene, triphenylene, and pyrene is preferable. Any one of compounds selected from pyridine derivatives, benzimidazole derivatives, imidazopyridine derivatives, metal complexes, and hydrocarbon compounds with fused rings is more preferable.

From the viewpoint of decreasing the driving voltage, the thickness of each of the electron injecting layer and the electron transporting layer is preferably not more than 500 nm.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one or two or more kinds of the materials selected from the above-exemplified materials or a multilayer structure composed of a plurality of layers having the same composition or different compositions.

The electron injecting layer preferably contains an electron donating dopant. By incorporating the electron donating dopant into the electron injecting layer, for example, there are brought such effects that the electron injecting properties are enhanced; that the driving voltage is lowered; and that the efficiency is enhanced. The electron donating dopant may be any one of organic materials and inorganic materials as long as it is capable of giving electrons to the material to be doped and generating radical anions. Examples thereof include dihydroimidazole compounds such as tetrathiafulvalene (TTF), tetrathianaphthacene (TTT), and bis-[1,3-d]ethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably 0.5% by mass to 30% by mass relative to the total mass of the compounds forming the electron injecting layer.

(B-2) Hole Blocking Layer

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order to prevent the energy movement of excitons produced in the light emitting layer and not lower the luminous efficiency, the $S_1$ energy of the organic compound constituting the hole blocking layer in a film state is preferably higher than the $S_1$ energy of the light emitting material.

As an example of the organic compound constituting the hole blocking layer, for example, the compound represented by the general formula (1) can be used.

Examples of the organic compounds constituting the hole blocking layer, other than the compound represented by the general formula (1), include aluminum complexes such as aluminum(III) bis(2-methyl-8-quinolinato) 4-phenylphenolate (abbreviated as "BAlq"), triazole derivatives, and phenanthroline derivatives such as 2,9-dimethyl-4,7-diphenyl-1,10-phenanthroline (abbreviated as "BCP").

The thickness of the hole blocking layer is preferably from 1 nm to 500 nm, more preferably from 3 nm to 100 nm, and still more preferably from 5 nm to 50 nm.

The hole blocking layer may have either a single layer structure composed of one or two or more kinds of the above-described materials or a multilayer structure composed of a plurality of layers having the same composition or different compositions.

The material which is used in the hole blocking layer preferably has higher $S_1$ energy than that of the light emitting material in view of color purity, luminous efficiency, and driving durability. The $S_1$ of the material used for the hole blocking layer in the film state is higher than the $S_1$ of the light emitting material by preferably 0.1 eV or more, more preferably 0.2 eV or more, further preferably 0.3 eV or more.

(B-3) Material Especially Preferably Used in Organic Layer, which is Preferably Disposed Between Cathode and Light Emitting Layer For the organic electroluminescent element according to the present invention, examples of the material which is especially preferably used in the materials for an organic layer, preferably disposed between the (B) cathode and the light emitting layer include the compound represented by the general formula (1), and compounds represented by the following general formula (P-1) and the following general formula (O-1).

The compounds represented by the general formula (O-1), and the compounds represented by the general formula (P-1) are hereunder described.

The organic electroluminescent element of the present invention preferably includes at least one organic layer between the light emitting layer and the cathode, and the organic layer preferably contains at least one compound represented by the following general formula (O-1) from the viewpoints of element efficiency and driving voltage. The general formula (O-1) is described below.

General Formula (O-1)

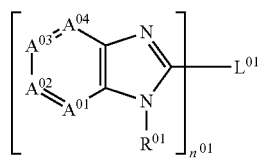

(In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and plural $R^A$s may be the same as or different from one another. $L^{O1}$ represents any of divalent to hexavalent linking groups composed of an aryl ring or a heteroaryl ring. $n^{O1}$ represents an integer of 2 to 6.)

$R^{O1}$ represents an alkyl group (of preferably 1 to 8 carbon atoms), an aryl group (of preferably 6 to 30 carbon atoms), or a heteroaryl group (of preferably 4 to 12 carbon atoms), which may have a substituent selected from the substituent group A. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group. Of these, an alkyl group and an aryl group are more preferable, with an aryl group being still more preferable. In the case where the aryl group of $R^{O1}$ has plural substituents, the plural substituents may be bonded to each other to form a 5- or 6-membered ring. The aryl group of $R^{O1}$ is preferably a phenyl group which may have a substituent selected from the substituent group A, more preferably a phenyl group which may be substituted with an alkyl group or an aryl group, and still more preferably an unsubstituted phenyl group or a 2-phenylphenyl group.

$A^{O1}$ to $A^{O4}$ each independently represent C—$R^A$ or a nitrogen atom. It is preferable that from 0 to 2 of $A^{O1}$ to $A^{O4}$ are nitrogen atoms; and it is more preferable that 0 or 1 of $A^{O1}$ to $A^{O4}$ is a nitrogen atom. It is preferable that all of $A^{O1}$ to $A^{O4}$ are C—$R^A$s, or $A^{O1}$ is a nitrogen atom, and $A^{O2}$ to $A^{O4}$ are C—$R^A$s; it is more preferable that $A^{O1}$ is a nitrogen atom, and $A^{O2}$ to $A^{O4}$ are C—$R^A$s; and it is still more preferable that $A^{O1}$ is a nitrogen atom, $A^{O2}$ to $A^{O4}$ are C—$R^A$s, and $R^A$s are all hydrogen atoms.

$R^A$ represents a hydrogen atom, an alkyl group (of preferably 1 to 8 carbon atoms), an aryl group (of preferably 6 to 30 carbon atoms), or a heteroaryl group (of preferably 4 to 12 carbon atoms), and may have a substituent selected from the substituent group A. In addition, plural $R^A$s may be the same as or different from one another. $R^A$ is preferably a hydrogen atom or an alkyl group, and more preferably a hydrogen atom.

$L^{O1}$ represents a divalent to hexavalent linking group composed of an aryl ring (of preferably 6 to 30 carbon atoms) or a heteroaryl ring (of preferably 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the substituent group A, and in the case where $L^{O1}$ has a substituent, the substituent is preferably an alkyl group, an aryl group, or a cyano group. Specific examples of $L^{O1}$ include the following.

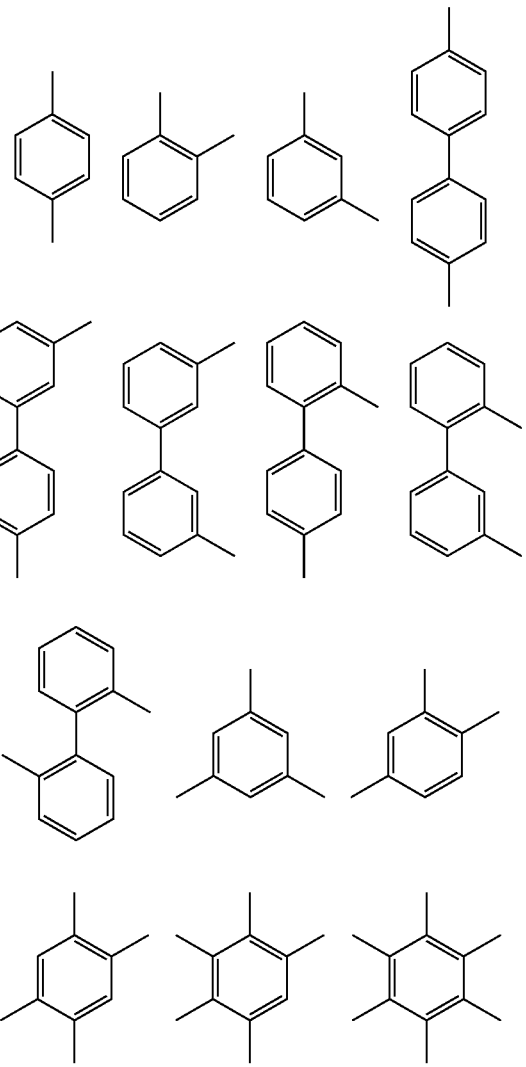

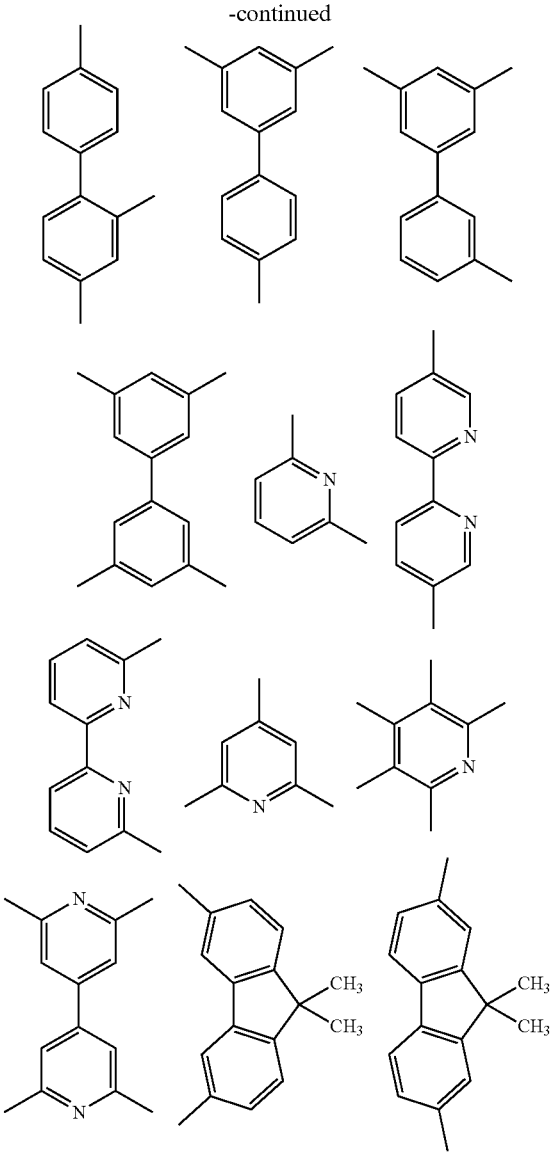
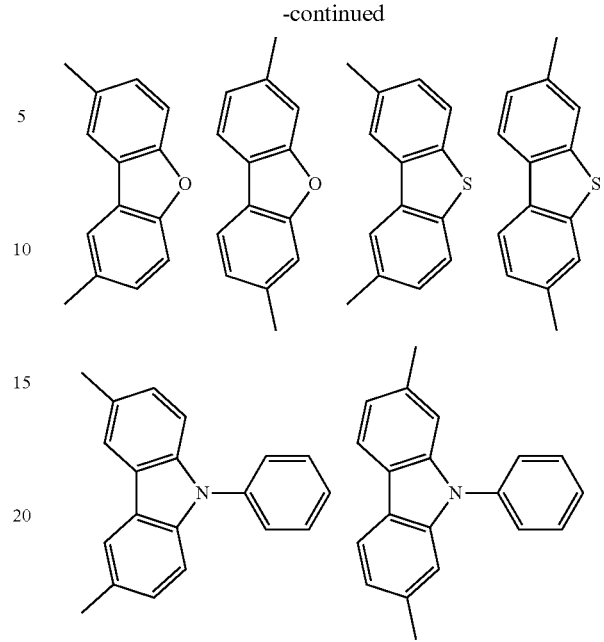

$n^{O1}$ represents an integer of from 2 to 6, preferably an integer of from 2 to 4, and more preferably 2 or 3. $n^{O1}$ is most preferably 3 from the viewpoint of element efficiency, or $n^{O1}$ is most preferably 2 from the viewpoint of element durability.

The glass transition temperature (Tg) of the compound represented by the general formula (O-1) is preferably from 100° C. to 300° C., more preferably from 120° C. to 300° C., and still more preferably from 140° C. to 300° C. from the viewpoint of stability at the time of storage at a high temperature, or stable operation during driving at a high temperature or against heat generation during driving.

Specific examples of the compounds represented by the general formula (O-1) are given below. It should be noted, however, the compounds represented by the general formula (O-1) that can be used in the present invention should not be narrowly construed as being limited to these specific examples.

OM-1

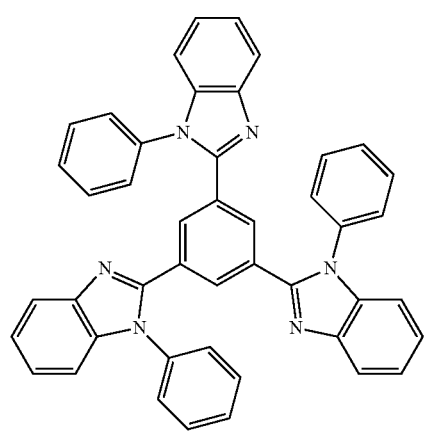

OM-2

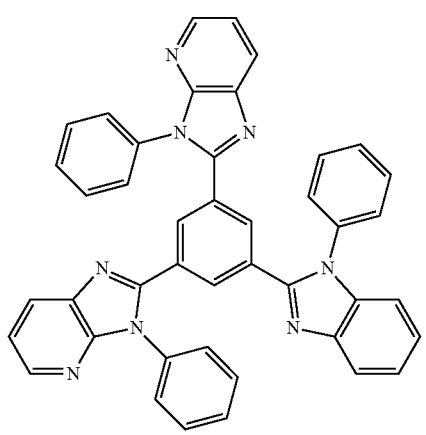

-continued
OM-3
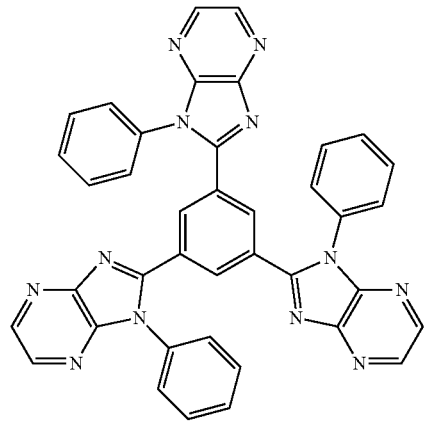
OM-4
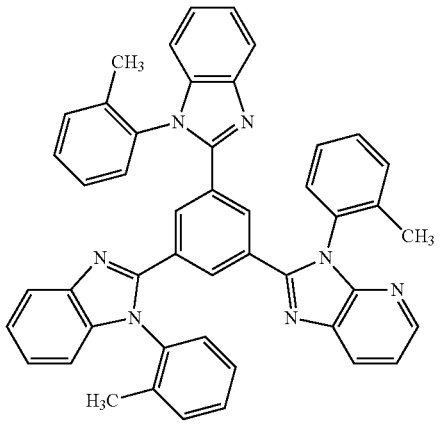
OM-5
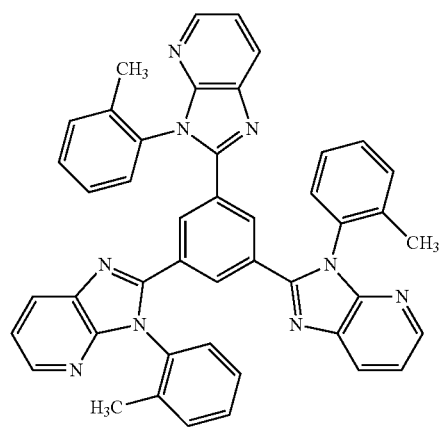
OM-6
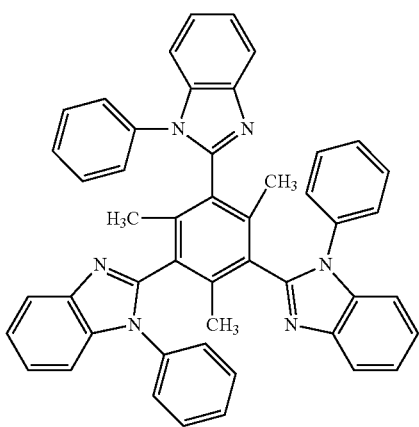
OM-7
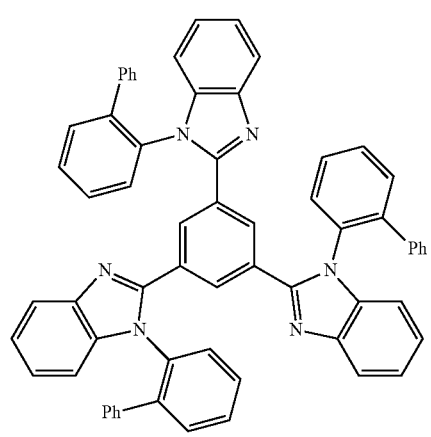
OM-8
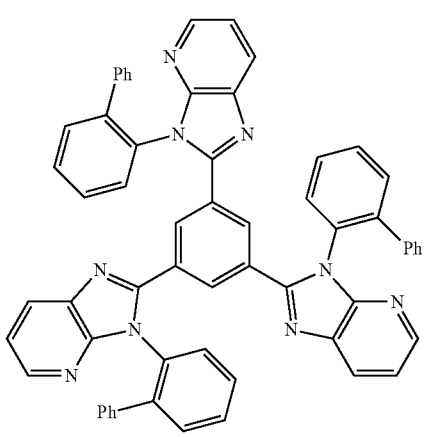

-continued
OM-9
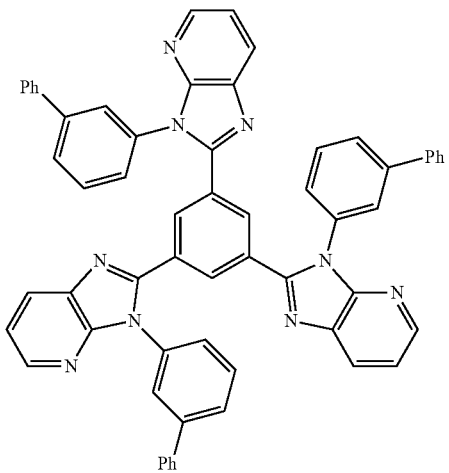
OM-10
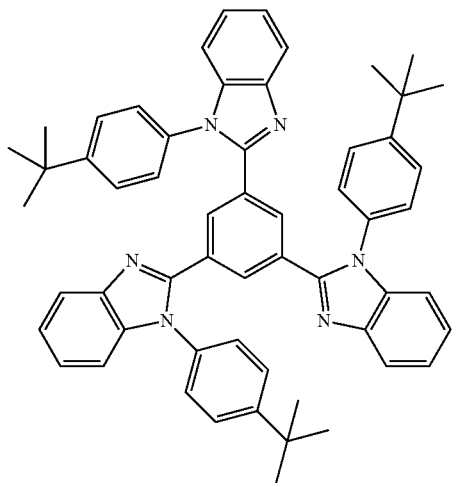
OM-11
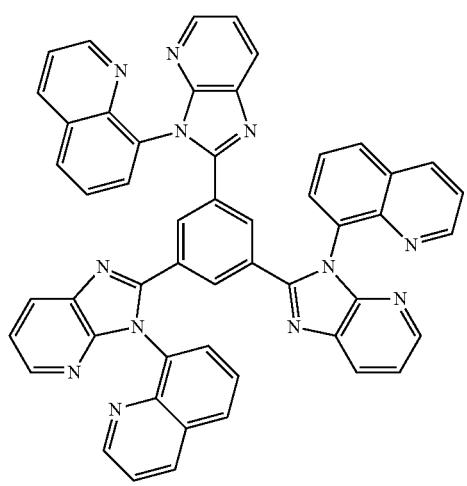
OM-12
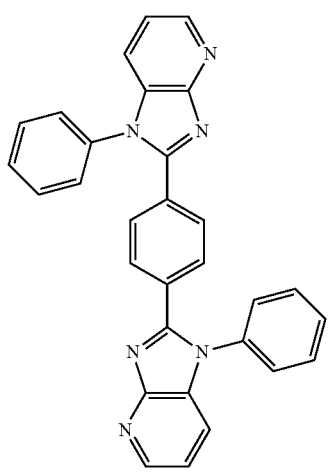
OM-13
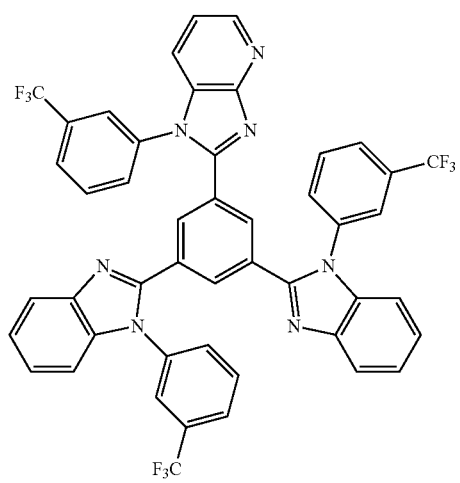
OM-14
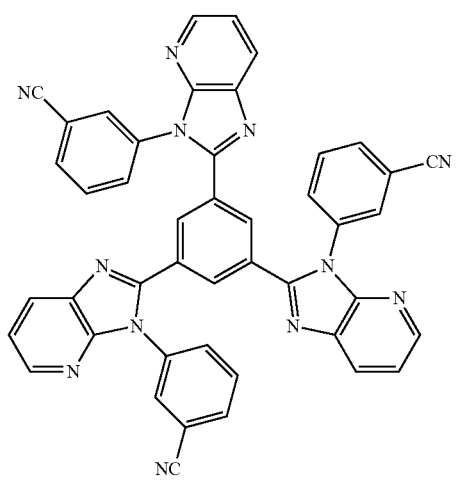

-continued
OM-15
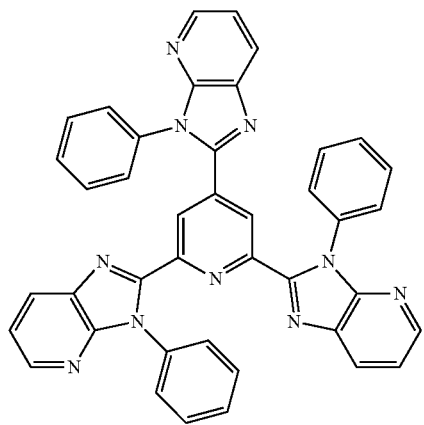
OM-16
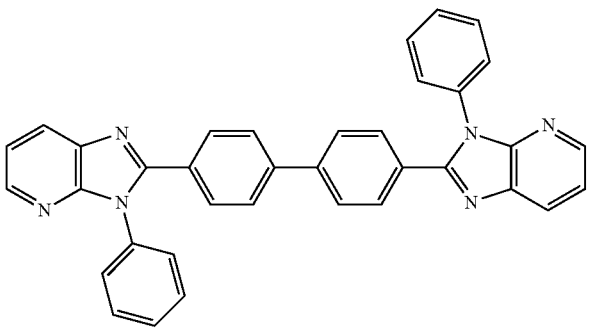
OM-17
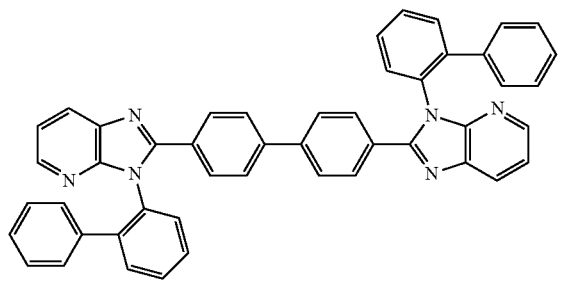
OM-18
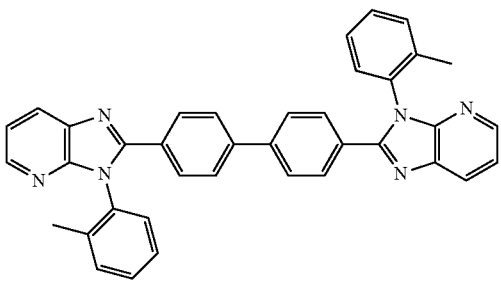
OM-19
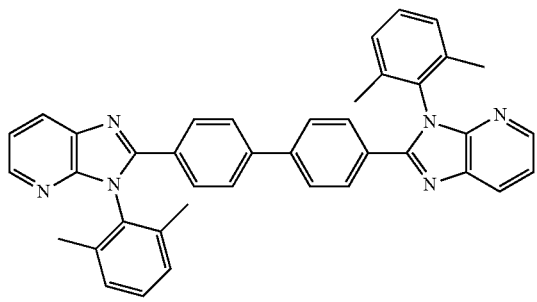
OM-20
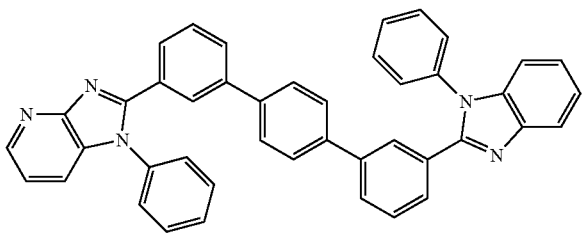
OM-21
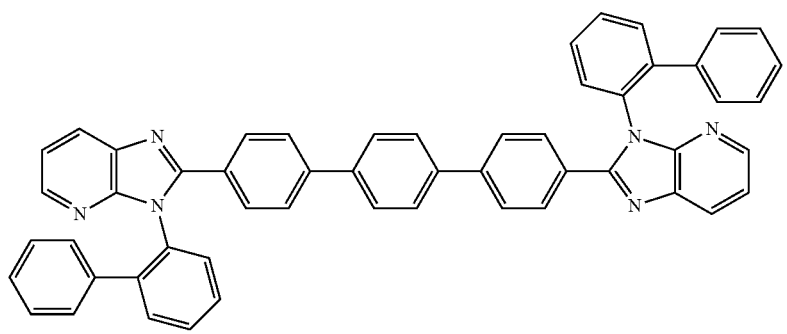

OM-22

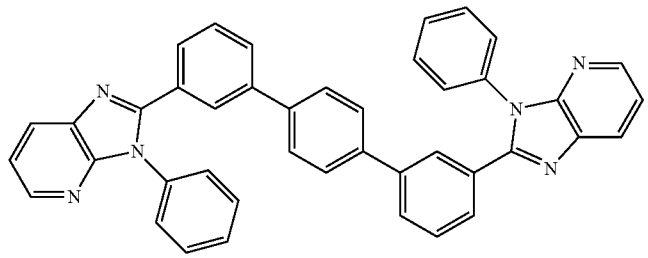

The compound represented by the general formula (O-1) can be synthesized by the method described in JP-A-2001-335776. After the synthesis, it is preferable that after performing purification by means of column chromatography, recrystallization, reprecipitation, or the like, purification is performed by means of sublimation purification. According to the sublimation purification, not only organic impurities can be separated, but inorganic salts, residual solvent, moisture, and the like can be effectively removed.

In the organic electroluminescent element according to the present invention, though the compound represented by the general formula (O-1) is preferably contained in the organic layer between the light emitting layer and the cathode, it is more preferably contained in the layer on the cathode side adjacent to the light emitting layer.

The compounds represented by the general formula (O-1) are contained in preferably 70 to 100% by mass, more preferably 85 to 100% by mass with respect to the total mass of the organic layer added.

The organic electroluminescent element of the present invention preferably contains at least one organic layer between the light emitting layer and the cathode, and the organic layer preferably contains at least one compound represented by the following general formula (P) from the viewpoints of element efficiency and driving voltage. The general formula (P) is described below. Note that the compounds represented by the general formula (P) below are distinguished from the pyrene derivative compounds represented by the general formula (p) preferably used as the light emitting material of the light emitting layer.

General Formula (P)

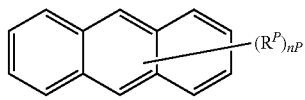

(In the general formula (P), $R^P$ represents an alkyl group (having preferably 1 to 8 carbon atoms), an aryl group (having preferably 6 to 30 carbon atoms), or a heteroaryl group (having preferably 4 to 12 carbon atoms), and these may have a substituent selected from the substituent group A. nP represents an integer of 1 to 10, and, when a plurality of $R^P$ exist, these may be the same or different. At least one $R^P$ is a substituent represented by the following general formulae (P-1) to (P-3).

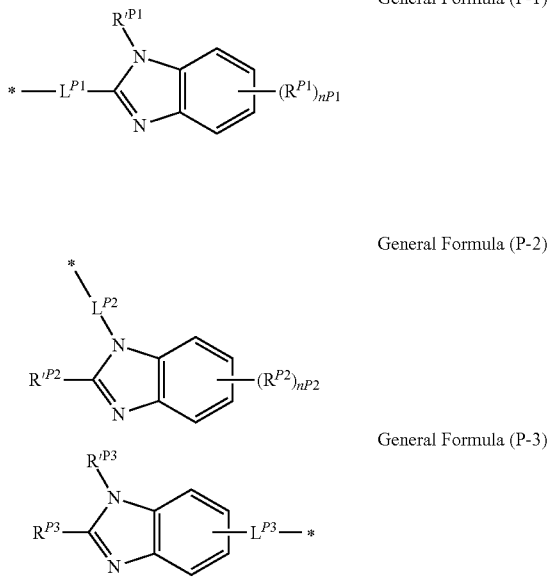

(In the general formulae (P-1) to (P-3), $R^{P1}$ to $R^{P3}$, and $R^{\prime P1}$ to $R^{\prime P3}$ each represent an alkyl group (having preferably 1 to 8 carbon atoms), an aryl group (having preferably 6 to 30 carbon atoms), or a heteroaryl group (having preferably 4 to 12 carbon atoms), and these may have a substituent selected from the substituent group A. $n^{P1}$ and $n^{P2}$ represent an integer of 0 to 4, and, when a plurality of $R^{P1}$ to $R^{P3}$ and a plurality of $R^{\prime P1}$ to $R^{\prime P3}$ exist, these may be the same or different. $L^{P1}$ to $L^{P3}$ represent single bonds, or divalent linking groups formed by aryl rings or heteroaryl rings. * represents the binding site for the anthracene ring of the general formula (P).)

Note that the $R^{P1}$ to $R^{P3}$ (P in capital letter) in the compounds represented by the general formula (P) are distinguished from the $R^{p1}$ to $R^{p3}$ (p in small letter) in the compounds represented by the general formula (p) preferably used as the light emitting material of the light emitting layer.

Preferred as substituents $R^P$ other than the substituents represented by (P-1) to (P-3) are aryl groups, more preferably any of phenyl groups, biphenyl groups, terphenyl groups, and naphthyl groups, further preferably naphthyl groups.

$R^{P1}$ to $R^{P3}$, and $R^{\prime P1}$ to $R^{\prime P3}$ are preferably aryl groups or heteroaryl groups, more preferably aryl groups, further preferably any of phenyl groups, biphenyl groups, terphenyl groups, and naphthyl groups, most preferably phenyl groups.

$L^{P1}$ to $L^{P3}$ are preferably single bonds, or divalent linking groups formed by aryl rings, more preferably any of single bonds, phenylene, biphenylene, terphenylene, and naphthylene, further preferably any of single bonds, phenylene, and naphthylene.

Specific examples of the compounds represented by the general formula (P) are given below. It should be noted, however, that the compounds represented by the general formula (P) that can be used in the present invention should not be narrowly construed as being limited to the following specific examples.
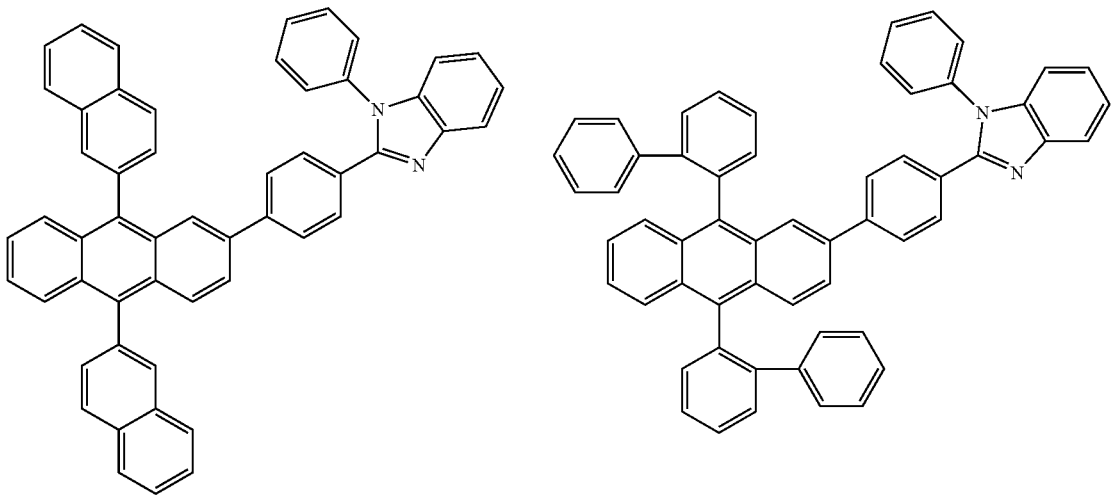
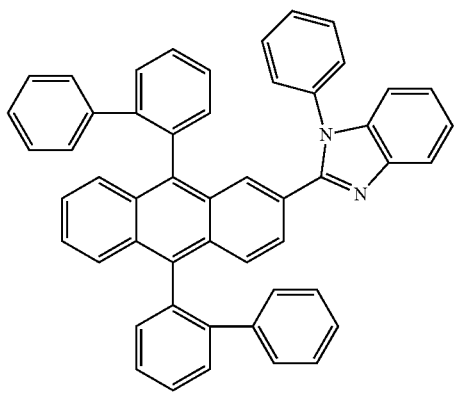
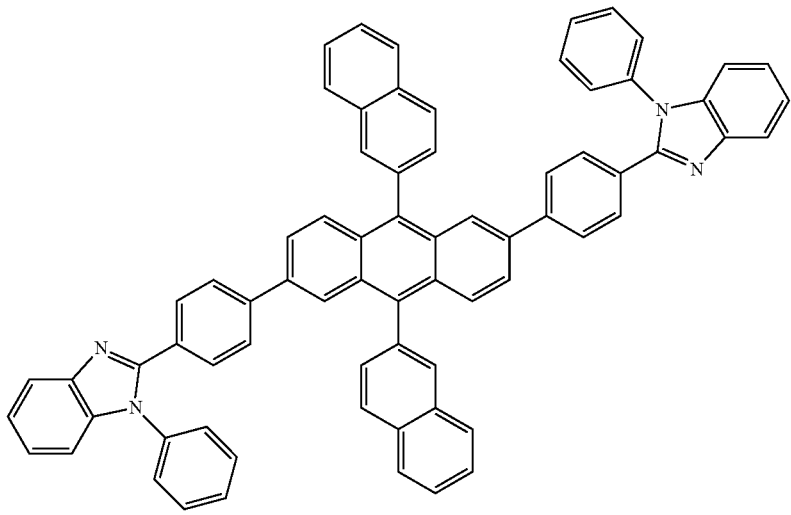

-continued
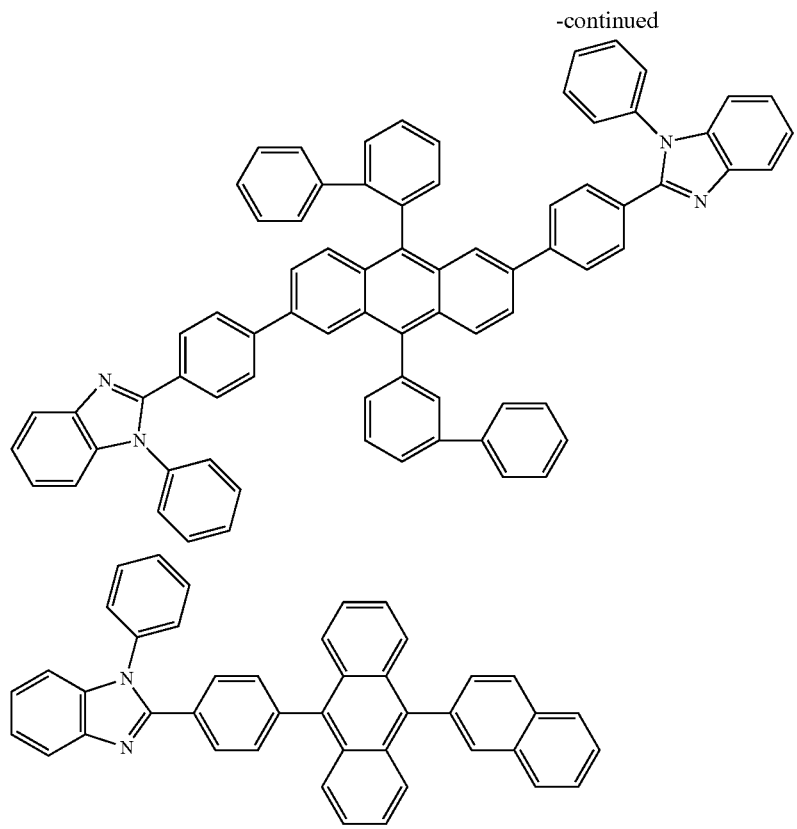
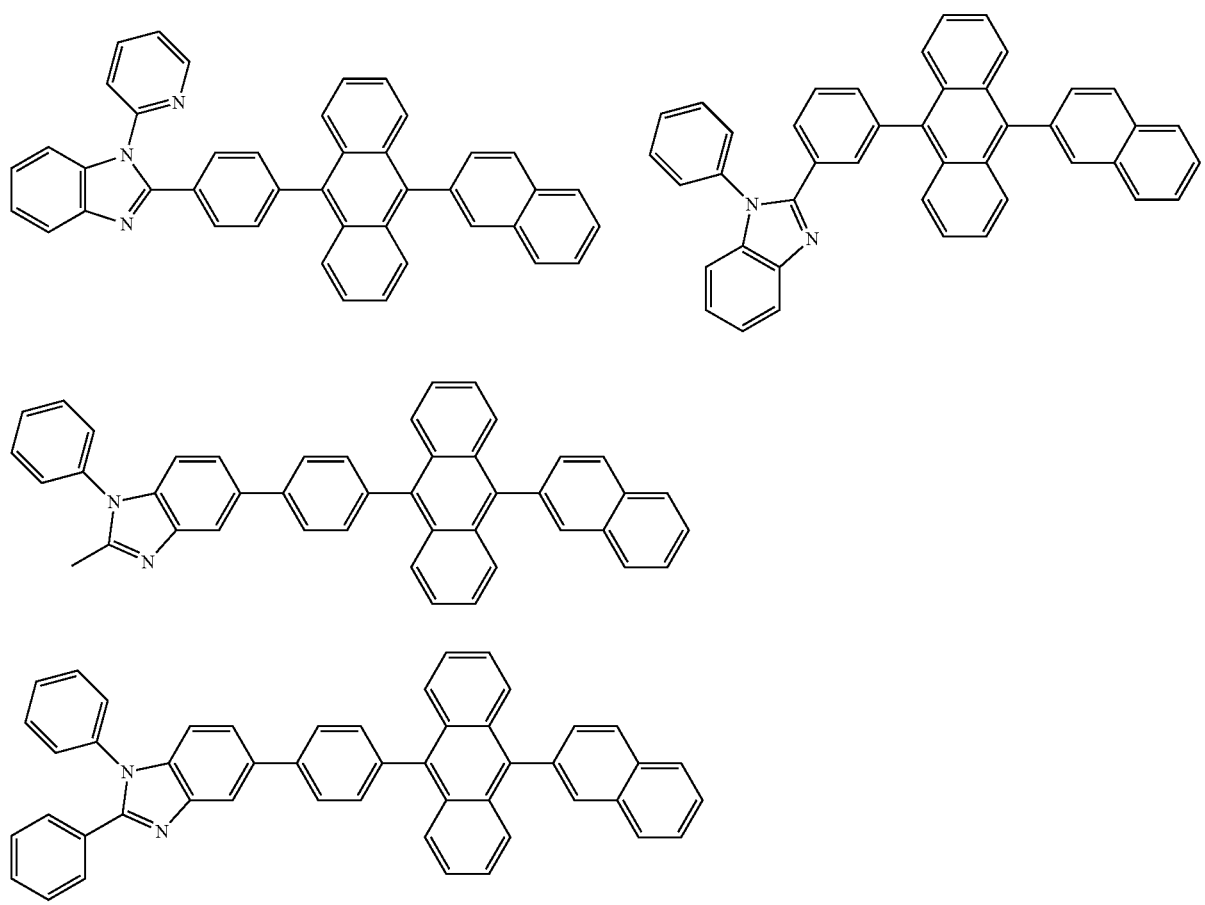

-continued

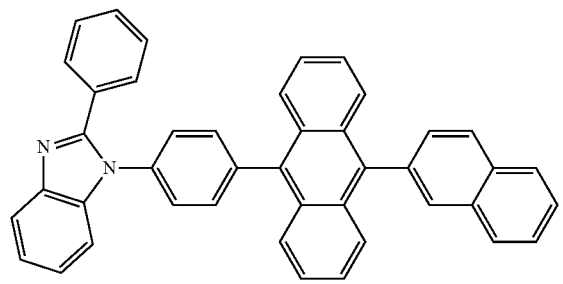
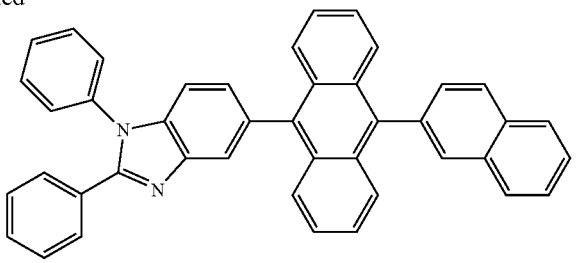

The compounds represented by the general formula (P) can be synthesized by using methods described in, for example, WO2003/060956, and WO2004/080975. After the synthesis, it is preferable that after performing purification by means of column chromatography, recrystallization, reprecipitation, or the like, purification is performed by means of sublimation purification. According to the sublimation purification, not only organic impurities can be separated, but inorganic salts, residual solvent, moisture, and the like can be effectively removed.

In the organic electroluminescent element according to the present invention, though the compound represented by the general formula (P) is preferably contained in the organic layer between the light emitting layer and the cathode, it is more preferably contained in the layer adjacent to the cathode.

The compounds represented by the general formula (P) are contained in preferably 70 to 100% by mass, more preferably 85 to 100% by mass with respect to the total mass of the organic layer added.

In the organic electroluminescent element of the present invention, other preferred examples of the materials for use in the electron injecting layer and the electron transporting layer include silole compounds described in, for example, JP-A-9-194487, phosphine oxide compounds described in, for example, JP-A-2006-73581, nitrogen-containing aromatic heterocyclic six-membered ring compounds described in, for example, JP-A-2005-276801, JP-A-2006-225320, and WO2005/085387, compounds having a nitrogen-containing aromatic heterocyclic six-membered structure and a carbazole structure as described in, for example, WO2003/080760, and WO2005/085387, and aromatic hydrocarbon compounds described in, for example, US2009/0009065, WO2010/134350, and JP-T 2010-535806 (the term "JP-T" as used herein means a published Japanese translation of a PCT patent application) (such as naphthalene compounds, anthracene compounds, triphenylene compounds, phenanthrene compounds, pyrene compounds, and fluoranthene compounds).

<Protective Layer>

In the present invention, the entirety of the organic electroluminescent element may be protected by a protective layer.

For the protective layer, the detailed description in paragraphs to [0170] of JP-A-2008-270736 can also be applied to the present invention. Incidentally, the materials for the protective layer may be either an inorganic material or an organic material.

<Sealing Enclosure>

For the organic electroluminescent element according to the present invention, the entirety of the element may be sealed using a sealing enclosure.

For the sealing enclosure, the detailed description in paragraph [0171] of JP-A-2008-270736 can be applied to the present invention.

<Driving Method>

The organic electroluminescent element according to the present invention can emit light by applying a direct current (it may include an alternate current component, if desired) voltage (usually from 2 volts to 15 volts) or a direct current between the anode and the cathode.

As a driving method of the organic electroluminescent element according to the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element according to the present invention is preferably 5% or more, more preferably 6% or more, further preferably 7% or more. As for the numerical value of the external quantum efficiency, a maximum value of the external quantum efficiency obtained when the organic electroluminescent element is driven at 20° C., or a value of the external quantum efficiency in the vicinity of from 300 to 400 cd/m$^2$ obtained when the element is driven at 20° C. can be employed.

The internal quantum efficiency of the organic electroluminescent element according to the present invention is preferably 30% or more, more preferably 50% or more, and still more preferably 70% or more. The internal quantum efficiency of the element is calculated by dividing the external quantum efficiency by the light extraction efficiency. Though the light extraction efficiency in usual organic EL elements is about 20%, by taking into consideration the shape of a substrate, the shape of an electrode, the film thickness of an organic layer, the film thickness of an inorganic layer, the refractive index of an organic layer, the refractive index of an inorganic layer, or the like, it is possible to increase the light extraction efficiency to 20% or more.

<Light Emitting Wavelength>

In the organic electroluminescent element according to the present invention, its light emitting wavelength is not limited, but the organic electroluminescent element is preferably used for blue or white emission. Preferably, the organic electroluminescent element of the present invention uses the compounds represented by the general formula (1) as light emitting material for emission, particularly for blue emission.

<Use of Organic Electroluminescent Element According to the Present Invention>

The organic electroluminescent element according to the present invention can be suitably used for display elements, displays, backlights, electrophotography, illumination light sources, recording light sources, exposure light sources, readout light sources, signs, billboards, interior decorations, optical communications, and the like. In particular, it is preferably used for devices to be driven in a region of high-intensity luminescence, such as a light emitting device, an illumination device, and a display device.

[Light Emitting Device]

The light emitting device according to the present invention comprises the organic electroluminescent element according to the present invention.

Next, the light emitting device according to the present invention is described with reference to FIG. 2.

The light emitting device of the present invention uses the organic electroluminescent element.

Figure 2:
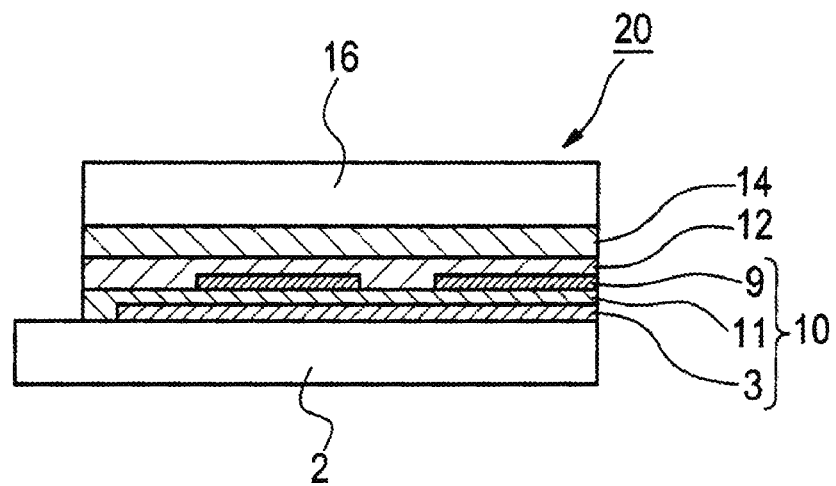
FIG. 2 is a schematic view showing one example of the light emitting device according to the present invention.

FIG. 2 is a cross-sectional view schematically showing one example of the light emitting device according to the present invention. A light emitting device 20 in FIG. 2 is constituted of a transparent substrate 2 (supporting substrate), an organic electroluminescent element 10, a sealing enclosure 16, and the like.

The organic electroluminescent element 10 is constituted by laminating an anode 3 (first electrode), an organic layer 11, and a cathode 9 (second electrode) in this order on the substrate 2. In addition, a protective layer 12 is laminated on the cathode 9, and a sealing enclosure 16 is further provided on the protective layer 12 via an adhesive layer 14. Incidentally, a part of each of the electrodes 3 and 9, a diaphragm, an insulating layer, and the like are omitted in FIG. 2.

Here, a photocurable adhesive such as an epoxy resin, or a thermosetting adhesive can be used for the adhesive layer 14, and for example, a thermosetting adhesive sheet can also be used as the adhesive layer 14.

The light emitting device according to the present invention is not particularly limited in its use, and it can be used as not only an illumination device but a display device of a television set, a personal computer, a mobile phone, electronic paper, or the like.

[Illumination Device]

The illumination device according to the present invention comprises the organic electroluminescent element according to the present invention.

Next, the illumination device according to the present invention is described with reference to FIG. 3.

Figure 3:
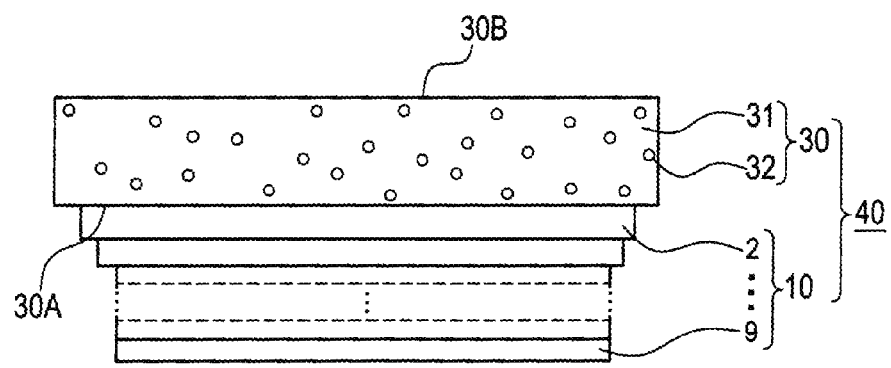
FIG. 3 is a schematic view showing one example of the illumination device according to the present invention.

FIG. 3 is a cross-sectional view schematically showing one example of the illumination device according to the present invention. As shown in FIG. 3, an illumination device 40 according to the present invention is provided with the above-described organic EL element 10 and a light scattering member 30. More specifically, the illumination device 40 is configured in such a manner that the substrate 2 of the organic EL element 10 and the light scattering member 30 are brought in contact with each other.

Though the light scattering member 30 is not particularly limited so far as it is able to scatter light, a member obtained by dispersing fine particles 32 in a transparent substrate 31 is used in FIG. 3. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is made incident onto a light incident surface 30A of the scattering member 30, the incident light is scattered by the light scattering member 30, and the scattered light is outputted as illuminating light from a light outputting surface 30B.

[Display Device]

The display device according to the present invention comprises the organic electroluminescent element according to the present invention.

The display device according to the present invention can be used for, for example, a display device of a television set, a personal computer, a mobile phone, electronic paper, or the like.

EXAMPLES

The characteristic features of the present invention are hereunder described in more detail with reference to the following Examples and Comparative Examples. The materials, use amounts, ratios, treatment details, treatment procedures, and the like shown in the following Examples can be appropriately modified so far as the gist of the present invention is not deviated. Accordingly, it should not be construed that the scope of the present invention is limited to the specific examples shown below.

Example 1

A compound (H-1) was synthesized according to the following scheme.

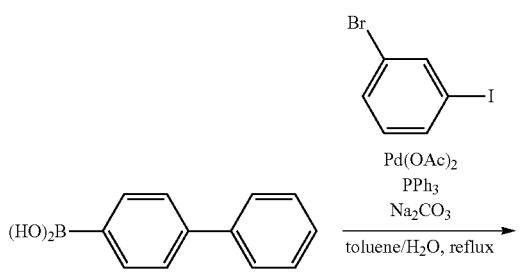

-continued
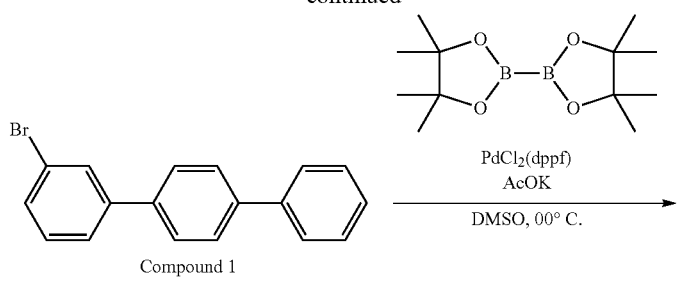
Compound 1
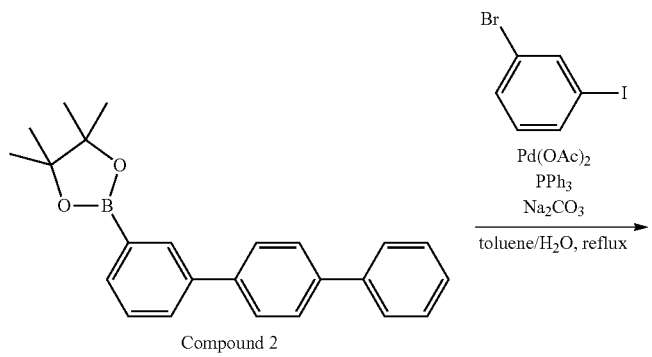
Compound 2
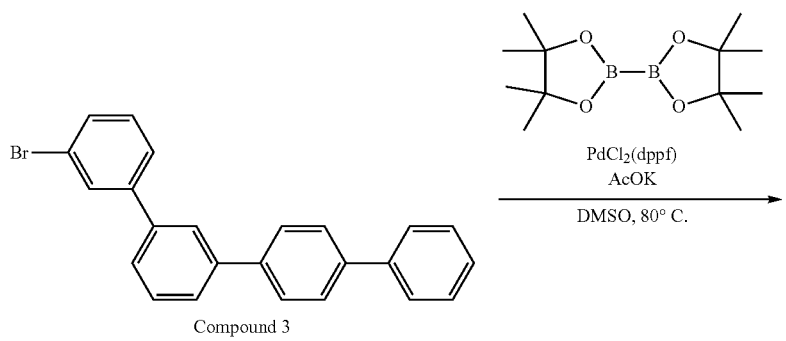
Compound 3
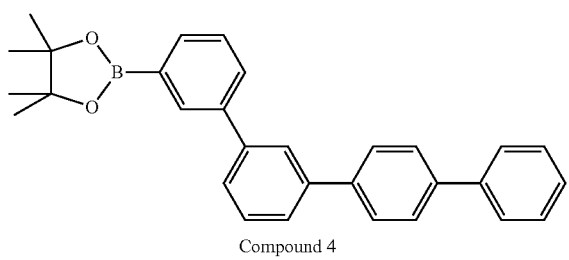
Compound 4
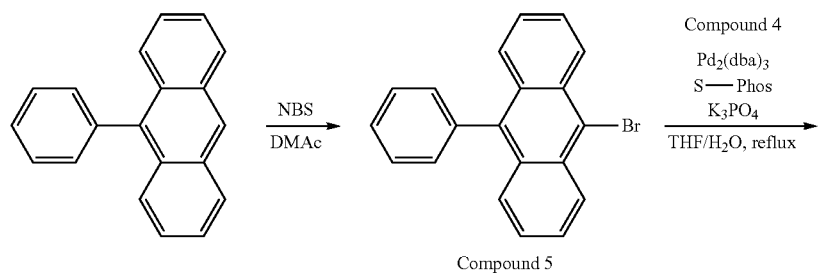
Compound 5

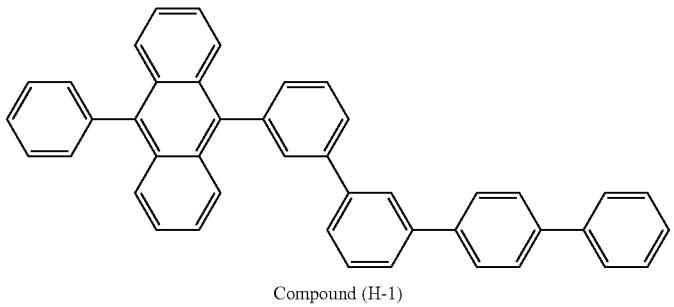 [SMILES: c1ccc(-c2ccc(-c3cccc(-c4cccc(-c5c6ccccc6c(-c6ccccc6)c6ccccc56)c4)c3)cc2)cc1]

Compound (H-1)

Sodium carbonate (171 g, 1.61 mol), 1-bromo-3-iodobenzene (77.3 mL, 806 mmol), toluene (400 mL), and water (800 mL) were charged into a 2-L three-neck flask, and were stirred at room temperature. The mixture was deaerated, and purged with nitrogen, and triphenylphosphine (21.2 g, 80.8 mmol), 4-biphenylboronic acid (80.0 g, 404 mmol), and palladium acetate (4.53 g, 20.2 mmol) were added. The reaction mixture was then refluxed and stirred under the nitrogen atmosphere for 7 hours. Then, the mixture was cooled to room temperature and ice-cooled. The precipitated solid was filtered, and washed with water and methanol to obtain compound 1 as a white solid (104 g).

The compound 1 (104 g, 336 mmol), bis(pinacolato)diboron (102 g, 402 mmol), potassium acetate (98.7 g, 1.01 mol), and anhydrous dimethylsulfoxide (1,000 mL) were added to a 2-L three-neck flask, and were stirred at room temperature. The mixture was deaerated, and purged with nitrogen, and a 1,1'-[bis(diphenylphosphino) ferrocene]dichloropalladium-.dichloromet bane adduct (13.7 g, 16.8 mmol) was added. The reaction mixture was stirred at 80° C. for 8 hours. Ice water (2,000 ml) was added after cooling the mixture to room temperature, and the mixture was extracted with ethyl acetate to concentrate the organic layer under reduced pressure. The product was then purified by column chromatography (silica gel, toluene) to obtain a compound 2 as a pale grey solid (44.0 g).

The compound 2 (44.0 g), 1-bromo-3-iodobenzene (23.6 mL), sodium hydroxide (14.9 g), toluene (220 mL), and water (220 mL) were added to a 2-L three-neck flask, and were stirred at room temperature. The mixture was deaerated, and purged with nitrogen, and triphenylphosphine (6.5 g), and palladium acetate (1.39 g) were added. The reaction mixture was refluxed and stirred under the nitrogen atmosphere for 6 hours. The mixture was cooled to room temperature, and stirred overnight. The precipitated solid was collected by filtration, and washed with water and methanol to obtain a compound 3 as a colorless solid (37.2 g).

The compound 3 (34 g), bis(pinacolato)diboron (34 g), potassium acetate (33 g), and anhydrous dimethylsulfoxide (350 mL) were charged into a 2-L three-neck flask, and the mixture was stirred at room temperature. The mixture was deaerated, and purged with nitrogen, and a 1,1'-[bis(diphenylphosphino) ferrocene]dichloropalladium.dichloromethane adduct (4.57 g) was added. The reaction mixture was stirred at 80° C. for 8 hours. The mixture was cooled to room temperature, and ice water (1,000 ml) was added. The mixture was then extracted with ethyl acetate to concentrate the organic layer under reduced pressure. The product was purified by column chromatography (silica gel, toluene) to obtain a compound 4 as a pale grey solid (20.0 g).

9-Phenylanthracene (46 g), and dimethylsulfoxide (500 ml) were charged into a 2-L three-neck flask, and the mixture was stirred for 1 hour after dropping an N-bromosuccinimide (36.18 g)/dimethylsulfoxide (190 ml) solution under a stream of nitrogen. The mixture was stirred at 38° C. for 2 hours, and brought back to room temperature. The mixture was then stirred for 2 hours after adding distilled water (500 ml), followed by filtration and washing with distilled water. The resulting yellow powder was transferred to a 1-L eggplant flask, and stirred under heat after adding methanol (600 ml). After being brought to room temperature, the mixture was washed with methanol, and dried to obtain a compound 5 as a yellow powder (60.5 g).

Figure 4:
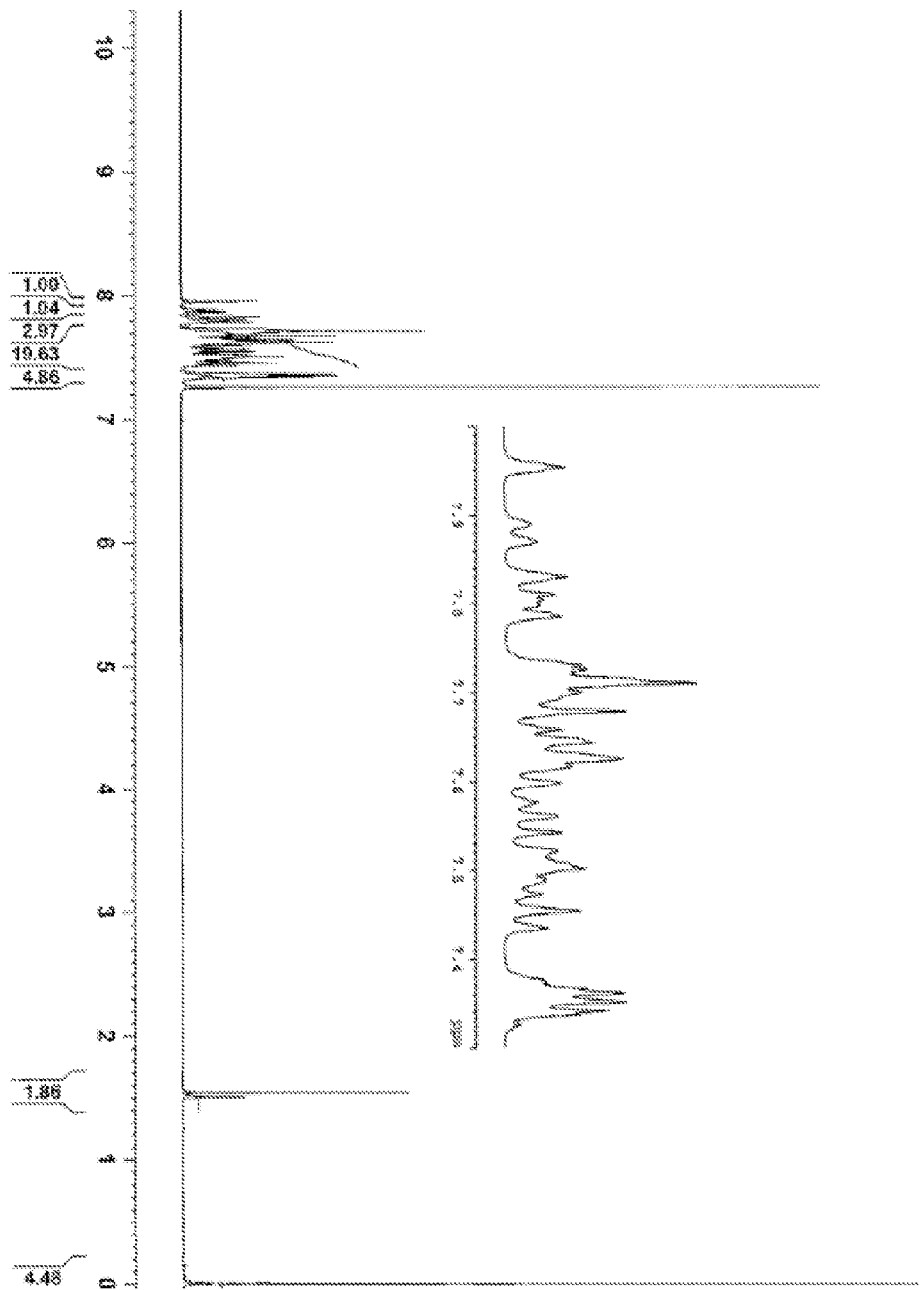
FIG. 4 is a $^1$H-NMR spectrum of the compound (H-1) of the present invention at 400 MHz.

Potassium triphosphate (3.82 g), the compound 5 (2.0 g), tetrahydrofuran (20 ml), and distilled water (10 ml) were added to a 100-ml three-neck flask, and were stirred at room temperature. Thereafter, S-Phos (0.296 g), the compound 4 (3.11 g), and $Pd_2(dba)_3$ (165 mg) were added, and the mixture was refluxed under heat for 14 hours after being deaerated and purged with nitrogen. After the reaction, toluene (20 ml) was added, and the aqueous layer was removed. The organic layer was concentrated under reduced pressure. The precipitate produced upon bringing the mixture to room temperature was filtered, and washed with methanol. After dissolving the precipitate again in THF, the organic layer was concentrated under reduced pressure after adding toluene. The precipitate produced upon bringing the mixture to room temperature was filtered, washed with methanol, and dried to obtain a white solid (3.12 g). The solid was subjected to sublimation purification to obtain a compound (H-1). The compound was identified by $^1$H-NMR at 400 MHz. The $^1$H-NMR spectrum of the synthesized compound (H-1) is shown in FIG. 4.

Examples 2 to 11
The following compounds (H-2) to (H-14) were synthesized by using the same method used for the compound (H-1).
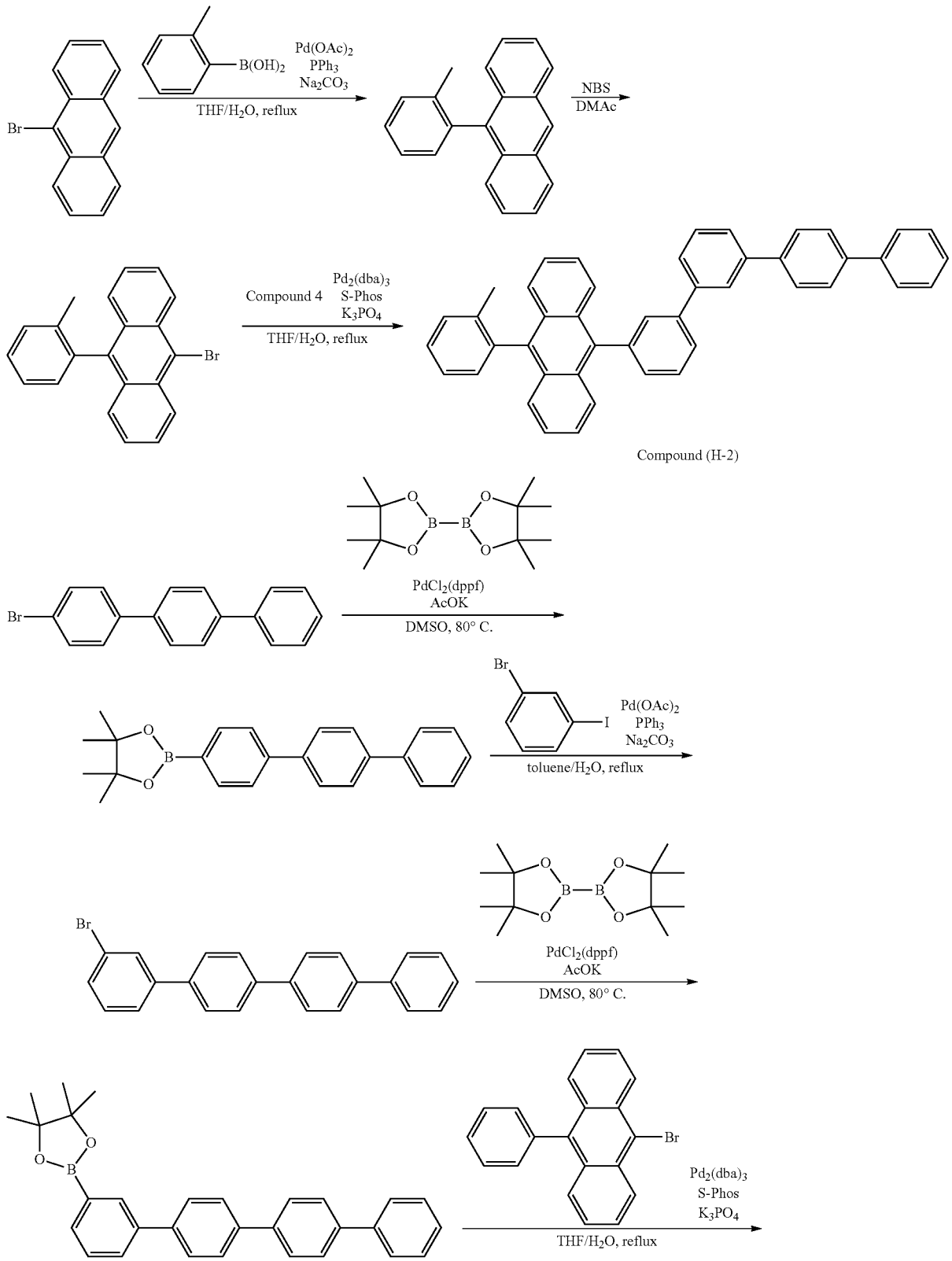

-continued
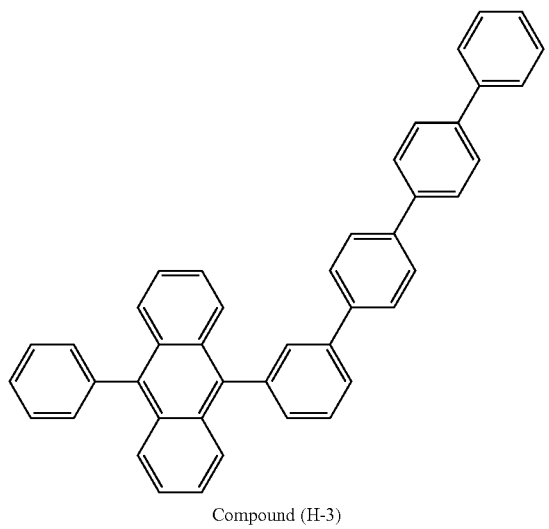
Compound (H-3)
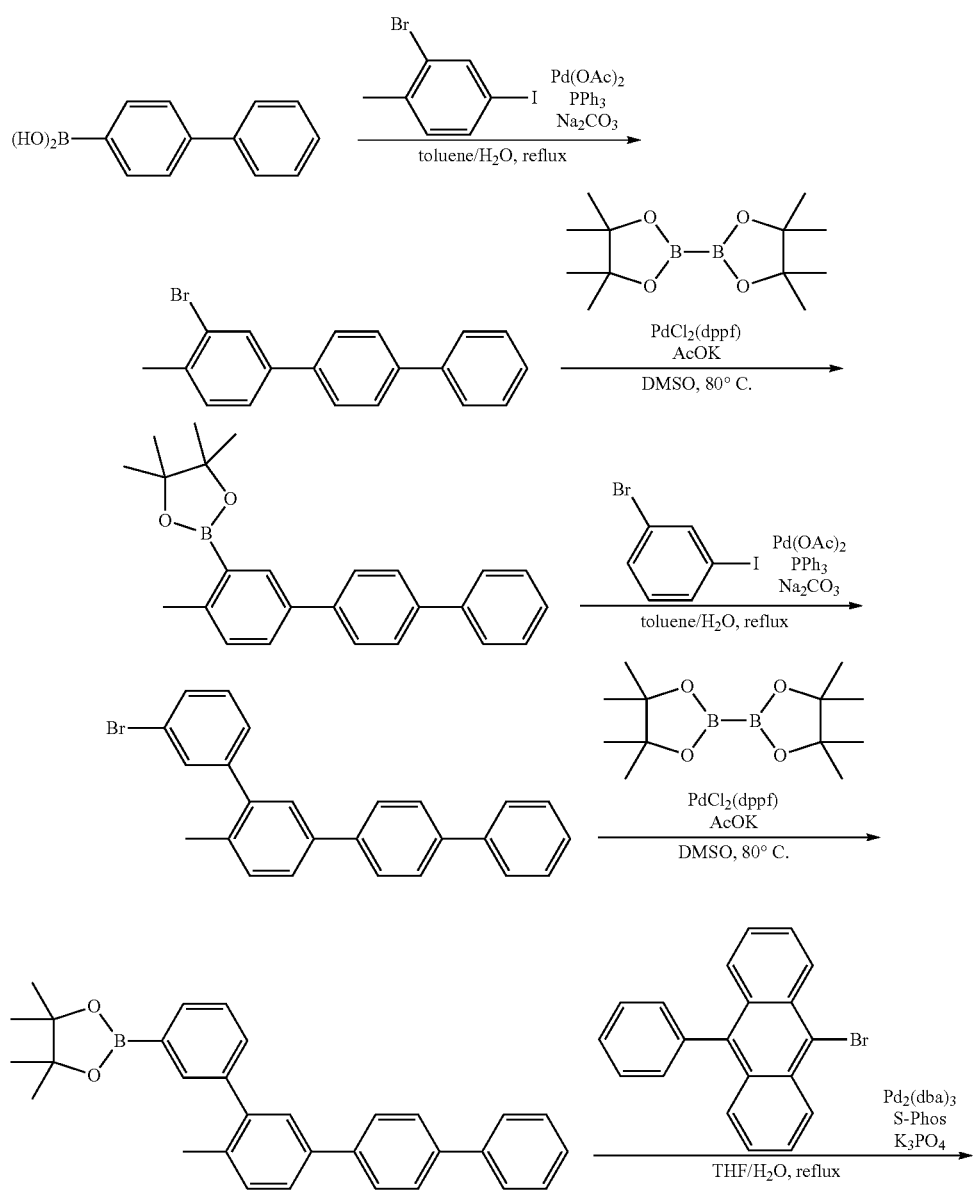

-continued
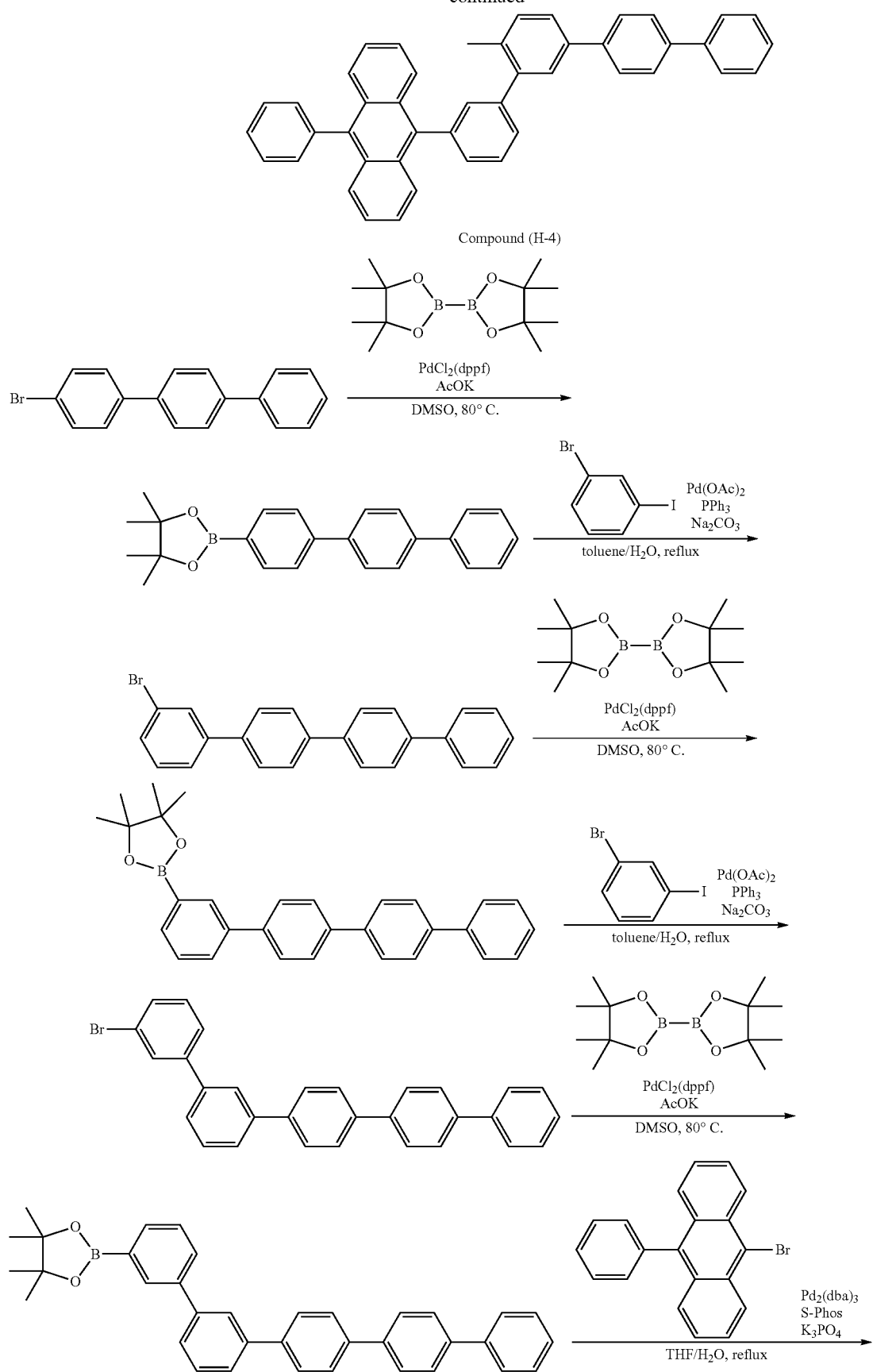
Compound (H-4)

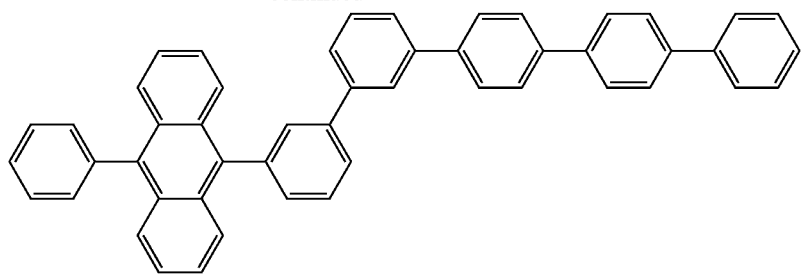
Compound (H-5)
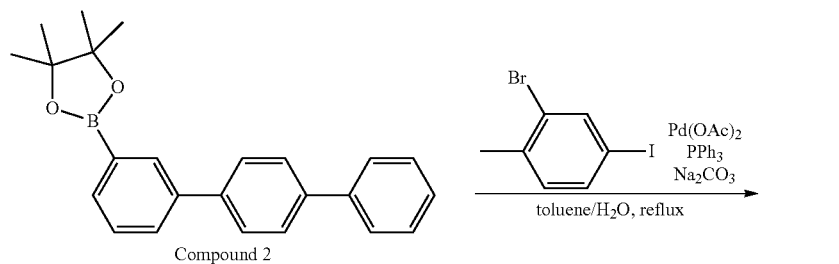
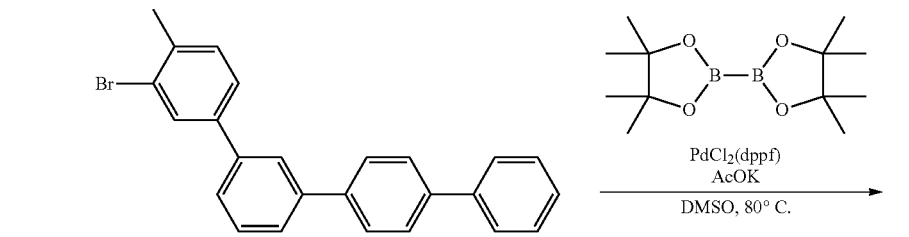
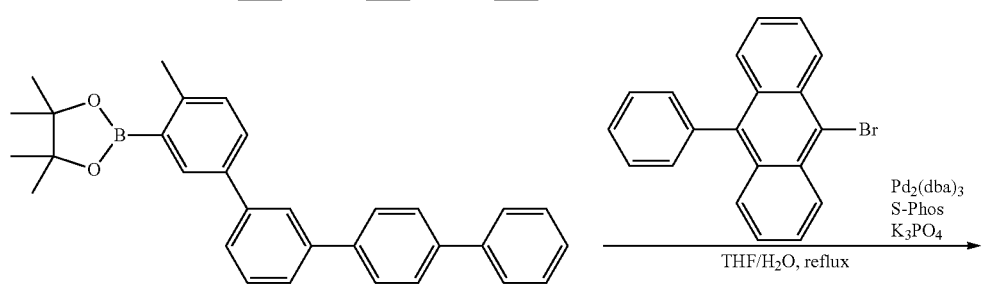
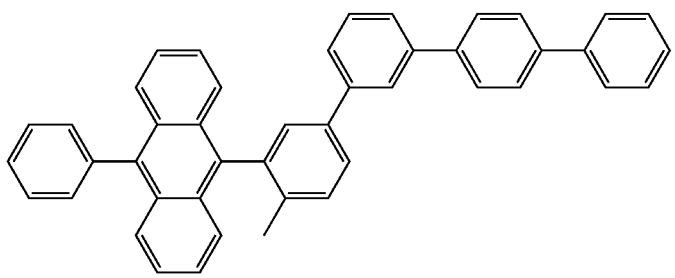
Compound (H-6)
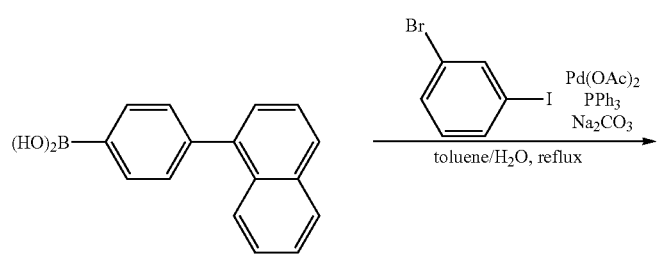

-continued
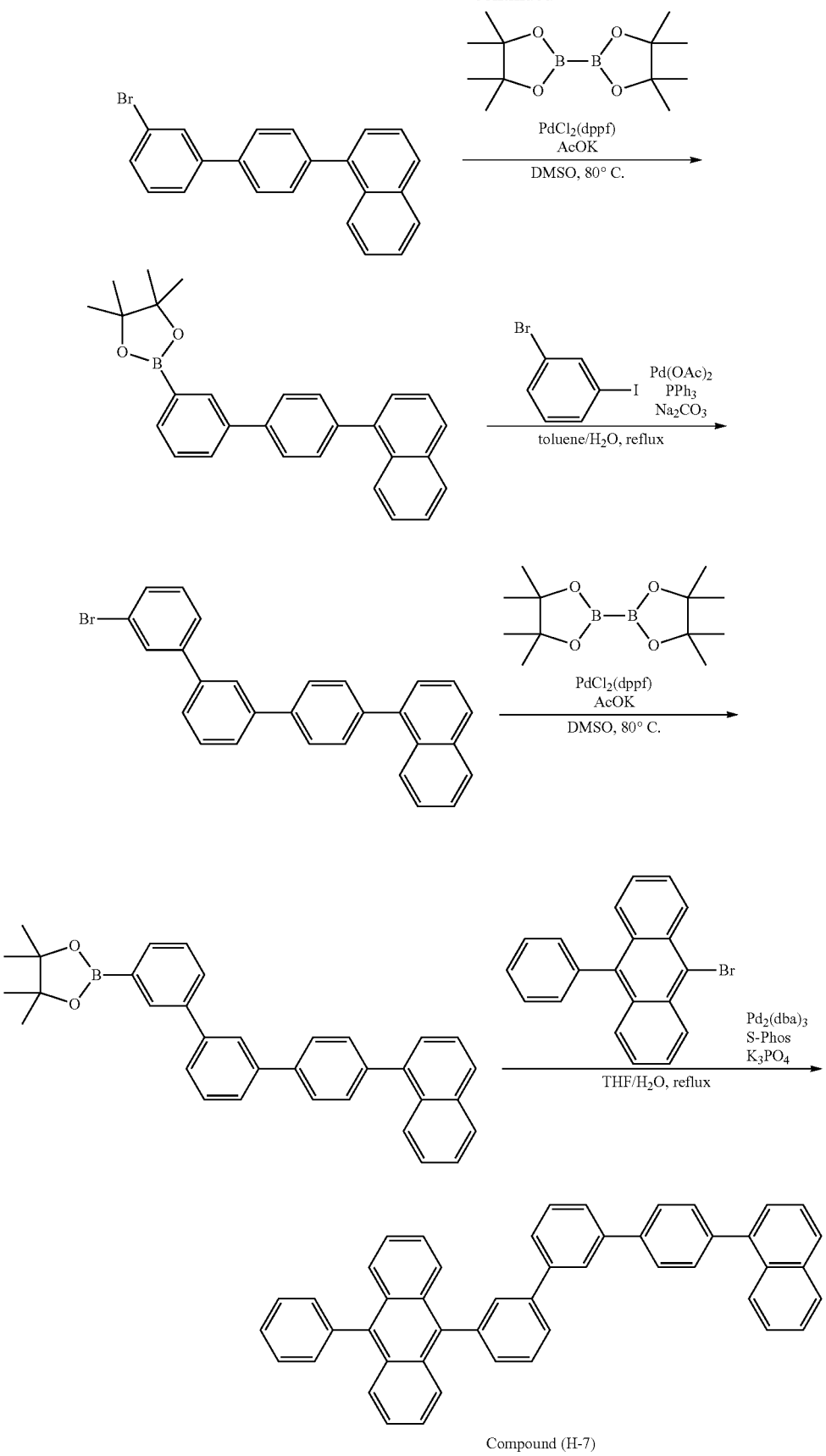
Compound (H-7)

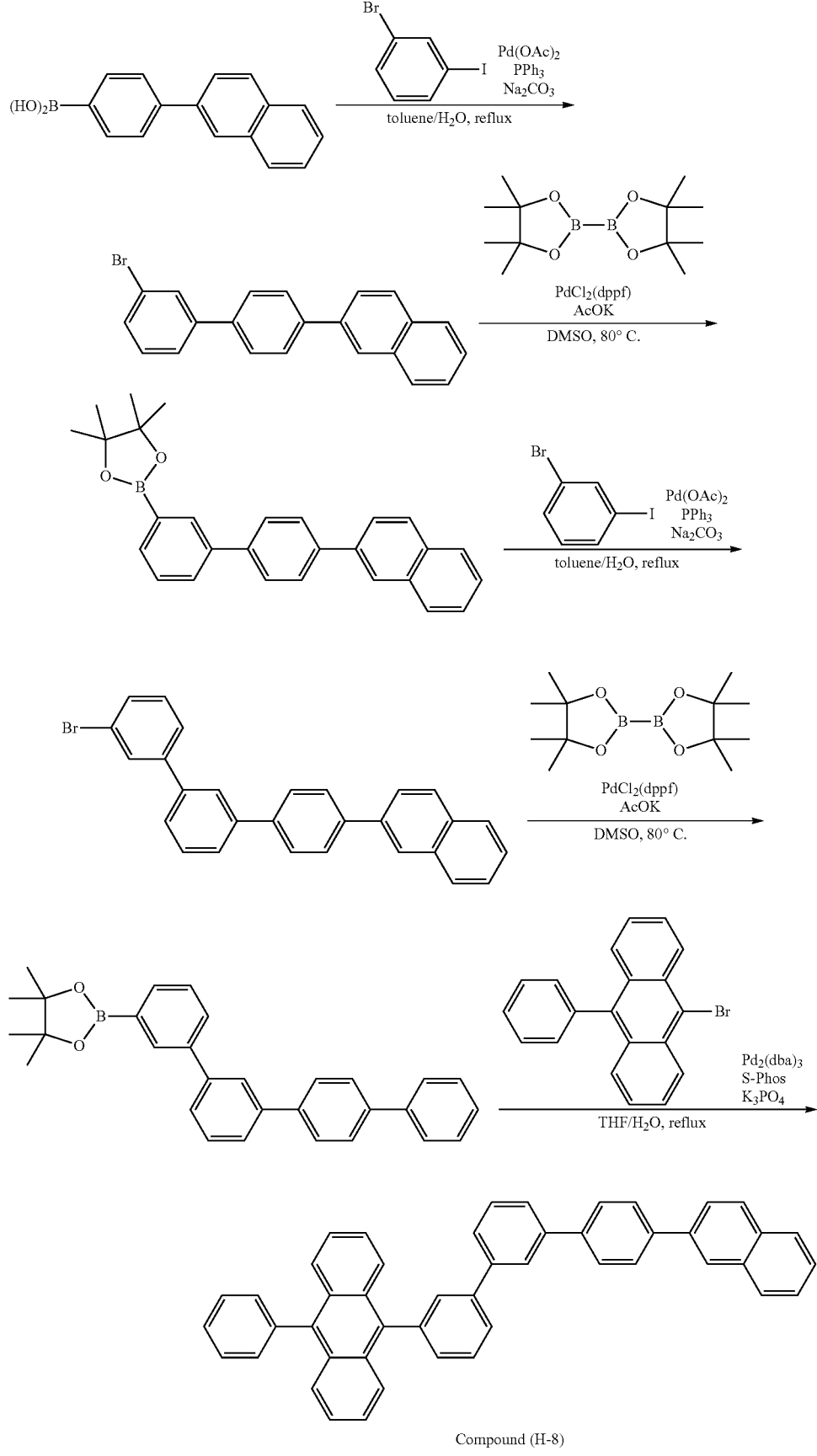
Compound (H-8)

-continued
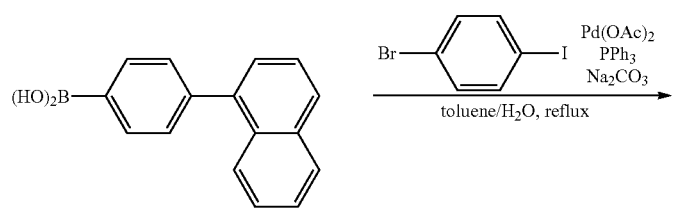
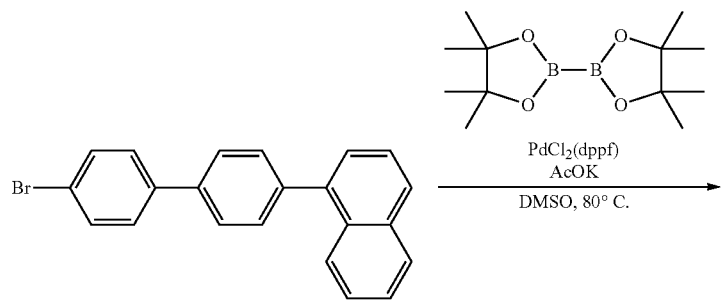
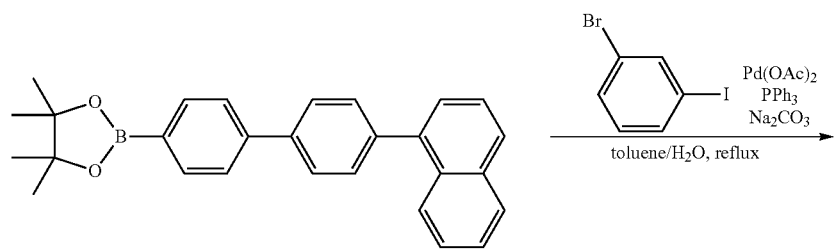
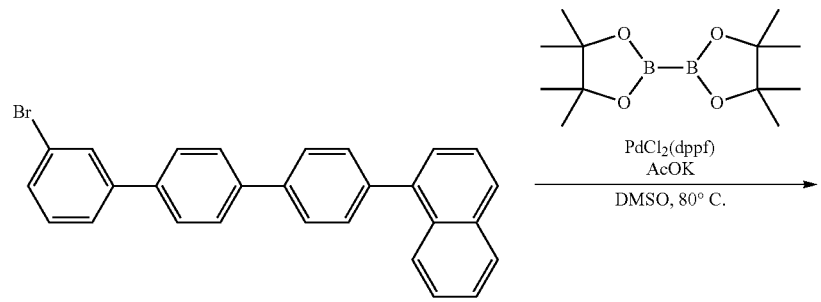
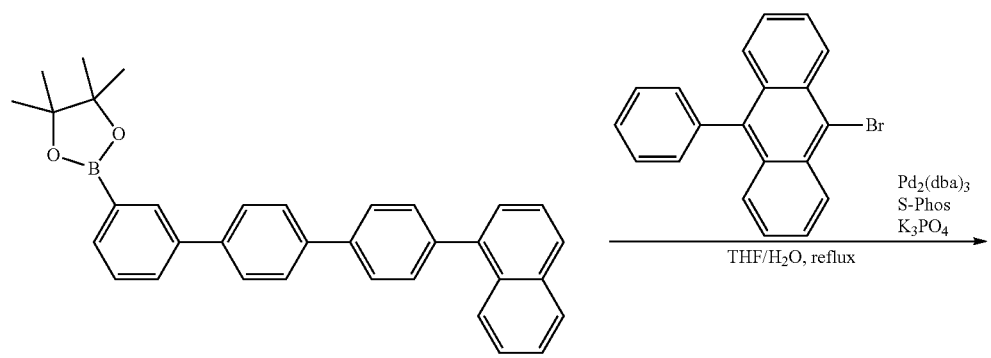

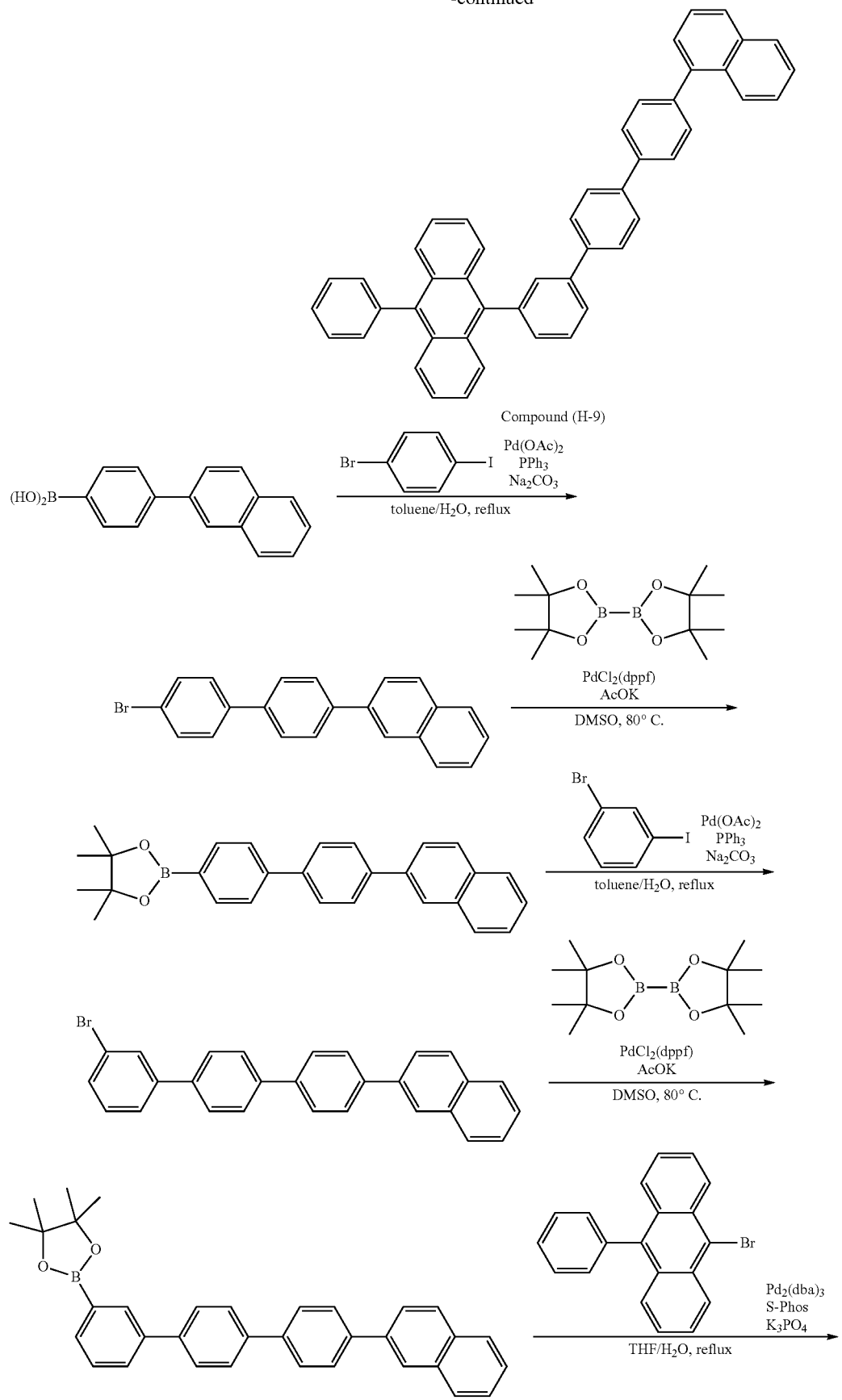

-continued
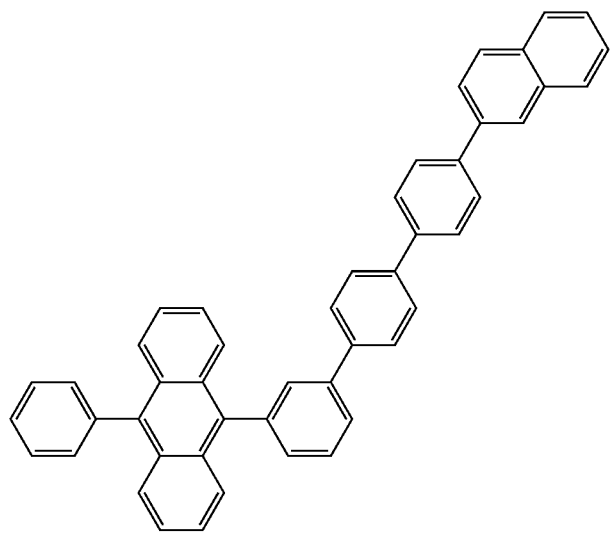
Compound (H-10)
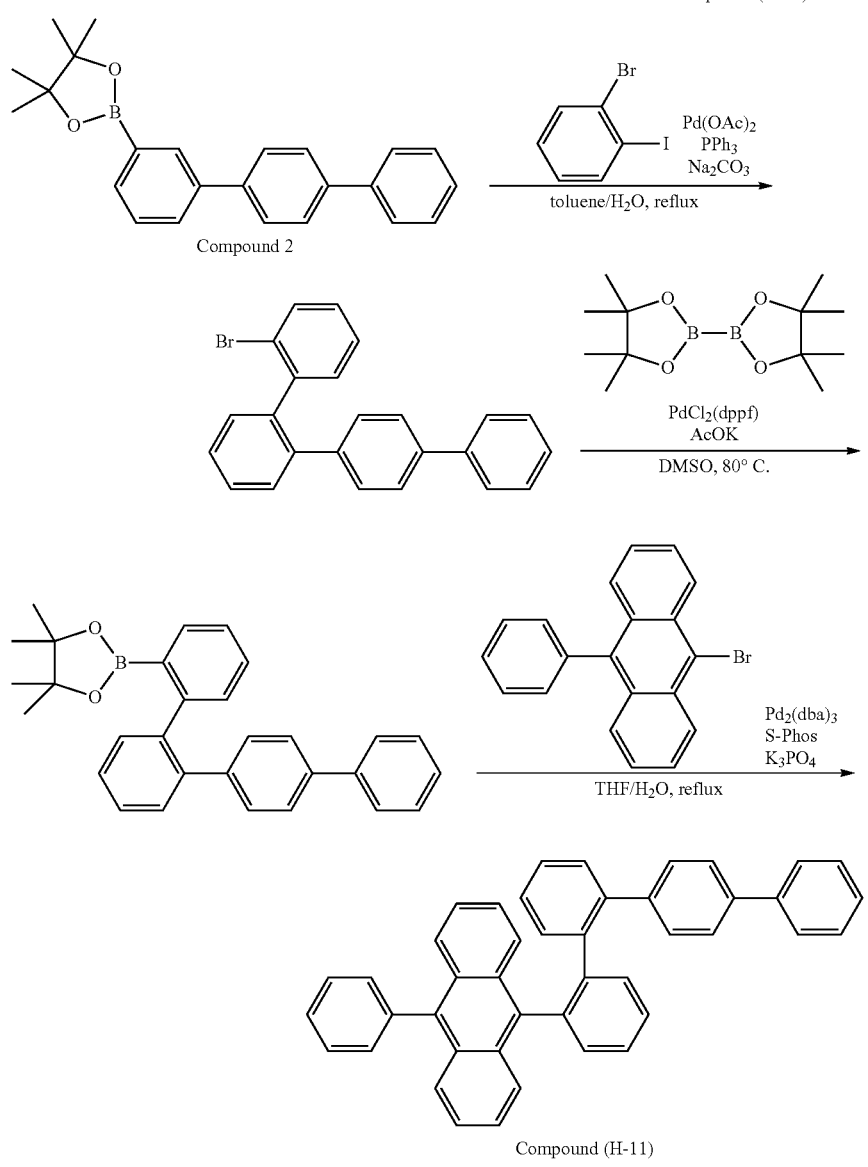
Compound (H-11)

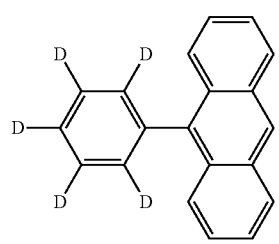
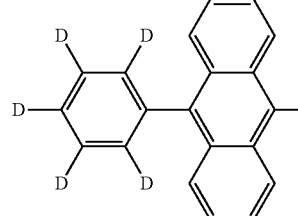
Compound (H-12)
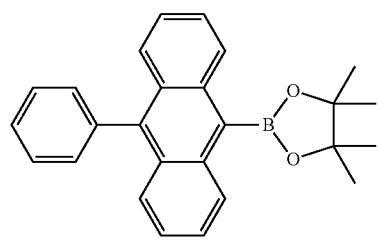
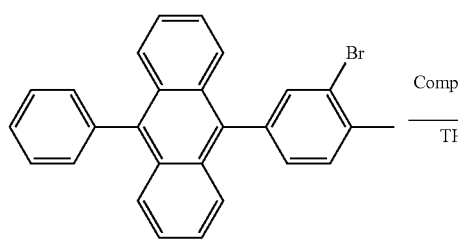
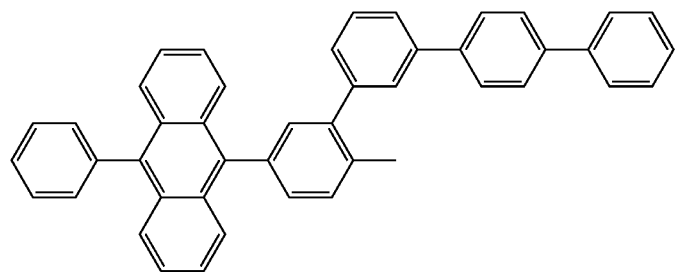
Compound (H-13)
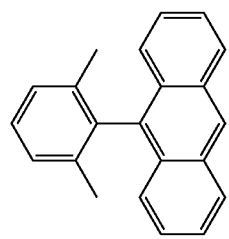

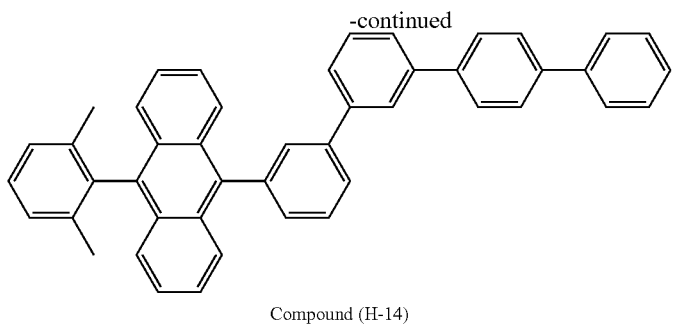

Compound (H-14)

<Evaluation of Material Physical Properties>
(Light Emitting Wavelength)

The compounds (H-1) to (H-14) of the present invention and compound D-2 (light emitting material; described later) were deposited on a quartz glass substrate (thickness: 0.7 mm, 2.5 cm square) in a 95:5 mass ratio by using a vacuum deposition method. As a result, a 50 nm-thick thin film was formed. The film was irradiated with 350-nm UV light, and the luminous spectrum of the emitted light was measured with a fluorescence spectrometer (JASCO Corporation; FP-6300) to read the maximum light emitting wavelength (nm).

Table 1 presents the results of the evaluation, using the following criteria.
Good: 435 nm or more and less than 455 nm
Acceptable: less than 435 nm
Poor: 455 nm or more

TABLE 1

| Host material | Light emitting material | Light emitting wavelength | Remarks |
|---|---|---|---|
| Compound (H-1) | Compound D-2 | Good | Present invention |
| Compound (H-2) | Compound D-2 | Good | Present invention |
| Compound (H-3) | Compound D-2 | Good | Present invention |
| Compound (H-4) | Compound D-2 | Good | Present invention |
| Compound (H-5) | Compound D-2 | Good | Present invention |
| Compound (H-6) | Compound D-2 | Good | Present invention |
| Compound (H-7) | Compound D-2 | Good | Present invention |
| Compound (H-8) | Compound D-2 | Good | Present invention |
| Compound (H-9) | Compound D-2 | Good | Present invention |
| Compound (H-10) | Compound D-2 | Good | Present invention |
| Compound (H-11) | Compound D-2 | Good | Present invention |
| Compound (H-12) | Compound D-2 | Good | Present invention |
| Compound (H-13) | Compound D-2 | Good | Present invention |
| Compound (H-14) | Compound D-2 | Good | Present invention |
| Comparative compound (1) | Compound D-2 | Good | Comparative example |
| Comparative compound (2) | Compound D-2 | Good | Comparative example |
| Comparative compound (3) | Compound D-2 | Good | Comparative example |
| Comparative compound (4) | Compound D-2 | Good | Comparative example |
| Comparative compound (5) | Compound D-2 | Good | Comparative example |
| Comparative compound (6) | Compound D-2 | Good | Comparative example |
| Comparative compound (7) | Compound D-2 | Good | Comparative example |
| Comparative compound (8) | Compound D-2 | Good | Comparative example |
| Comparative compound (9) | Compound D-2 | Good | Comparative example |

Example 101

Fabrication and Evaluation of Element

A glass substrate having an ITO film measuring 0.5 mm in thickness and 2.5 cm square in size (Geomatec Co., Ltd.; surface resistance 10Ω/□) was placed in a washing container. After ultrasonic washing in 2-propanol, the substrate was UV-ozone treated for 30 min. The following organic compound layers were deposited in order on the transparent anode (ITO film), using a vacuum deposition method.

First layer: HAT-CN; thickness 10 nm

Second layer: HTM-1; thickness 30 nm

Third layer: Compound (H-1) and compound (D-1) (mass ratio 95:5); thickness 30 nm Fourth layer: ETM-1; thickness 30 nm Then, lithium fluoride (1 nm) and metallic aluminum (100 nm) were deposited thereon in this order to make a cathode.

The resulting laminate was put in a glove box purged with a nitrogen gas without bringing it into contact with the atmosphere and then sealed with a sealing can made of glass and an ultraviolet ray-curable adhesive (XNR5516HV, manufactured by Nagase-CIBA Ltd.). As a result, organic electroluminescent elements 1 to 10 having a square light emitting portion (2 mm×2 mm), and comparative organic electroluminescent elements 1 to 5 were obtained. Each organic electroluminescent element was tested, as follows. Table 2 presents the results of the evaluation conducted for luminous efficiency, color purity, and changes in drive chromaticity.

Hole Injecting Layer (First Layer)

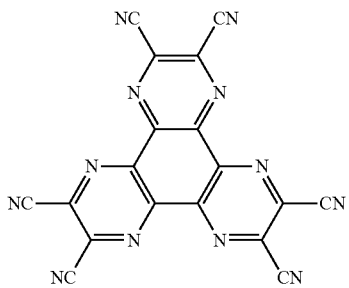
HAT-CN

Hole Transporting Material (Second Layer)

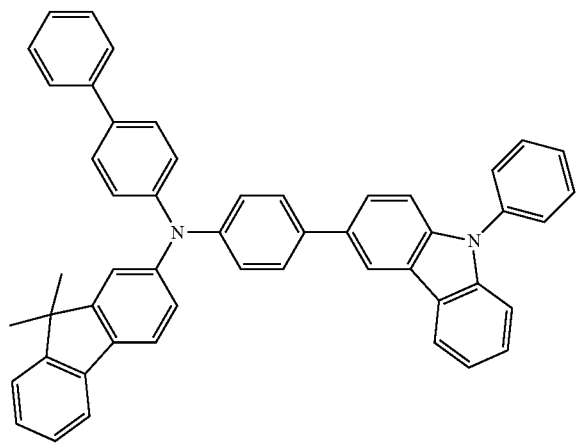
HTM-1

Light Emitting Layer Material (Third Layer)

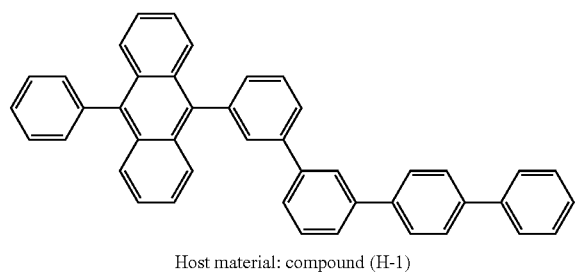
Host material: compound (H-1)

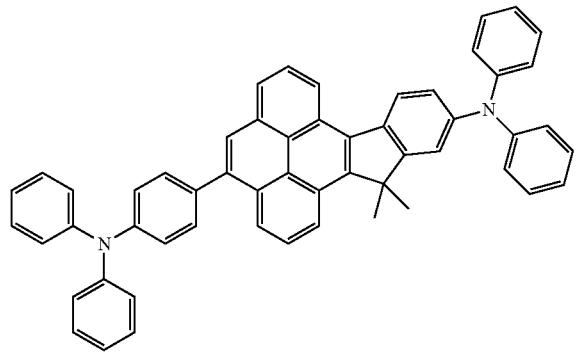
Light emitting material: compound (D-1)

Electron Transporting Material (Fourth Layer)

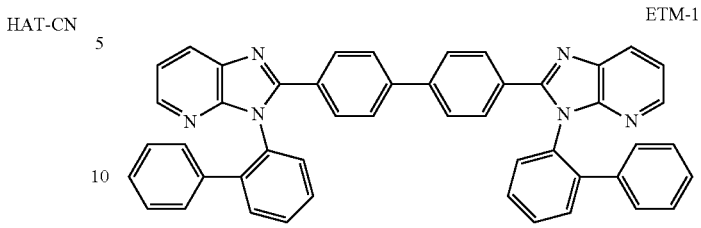
ETM-1

(b) Color Purity

Chromaticity (x, y) was determined from the luminous spectrum of each organic electroluminescent element emitting light at a luminance of 1,000 cd/m² (CIE1931 color system). The y values were evaluated according to the following criteria. The results are presented in Table 2.
Excellent: less than 0.10
Good: 0.10 or more and less than 0.12
Poor: 0.12 or more and less than 0.15

(a) Luminous Efficiency

A direct current voltage was applied to each of the elements by using a source measure unit 2400, manufactured by Toyo Corporation to allow the organic electroluminescent element to emit light. The luminance was measured by a luminance meter BM-8, manufactured by Topcon Corporation. The luminous spectrum and the light emitting wavelength were measured by a spectrum analyzer PMA-11, manufactured by Hamamatsu Photonics K.K. On the basis of these values, the external quantum efficiency ($\eta$) at a luminance in the vicinity of 1,000 cd/m² was calculated by a luminance conversion method. The results are presented in Table 2.
Excellent: external quantum efficiency of 4.5% or more
Good: external quantum efficiency of 4.0% or more and less than 4.5%
Acceptable: external quantum efficiency of 3.0% or more and less than 3.5%
Poor: external quantum efficiency of less than 3.0%

For practical applications, the external quantum efficiency needs to be either Good or Excellent.

(c) Durability (Luminance Deterioration at Initial Stage of Lighting)

A direct current voltage was applied at room temperature (20° C.) to each of the elements to continuously emit light such that the luminance reached 500 cd/m², and a time required until the luminance reached 475 cd/m² was defined as an index of durability (luminance deterioration at the initial stage of lighting). The results are presented in Table 2.
Excellent: 60 hours or more
Good: 40 hours or more and less than 60 hours
Acceptable: 20 hours or more and less than 40 hours
Poor: 0 hour or more and less than 20 hours For practical applications, the luminance deterioration at the initial stage of lighting needs to be either Good or Excellent.

Examples 102 to 114, and Comparative Examples 101 to 109

Organic electroluminescent elements of Examples 102 to 114, and Comparative Examples 101 to 109 were produced in the same manner as in Example 101, except that the following host materials were used for the light emitting layer. The organic electroluminescent element of each Example and Comparative Example was evaluated in the same manner as in Example 101. The results are presented in Table 2.

Comparative Compound (1)
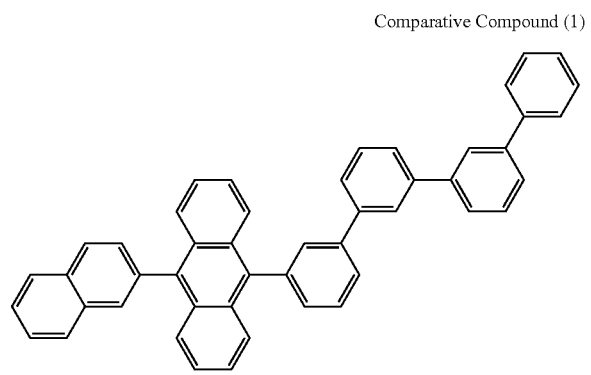
Comparative Compound (2)
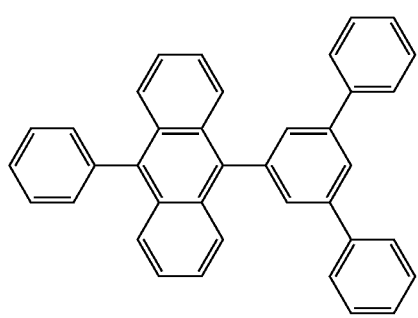
Comparative Compound (3)
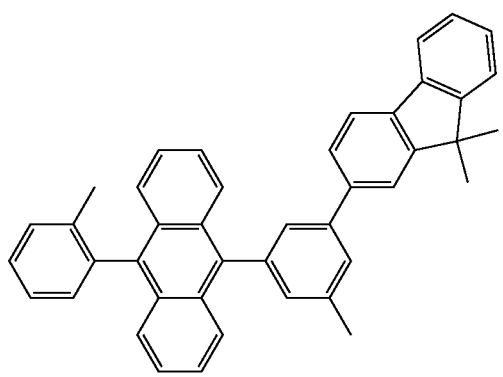
Comparative Compound (4)
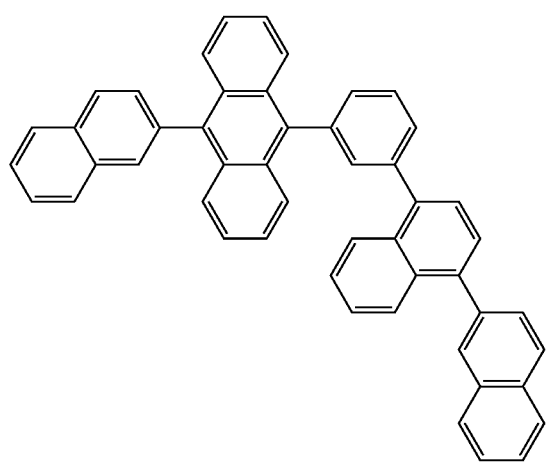
Comparative Compound (5)
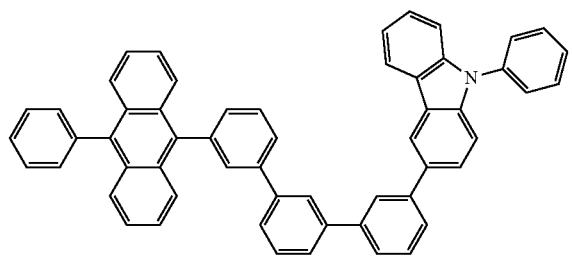
Comparative Compound (6)
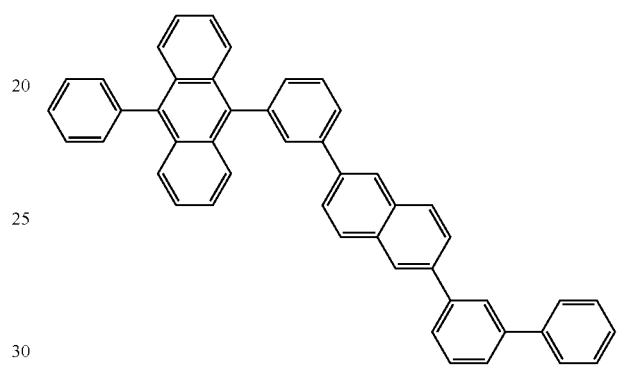
Comparative Compound (7)
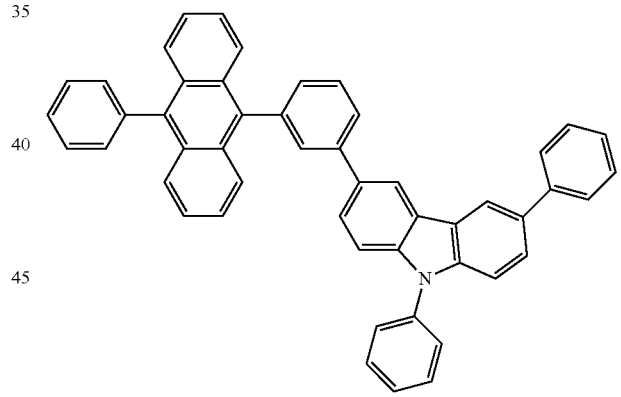
Comparative Compound (8)
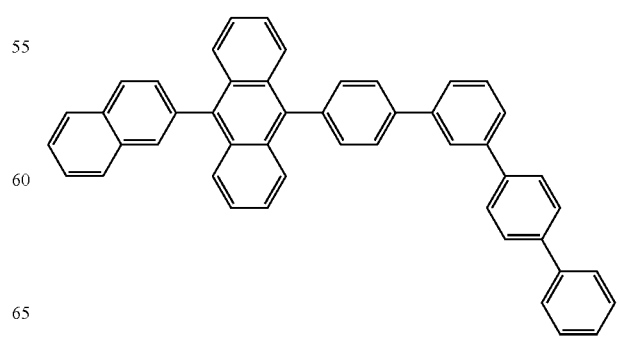

Comparative Compound (9)

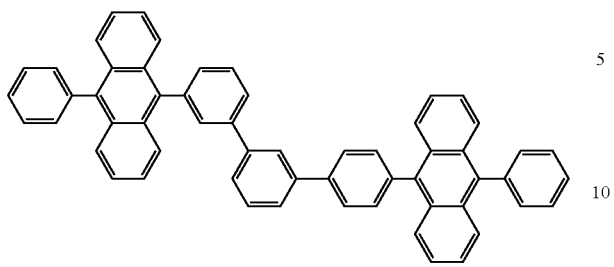

Comparative compound (1): compound AN-13 of WO2006/104044
Comparative compound (2): compound E87 of JP-A-2010-6818
Comparative compound (3): compound 81 of KR10-2011-0123701
Comparative compound (4): compound AN-35 of WO2006/104044
Comparative compound (5): compound AN-65 of WO2006/104044
Comparative compound (6): compound AN-86 of WO2006/104044
Comparative compound (7): compound AN-66 of WO2006/104044
Comparative compound (8): compound AN-98 of WO2006/104044
Comparative compound (9): compound AN-26 of WO2006/085434

Examples 201 to 214, and Comparative Examples 201 to 209

Organic electroluminescent elements of Examples 201 to 214 and Comparative Examples 201 to 209 were produced in the same manner as in Examples 101 to 114 and Comparative Examples 101 to 109, except that the following compound (D-2) was used as the light emitting material used for the light emitting layer. The organic electroluminescent element of each Example and Comparative Example was evaluated in the same manner as in Example 101. The results are presented in Table 2.

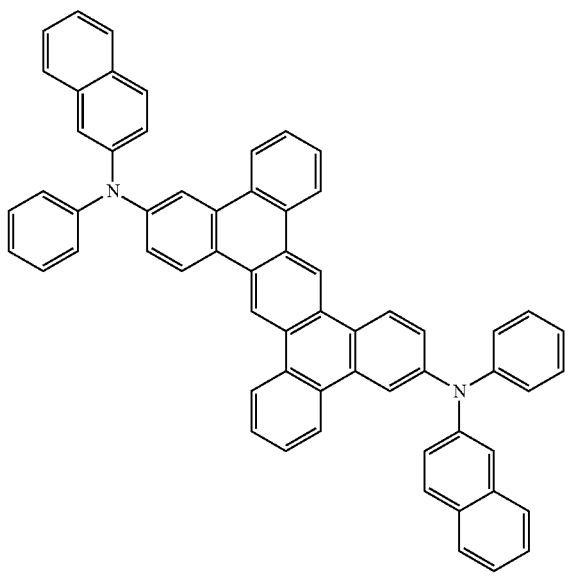

Light emitting material: Compound (D-2)

TABLE 2

| | Host material | Light emitting material | Color purity | Light emitting efficiency | Luminance deterioration at the initial stage of lighting (durability LT95) |
|---|---|---|---|---|---|
| Ex. 101 | (H-1) | D-1 | Good | Excellent | Excellent |
| Ex. 102 | (H-2) | D-1 | Good | Excellent | Good |
| Ex. 103 | (H-3) | D-1 | Good | Excellent | Good |
| Ex. 104 | (H-4) | D-1 | Good | Excellent | Good |
| Ex. 105 | (H-5) | D-1 | Good | Excellent | Excellent |
| Ex. 106 | (H-6) | D-1 | Good | Excellent | Good |
| Ex. 107 | (H-7) | D-1 | Good | Good | Good |
| Ex. 108 | (H-8) | D-1 | Good | Good | Good |
| Ex. 109 | (H-9) | D-1 | Good | Good | Good |
| Ex. 110 | (H-10) | D-1 | Good | Good | Good |
| Ex. 111 | (H-11) | D-1 | Good | Excellent | Good |
| Ex. 112 | (H-12) | D-1 | Good | Excellent | Excellent |
| Ex. 113 | (H-13) | D-1 | Good | Excellent | Good |
| Ex. 114 | (H-14) | D-1 | Good | Excellent | Good |
| Ex. 201 | (H-1) | D-2 | Excellent | Good | Excellent |
| Ex. 202 | (H-2) | D-2 | Excellent | Good | Good |
| Ex. 203 | (H-3) | D-2 | Excellent | Good | Good |
| Ex. 204 | (H-4) | D-2 | Excellent | Good | Good |
| Ex. 205 | (H-5) | D-2 | Excellent | Good | Excellent |
| Ex. 206 | (H-6) | D-2 | Excellent | Good | Good |
| Ex. 207 | (H-7) | D-2 | Excellent | Good | Good |
| Ex. 208 | (H-8) | D-2 | Excellent | Good | Good |
| Ex. 209 | (H-9) | D-2 | Excellent | Good | Good |
| Ex. 210 | (H-10) | D-2 | Excellent | Good | Good |
| Ex. 211 | (H-11) | D-2 | Excellent | Excellent | Good |
| Ex. 212 | (H-12) | D-2 | Excellent | Good | Excellent |
| Ex. 213 | (H-13) | D-2 | Excellent | Excellent | Good |

TABLE 2-continued

| | Host material | Light emitting material | Color purity | Light emitting efficiency | Luminance deterioration at the initial stage of lighting (durability LT95) |
|---|---|---|---|---|---|
| Ex. 214 | (H-14) | D-2 | Excellent | Excellent | Good |
| Com. Ex. 101 | Comparative compound (1) | D-1 | Good | Acceptable | Poor |
| Com. Ex. 201 | Comparative compound (1) | D-2 | Excellent | Poor | Acceptable |
| Com. Ex. 102 | Comparative compound (2) | D-1 | Good | Good | Poor |
| Com. Ex. 202 | Comparative compound (2) | D-2 | Excellent | Acceptable | Acceptable |
| Com. Ex. 103 | Comparative compound (3) | D-1 | Good | Good | Poor |
| Com. Ex. 203 | Comparative compound (3) | D-2 | Excellent | Good | Poor |
| Com. Ex. 104 | Comparative compound (4) | D-1 | Good | Acceptable | Acceptable |
| Com. Ex. 204 | Comparative compound (4) | D-2 | Excellent | Poor | Acceptable |
| Com. Ex. 105 | Comparative compound (5) | D-1 | Good | Acceptable | Poor |
| Com. Ex. 205 | Comparative compound (5) | D-2 | Excellent | Acceptable | Poor |
| Com. Ex. 106 | Comparative compound (6) | D-1 | Good | Acceptable | Acceptable |
| Com. Ex. 206 | Comparative compound (6) | D-2 | Excellent | Acceptable | Acceptable |
| Com. Ex. 107 | Comparative compound (7) | D-1 | Good | Acceptable | Poor |
| Com. Ex. 207 | Comparative compound (7) | D-2 | Excellent | Acceptable | Poor |
| Com. Ex. 108 | Comparative compound (8) | D-1 | Good | Poor | Acceptable |
| Com. Ex. 208 | Comparative compound (8) | D-2 | Excellent | Poor | Acceptable |
| Com. Ex. 109 | Comparative compound (9) | D-1 | Good | Poor | Acceptable |
| Com. Ex. 209 | Comparative compound (9) | D-2 | Excellent | Poor | Acceptable |

It was found from the results presented in Table 2 that the organic electroluminescent elements of the Examples in which the compounds of the present invention were used as the host material of the light emitting layer had high luminous efficiency, and slow luminance deterioration rates in the initial stage of lighting.

On the other hand, the comparative organic electroluminescent elements in which the comparative compounds (1) to (9) were used as the host material of the light emitting layer all had fast luminance deterioration rates in the initial stage of lighting, and were not desirable. The results were also unsatisfactory in terms of luminous efficiency.

DESCRIPTION OF REFERENCE NUMERALS AND SIGNS

2 Substrate
3 Anode
4 Hole injecting layer
5 Hole transporting layer
6 Light emitting layer
7 Hole blocking layer
8 Electron transporting layer
9 Cathode
10 Organic electroluminescent element
11 Organic layer
12 Protective layer
14 Adhesive layer
16 Sealing enclosure
20 Light emitting device
30 Light scattering member
31 Transparent substrate
30A Light incident surface
30B Light outputting surface
32 Fine particles
40 Illumination device

What is claimed:

1. A compound represented by the following general formula (1):

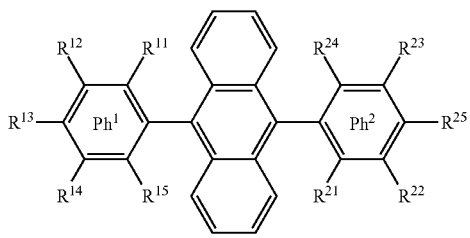

General Formula (1)

wherein: $Ph^1$ represents a phenyl group, and $Ph^2$ represents a phenylene group; $R^{11}$ to $R^{15}$ each independently represent a hydrogen atom, an alkyl group, or a silyl group, and $R^{11}$ to $R^{15}$ are not bound to each other to form a ring; any one of $R^{21}$ to $R^{24}$ represents a group represented by the general formula (1A) or (1B) below, and the other $R^{21}$ to $R^{24}$ each independently represent hydrogen atoms or alkyl groups, and $R^{21}$ to $R^{24}$ are not bound to each other to form a ring; $R^{25}$ represents a hydrogen atom, an alkyl group, or a silyl group General Formula (1A)

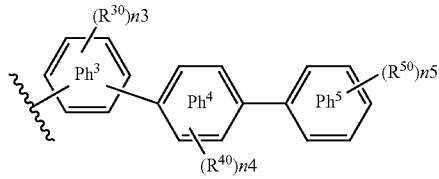

wherein: $Ph^i$ represents a phenylene group, $Ph^4$ represents a p-phenylene group, and $Ph^5$ represents a phenyl group; $R^{30}$ and $R^{40}$ each independently represent an alkyl group, n3 and n4 each independently represent an integer of 0 to 4, and, when n3 and n4 are 2 or more, a plurality of $R^{30}$, a plurality of $R^{40}$, and $R^{30}$ and $R^{40}$ are not connected to each other to form a ring; $R^{50}$ represents a substituent, n5 represents an integer of 0 to 5, and, when n5 is 2 or more, a plurality of $R^{50}$ may be connected to each other to form an aromatic hydrocarbon ring, with the proviso that when a plurality of $R^{50}$ are connected to each other to form an aromatic hydrocarbon ring, then $Ph^5$ as a whole is not further substituted with an aromatic hydrocarbon ring; $R^{40}$ and $R^{50}$ are not connected to each other to form a ring;

General Formula (1B)

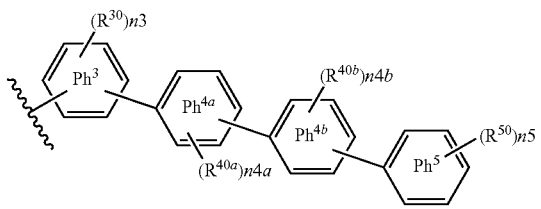

wherein: $Ph^3$, $Ph^{4a}$, and $Ph^{4b}$ each independently represent a phenylene group (at least one of $Ph^{4a}$ and $Ph^{4b}$ representing a p-phenylene group; $Ph^5$ represents a phenyl group; $R^{30}$, $R^{40a}$, and $R^{40b}$ each independently represent an alkyl group, n3, n4a, n4b each independently represent an integer of 0 to 4, and, when n3, n4a, and n4b are 2 or more, a plurality of $R^{30}$, a plurality of $R^{40a}$, a plurality of $R^{40b}$, $R^{30}$ and $R^{40a}$, and $R^{40a}$ and $R^{40b}$ are not connected to each other to form a ring; $R^{50}$ represents a substituent, $Ph^5$ represents a phenyl group, n5 represents an integer of 0 to 5, and, when n5 is 2 or more, a plurality of $R^{50}$ may be connected to each other to form an aromatic hydrocarbon ring, with the proviso that when a plurality of $R^{50}$ are connected to each other to form an aromatic hydrocarbon ring, then $Ph^5$ as a whole is not further substituted with an aromatic hydrocarbon ring; $R^{40b}$ and $R^{50}$ are not connected to each other to form a ring.

2. The compound according to claim 1, wherein the $R^{22}$ or $R^{23}$ in the compound represented by the general formula (1) is a group represented by the general formula (1A) or (1B).

3. The compound according to claim 1, wherein the $Ph^3$ in the compound represented by the general formula (1) is a m-phenylene group.

4. The compound according to claim 1, wherein one of the $R^{21}$ to $R^{24}$ in the compound represented by the general formula (1) is a group represented by the general formula (1A).

5. The compound according to claim 1, which is represented by any one of the following (H-1) to (H-14):

(H-1)

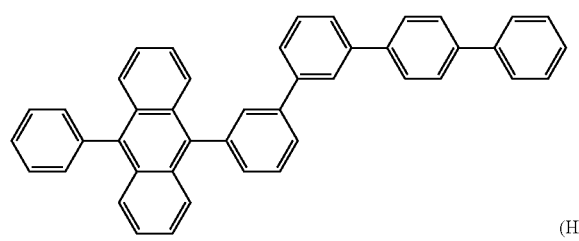

(H-2)

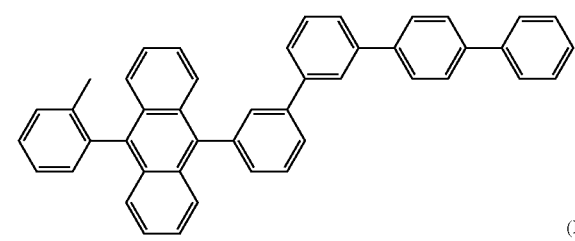

(H-3)

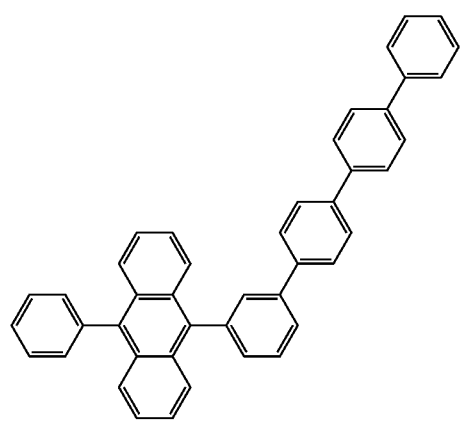

(H-4)

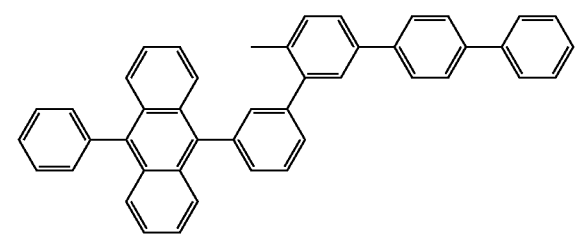

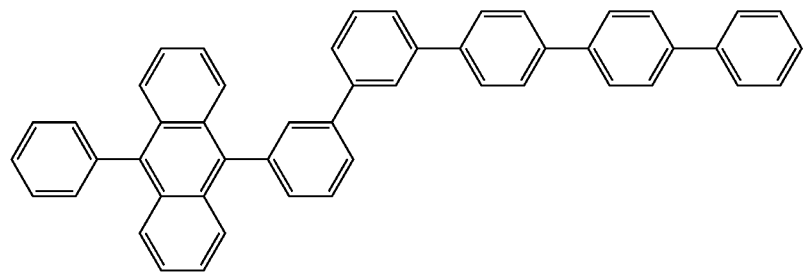
(H-5)
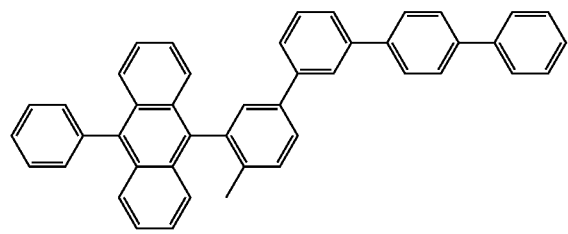
(H-6)　(H-7)
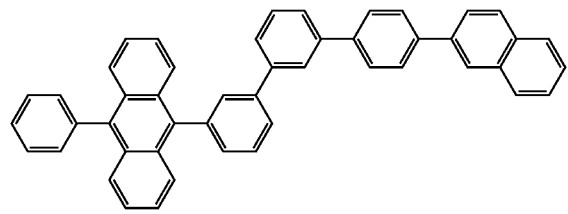
(H-8)　(H-9)
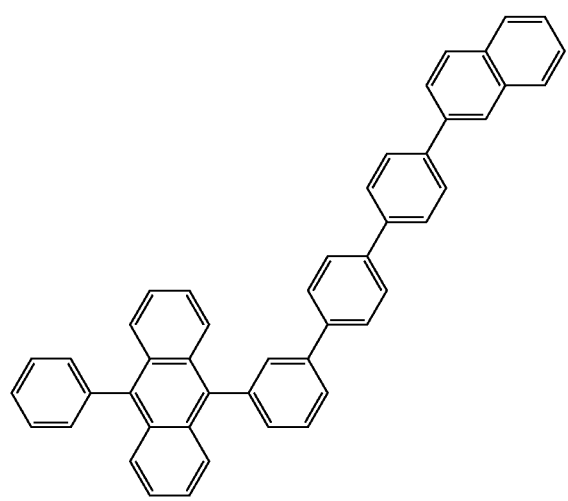
(H-10)　(H-11)

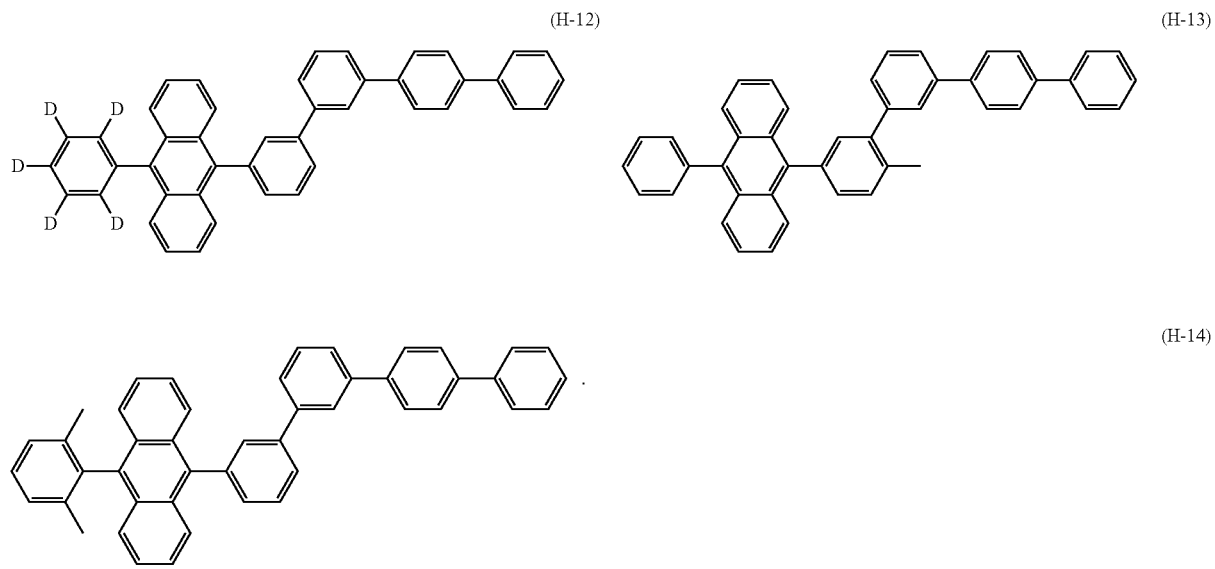

(H-12) (H-13) (H-14)

6. A charge transporting material comprising the compound of claim 1.

7. An organic electroluminescent element comprising the compound according to claim 1.

8. The organic electroluminescent element of claim 7 further including: a substrate; a pair of electrodes including an anode and a cathode, disposed on the substrate; and at least one organic layer including a light emitting layer, disposed between the electrodes, wherein at least one organic layer includes the compound.

9. The organic electroluminescent element according to claim 8, wherein the $R^{22}$ or $R^{23}$ in the compound represented by the general formula (1) is a group represented by the general formula (1A) or (1B).

10. The organic electroluminescent element according to claim 8, wherein the $Ph^3$ in the compound represented by the general formula (1) is a m-phenylene group.

11. The organic electroluminescent element according to claim 8, wherein $Ph^3$, $Ph^4$, and $Ph^5$ in the group represented by the general formula (1A) in the compound represented by the general formula (1) form a substituted or unsubstituted p-terphenylene structure, or that $Ph^{4a}$, $Ph^{4b}$, and $Ph^5$ in the group represented by the general formula (1B) form a substituted or unsubstituted p-terphenylene structure.

12. The organic electroluminescent element according to claim 8, wherein one of the $R^{21}$ to $R^{24}$ in the compound represented by the general formula (1) is a group represented by the general formula (1A).

13. The organic electroluminescent element according to claim 8, wherein the compound represented by the general formula (1) is contained in the light emitting layer.

14. The organic electroluminescent element according to claim 8, wherein the same organic layer as the organic layer containing the compound represented by the general formula (1) contains a compound represented by the following general formula (p-4):

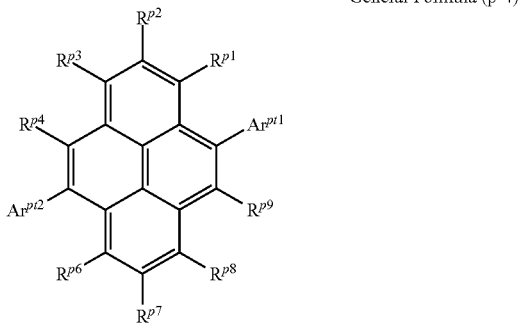

General Formula (p-4)

wherein $Ar^{p41}$ and $Ar^{p42}$ each independently represent a hydrogen atom, an aryl group, or a heteroaryl group, wherein the aryl or heteroaryl group may be substituted, and at least one of $Ar^{p41}$ and $Ar^{p42}$ represents an aryl group or a heteroaryl group;

$R^{p1}$ to $R^{p4}$ and $R^{p6}$ to $R^{p9}$ are each independently a hydrogen atom, or a substituent selected from the group consisting of an alkyl group, an aryl group, or a heteroaryl group; and any adjacent substituents may be bound to each other via a single bond or a linking group to form a ring.

15. The organic electroluminescent element according to claim 8, wherein the same organic layer as the organic layer containing the compound represented by the general formula (1) contains a compound represented by the following general formula (PT-2):

General Formula (PT-2)

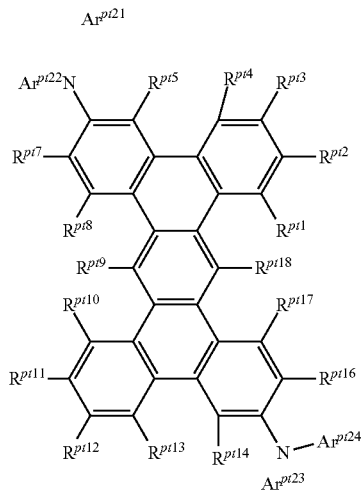

wherein $R^{pt1}$ to $R^{pt5}$, $R^{pt7}$ to $R^{pt14}$, and $R^{pt16}$ to $R^{pt18}$ represent hydrogen atoms; and $Ar^{pt21}$ to $Ar^{pt24}$ are each independently an aryl group that may be substituted.

16. The organic electroluminescent element according to claim 8, wherein the same organic layer as the organic layer containing the compound represented by the general formula (1) contains a compound represented by the following general formula (ch-1):

General Formula (ch-1)

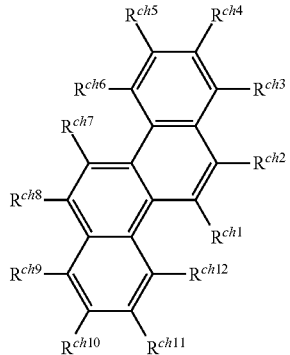

wherein $R^{ch1}$, $R^{ch3}$ to $R^{ch7}$ and $R^{ch9}$ to $R^{ch12}$ represent hydrogen atoms; and $R^{ch8}$ and $R^{ch2}$ are each independently a diarylamino group.

17. A light emitting device comprising the organic electroluminescent element of claim 8.

18. A display device comprising the organic electroluminescent element of claim 8.

19. An illumination device comprising the organic electroluminescent element of claim 8.

* * * * *